US009879306B2

(12) United States Patent
Binkowski et al.

(10) Patent No.: US 9,879,306 B2
(45) Date of Patent: Jan. 30, 2018

(54) LUCIFERASE BIOSENSORS FOR CAMP

(71) Applicant: PROMEGA CORPORATION, Madison, WI (US)

(72) Inventors: Brock Binkowski, Sauk City, WI (US); Lance P. Encell, Fitchburg, WI (US); Monika G. Wood, Mt. Horeb, WI (US); Keith V. Wood, Madison, WI (US); Kris Zimmerman, Madison, WI (US); Paul Otto, Madison, WI (US); Gediminas Vidugiris, Fitchburg, WI (US); Pete Stecha, New Glarus, WI (US)

(73) Assignee: PROMEGA CORPORATION, Madison, WI (US)

( * ) Notice: Subject to any disclaimer, the term of this patent is extended or adjusted under 35 U.S.C. 154(b) by 0 days.

(21) Appl. No.: 14/695,944

(22) Filed: Apr. 24, 2015

(65) Prior Publication Data

US 2015/0299765 A1 Oct. 22, 2015

Related U.S. Application Data

(62) Division of application No. 12/454,643, filed on May 19, 2009, now Pat. No. 9,045,730.

(60) Provisional application No. 61/119,983, filed on Dec. 4, 2008, provisional application No. 61/054,374, filed on May 19, 2008.

(51) Int. Cl.

| | |
|---|---|
| ***C12Q 1/66*** | (2006.01) |
| ***C12Q 1/00*** | (2006.01) |
| ***C12N 9/02*** | (2006.01) |
| ***G01N 33/573*** | (2006.01) |
| ***C12Q 1/68*** | (2006.01) |
| ***G01N 33/74*** | (2006.01) |

(52) U.S. Cl.

CPC ............. *C12Q 1/66* (2013.01); *C12N 9/0004* (2013.01); *C12N 9/0069* (2013.01); *C12Q 1/008* (2013.01); *C12Q 1/6876* (2013.01); *G01N 33/5735* (2013.01); *G01N 33/74* (2013.01); *C07K 2319/20* (2013.01); *C07K 2319/61* (2013.01); *C12Y 113/12* (2013.01); *C12Y 114/00* (2013.01); *G01N 2333/726* (2013.01); *G01N 2333/90241* (2013.01)

(58) Field of Classification Search

CPC .................................................. C12N 9/0069

See application file for complete search history.

(56) References Cited

U.S. PATENT DOCUMENTS

| | | | |
|---|---|---|---|
| 5,097,026 | A | 3/1992 | Jahnsen |
| 6,251,667 | B1 | 6/2001 | Habener et al. |
| 6,270,964 | B1 | 8/2001 | Michnick et al. |
| 6,294,330 | B1 | 9/2001 | Michnick et al. |
| 6,406,856 | B1 | 6/2002 | Glover et al. |
| 6,428,951 | B1 | 8/2002 | Michnick et al. |
| 6,573,059 | B1 | 6/2003 | Reymond |
| 6,602,677 | B1 | 8/2003 | Wood et al. |
| 6,762,026 | B1 | 7/2004 | Sugiyama |
| 6,808,874 | B2 | 10/2004 | Griffiths |
| 6,855,515 | B1 | 2/2005 | Rosen et al. |
| 6,890,745 | B1 | 5/2005 | Leng |
| 6,936,687 | B1 | 8/2005 | Komoriya et al. |
| 7,083,911 | B2 | 8/2006 | Wood et al. |
| 7,241,584 | B2 | 7/2007 | Wood et al. |
| 7,452,663 | B2 | 11/2008 | Wood et al. |
| 7,700,310 | B2 | 4/2010 | Somberg et al. |
| 7,732,128 | B2 | 6/2010 | Wood et al. |
| 7,741,067 | B2 | 6/2010 | Hawkins et al. |
| 7,927,816 | B2 | 4/2011 | Reed et al. |
| 7,927,871 | B2 | 4/2011 | Packard et al. |
| 8,030,017 | B2 | 10/2011 | Wood et al. |
| 8,183,036 | B2 | 5/2012 | Fan et al. |
| 8,227,572 | B2 | 7/2012 | Leitch et al. |
| 8,673,558 | B2 | 3/2014 | Fan et al. |
| 8,735,559 | B2 | 5/2014 | Binkowski et al. |
| 2002/0022220 | A1 | 2/2002 | Izevbigie |
| 2002/0132327 | A1 | 9/2002 | Hay et al. |
| 2002/0150885 | A1 | 10/2002 | Weber et al. |
| 2002/0151014 | A1 | 10/2002 | Campbell |
| 2003/0003506 | A1 | 1/2003 | Umezawa et al. |
| 2003/0053995 | A1 | 3/2003 | Hung et al. |
| 2003/0068801 | A1 | 4/2003 | Wood et al. |
| 2003/0092098 | A1 | 5/2003 | Bryan et al. |
| 2003/0104507 | A1 | 6/2003 | Wood et al. |
| 2003/0170850 | A1 | 9/2003 | Cardone et al. |
| 2003/0203407 | A1 | 10/2003 | Craig et al. |

(Continued)

FOREIGN PATENT DOCUMENTS

| | | |
|---|---|---|
| EP | 1097992 | 5/2001 |
| EP | 1229330 | 8/2002 |

(Continued)

OTHER PUBLICATIONS

Wikipedia G Protein Coupled Receptor entry https://en.wikipedia.org/wiki/G_protein%E2%80%93coupled_receptor, retrieved Sep. 27, 2016.*

(Continued)

*Primary Examiner* — Rebecca E Prouty

(74) *Attorney, Agent, or Firm* — Michael Best & Friedrich LLP

(57) ABSTRACT

A modified luciferase protein which is a sensor for molecules including cAMP is provided. The modified luciferase protein includes one or more heterologous amino acid sequences, at least one of which directly or indirectly interacts with cAMP.

3 Claims, 16 Drawing Sheets

(56) References Cited

U.S. PATENT DOCUMENTS

| | | | |
|---|---|---|---|
| 2003/0232404 | A1 | 12/2003 | Wood et al. |
| 2004/0096926 | A1 | 5/2004 | Packard et al. |
| 2004/0101922 | A1 | 5/2004 | Somberg et al. |
| 2004/0157272 | A1 | 8/2004 | Cardone et al. |
| 2005/0026171 | A1 | 2/2005 | Hawkins et al. |
| 2005/0054573 | A1 | 3/2005 | Werner et al. |
| 2005/0153310 | A1 | 7/2005 | Fan et al. |
| 2005/0170442 | A1 | 8/2005 | Kupcho et al. |
| 2005/0176071 | A1 | 8/2005 | Nikiforov et al. |
| 2005/0181452 | A1 | 8/2005 | Westwick et al. |
| 2006/0048592 | A1 | 3/2006 | Wood et al. |
| 2006/0110364 | A1 | 5/2006 | Harding |
| 2006/0183212 | A1 | 8/2006 | Wood et al. |
| 2007/0184493 | A1 | 8/2007 | Packard et al. |
| 2008/0199898 | A1 | 8/2008 | Packard et al. |
| 2008/0206798 | A1 | 8/2008 | Wood et al. |
| 2009/0075292 | A1 | 3/2009 | Reed et al. |
| 2009/0137019 | A1 | 5/2009 | Wood et al. |
| 2009/0215864 | A1 | 8/2009 | Feinstein |
| 2009/0253131 | A1 | 10/2009 | Wigdal et al. |
| 2009/0286299 | A1 | 11/2009 | Ronaghi et al. |
| 2009/0305280 | A1 | 12/2009 | Binkowski et al. |
| 2009/0311769 | A1 | 12/2009 | Wood et al. |
| 2010/0021949 | A1 | 1/2010 | Somberg et al. |
| 2010/0297620 | A1 | 11/2010 | Umezawa et al. |
| 2011/0039257 | A1 | 2/2011 | Binkowski et al. |
| 2012/0009647 | A1 | 1/2012 | Wood et al. |
| 2012/0117667 | A1 | 5/2012 | Klaubert et al. |
| 2012/0174242 | A1 | 7/2012 | Binkowski et al. |
| 2014/0273156 | A1 | 9/2014 | Fan et al. |
| 2014/0298500 | A1 | 10/2014 | Binkowski et al. |
| 2014/0308211 | A1 | 10/2014 | Binkowski et al. |
| 2016/0115522 | A1 | 4/2016 | Binkowski et al. |

FOREIGN PATENT DOCUMENTS

| | | |
|---|---|---|
| JP | 5501862 | 4/1993 |
| JP | 2002315589 | 10/2002 |
| JP | 2012/090635 | 5/2012 |
| WO | WO 95/18853 | 7/1995 |
| WO | WO 00/14267 | 3/2000 |
| WO | 00/24878 | 5/2000 |
| WO | WO 00/24768 | 5/2000 |
| WO | WO 00/75332 | 12/2000 |
| WO | WO 01/20002 | 3/2001 |
| WO | WO 02/06458 | 1/2002 |
| WO | WO 02/08766 | 1/2002 |
| WO | WO 02/16944 | 2/2002 |
| WO | WO 02/059262 | 8/2002 |
| WO | WO 03/066883 | 8/2003 |
| WO | WO 2004/027094 | 4/2004 |
| WO | WO 2004/038039 | 5/2004 |
| WO | WO 2004/043992 | 5/2004 |
| WO | WO 2004/059294 | 7/2004 |
| WO | WO 2004/081189 | 9/2004 |
| WO | WO 2005/015161 | 2/2005 |
| WO | WO 2005/038029 | 4/2005 |
| WO | WO 2005/052186 | 6/2005 |
| WO | WO 2006/023972 | 3/2006 |
| WO | WO 2007/120522 | 10/2007 |
| WO | 2008/030968 | 3/2008 |
| WO | 2009/049892 | 4/2009 |
| WO | WO 2009/142735 | 11/2009 |
| WO | WO 2011/143339 | 11/2011 |
| WO | WO 2013/071237 | 5/2013 |

OTHER PUBLICATIONS

Goodsell, "PDB Molecule of the Month: Estrogen Receptor," http://www.rcsb.org/pdb/molecules/pdb45_1.html, (observed Dec. 8, 2003) 2 pages.

Baird, G.S. et al., "Circular permutation and receptor insertion within green fuorescent proteins," Proc. Natl. Acad. Sci. USA (1999) 96:11241-11246.

Berman, H.M.et al., "The cAMP binding domain: an ancient signaling module," Proc. Natl. Acad. Sci. USA (2000) 102(1):45-50.

Binkowski et al., Engineered luciferases for molecular sensing in living cells, Current Opinion in Biotechnology, vol. 20, Iss. 1, Feb. 2009, pp. 14-18.

Bos, J.L., "Epac: a new cAMP target and new avenues in cAMP research," Nat. Rev. Mol. Cell. Biol. (2003) 4:733-738.

Burbelo, P.D. et al., "Detecting protein-protein interactions using renilla luciferase fusion proteins," Biotech. (2002) 33(5):1044-1049.

Chong, S. et al., "Single-column purification of free recombinant proteins using a self-cleavable affinity tag derived from a protein splicing element," Gene (1997) 192:271-281.

Daugherty et al., "Quantitative analysis of the effect of the mutation frequency on the affinity maturation of single chain Fv antibodies," PNAS USA 97(5):2029-2034 (2000).

Dremier, S. et al., "Search for new cyclic AMP-binding proteins," FEBS Left. (2003) 546:103-107.

Fan, F. et al., "Novel genetically encoded biosensors using firefly luciferase," ACS Chemical Biology (2008) 3(6):346-351.

Genbank Accession No. AF115480, Sequence ID No. 123, "Mus musculus cAMP-dependent Rap1 guanine-nucleotide exchange factor mRNA, complete cds" (1999) 2 pages.

Genbank Accession No. AF192755, Seq. ID No. 125, "Trypanosoma brucei cyclic nucleotide phophodiesterase (PDE) gene, complete cds" (2002) 2 pages.

Genbank Accession No. M124921, "Rat type II cAMP-dependent protein kinase regulatory subunit mRNA, 3' end" (2002) 2 pages.

Genbank Accession No. NM_002734, "*Homo sapiens* protein kinase, cAMP-dependent, regulatory, type I, alpha (tissue specific extinguisher1), (PRKAR1A), transcript variant 1, mRNA," (2010) 5 pages.

Graf, R. et al., "Random circular permutation of genes and expressed polypeptide chains: application of the method to the catalytic chains of aspartate transcarbamoylase," Proc. Natl. Acad. Sci. USA (1996) 93:11591-11596.

Greer, L.F. et al., "Imaging of light emission from the expression of luciferases in living cells and organisms: a review," Luminescence (2002) 17(1):43-74.

Hanks, S.K. et al., "The eukaryotic protein kinase super family: kinase (catalytic) domain structure and classification," FASEB J. (1995) 9:576-596.

Heinemann, U. et al., "Circular permutation of polypeptide chains: implications for protein folding and stability," Prog. Biophys. Mol. Biol. (1995) 64(2-3):121-143.

Kaihara, A. et al., "Locating a protein-protein interaction in living cells via split renilla luciferase complementation," Anal. Chem. (2003) 75(16):4176-4181.

Kim et al., Circularly permutated bioluminescent probes for illuminating ligand-activated protein dynamics, Bioconjugate Chem, 2008, 19, pp. 2480-2486.

Kunkel, "Rapid and efficient site-specific mutagenesis without phenotypic selection," PNAS USA 82(2):488-492 (1985).

Laxman, B. et al., "Noninvasive real-time imaging of apoptosis," Proc. Natl. Acad. Sci. USA (2002) 99(26):16551-16555.

Leclerc, G.M. et al., "Development of a destabilized firefly luciferase enzyme for measurement of gene expression," BioTech. (2000) 29(3):590-601.

Lee, J-C., "Development of a cell-based assay for monitoring specific hepatitis C virus NS3/4A protease activity in mammalian cells," Anal. Biochem. (2003) 316(2):162-170.

Li, I.T. et al., "Protein biosensors based on the principle of fluorescene resonance energy transfer for monitoring cellular dynamics," Biotech. Lett. (2006) 28(24):1971-1982.

Littlewood, T.D. et al., "A modified oestrogen receptor ligand-binding domain as an improved switch for the regulation of heterologous proteins," Nucl. Acids Res. (1995) 23(10):1686-1690.

Lorenz, W. et al., "Isolation and expression of a cDNA encoding renilla reniformis luciferase," Proc. Natl. Academ. Sci. USA, May 1991, vol. 88, pp. 4438-4442.

(56) References Cited

OTHER PUBLICATIONS

Luker, K.E. et al., "Kinetics of regulated protein-protein interactions revealed with firefly luciferase complementation imaging in cells and living animals," Proc. Natl. Acad. Sci. USA (2004) 101(33):12288-12293.
Lykens et al., "Perforin is a critical physiologic regulator of T-cell activation," Blood, 118:618-626 (2011).
Maldonado, F. et al., "A cDNA clone encoding human cAMP-dependent protein kinase catalytic subunit calpha," Nucl. Acids Res. (1988) 16(16):8189-8190.
Massoud, T.F. et al., "Molecular imaging of homodimeric protein-protein interactions in living subjects," The FASEB Journal (2004) 18:1105-1107.
Mayer, B.J. et al., "Signalling through SH2 and SH3 domains," Trends Cell Biol. (1993) 3:8-13.
Michel, P. et al., "Expression and purification of polyhistidine-tagged firefly luciferase in insect cells—a potential alternative for process scale-up," J. Biotech., Short Technical Reports (2001) 85(1):49-56.
Murray et al., "Codon usage in plant genes" NAR 17: 477-498 (1989).
Nagai, T. et al., Circularly permuted green fluorescent proteins engineered to sense Ca2+, Proc. Natl. Acad. Sci. USA, 2001, 98, pp. 3197-3202.
Nikolaev, V.O. et al., "Novel single chain cAMP sensors for receptor-induced signal propagation," J. Biol. Chem. (2004) 279(36):37215-37218.
Niles, A.L. et al., "Caspase activity assays," Meth. Mol. Biol. (2008) 414:137-150.
Øyen, O. et al., "Human testis cDNA for the regulatory subunit R11α of cAMP-dependent protein kinase encodes an alternative amino-terminal region," FEBS Left. (1989) 246(1-2):57-64.
Ozawa, T. et al., "Split luciferase as an optical probe for detecting protein-protein interactions in mammalian cells based on protein splicing," Anal. Chem. (2001) 73(11):2516-2521.
Paulmurugan, R. et al., "An intramolecular folding sensor for imaging estrogen receptor-ligand interactions," Proc. Natl. Acad. Sci. USA (2006) 103(43):15883-15888.
Paulmurugan, R. et al., "Molecular imaging of drug-modulated protein-protein interactions in living subjects," Cancer Res. (2004) 64:2113-2119.
Paulmurugan, R. et al., "Monitoring protein-protein interactions using split synthetic renilla luciferase protein-fragment-assisted complementation," Anal. Chem. (2003) 75(7):1584-1589.
Paulmurugan, R. et al., "Novel fusion protein approach for efficient high-throughput screening of small molecule-mediating protein-protein interactions in cells in living animals," Cancer Res. (2005) 65(16):7413-7420.
Paulmurugan, R. eta l., "Noninvasive imaging of protein-protein interactions in living subjects by using reporter protein complementation and reconsittution strategies," Proc. Natl. Acad. Sci. USA (2002) 99(24):15608-15613.
Plainkum, P. et al., "Creation of a zymogen," Nature Structural Biology (2003) 10(2):115-119.
Qian, Z. et al., "Improving the catalytic activity of candida antarctica lipase B by circular permutation," J. Am. Chem. Soc. (2005) 127:13466-13467.
Sadowski, I. et al., "A noncatalytic domain conserved among cytoplasmic protein-tyrosine kinases modifies the kinase function and transforming activity of fujinami sarcoma virus P130 gaag-fps," Mol. Cell. Biol. (1986) 6:4396-4408.
Sala-Newby, G., "Engineering a bioluminescent indicator for cyclic AMP-dependent protein kinase," Biochem. J. (1991) 279(Part 3):727-732.
Sala-Newby, G., "Engineering firefly luciferase as an indicator of cyclic AMP-dependent protein kinase in living cells," FEBS Letters (1992) 307(2):241-244.
Siehler, S., "Cell-based assays in GPCR drug discovery," Biotechnol. J. (2008) 3:471-483.
Spotts, J.M. et al., "Time-lapse imaging of a dynamic phosphorylation-dependent protein-protein interaction in mammalian cells," Proc. Natl Acad. Sci. USA (2002) 99(23):15142-15147.
Tanenbaum, D.M. et al., "Crystallographic comparison of the estrogen and progesterone receptor's ligand binding domains," Proc. Natl. Acad. Sci. USA (1998) 95:5998-6003.
Umezawa, Y., "Assay and screening methods for bioactive substances based on cellular signalling pathways," Reviews in Mol. Biotech. (2001) 82:357-370.
Wada et al., "Codon usage tabulated from the GenBank genetic sequence data" NAR 18: 2367-2411 (1990).
Wang, X. et al., "Effect of removal of the N-terminal amino acid residues on the activity and conformation of firefly luciferase," Intl. J. Biochem. Cell Biol. (2002) 34(8):983-991.
Waud, J.P. et al., "Engineering the C-terminus of firefly luciferase as an indicator of covalent modification of proteins," Biochim. Biophys. Acta (1996) 1292(1):89-98.
Wigdal, S.S. et al., "A novel bioluminescent protease assay using engineered firefly luciferase," Curr. Chem. Genomics (2008) 2(1):16-28.
Wiley, S.R. et al., "Identification and characterization of a new member of the TNF family that induces apoptosis," Immunity (1995) 3(6):673-682.
Ye, L. et al., "Cloning and sequencing of a cDNA for firefly luciferase from photuris pennsylvanica," Biochimica et Biophysica Acta (1997) 1339:39-52.
Zagotta, W.N. et al., "Structural basis for modulation and agonist specificity of HCN pacemaker channels," Nature (2003) 425:200-205.
Zako, T. et al., "Luminescent and substrate binding activities of firefly luciferase N-terminal domain," Biochim. Biophys. Acta—Proteins & Proteomics (2003) 1649(2):183-189.
Zhang et al., "A Simple Statistical Parameter for Use in Evaluation and Validation of High Throughput Screening Assays," Biomol Screen. 4:67-73 (1999).
Zhang, J. et al., "Creating new fluorescent probes for cell biology," Mol. Cell Biol. (2002) 3:906-918.
Zhao, H. et al., "Emission spectra of bioluminescent reporters and interaction with mammalian tissue determine the sensitivity of detection in vivo," J. Biomed. Optics (2005) 10(4):041230-1-041230-9.
De Wet, J.R., et al., 1987, "Firefly luciferase gene: structure and expression in mammalian cells", Molecular and Cellular Biology, vol. 7, No. 2, pp. 725-737.
Tatsumi, H., et al., 1992, "Molecular cloning and expression in *Escherichia coli* of a eDNA clone encoding luciferase of a firefly, Lucio Ia lateralis", Biochimica et Biophysica Acta, vol. 1131, pp. 161-165.
Devine, J.H., et al., 1993, "Luciferase from the East European firefly Luciola mingrelica: cloning and nucleotide sequence of the eDNA, overexpression in *Escherichia coli* and purification of the enzyme", Biochimica et Biophysica Acta, vol. 1173, pp. 121-132.
Sala-Newby, G.B., et al., 1996, "Sequence and biochemical similarities between the luciferases of the glow-worm Lampyris noctiluca and the firefly Photinus pyralis", Biochemical Journal, vol. 313, pp. 761-767.
Alipour B.S., et al., 2004, "Molecular cloning, sequence analysis, and expression of a eDNA encoding the luciferase from the glow-worm, Lampyris turkestanicus", Biochemical and Biophysical Research Communications, vol. 325, pp. 215-222.
Viviani, V. R., et al., 2004, "Cloning and characterization of the eDNA for the Brazilian Cratomorphus distinctus larval firefly luciferase: similarities with European Lampyris noctiluca and Asiatic Pyrocoelia luciferases", Comparative Biochemistry and Physiology, Part B, vol. 139, pp. 151-156.
Li, X., et al., 2006, "Phylogenetic relationship of the firefly, Diaphanes pectineal is based on the DNA sequence and gene structure of luciferase", Dong Wu Xue Za Zhi [Zoological Research], vol. 27, No. 4, pp. 367-374.
Oba, Y., et al., 2010, "Identification and characterization of a luciferase isotype in the Japanese firefly, Luciola cruciata, involving in the dim glow of firefly eggs", Biochemistry, vol. 49, pp. 10788-10795.

(56) References Cited

OTHER PUBLICATIONS

Wilson et al., Annu. Rev. Cell Dev. Biol., 1998, vol. 14, pp. 197-230.
Canadian Patent Office Action for Application No. 2648263 dated Feb. 8, 2011 (4 pages).
Chinese Patent Office Action for Application No. 200780020577.7 dated Jun. 4, 2010 (9 pages) with translation.
European Patent Office Action for Application No. 07754666.1 dated Jan. 11, 2010 (3 pages).
European Patent Office Action for Application No. 07754666.1 dated Feb. 13, 2009 (6 pages).
European Patent Office Action for Application No. 07754666.1 dated Aug. 19, 2011 (4 pages).
European Patent Office Partial Search Report for Application No. 11155576.9 dated May 3, 2011 (7 pages).
European Patent Office Action for Application No. 11155576.9 dated Sep. 9, 2011 (12 pages).
European Patent Office Action for Application No. 07754666.1 dated Jun. 11, 2012 (4 pages).
European Patent Office Action for Application No. 07754666.1 dated Mar. 25, 2013 (4 pages).
European Patent Office Action for Application No. 11155576.9 dated Nov. 20, 2013 (4 pages).
European Patent Office Action for Application No. 07754666.1 dated Feb. 11, 2014 (5 pages).
European Patent Office Action for Application No. 04809862.8 dated Mar. 19, 2007 (3 pages).
European Patent Office Examination Report for Application No. 04809862.8 dated Dec. 28, 2007 (3 pages).
European Patent Office Action for Application No. 04809862.8 dated Apr. 8, 2009 (4 pages).
European Patent Office Examination Report for Application No. 04809862.8 dated Dec. 23, 2009 (4 pages).
European Patent Office Action for Application No. 04809862.8 dated Dec. 1, 2010 (4 pages).
European Patent Office Action for Application No. 10182746.7 dated Feb. 10, 2011 (7 pages).
European Patent Office Action for Application No. 10182746.7 dated Jan. 17, 2013 (4 pages).
European Patent Office Action for Application No. 10182746.7 dated Nov. 21, 2013 (3 pages).
European Patent Office Action for Application No. 10182742.6 dated Jan. 10, 2013 (5 pages).
European Patent Office Action for Application No. 10182742.6 dated Oct. 15, 2013 (4 pages).
European Patent Office Action for Application No. 10182742.6 dated Apr. 2, 2014 (5 pages).
European Patent Office Action for Application No. 09750966.5 dated Apr. 19, 2011 (3 pages).
European Patent Office Action for Application No. 11720279.6 dated Sep. 24, 2013 (7 pages).
European Patent Office Action for Application No. 11720279.6 dated May 2, 2014 (5 pages).
Invitation to Pay Additional Fees and Partial Search Report for Application No. PCT/US2007/008176 dated Feb. 10, 2007 (7 pages).
Invitation to Pay Additional Fees and Partial Search Report for Application No. PCT/US2004/032705 dated May 19, 2005 (9 pages).
International Search Report and Written Opinion for Application No. PCT/US2009/003132 dated Nov. 12, 2009 (10 pages).
International Search Report and Written Opinion for Application No. PCT/US2011/036110 dated Jul. 28, 2011 (15 pages).
PCT/US2012/064675 Invitation to Pay Additional Fees and International Search Report dated Jan. 31, 2013 (9 pages).
PCT/US2012/064675 International Search Report and Written Opinion dated Apr. 3, 2013 (19 pages).
Japanese Patent Office Action for Application No. 2006-534242 dated Sep. 1, 2010 (9 pages).
Japanese Patent Office Action for Application No. 2006-534242 dated Dec. 15, 2011 (6 pages) with English translation.
Japanese Patent Office Action for Application No. 2011-43966 dated May 1, 2013 (6 pages) English translation.
Japanese Patent Office Action for Application No. 2006-534242 dated Feb. 4, 2014 (8 pages, English translation included).
Japanese Patent Office Action for Application No. 2011-43966 dated Jul. 2, 2014 (7 pages, English translation included).
Japanese Patent Office Action for Application No. 2011-043966 dated Feb. 25, 2015 (6 pages—English summary included).
Japanese Patent Office Action for Application No. 2009-504249 dated Jun. 9, 2011 (10 pages).
Japanese Patent Office Action for Application No. 2011-269846 dated May 14, 2012 (Original and English Translation, 8 pages).
Japanese Patent Office Action for Application No. 2009-504249 dated May 10, 2012 (English Translation Only, 4 pages).
Japanese Patent Office Action for Application No. 2009-504249 dated Feb. 7, 2013 (Original and English Translation, 7 pages).
Japanese Patent Office Action for Application No. 2012-248580 dated May 1, 2014 (5 pages, English translation included).
Japanese Patent Office Action for Application No. 2009-504249 dated May 26, 2014 (5 pages, English translation included).
Japanese Patent Office Action for Application No. 2009-504249 dated Dec. 8, 2014 (2 pages).
Japanese Patent Office Action for Application No. 2011-510512 dated Nov. 25, 2013 (Original, 5 pages).
Singapore Patent Office Search Report and Written Opinion for Application No. 200807470-0 dated Jan. 29, 2010 (17 pages).
United States Patent Office Action for U.S. Appl. No. 10/957,433 dated Jan. 7, 2010 (6 pages).
United States Patent Office Action for U.S. Appl. No. 10/957,433 dated Jul. 21, 2009 (8 pages).
United States Patent Office Action for U.S. Appl. No. 10/957,433 dated Feb. 12, 2009 (5 pages).
United States Patent Office Action for U.S. Appl. No. 10/957,433 dated Sep. 4, 2008 (7 pages).
United States Patent Office Action for U.S. Appl. No. 10/957,433 dated Mar. 21, 2008 (10 pages).
United States Patent Office Action for U.S. Appl. No. 10/957,433 dated Mar. 11, 2011 (6 pages).
United States Patent Office Action for U.S. Appl. No. 10/957,433 dated Jan. 31, 2012 (3 pages).
United States Patent Office Action for U.S. Appl. No. 13/454,464 dated Apr. 30, 2013 (8 pages).
United States Patent Office Action for U.S. Appl. No. 11/732,105 dated Jun. 7, 2011 (22 pages).
United States Patent Office Action for U.S. Appl. No. 11/732,105 dated Nov. 23, 2011 (19 pages).
United States Patent Office Action for U.S. Appl. No. 11/732,105 dated Sep. 4, 2013 (10 pages).
United States Patent Office Action for U.S. Appl. No. 11/732,105 dated May 23, 2014 (10 pages).
United States Patent Office Action for U.S. Appl. No. 13/105,648 dated Jun. 20, 2013 (14 pages).
United States Patent Office Notice of Allowance for U.S. Appl. No. 13/105,648 dated Jan. 10, 2014 (12 pages).
United States Patent Office Action for U.S. Appl. No. 11/732,105 dated Oct. 9, 2014 (11 pages).
United States Patent Office Action for U.S. Appl. No. 13/674,655 dated Oct. 27, 2014 (21 pages).
United States Patent Office Action for U.S. Appl. No. 14/180,451 dated Feb. 11, 2015 (9 pages).
United States Patent Office Action for U.S. Appl. No. 14/269,669 dated Feb. 2, 2015 (11 pages).
United States Patent Office Action for U.S. Appl. No. 14/269,689 dated Feb. 4, 2015 (16 pages).
United States Patent Office Action for U.S. Appl. No. 13/674,655 dated Apr. 1, 2015 (10 pages).
Japanese Patent Office Action for Application No. 2014-266438 dated Jun. 20, 2016 (8 pages including translation).
Japanese Patent Office Action for Application No. 2011-510512 dated Mar. 9, 2016 (12 pages including translation).

(56) References Cited

OTHER PUBLICATIONS

Kanno Akira et al., "Detection of apoptosis using cyclic luciferase in living mammals," Methods in Molecular Biology, 2009, vol. 574, pp. 105-114.
United States Patent Office Notice of Allowance for U.S. Appl. No. 14/269,669 dated Jan. 13, 2016 (9 pages).
United States Patent Office Notice of Allowance for U.S. Appl. No. 11/732,105 dated Feb. 8, 2016 (15 pages).
Japanese Patent Office Action for Application No. 2014-266438 dated Oct. 28, 2015 (5 pages—including translation).
United States Patent Office Final Action for U.S. Appl. No. 11/732,105 dated Oct. 9, 2015 (11 pages).
United States Patent Office Notice of Allowance for U.S. Appl. No. 13/674,655 dated Nov. 5, 2015 (10 pages).
Thornberry, N. A., 1997, "A combinatorial approach defines specificities of members of the caspase family and granzyme B. Functional relationships established for key mediators of apoptosis", The Journal of Biological Chemistry, vol. 272, No. 29, pp. 17907-17911.
Li, H., et al., 1998, "Cleavage of BID by caspase 8 mediates the mitochondrial damage in the Fas pathway of apoptosis", Cell, vol. 94, pp. 491-501.
Gross, A., et al., 1999, "Caspase cleaved BID targets mitochondria and is required for cytochrome c release, while BCL-XL prevents this release but not tumor necrosis factor-R1/Fas death", The Joumal of Biological Chemistry, vol. 274, No. 2, pp. 1156-1163.
United States Patent Office Final Action for U.S. Appl. No. 14/269,669 dated Jul. 20, 2015 (11 pages).
United States Patent Office Notice of Allowance for U.S. Appl. No. 14/269,689 dated Sep. 25, 2015 (9 pages).
United States Patent Office Final Action for U.S. Appl. No. 14/180,451 dated Jul. 29, 2015 (5 pages).
Nagai, T. et al., "Development of a GFP variant with fast and efficient maturation properties," Seibutsu Butsuri, The Biophysical Society of Japan, (2002) 42(6):305-308.
European Patent Office Action for Application No. 11155576.9 dated Jul. 13, 2012 (4 pages).
International Search Report and Written Opinion for Application No. PCT/US2007/008176 dated Dec. 27, 2007 (18 pages).
International Search Report and Written Opinion for Application No. PCT/US2004/032705 dated Dec. 9, 2005 (20 pages).
United States Patent Office Action for U.S. Appl. No. 10/957,433 dated Oct. 12, 2007 (9 pages).
United States Patent Office Action for U.S. Appl. No. 12/454,643 dated Jan. 31, 2012 (13 pages).
United States Patent Office Final Rejection for U.S. Appl. No. 12/454,643 dated Jun. 15, 2012 (9 pages).
United States Patent Office Action for U.S. Appl. No. 12/454,643 dated Jun. 24, 2014 (14 pages).
United States Patent Office Notice of Allowance for U.S. Appl. No. 12/454,643 dated Jan. 26, 2015 (19 pages).
Japanese Patent Office Action for Application No. 2011-510512 dated Oct. 3, 2016 (6 pages including translation).
United States Patent Office Action for U.S. Appl. No. 14/990,279 dated Dec. 28, 2016 (13 pages).
Packard et al., "Granzyme B activity in Target Cells Detects Attack by Cytotoxic Lymphocytes," The Journal of Immonology, 2007, vol. 179, No. 6, pp. 3812-3820.
European Patent Office Action for Application No. 12791055.2 dated May 30, 2017 (7 pages).
Japanese Patent Office Action for Application No. 2014-266438 dated Jun. 5, 2017 (10 pages, English translation included).
United States Patent Office Notice of Allowance for U.S. Appl. No. 14/990,279 dated May 8, 2017 (8 pages).
United States Patent Office Action for U.S. Appl. No. 14/990,279 dated Jul. 12, 2016 (12 pages).
Wigdal et al., "Sensitive and Flexible Protease Assay without the Need for Chemical Synthesis," Promega Corporation, 2009, pp. 1-9.
European Patent Office Action for Application No. 151897253 dated Sep. 4, 2017 (8 pages).
United States Patent Office Action for U.S. Appl. No. 15/168,631 dated Nov. 16, 2017 (11 pages).

* cited by examiner

| FSK at 3 uM | EC50 (nM) | S/B |
| --- | --- | --- |
| L9 + FSK | 24 | 3.1 |
| L9 No FSK | 22 | 3.1 |
| GS358 + FSK | 40 | 1.6 |
| GS358 No FSK | 24 | 2.5 |

LUCIFERASE BIOSENSORS FOR CAMP

CROSS-REFERENCE TO RELATED APPLICATIONS

This application is a divisional of U.S. application Ser. No. 12/454,643 filed May 19, 2009, now U.S. Pat. No. 9,045,730 which claims priority to U.S. Provisional Application No. 61/054,374 filed on May 19, 2008 and U.S. Provisional Application No. 61/119,983 filed on Dec. 4, 2008, all of which are incorporated herein by reference in their entirety.

FIELD OF THE INVENTION

This invention relates to the field of biochemical assays and reagents. More specifically, this invention relates to modified luciferases and to methods for their use.

BACKGROUND

Luciferases are enzymes that catalyze the oxidation of a substrate (e.g., luciferin) with the concomitant release of photons of light. Luciferases have been isolated from numerous species, including Coleopteran arthropods and many sea creatures. Because it is easily detectable and its activity can be quantified with high precision, luciferases have been used widely to study gene expression and protein localization. Unlike green fluorescent protein (GFP), which requires up to 30 minutes to form its chromophore, the products of luciferases can be detected immediately upon completion of synthesis of the polypeptide chain (if substrate and oxygen are also present). In addition, no post-translational modifications are required for enzymatic activity, and the enzyme contains no prosthetic groups, bound cofactors, or disulfide bonds. Luciferases are useful reporters in numerous species and in a wide variety of cells.

Luciferases possess additional features that render them particularly useful as reporter molecules for biosensing, i.e., molecules which reveal molecular properties of a system. Biosensors (i.e., sensors which comprise a biological component) generally function by means of a two-step process: signal generation mediated through a biological component, and signal transduction and/or amplification through an electrical component. Signal generation is typically achieved through binding, energy transfer or catalysis. Signal generation by enzymatic catalysis can be particularly useful due to the inherent efficiency and specificity of these chemical processes. Most catalytic reactions generate less than the energy of hydrolysis for two molecules of ATP, or about 70 kJ/mole. However, the luminescence elicited by luciferases has much higher energy content. For instance, the reaction catalyzed by firefly luciferase (560 nm) emits 214 kJ/mole of energy. Furthermore, luciferases are also highly efficient at converting chemical energy into photons, i.e., they have high quantum yields. Luciferases are thus extremely efficient for generating detectable signals.

Luciferase biosensors have been described. For example, Sala-Newby et al. (Biochem J. 279:727 (1991)) disclose that a *Photinus pyralis* luciferase cDNA was modified to generate cyclic AMP-dependent protein kinase phosphorylation sites. In particular, a valine at position 217 was mutated to arginine to generate a site, RRFS (SEQ ID NO:1), and the heptapeptide kemptide, the phosphorylation site of the porcine pyruvate kinase, was added at the N- or C-terminus of the luciferase. Sala-Newby et al. relate that the proteins carrying phosphorylation sites were characterized for their specific activity, pI, effect of pH on the color of the light emitted, and effect of the catalytic subunit of protein kinase A in the presence of ATP. They found that only one of the recombinant proteins (RRFS; SEQ ID NO:1) was significantly different from wild-type luciferase and that the RRFS (SEQ ID NO:1) mutant had a lower specific activity, lower pH optimum, emitted greener light at low pH and, when phosphorylated, decreased its activity by up to 80%. It is disclosed that the latter effect was reversed by phosphatase.

Waud et al. (BBA 1292: 89 (1996)) engineered protein kinase recognition sequences and proteinase sites into a *Photinus pyralis* luciferase cDNA. Two domains of the luciferase were modified by Waud et al.; one between amino acids 209 and 227 and the other at the C-terminus between amino acids 537 and 550. Waud et al. disclose that the mutation of amino acids between residues 209 and 227 reduced bioluminescent activity to less than 1% of wild-type recombinant, while engineering peptide sequences at the C-terminus resulted in specific activities ranging from 0.06%-120% of the wild-type recombinant luciferase. Waud et al. also disclose that addition of a cyclic AMP dependent protein kinase catalytic subunit to a variant luciferase incorporating the kinase recognition sequence, LRRASLG (SEQ ID NO:2), with a serine at amino acid position 543, resulted in a 30% reduction activity. Alkaline phosphatase treatment restored activity. Waud et al. further disclose that the bioluminescent activity of a variant luciferase containing a thrombin recognition sequence, LVPRES (SEQ ID NO:3), with the cleavage site positioned between amino acids 542 and 543, decreased by 50% when incubated in the presence of thrombin.

Ozawa et al. (Analytical Chemistry 73: 2516 (2001)) describe a biosensor based on protein splicing-induced complementation of rationally designed fragments of firefly luciferase. Protein splicing is a posttranslational protein modification through which inteins (internal proteins) are excised out from a precursor fusion protein, ligating the flanking exteins (external proteins) into a contiguous polypeptide. It is disclosed that the N- and C-terminal intein DnaE from *Synechocystis* sp. PCC6803 were each fused respectively to N- and C-terminal fragments of a luciferase. Protein-protein interactions trigger the folding of DnaE intein, resulting in protein splicing, and thereby the extein of ligated luciferase recovers its enzymatic activity. Ozawa et al. disclose that the interaction between known binding partners, phosphorylated insulin receptor substrate 1 (IRS-1) and its target N-terminal SH2 domain of PI 3-kinase, was monitored using a split luciferase in the presence insulin.

Paulmurugan et al. (PNAS USA 99: 3105 (2002)) employed a split firefly luciferase-based assay to monitor the interaction of two proteins, i.e., MyoD and Id, in cell cultures and in mice using both complementation strategy and an intein-mediated reconstitution strategy. To retain reporter activity, in the complementation strategy, fusion proteins need protein interaction, i.e., via the interaction of the protein partners MyoD and Id, while in the reconstitution strategy, the new complete beetle luciferase formed via intein-mediated splicing maintains it activity even in the absence of a continuing interaction between the protein partners.

A protein fragment complementation assay is disclosed in Michnick et al. (U.S. Pat. Nos. 6,270,964, 6,294,330 and 6,428,951). Specifically, Michnick describe a split murine dihydrofolate reductase (DHFR) gene-based assay in which an N-terminal fragment of DHFR and a C-terminal fragment of DHFR are each fused to a GCN4 leucine zipper sequence. DHFR activity was detected in cells which expressed both fusion proteins. Michnick et al. also describe another complementation approach in which nested sets of Si nuclease generated deletions in the aminoglycoside kinase (AK) gene are introduced into a leucine zipper construct, and the resulting sets of constructs introduced to cells and screened for AK activity.

SUMMARY OF THE INVENTION

The invention provides an improved gene product, e.g., a modified luciferase such as a modified beetle luciferase, for instance, a modified firefly or click beetle luciferase, a modified anthozoan luciferase such as a *Renilla* luciferase, or a modified copepod or decapod luciferase comprising a heterologous, non-native mutant cAMP binding site having one or more altered activities.

cAMP binding sites (domains) useful to prepare mutant cAMP binding domain for use in the modified luciferases of the invention include but are not limited to cAMP binding domain in exchange protein directly activated by cAMP (Epac) (Bos et al., Nat. Rev. Mol. Cell. Biol. 4:733 (2003); NCBI Accession No. AF115480; SEQ ID NO:123)), including Epac 2B, Epac 1 (Nikolav, J. Biol. Chem. 279:372 (2004)), and Epac IIA; human RIα residues 245-381 (Genbank Accession No. BL036285; SEQ ID NO:124); cyclic nucleotide gated ion channels such as hyperpolarization-activated cyclic nucleotide modulated channel (Zagotta et al., Nature 425: 730 (2003)); neuropathy target esterase (Dremier et al., FEBS Lett. 546:163 (2003)); PKA regulatory type IIβ subunit (see, e.g., NCBI Accession No. M124921), e.g., PKA IIβA and PKA IIβB; PKA regulatory type Iα subunit, e.g., PKA IαA and PKA IαB, PKG IIA, PKG IIB; GAF A domain from *Trypanosoma brucei* PDE residues 241-375 (Genbank Accession No. AF192755; SEQ ID NO:125); and catabolite activating protein. In one embodiment, the cAMP binding domain includes a protein fold from a native protein which protein fold has substantially the same three-dimensional structure as the cAMP binding site of, for instance, RIIβB, and an amino acid residue that is different than the residue at a position corresponding to residue 266, 282, 284, 286, 296, 316, 333, 338, 382, 389, 404 or 407 of RIIβB having SEQ ID NO:4, which different residue results in an altered affinity for cAMP. In one embodiment, the cAMP binding domain includes a protein fold from a native protein that binds cAMP which protein fold has substantially the same three-dimensional structure as the cAMP binding site of RIIβB and an amino acid residue that is different than the residue at a position corresponding to residue 266, 282, 284, 286, 296, 316, 333, 338, 382, 389, 404 or 407 of RIIβB having SEQ ID NO:4, which results in an altered affinity for cAMP, e.g., an increase in the $EC_{50}$ for activation, and/or results in an enhanced response in live cells, for instance, as a result of decreased binding under basal conditions.

In one embodiment, the mutant cAMP binding site has one or more substitutions that enhance the bioluminescence signal of the modified luciferase, enhance the response of the modified luciferase to an agent that alters the amount of cAMP in a cell, or both, relative to a corresponding luciferase with a cAMP binding site that lacks the one or more substitutions. In one embodiment, the one or more substitutions are at a position corresponding to residue 266, 282, 284, 286, 296, 316, 333, 338, 382, 389, 404 or 407 of RIIβB having SEQ ID NO:4. In one embodiment, the residue in the mutant cAMP binding site corresponding to residue 266 is not M, the residue in the mutant cAMP binding site corresponding to residue 282 is not F, the residue in the mutant cAMP binding site corresponding to residue 286 is not L, the residue in the mutant cAMP binding site corresponding to residue 296 is not V, the residue in the mutant cAMP binding site corresponding to residue 333 is not V, or the residue in the mutant cAMP binding site corresponding to residue 404 is not V. In one embodiment, the one or more substitutions are at a position corresponding to residue 266, 282, 284, 286, 296, 316, 333, 338, 382, 389, 404 or 407 of RIIβB having SEQ ID NO:4. For example, the residue in the mutant cAMP binding site corresponding to residue 389 is not M, the residue in the mutant cAMP binding site corresponding to residue 284 is not E, the residue in the mutant cAMP binding site corresponding to residue 308 is not D, or residue in the mutant cAMP binding site corresponding to residue 286 is not L. In one embodiment, the mutant cAMP binding site has at least about 80%, 85%, 90%, 95%, or 99%, but not 100%, amino acid sequence identity to the cAMP binding site in SEQ ID NO:4, SEQ ID NO:5, or SEQ ID NO:6, e.g., residues 266 to 414 in SEQ ID NO:4, residues 284 to 381 in SEQ ID NO:5 or residues 241 to 375 in SEQ ID NO:6.

In one embodiment, the modified luciferase has a detectable activity and includes an insertion of one or more amino acids relative to a corresponding unmodified luciferase at a site or in a region which is tolerant to modification, which insertion includes an amino acid sequence which directly interacts with cAMP, e.g., an insertion which includes a recognition sequence for cAMP, or indirectly interacts with cAMP, e.g., via another molecule. In one embodiment, a modified luciferase comprises an insertion of 10 or more, e.g., 20, 50, 100, 200, 300 or more, but less than about 1000, or any integer in between, amino acid residues. In one embodiment, the modified luciferase with an insertion further comprises a deletion of luciferase sequences, e.g., a deletion of 1 or more, but less than about 100, for instance less than 50, 40, 30, 20, 10 or 5, or any integer in between, residues.

Hence, in one embodiment, a modified luciferase of the invention comprises an amino acid sequence which is circularly permuted relative to the amino acid sequence of a corresponding luciferase, such as an unmodified wild type luciferase, resulting in a new N- and C-terminus in the circularly permuted luciferase, at least one of which is at a site or in a region which is tolerant to modification, and is engineered to have functionality by introducing a heterologous amino acid sequence which directly or indirectly interacts with cAMP. In another embodiment, the circularly permuted luciferase includes other modifications, including but not limited to insertions and/or deletions internal to the N- or C-terminus of the circularly permuted luciferase, for instance, another insertion and/or a deletion, e.g., at or near the N- and C-terminus of the corresponding unmodified luciferase such as at residues corresponding to residues 1 to about 10 or about 30, or any integer in between, of the N-terminus and/or corresponding to the last residue or about the last 30, e.g., last 15, or any integer in between 1 and 30, residues of the C-terminus of the corresponding unmodified luciferase. In one embodiment, the amino acid sequence that interacts with cAMP is flanked by at least one linker, e.g., flanked at each end, such as a peptide linker, which linkers may be the same or different, which optionally improve luminescence and/or response, e.g., to forskolin or isoproterenol. In one embodiment, the amino acid sequence that interacts with cAMP is flanked by at least one linker at the N-terminus, which optionally improves luminescence and/or response to forskolin or isoproterenol, or foskolin and dopamine. In one embodiment, the linker has at least one of the following sequences: GSSGGSGGSGGG, GSSSDSDSSAGS, GSNDSSGGSEGG, GSNG-GFDSSEGG, GSIRWSGLSGGD, GSRGGSVYSEGG, GSSEGSSDFGGD, GSIVVSCSSEGG, GSNWDSGC-SREG, GSNWDSGCSREC, GSSGCTGDAGGS, GSN-WDSGCSRQC, GSS/NS/D/GD/S/GS/FD/GS/GSA/EGS/G, GSI/R/SR/G/EW/GSGN/SL/Y/DS/FG/EGD/G, GSI/N/SV/W/GV/D/CS/TC/GS/C/DS/AE/R/GG/EG/S, GSI/SV/G/AV/GS/CG/DG/D/SS/AG/EG/EG/N, GSI/N/SV/W/G/AV/D/C/GS/T/CC/GS/C/DS/AE/R/GG/EG/S, GSIAGCGDAGEG, GSNWDSGCSRE, GSIAGCGDAGEG, GSNWDSGC-SREG, NWDSGCSREG, or IAGCGDAGEG (SEQ ID Nos. 41-57 and 126-131 respectively). A linker employed in the biosensor of the invention is an amino acid sequence, the presence of which in the biosensor does not substantially decrease the activity of that biosensor, e.g., does not decrease the activity by more than 10-fold, such as by no more that 4-fold, or no more than 2-fold, relative to a corresponding biosensor that lacks the linker(s), and/or the presence of the linker employed in the biosensor of the invention increases luminescence or response to agents such as forskolin or isoproterenol, or both, relative to a corresponding biosensor that lacks the linker(s) or a corresponding biosensor having the linker(s) GSSGGSGGSGGG (SEQ ID NO:41), or relative to both corresponding biosensors. In one embodiment, a linker containing biosensor has one of SEQ ID Nos. 42-57 or 126-131 flanking a mutant amino acid sequence that interacts with cAMP and has increased luminescence or an increased response to forskolin or isoproterenol, or both, relative to a corresponding biosensor having the linker(s) GSSGGSGGSGGG (SEQ ID NO:41).

The peptide linker of the invention may be employed to separate two polypeptides, each of which has an activity, or two polypeptide fragments, which individually have little or no activity but together have activity or increased activity corresponding to an activity of one of the full length polypeptides relative to the individual fragments. In one embodiment, the invention provides a polynucleotide comprising a nucleic acid sequence comprising an open reading frame for a first protein or a fragment of a first protein fused to a peptide linker fused to a second protein or a fragment of a second protein. In one embodiment, the fragment of a first protein is a fragment of a luciferase and the fragment of a second protein is a different fragment of the luciferase, e.g., the first fragment has residues 234 to 544 of a firefly luciferase and the second fragment has residues 4 to 233 of a firefly luciferase or the first fragment has residues 359 to 544 of a firefly luciferase and the second fragment has residues 4 to 355 of a firefly luciferase, e.g., the luciferase sequences are circularly permuted. In one embodiment, the fragment of a first protein is a fragment of a luciferase and the fragment of a second protein is a fragment of a protein that is not a luciferase, e.g., it is a hydrolase such as a dehalogenase. In another embodiment, the fragment of a first protein is a fragment of a luciferase and the fragment of a second protein is a fragment of a different luciferase. In another embodiment, the first protein is a luciferase and the second protein is a different luciferase. In yet another embodiment, the first protein is a luciferase and the second protein is a protein that is not a luciferase.

The peptide linker of the invention may also be employed to separate three polypeptide fragments or two polypeptide fragments and another polypeptide, where the fragments have little or no activity but together have activity or increased activity corresponding to an activity of one of the full length polypeptides relative to the individual fragments. Thus, in one embodiment, the invention provides a polynucleotide comprising a nucleic acid sequence comprising an open reading frame for a first protein or a fragment of a first protein fused to a first peptide linker fused to a second protein or a fragment of a second protein, e.g. a domain of a protein with binding or catalytic activity, fused to a second peptide linker fused to a third protein or a fragment of a third protein. In one embodiment, the fragment of a first protein is a fragment of a luciferase, the fragment of a third protein is a different fragment of the luciferase, and the second protein or the fragment thereof is not a luciferase. In another embodiment, the fragment of the first protein is a fragment of a luciferase, the second protein or the fragment thereof is not a luciferase, and the fragment of a third protein is a fragment that restores or increases the luciferase activity of the first fragment. In another embodiment, the second protein or the fragment thereof is not a luciferase, the fragment of a third protein is a fragment of a luciferase, and the fragment of the first protein is a fragment of the luciferase that restores or increases the luciferase activity of the first fragment. In one embodiment, the second fragment has a cAMP binding site.

In one embodiment, a peptide linker of the invention is positioned N-terminal to a cAMP binding site in a cAMP biosensor of the invention, e.g., one having firefly luciferase or click beetle luciferase sequences. In one embodiment, a peptide linker of the invention is positioned C-terminal to a cAMP binding site in a cAMP biosensor of the invention. In one embodiment, a peptide linker of the invention is positioned N-terminal and C-terminal to a cAMP binding site in a cAMP biosensor of the invention, and optionally the peptide linkers have different sequences and/or different lengths. The use of peptide linkers of the invention may result in biosensors with improved properties, e.g., in assays with endogenous or exogenous Gs- or Gi-coupled 7 transmembrane receptors, relative to the linker GSSGGSGSGGG (SEQ ID NO:41).

In one embodiment, a peptide linker of the invention is positioned N-terminal to a peptide sequence which is capable of directly or indirectly interacting with a molecule of interest, e.g., a molecule to be detected. In one embodiment, a peptide linker of the invention is positioned C-terminal to that peptide sequence in a biosensor of the invention. In one embodiment, a peptide linker of the invention is positioned N-terminal and C-terminal to peptide sequence which is capable of directly or indirectly interacting with a molecule to be detected.

In one embodiment, in the absence of cAMP, the activity of a modified luciferase of the invention is less than the activity of a corresponding unmodified luciferase, e.g., the reporter activity of the modified luciferase is about 0.001%, 0.01%, 0.1%, 1%, 10%, 20%, 50%, 70% or more, but less than 100% that of a corresponding unmodified luciferase, the activity of which modified luciferase is optionally detectable. In another embodiment, in the absence of cAMP, the activity of a modified luciferase of the invention is substantially the same or greater than the activity of a corresponding unmodified luciferase, e.g., the reporter activity of the modified luciferase of the invention is about 1.5-fold, e.g., at least 2-, 3- or 5-fold or more, that of a corresponding unmodified luciferase. In the presence of cAMP, the activity of the modified luciferase of the invention is detectably altered. For instance, a detectable alteration in activity of a modified luciferase in the presence of cAMP is an alteration of at least 0.001%, 0.01%, 0.1%, 1%, 10%, or 100%, and up to 2-fold, 4-fold, 10-fold, 100-fold, 1,000-fold, 10,000-fold or more, relative to the activity of the modified luciferase in the absence of cAMP. Thus, the physical proximity of cAMP which interacts with a modification present in the modified luciferase but not the corresponding unmodified luciferase, alters, e.g., decreases, eliminates or increases, the activity of the modified luciferase. In one embodiment, the luminescent signal of a modified luciferase of the invention in the presence of cAMP is increased relative to the luminescent signal of a corresponding luciferase with a heterologous native cAMP binding domain in the presence of cAMP.

The amino acid sequence of the modified luciferase is different than the amino acid sequence of a corresponding unmodified luciferase (native, wild-type or parental), e.g., a mutant luciferase with one or more substitutions in the luciferase sequences as a result of an insertion of heterologous amino acid sequences at a site (residue) or in a region in the luciferase which is tolerant to modification, e.g., tolerant to an insertion, a deletion, circular permutation, or any combination thereof. In one embodiment, in addition to the insertion of heterologous amino acid sequences, the luciferase sequences of the modified luciferase are circularly permuted relative to the amino acid sequence of a corresponding unmodified luciferase (native, wild-type luciferase) wherein the permutation is at a site (residue) or in a region that is tolerant to modification. In one embodiment, the regions which are tolerant to modification include surface loops between secondary structures, such as beta sheets or alpha helices, found on the native, wild-type luciferase. The heterologous amino acid sequences may be internal relative to the N- or C-terminus of a wild-type or circularly permuted luciferase, or may be at the N- and/or C-terminus of a wild-type or circularly permuted luciferase, and may include a deletion of luciferase sequences at the modification sites. In one embodiment, the one or more heterologous amino acid sequences which directly or indirectly interact with cAMP are at or near the N-terminal and/or C-terminal residues of a circularly permuted or a noncircularly permuted luciferase. In one embodiment, the one or more heterologous amino acid sequences which directly or indirectly interact with cAMP are not at or near the N-terminal and/or C-terminal residues of a circularly permuted luciferase or a nonpermuted luciferase, i.e., the heterologous sequences are internal to the N- and C-termini. In one embodiment, the modified luciferase may be circularly permuted, have one or more discreet (isolated) heterologous amino acid sequences, at least one of which directly or indirectly interacts with cAMP, and optionally may include the deletion of one or more amino acids, e.g., at a site(s) or in a region(s) tolerant to modification including the N- and/or C-terminus of the unmodified luciferase, so long as the resulting modified luciferase has bioluminescent activity before and/or after the interaction with cAMP, e.g., bioluminescent activity is altered after interaction with cAMP, such as an alteration in light intensity, color or kinetic profile.

A deletion within the scope of the invention includes a deletion of one or more amino acid residues at a site or in a region of a luciferase sequence that is tolerant to a deletion. The modified luciferase may include deletions at the N- and C-terminus of 1 to about 10 or about 30, residues, or any integer in between, e.g., 15 residues, corresponding to the N- or C-terminus of the unmodified luciferase. The length of the deletion may be greater than 30 residues depending on the particular luciferase and the length of a desirable deletion may be determined by routine deletion analysis.

A beetle luciferase may be modified at a residue, for instance, residue 21, 25, 117, 358, 376, 379, 398, 399, 400, 401, 402, 403, 405, 406, 407, 409 or 490, or in a region corresponding to residue 15 to 30, e.g., residue 21 or 25, residue 112 to 122, e.g., residue 117, residue 352 to 362, for instance, residue 358, residue 371 to 384, e.g., residue 379, residue 393 to 414, or residue 485 to 495, of a click beetle luciferase, e.g., one having SEQ ID NO:9, or at residue 7, 37, 47, 75, 83, 107, 121, 144, 160, 174, 188, 198, 205, 225, 233, 242, 255, 268, 308, 316, 358, 377, 403, 435, 490 or 540, or in a region corresponding to residue 2 to 12, residue 32 to 53, e.g., residue 32 to 43 or residue 42 to 52, residue 70 to 88, e.g., residue 70 to 80 or residue 78 to 88, residue 102 to 126, e.g., residue 102 to 112 or residue 116 to 126, residue 139 to 165, residue 183 to 203, residue 220 to 247, e.g., residue 228 to 238, residue 262 to 273, residue 303 to 313, residue 353 to 408, residue 485 to 495, or residue 535 to 546 of a firefly luciferase, e.g., one having SEQ ID NO:106, 118, or 120. The residue numbering is based on that in an unmodified (native) click beetle or firefly luciferase sequence. Corresponding positions may be identified by aligning luciferase sequences using, for instance, sequence alignment programs. Residues or regions in a luciferase tolerant to modification may be employed as sites to circularly permute the luciferase or for an insertion.

The invention further includes a modified anthozoan luciferase having at least one modification at a site or in a region which is tolerant to modification, including but not limited to at a residue corresponding to residue 2, 30, 31, 42, 45, 46, 68, 69, 90, 91, 92, 110, 111, 150, 151, 168, 169, 193, 207, 208, 223, 224, 251, 259, 274, or 311 or in a region corresponding to residue 2 to 12, residue 26 to 36, residue 37 to 47, residue 64 to 74, residue 86 to 97, e.g., residue 90 or 91, residue 96 to 116, residue 147 to 157, residue 218 to 234, e.g., residue 223, 234, 228, 229 or 230, or residue 301 to 311 of a *Renilla* luciferase (Genbank ID AF025843), e.g., one having SEQ ID NO:116. The residue numbering is based on that in an unmodified (native) *Renilla* luciferase sequence. Corresponding positions may be identified by aligning luciferase sequences using, for instance, sequence alignment programs. Residues or regions in a luciferase tolerant to modification may be employed as sites to circularly permute the luciferase or for an insertion.

Further included is a modified crustacean luciferase, e.g., a copepod luciferase, having at least one modification at a site or in a region which is tolerant to modification, including but not limited to in a region corresponding to residue 43 to 53, residue 63 to 73, residue 79 to 89, residue 95 to 105, residue 105 to 115, residue 109 to 119, residue 121 to 131 or residue 157 to 168 of a *Gaussia* luciferase, e.g., one having SEQ ID NO:121, or in a region corresponding to residue 45 to 55 or residue 79 to 89 of a mature *Oplophorus* luciferase, e.g., one having SEQ ID NO:122. The residue numbering is based on that in an unmodified (native) *Gaussia* luciferase sequence or the *Oplophorus* luciferase sequence with a molecular weight of 19 kDa. Corresponding positions may be identified by aligning luciferase sequences using, for instance, sequence alignment programs. Residues or regions in a luciferase tolerant to modification may be employed as sites to circularly permute the luciferase or for an insertion.

Accordingly, a modified luciferase of the invention may be employed as a biosensor.

The invention also provides an isolated nucleic acid molecule (polynucleotide) comprising a nucleic acid sequence encoding a modified luciferase of the invention. Further provided is an isolated nucleic acid molecule comprising a nucleic acid sequence encoding fusion protein comprising a modified luciferase and one or more amino acid residues at the N-terminus (a N-terminal fusion partner) and/or C-terminus (a C-terminal fusion partner) of the modified luciferase. Thus, as used herein, a "fusion protein" is a polypeptide which includes one or more amino acids at the N-terminus and/or C-terminus of a modified luciferase of the invention. In one embodiment, the presence of one or more fusion partners in the fusion protein does not substantially alter the detectable activity of the fusion protein relative to a corresponding modified luciferase. The N- or C-terminal fusion partner may be a sequence used for purification, e.g., a glutathione S-transferase (GST) or a polyHis sequence, a sequence intended to alter a property of the modified luciferase, e.g., a protein destabilization sequence, a protein or nucleic acid interaction sequence (e.g., a binding sequence), a subcellular localization sequence, or a sequence which has a property which is distinguishable from one or more properties of the luciferase in the fusion protein. In one embodiment, the fusion protein comprises a modified luciferase and a fusion partner which is a reporter protein that is different than the luciferase, which reporter protein is useful as an intramolecular control, e.g., a fluorescent protein or another luciferase. In another embodiment, the invention includes a vector comprising a nucleic acid sequence encoding a fusion protein comprising a modified luciferase of the invention and a nucleic acid fragment which encodes a reporter protein that is different than the luciferase in the modified luciferase. In one embodiment, the mutant cAMP binding domain containing luciferase of the invention further includes a subcellular localization signal, which is useful to detect subcellular localization and/or concentration of cAMP.

Optionally, optimized nucleic acid sequences, e.g., human codon optimized sequences, encoding at least the luciferase, and in one embodiment the modified luciferase or a fusion protein comprising a modified luciferase, are employed in the nucleic acid molecules of the invention, as those optimized sequences can increase the strength of the signal for luciferase. The optimization of nucleic acid sequences is known to the art, see, for example, WO 02/16944.

The invention also includes a stable cell line that expresses a modified luciferase, or fusion protein of the invention, as well as an expression cassette comprising a nucleic acid molecule encoding the modified luciferase or fusion protein of the invention, and a vector (e.g., a plasmid, virus, or defective viral particles) capable of expressing the nucleic acid molecule of the invention in a host cell. In one embodiment, the expression cassette comprises a promoter, e.g., a constitutive or regulatable promoter, operably linked to the nucleic acid sequence. In one embodiment, the expression cassette contains an inducible promoter. Also provided is a host cell, e.g., a prokaryotic cell or an eukaryotic cell such as a plant or vertebrate cell, e.g., a mammalian cell, including but not limited to a human, non-human primate, canine, feline, bovine, equine, ovine or rodent (e.g., rabbit, rat, ferret or mouse) cell, which comprises the expression cassette or vector of the invention, and a kit which comprises the nucleic acid molecule, expression cassette, vector, host cell or modified luciferase or fusion protein of the invention.

For instance, a vector encoding a modified luciferase comprising an insertion of a cAMP binding site of the invention, or a modified luciferase comprising an insertion of a cAMP binding site of the invention, is mixed with a sample, e.g., a cell, cell lysate, in vitro transcription/translation mixture, or supernatant, and the activity of the modified luciferase in the sample detected or determined, e.g., optionally at one or more time points, or relative to a control sample without cAMP or having a differing amount of cAMP. An alteration in luminescent activity in the sample, for instance, over time, and/or relative to a control, e.g., a cell having a specified amount of cAMP, indicates the presence or amount of cAMP in the sample, or change in amount of cAMP related to experimental condition. In one embodiment, a cell is contacted with a vector comprising a promoter, e.g., a regulatable or constitutive promoter, and a nucleic acid sequence encoding a modified luciferase of the invention which comprises an insertion which interacts with the cyclic nucleotide. In one embodiment, a transfected cell is cultured under conditions in which the promoter induces transient expression of the modified luciferase, and the presence or amount of luminescence determined. In another embodiment, a modified luciferase of the invention which comprises an insertion which interacts with the cAMP and a sample suspected of having a cAMP are mixed. Then the amount of luminescence is determined. The invention thus provides a method of detecting the amount of cAMP.

BRIEF DESCRIPTION OF THE FIGURES

FIG. 7A) Basal activity of various cAMP biosensors with linkers over time. FIG. 7B) Activity of various cAMP biosensors with linkers after isoproterenol induction. FIG. 7C) Response of various cAMP biosensors with linkers.

FIG. 8A) Fold response over time in 293 cells expressing a CPM-FF Luc/mutant RIIβB cAMP biosensor with a modified linker (L9) and treated with isoproterenol relative to 293 cells expressing a CPM-FF Luc/mutant RIIβB cAMP biosensor with a GSSGGSGGSGGG (SEQ ID NO: 41) linker. FIG. 8B) Fold change in RLU versus t=0 in the presence or absence of forskolin for HEK293/D2 cells expressing the CPM-FF Luc/mutant RIIβB cAMP biosensor L9 or a CPM-FF Luc/mutant RIIβB cAMP biosensor with GSSGGSGGSGGG (SEQ ID NO:41) linker.

DETAILED DESCRIPTION OF THE INVENTION

Definitions

Figure 1:
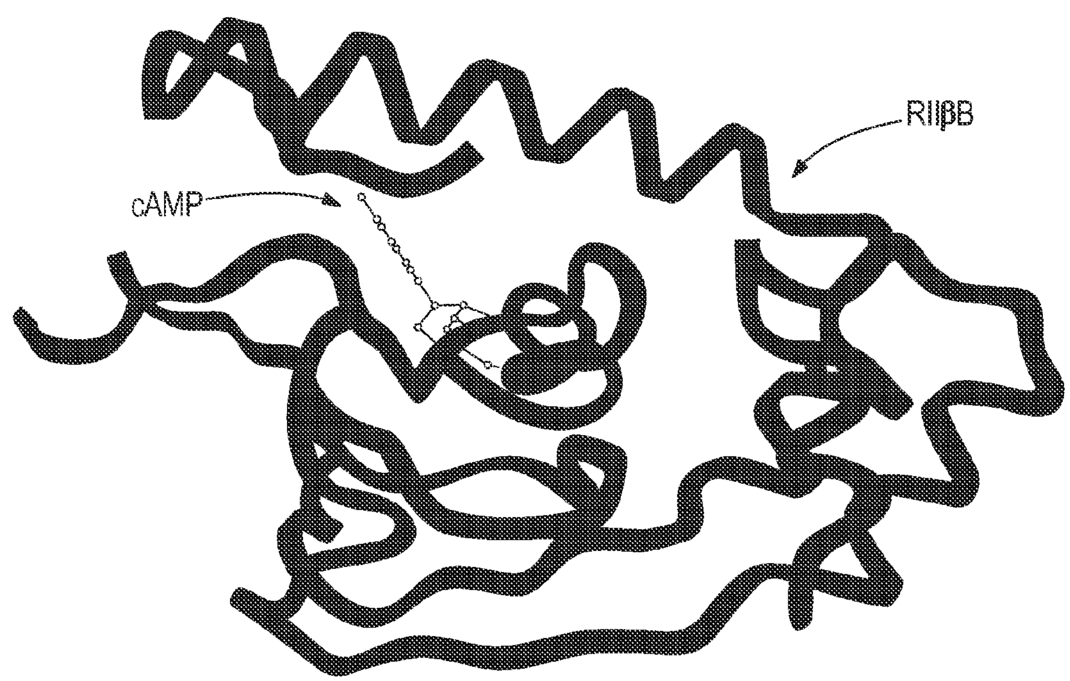
FIG. 1. PKA regulatory subunit type IIβ (RIIβB). X-ray crystal structure of rat RIIβB amino acids 264-412 (PDB 1CX4). RIIβB is rendered as a red ribbon; cAMP is rendered as ball and stick. The primary sequence similarity between rat (amino acids 264-412) and human RIIβB (amino acids 266-414) is 96.6% (program Megalign, DNAStar).
Figure 2:
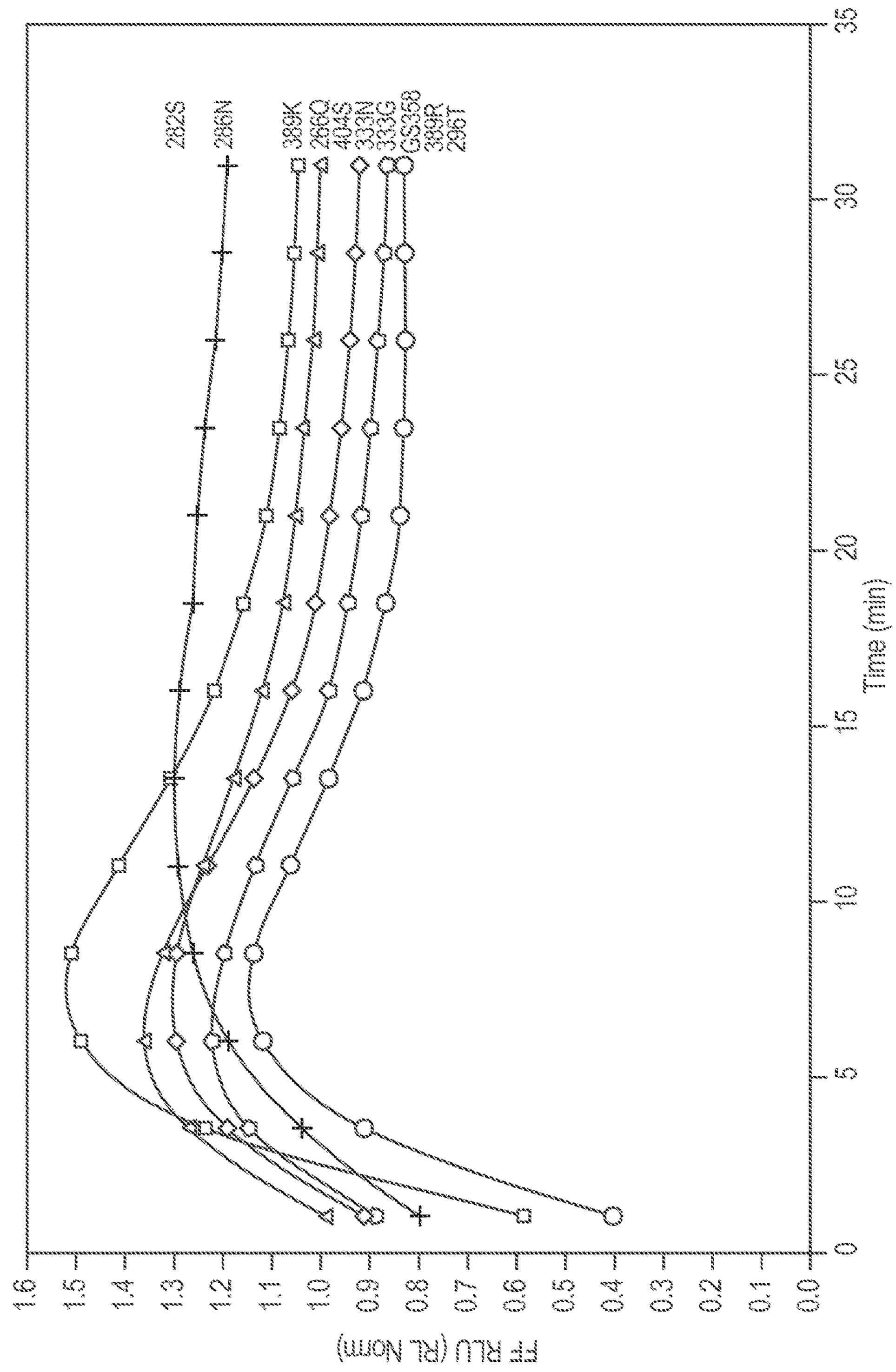
FIG. 2. Fold induction over time for circularly-permuted firefly luciferase (CPM-FF Luc/mutant RIIβB cAMP biosensors treated with isoproterenol.
Figure 3:
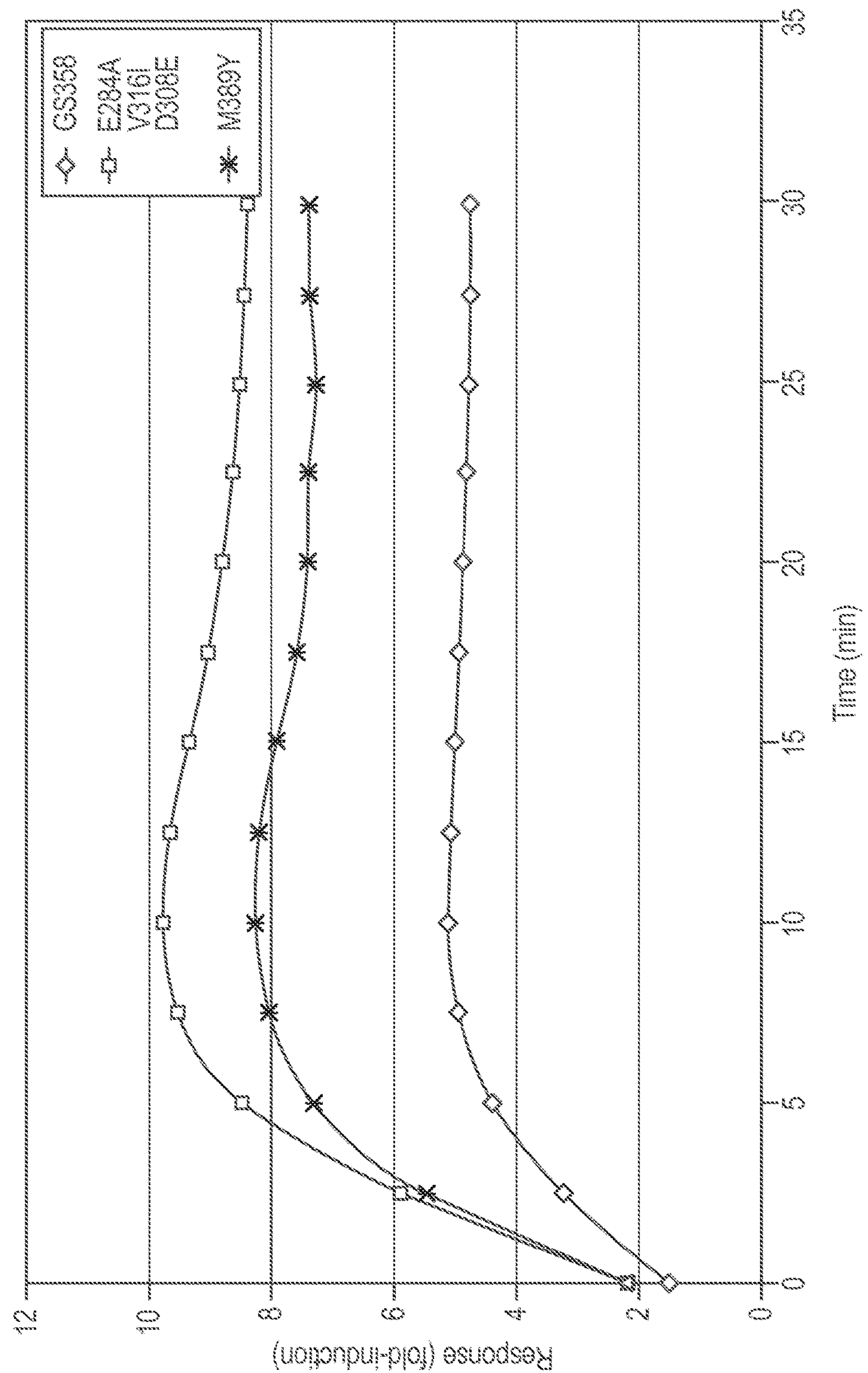
FIG. 3. Fold induction over time for CPM-FF Luc/mutant RIIβB cAMP biosensors treated with isoproterenol.
Figure 4:
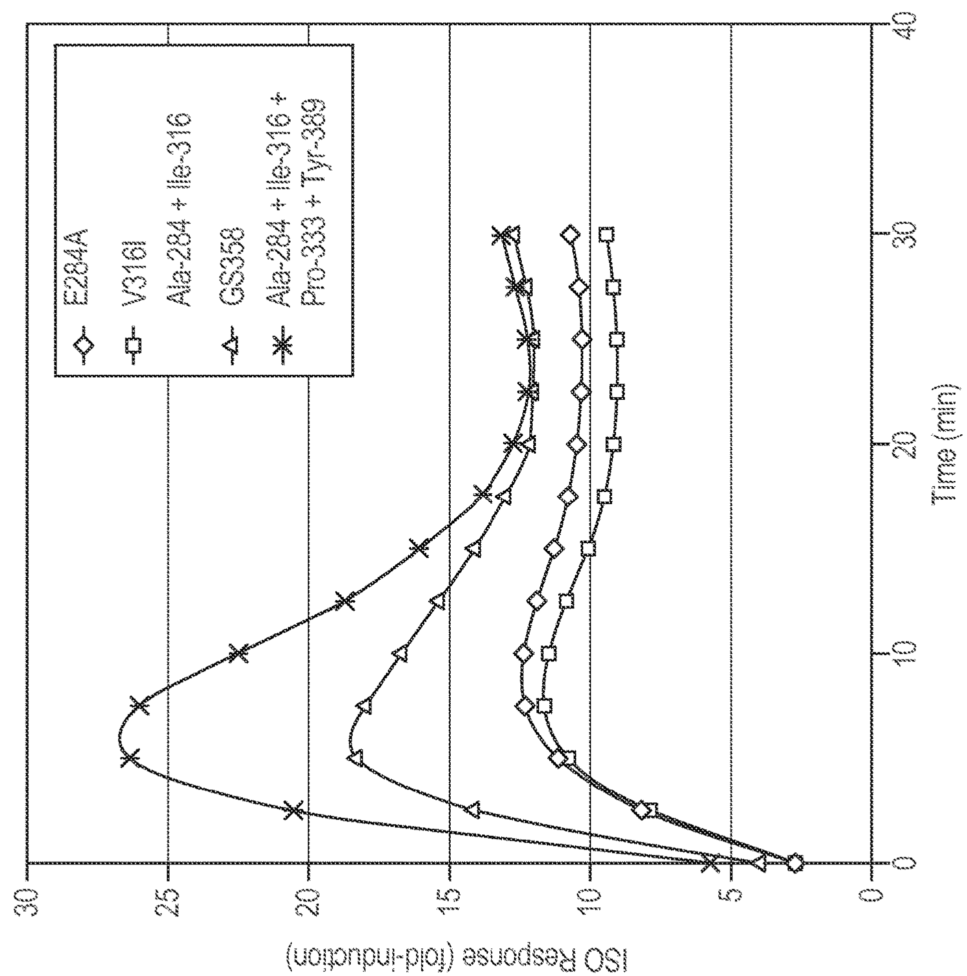
FIG. 4. Fold induction over time for CPM-FF Luc/mutant RIIβB cAMP biosensors treated with isoproterenol.
Figure 5:
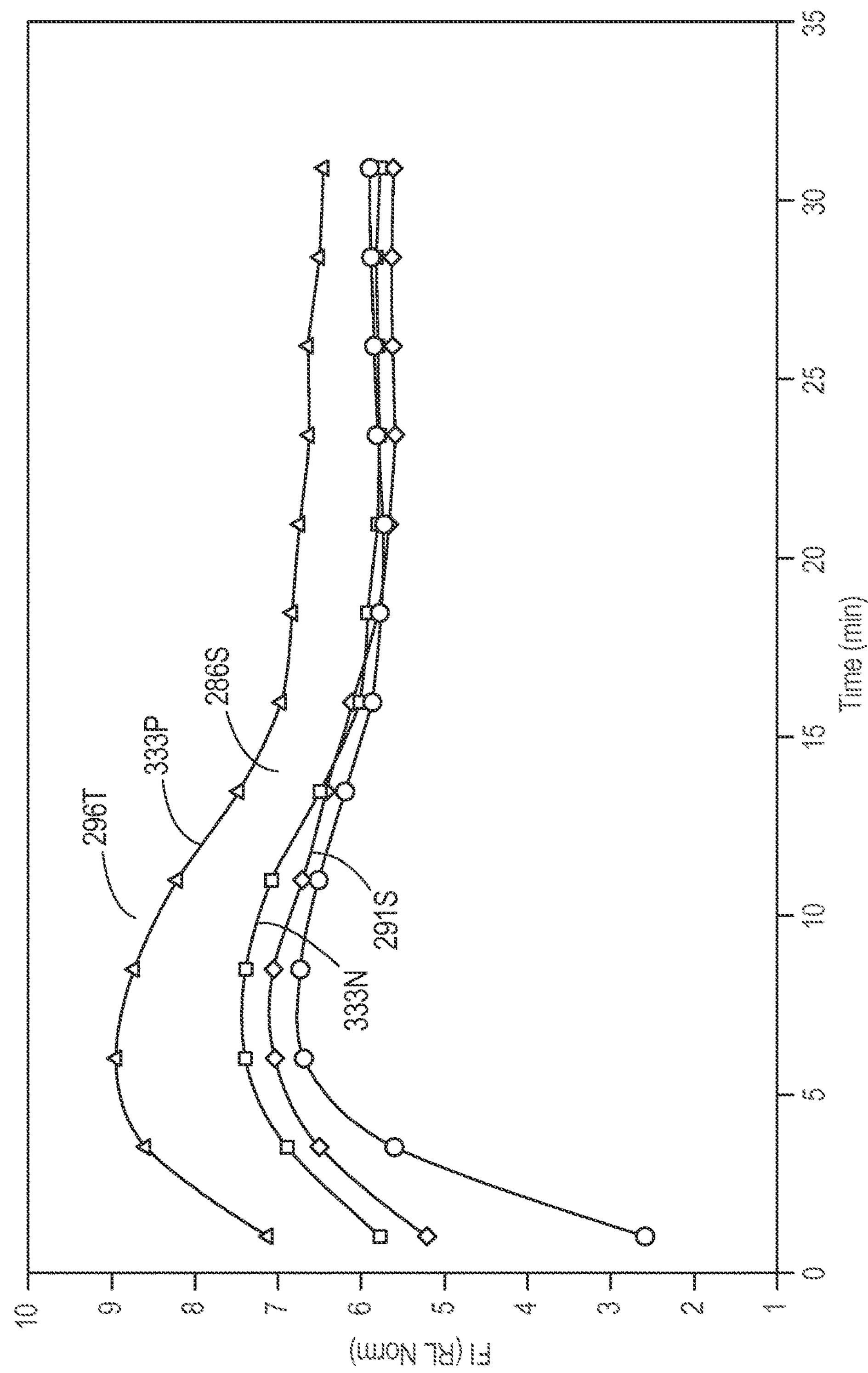
FIG. 5. Fold induction over time for CPM-FF Luc/mutant RIIβB cAMP biosensors treated with isoproterenol.
Figure 6:
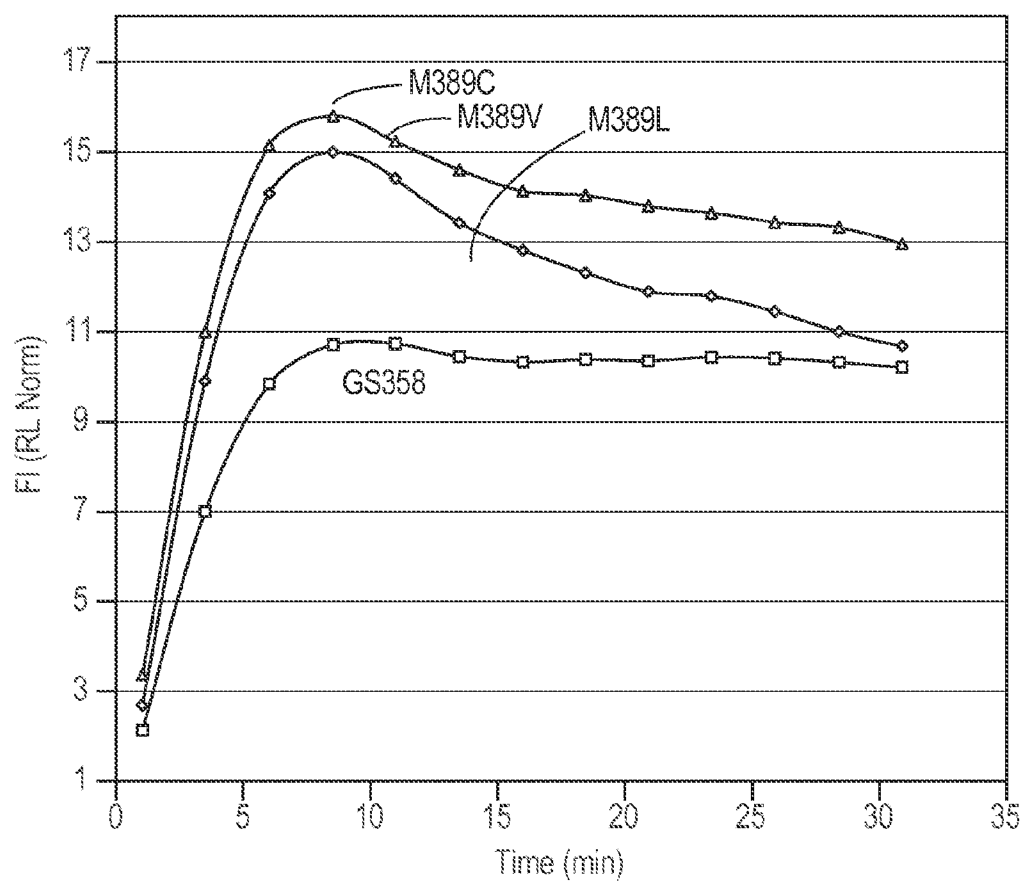
FIG. 6. Fold induction over time for CPM-FF Luc/mutant RIIβB cAMP biosensors treated with isoproterenol.
Figure 7A:
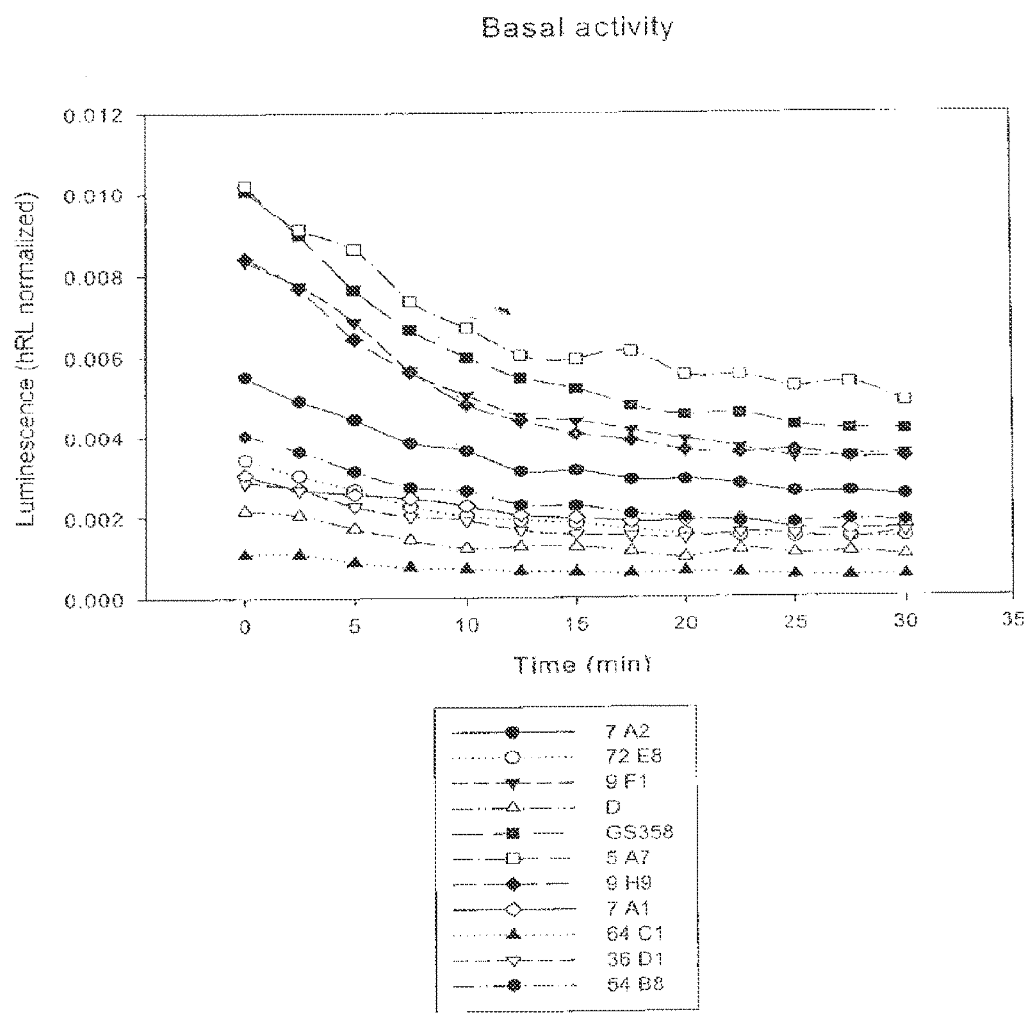
FIGS. 7A-C.
Figure 7B:
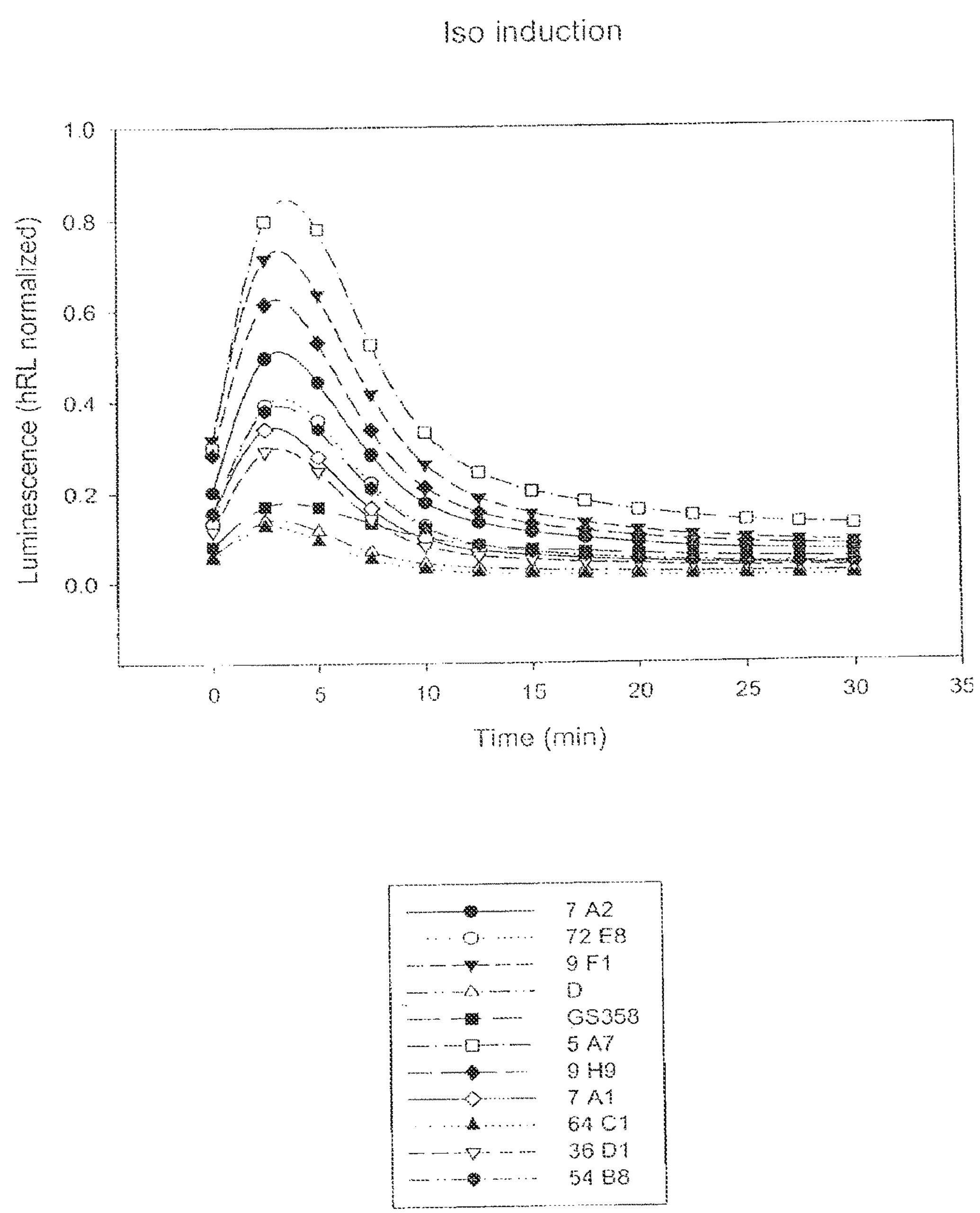
Figure 7C:
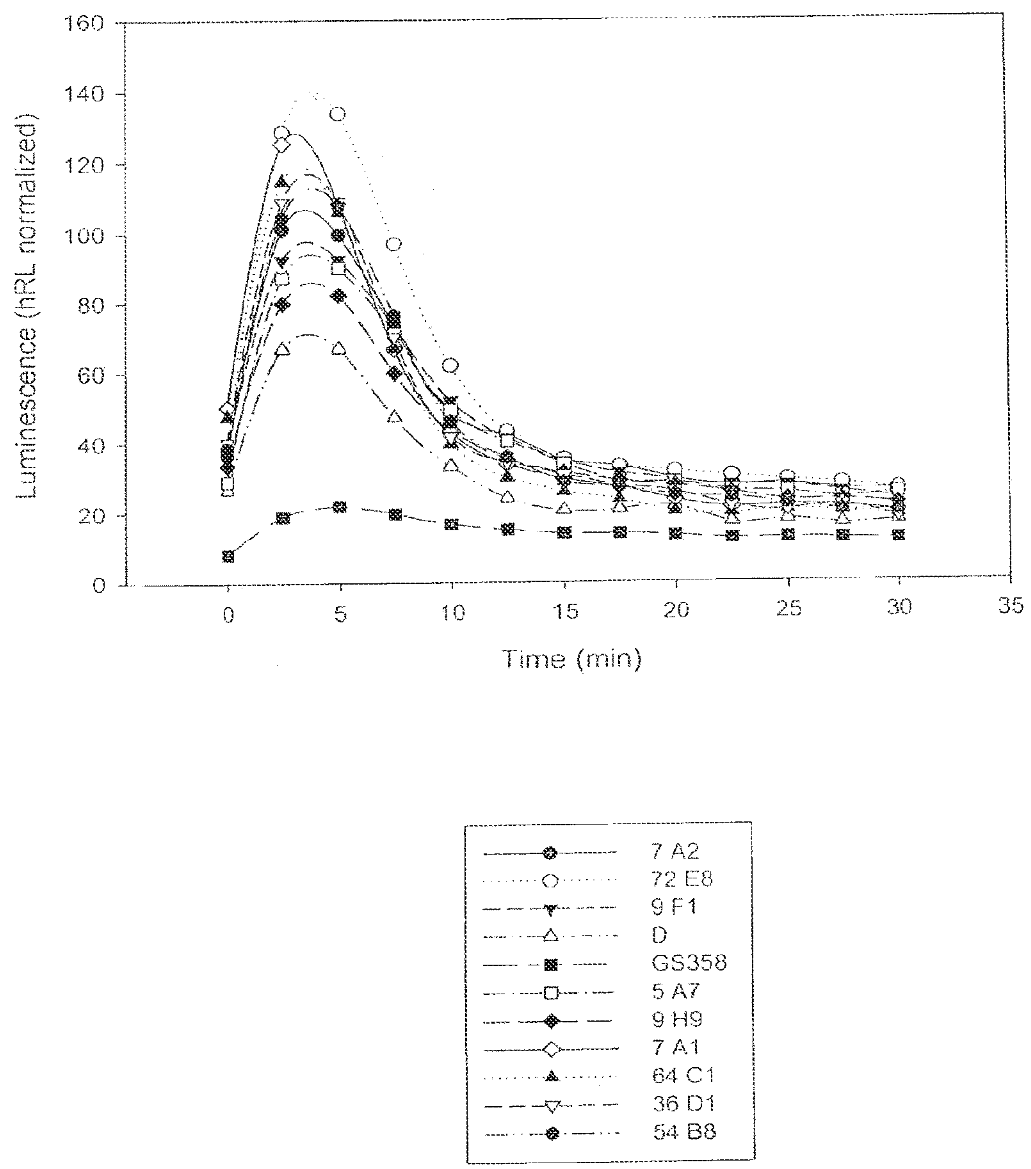

All amino acid residues identified herein are in the natural L configuration. In keeping with standard polypeptide nomenclature, abbreviations for amino acid residues are as shown in the following Table of Correspondence.

TABLE OF CORRESPONDENCE

| 1 Letter | 3 Letter | AMINO ACID |
|---|---|---|
| Y | Tyr | L tyrosine |
| G | Gly | L-glycine |
| F | Phe | L phenylalanine |
| M | Met | L methionine |
| A | Ala | L alanine |
| S | Ser | L serine |
| I | Ile | L isoleucine |
| L | Leu | L leucine |
| T | Thr | L threonine |
| V | Val | L valine |
| P | Pro | L proline |
| K | Lys | L lysine |
| H | His | L histidine |
| Q | Gln | L glutamine |
| E | Glu | L glutamic acid |
| W | Trp | L tryptophan |
| R | Arg | L arginine |
| D | Asp | L aspartic acid |
| N | Asn | L asparagine |
| C | Cys | L cysteine |

The terms "cell," "cell line," "host cell," as used herein, are used interchangeably, and all such designations include progeny or potential progeny of these designations. By "transformed cell" is meant a cell into which (or into an ancestor of which) has been introduced a nucleic acid molecule of the invention. Optionally, a nucleic acid molecule of the invention may be introduced into a suitable cell line so as to create a stably-transfected cell line capable of producing the protein or polypeptide encoded by the gene. Vectors, cells, and methods for constructing such cell lines are well known in the art. The words "transformants" or "transformed cells" include the primary transformed cells derived from the originally transformed cell without regard to the number of transfers. All progeny may not be precisely identical in DNA content, due to deliberate or inadvertent mutations. Nonetheless, mutant progeny that have the same functionality as screened for in the originally transformed cell are included in the definition of transformants.

As used herein, the term "heterologous" nucleic acid sequence or protein refers to a sequence that relative to a reference sequence has a different source, e.g., originates from a foreign species, or, if from the same species, it may be substantially modified from the original form. The term "homology" refers to a degree of complementarity between two or more sequences. There may be partial homology or complete homology (i.e., identity). Homology is often measured using sequence analysis. Such software matches similar sequences by assigning degrees of homology to various substitutions, deletions, insertions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

The term "in vitro" refers to an artificial environment and to processes or reactions that occur within an artificial environment. In vitro environments include, but are not limited to, test tubes and cell lysates. The term "in vivo" refers to the natural environment (e.g., an animal or a cell) and to processes or reaction that occur within a natural environment.

The term "isolated" when used in relation to a nucleic acid or polypeptide, as in "isolated oligonucleotide", "isolated polynucleotide", "isolated protein" or "isolated polypeptide" refers to a nucleic acid or amino acid sequence that is identified and separated from at least one contaminant with which it is ordinarily associated in its source. Thus, an isolated nucleic acid or isolated polypeptide is present in a form or setting that is different from that in which it is found in nature. In contrast, non isolated nucleic acids (e.g., DNA and RNA) or non-isolated polypeptides (e.g., proteins and enzymes) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs that encode a multitude of proteins. However, isolated nucleic acid includes, by way of example, such nucleic acid in cells ordinarily expressing that nucleic acid where the nucleic acid is in a chromosomal location different from that of natural cells, or is otherwise flanked by a different nucleic acid sequence than that found in nature. The isolated nucleic acid or oligonucleotide may be present in single stranded or double stranded form. When an isolated nucleic acid or oligonucleotide is to be utilized to express a protein, the oligonucleotide contains at a minimum, the sense or coding strand (i.e., the oligonucleotide may single stranded), but may contain both the sense and anti sense strands (i.e., the oligonucleotide may be double stranded).

The term "nucleic acid molecule', "polynucleotide", or "nucleic acid sequence" as used herein, refers to nucleic acid, DNA or RNA, that comprises coding sequences necessary for the production of a polypeptide or protein precursor. The encoded polypeptide may be a full-length polypeptide, a fragment thereof (less than full-length), or a fusion of either the full-length polypeptide or fragment thereof with another polypeptide, yielding a fusion polypeptide.

A polynucleotide having a nucleotide sequence encoding a protein or polypeptide means a nucleic acid sequence comprising the coding region of a gene, or in other words the nucleic acid sequence encodes a gene product. The coding region may be present in either a cDNA, genomic DNA or RNA form. When present in a DNA form, the oligonucleotide may be single stranded (i.e., the sense strand) or double stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region. Other regulatory elements include, but are not limited to, transcription factor binding sites, splicing signals, polyadenylation signals, termination signals and enhancer elements.

By "peptide," "protein" and "polypeptide" is meant any chain of amino acids, regardless of length or post-translational modification (e.g., glycosylation or phosphorylation). The nucleic acid molecules of the invention may also encode a variant of a naturally-occurring protein or polypeptide fragment thereof, which has an amino acid sequence that is at least 60%, 70%, 80%, 85%, 90%, 95% or 99% identical to the amino acid sequence of the naturally-occurring (native or wild-type) protein from which it is derived. For example, a coleopteran luciferase has at least 60%, 70%, 80%, 85%, 90%, 95% or 99% amino acid sequence identity to one of SEQ ID Nos. 9, 106, 118 or 120; a firefly luciferase has at least 60%, 70%, 80%, 85%, 90%, 95% or 99% amino acid sequence identity to one of 106, 118 or 120; a click beetle luciferase has at least 60%, 70%, 80%, 85%, 90%, 95% or 99% amino acid sequence identity to SEQ ID NO:9; an anthozoan luciferase has at least 60%, 70%, 80%, 85%, 90%, 95% or 99% amino acid sequence identity to SEQ ID NO:116; a copepod luciferase has at least 60%, 70%, 80%, 85%, 90%, 95% or 99% amino acid sequence identity to SEQ ID NO:121; and decapod luciferase has at least 60%, 70%, 80%, 85%, 90%, 95% or 99% amino acid sequence identity to SEQ ID NO: 122. The term "fusion polypeptide" or "fusion protein" refers to a chimeric protein containing a reference protein (e.g., luciferase) joined at the N- and/or C-terminus to one or more heterologous sequences (e.g., a non luciferase polypeptide). In some embodiments, a modified polypeptide, fusion polypeptide or a portion of a full-length polypeptide of the invention, may retain at least some of the activity of a corresponding full-length functional (nonchimeric) polypeptide. In other embodiments, in the absence of an exogenous agent or molecule of interest, a modified polypeptide, fusion polypeptide or portion of a full-length functional polypeptide of the invention, may lack activity relative to a corresponding full-length functional polypeptide. In other embodiments, a modified polypeptide, fusion polypeptide or portion of a full-length functional polypeptide of the invention in the presence of an exogenous agent may retain at least some or have substantially the same activity, or alternatively lack activity, relative to a corresponding full-length functional polypeptide.

As used herein, "pure" means an object species is the predominant species present (i.e., on a molar basis it is more abundant than any other individual species in the composition), and in one embodiment a substantially purified fraction is a composition wherein the object species comprises at least about 50 percent (on a molar basis) of all macromolecular species present. Generally, a "substantially pure" composition will comprise more than about 80 percent of all macromolecular species present in the composition, more in one embodiment more than about 85%, about 90%, about 95%, or about 99%. For instance, the object species is purified to essential homogeneity (contaminant species cannot be detected in the composition by conventional detection methods) wherein the composition consists essentially of a single macromolecular species.

Nucleic acids are known to contain different types of mutations. A "point" mutation refers to an alteration in the sequence of a nucleotide at a single base position from the wild-type sequence. Mutations may also refer to insertion or deletion of one or more bases, so that the nucleic acid sequence differs from a reference, e.g., a wild-type, sequence.

The terms "recombinant vector" and "expression vector" as used herein refer to DNA or RNA sequences containing a desired coding sequence and appropriate DNA or RNA sequences necessary for the expression of the operably linked coding sequence in a particular host organism. Prokaryotic expression vectors include a promoter, a ribosome binding site, an origin of replication for autonomous replication in a host cell and possibly other sequences, e.g. an optional operator sequence, optional restriction enzyme sites. A promoter is defined as a DNA sequence that directs RNA polymerase to bind to DNA and to initiate RNA synthesis. Eukaryotic expression vectors include a promoter, optionally a polyadenlyation signal and optionally an enhancer sequence.

The term "vector" is used in reference to nucleic acid molecules into which fragments of DNA may be inserted or cloned and can be used to transfer DNA segment(s) into a cell and capable of replication in a cell. Vectors may be derived from plasmids, bacteriophages, viruses, cosmids, and the like.

The term "wild-type" as used herein, refers to a gene or gene product that has the characteristics of that gene or gene product isolated from a naturally occurring source. A wild-type gene is that which is most frequently observed in a population and is thus arbitrarily designated the "wild-type" form of the gene. In contrast, the term "mutant" refers to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

Exemplary Polynucleotides and Proteins for cAMP Biosensors

The invention includes cAMP luciferase biosensors including circularly permuted cAMP luciferase biosensors, which luciferase sequence may include deletions of residues at the original (wild type) N- or C-termini, or both, e.g., deletion of 1 to 3 or more residues at the N-terminus and 1 to 6 or more residues at the C-terminus, as well as sequences that directly or indirectly interact with cAMP. The luciferase sequences of a modified luciferase are the same or are substantially the same as the amino acid sequence of a corresponding unmodified luciferase. A polypeptide or peptide having substantially the same sequence means that an amino acid sequence is largely, but may not entirely be, the same and retains a functional activity of the sequence to which it is related. In general, two amino acid sequences are substantially the same or substantially homologous if they are at least 80% identical, e.g., have at least 85%, 90%, 95%, 99% or more identity.

Homology or identity is often measured using sequence analysis software. Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

Methods of alignment of sequence for comparison are well-known in the art. Optimal alignment of sequences for comparison can be conducted by the local homology algorithm of Smith et al. (Adv. Appl. Math. 2: 482 (1981)), by the homology alignment algorithm of Needleman et al. (J. Mol. Biol. 48: 443 (1970)), by the search for similarity method of Person et al. (1988), by computerized implementations of these algorithms (GAP, BESTFIT, FASTA, and TFASTA), or by manual alignment and visual inspection.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA. Alignments using these programs can be performed using the default parameters. The CLUSTAL program is well described by Higgins et al. (Gene 73: 237 (1988)); Higgins et al. (CABIOS 5: 157 (1989)); Corpet et al. NAR 16: 1088 (1988); Huang et al. (CABIOS 8: 155 (1992)); and Pearson et al. (Methods Mol. Biol. 24: 307 (1994)). The ALIGN program is based on the algorithm of Myers and Miller (LABIOS 4: 11 (1988)). The BLAST programs of Altschul et al. (J. Mol. Biol. 215: 403 (1990)), are based on the algorithm of Karlin and Altschul (PNAS USA 90: 5873 (1993)).

Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. J. Mol. Biol. 215: 403 (1990)). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences (see, e.g., Karlin & Altschul PNAS USA 90: 5873 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, e.g., less than about 0.01, for instance, less than about 0.001.

To obtain gapped alignments for comparison purposes, Gapped BLAST (in BLAST 2.0) can be utilized as described in Altschul et al. (NAR 25: 3389 (1997)). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff. PNAS USA 89: 10915(1989)). See http://www.ncbi.nlm.nih.gov.

In particular, a polypeptide may be substantially related but for a conservative variation. A conservative variation denotes the replacement of an amino acid residue by another, biologically similar residue. Examples of conservative variations include the substitution of one hydrophobic residue such as isoleucine, valine, leucine or methionine for another, or the substitution of one polar residue for another such as the substitution of arginine for lysine, glutamic for aspartic acids, or glutamine for asparagine, and the like. Other illustrative examples of conservative substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine to leucine.

In one embodiment, a polynucleotide of the invention is optimized for expression in a particular host. As used herein, optimization includes codon optimization as well as, in eukaryotic cells, introduction of a Kozak sequence, and/or one or more introns. Thus, a nucleic acid molecule may have a codon composition that differs from that of a wild-type nucleic acid sequence encoding an unmodified luciferase at more than 30%, 35%, 40% or more than 45%, e.g., 50%, 55%, 60% or more of the codons. Preferred codons for use in the invention are those which are employed more frequently than at least one other codon for the same amino acid in a particular organism and, optionally, are also not low-usage codons in that organism and are not low-usage codons in the organism used to clone or screen for the expression of the nucleic acid molecule. Moreover, preferred codons for certain amino acids (i.e., those amino acids that have three or more codons,), may include two or more codons that are employed more frequently than the other (non-preferred) codon(s). The presence of codons in the nucleic acid molecule that are employed more frequently in one organism than in another organism results in a nucleic acid molecule which, when introduced into the cells of the organism that employs those codons more frequently, is expressed in those cells at a level that is greater than the expression of the wild-type or parent nucleic acid sequence in those cells.

In one embodiment of the invention, the codons that are different are those employed more frequently in a mammal, while in another embodiment the codons that are different are those employed more frequently in a plant. A particular type of mammal, e.g., human, may have a different set of preferred codons than another type of mammal. Likewise, a particular type of plant may have a different set of preferred codons than another type of plant. In one embodiment of the invention, the majority of the codons which differ are ones that are preferred codons in a desired host cell. Preferred codons for mammals (e.g., humans) and plants are known to the art (e.g., Wada et al. NAR 18: 2367(1990); Murray et al. NAR 17: 477 (1989))

The modified luciferase proteins or fusion proteins of the invention may be prepared by recombinant methods or by solid phase chemical peptide synthesis methods. Such methods have been known in the art since the early 1960's (Merrifield. J. Am. Chem. Soc. 2149(1963); Stewart et al., Solid Phase Peptide Synthesis, 2nd ed., Pierce Chemical Co., Rockford, Ill., pp. 11-12)) and have recently been employed in commercially available laboratory peptide design and synthesis kits (Cambridge Research Biochemicals).

II. Fusion Partners Useful with the Modified Luciferase of the Invention

The polynucleotide of the invention which encodes a modified luciferase may be employed with other nucleic acid sequences, e.g., a native sequence such as a cDNA or one which has been manipulated in vitro, e.g., to prepare N-terminal, C-terminal, or N- and C-terminal fusion proteins, e.g., a fusion with a protein encoded by a different reporter gene including a selectable marker. Many examples of suitable fusion partners are known to the art and can be employed in the practice of the invention.

Fusion partners include but are not limited to affinity domains or other functional protein sequences, such as those having an enzymatic activity. For example, a functional protein sequence may encode a kinase catalytic domain (Hanks and Hunter. FASEB J. 9: 576(1995)), producing a fusion protein that can enzymatically add phosphate moieties to particular amino acids, or may encode a Src Homology 2 (SH2) domain (Sadowski et al. Mol. Cell. Bio. 6: 4396(1986); Mayer and Baltimore. Trends Cell. Biol. 3: 8(1993)), producing a fusion protein that specifically binds to phosphorylated tyrosines.

Affinity domains are generally peptide sequences that can interact with a binding partner, e.g., such as one immobilized on a solid support. DNA sequences encoding multiple consecutive single amino acids, such as histidine, when fused to the expressed protein, may be used for one-step purification of the recombinant protein by high affinity binding to a resin column, such as nickel sepharose. Sequences encoding peptides, such as the chitin binding domain (which binds to chitin), glutathione-S-transferase (which binds to glutathione), biotin (which binds to avidin and strepavidin), and the like, can also be used for facilitating purification of the protein of interest. The affinity domain can be separated from the protein of interest by methods well known in the art, including the use of inteins (protein self-splicing elements (Chong et al. Gene 192: 271(1997)). Exemplary affinity domains include HisV5 (HHHHH) (SEQ ID NO:15), HisX6 (HHHHHH) (SEQ ID NO:16), C-myc (EQKLISEEDL) (SEQ ID NO:17), Flag (DYKDDDDK) (SEQ ID NO:14), Step-Tag (WSHPQFEK) (SEQ ID NO:18), hemagluttinin, e.g., HA Tag (YPYDVPDYA) (SEQ ID NO:19), GST, thioredoxin, cellulose binding domain, RYIRS (SEQ ID NO:20), Phe-His-His-Thr (SEQ ID NO:21), chitin binding domain, S-peptide, T7 peptide, SH2 domain, C-end RNA tag, WEAAAREACCRECCARA (SEQ ID NO:22), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, 5100 proteins, parvalbumin, calbindin D9K, calbindin D28K, and calretinin, inteins, biotin, streptavidin, MyoD, Id, leucine zipper sequences, and maltose binding protein. In one embodiment, the fusion partner is a sequence useful to purify a fusion protein, e.g., a His or GST tag, and in one embodiment the purification tag is fused to the N- or C-terminus of a circularly permuted luciferase.

III. Vectors and Host Cells Encoding the Modified Luciferase or Fusions Thereof

Once a desirable nucleic acid molecule encoding a modified luciferase or a fusion thereof is prepared, an expression cassette encoding the modified luciferase or a fusion protein comprising the modified luciferase is prepared. For example, a nucleic acid molecule comprising a nucleic acid sequence encoding a modified luciferase is optionally operably linked to transcription regulatory sequences, e.g., one or more enhancers, a promoter, a transcription termination sequence or a combination thereof, to form an expression cassette. The nucleic acid molecule or expression cassette may be introduced to a vector, e.g., a plasmid or viral vector, which optionally includes a selectable marker gene, and the vector introduced to a cell of interest, for example, a prokaryotic cell such as *E. coli, Streptomyces* spp., *Bacillus* spp., *Staphylococcus* spp. and the like, as well as eukaryotic cells including a plant (dicot or monocot), fungus, yeast, e.g., *Pichia, Saccharomyces* or *Schizosaccharomyces*, or a mammalian cell. Exemplary mammalian cells include bovine, caprine, ovine, canine, feline, non-human primate, e.g., simian, and human cells. Exemplary mammalian cell lines include, but are not limited to, CHO, COS, 293, Hela, CV-1, SH-SY5Y, HEK293, and NIH3T3 cells.

The expression of an encoded modified luciferase may be controlled by any promoter capable of expression in prokaryotic cells or eukaryotic cells. Exemplary prokaryotic promoters include, but are not limited to, SP6, T7, T5, tac, bla, trp, gal, lac or maltose promoters. Exemplary eukaryotic promoters include, but are not limited to, constitutive promoters, e.g., viral promoters such as CMV, SV40 and RSV promoters, as well as regulatable promoters, e.g., an inducible or repressible promoter such as the tet promoter, the hsp70 promoter and a synthetic promoter regulated by CRE. The nucleic acid molecule, expression cassette and/or vector of the invention may be introduced to a cell by any method including, but not limited to, calcium-mediated transformation, electroporation, microinjection, lipofection and the like.

IV. Exemplary Uses

The modified luciferases or fusions thereof are useful for any purpose including, but not limited to, detecting the amount or presence of cAMP (a biosensor), isolating a particular molecule, detecting conformational changes in a particular molecule, e.g., due to binding, facilitating high or low throughput screening, detecting protein-protein, protein-DNA or other protein-based interactions, or selecting or evolving biosensors. For instance, a modified luciferase or a fusion thereof, is useful to detect, e.g., in an in vitro or cell-based assay, the amount, presence or activity of cAMP (for example, by inserting a cAMP binding site into a luciferase protein); to identify recognition sites or to detect substrate specificity, e.g., using a modified luciferase with a selected recognition sequence or a library of modified luciferases having a plurality of different sequences with a single molecule of interest or a plurality (for instance, a library) of molecules; to select or evolve biosensors or molecules of interest; or to detect protein-protein interactions via complementation or binding, e.g., in an in vitro or cell-based approach. In one embodiment, a modified luciferase which includes a cAMP binding site is contacted with a random library or mutated library of molecules, and molecules identified which interact with the site. In another embodiment, a library of modified luciferases having a plurality cAMP binding sites is contacted with a molecule, and modified luciferases which interact with the molecule identified. In one embodiment, a modified luciferase or fusion thereof, is useful to detect, e.g., in an in vitro or cell-based assay, the amount or presence of cAMP (for example, by inserting a cAMP binding site into a circularly permuted luciferase), to screen for inhibitors or activators, e.g., inhibitors or activators of cAMP, inhibitors or activators of cAMP binding to a cAMP binding site or inhibitors or activators of G protein coupled receptors (GPCR), to identify recognition sites or to detect substrate specificity, e.g., using a modified luciferase with a selected recognition sequence or a library of modified luciferases having a plurality of different sequences with a single molecule of interest or a plurality (for instance, a library) of molecules, to select or evolve cAMP binding sites, or in whole animal imaging.

The invention also provides methods of screening for agents ("test" agents) capable of modulating the amount of cAMP. "Modulation" refers to an alteration of a property; such enhancement or inhibition of a biological or chemical activity, where the alteration may be contingent on the occurrence of a specific event, such as activation of a signal transduction pathway, and/or may be manifest only in particular cell types. A "modulator" refers to an agent (naturally occurring or non-naturally occurring), such as, for example, a biological macromolecule (e.g., nucleic acid, protein, non-peptide, or organic molecule), small molecules, an extract made from biological materials such as bacteria, plants, fungi, or animal (particularly mammalian) cells or tissues, or any other agent. Modulators are evaluated for potential activity as inhibitors or activators (directly or indirectly) of a biological process or processes (e.g., agonist, partial antagonist, partial agonist, or antagonist) by inclusion in the screening assays described herein. The activities (or activity) of a modulator may be known, unknown or partially known. Such modulators can be screened using the methods of the invention. The term "test agent" refers to an agent to be tested by one or more screening method(s) of the invention as a putative modulator. Usually, various predetermined concentrations are used for screening such as 0.01 μM, 0.1 μM, 1.0 μM, and 10.0 μM. Controls can include the measurement of a signal in the absence of the test agent, comparison to an agent known to modulate the target, or comparison to a sample (e. a cell, tissue or organism) before, during and/or after contacting with the test agent.

In one embodiment, a modified luciferase of the invention is useful as a substrate to study agents or conditions that modulate an interaction between a cAMP binding site in the modified luciferase and a molecule of interest such as a cyclic nucleotide, agents or conditions that modulate the presence or amount of a cyclic nucleotide, or agents or conditions that modulate molecules such as receptors that are associated with intracellular cyclic nucleotide concentrations. In particular, the invention contemplates modified luciferase proteins in which the insertion includes a cAMP binding site. Thus, when the molecule of interest is cAMP, the invention provides a method to determine the presence or the amount of cAMP in a sample by contacting the sample with a modified luciferase polypeptide of the invention and measuring changes in luciferase activity. The modified luciferase protein of the invention can be used for, among other things, monitoring the amount or presence of cAMP or molecules that alter the amount or presence of cAMP inside a cell that has the modified luciferase.

The assays of the invention can be used to screen drugs to identify compounds that alter the amount, for example, of cyclic nucleotide or alter the binding of a cyclic nucleotide to a cyclic nucleotide binding site. In one embodiment, the assay is performed on a sample in vitro containing cAMP. A sample containing a known amount of cAMP is mixed with a modified luciferase of the invention and with a test agent. The amount of the luciferase activity in the sample is then determined. Then the amount of activity per mole of cAMP in the presence of the test agent may be compared with the activity per mole of cAMP in the absence of the test agent. A difference indicates that the test agent alters the amount of cAMP or binding of cAMP to the cAMP binding site.

In one embodiment, cells are conditioned or contacted with an agent suspected of directly or indirectly modulating, for instance, cAMP amount or binding. The cells or cells in culture are lysed and the amount of cAMP measured. For example, a lysed cell sample containing a known or unknown amount of cAMP is mixed with a modified luciferase of the invention. The amount of cAMP in the sample is then determined as above by determining the degree of modified luciferase activity in a control or non-treated sample and the treated lysed cellular sample. The activity or inhibition can be calculated based on a per microgram or milligram protein in the sample. Typically, the difference is calibrated against standard measurements to yield an absolute amount of cAMP.

The materials and composition for use in the assay of the invention are ideally suited for the preparation of a kit. Such a kit may comprise a carrier means containing one or more container means such as vials, tubes, and the like, each of the container means comprising one of the separate elements to be used in the method. One of the containers comprises a modified luciferase or polynucleotide (e.g., in the form of a vector) of the invention. A second container may contain a substrate for the modified luciferase.

The invention will be further described by the following non-limiting examples.

Example I

Exemplary Sites Tolerant to Modification in Luciferases

To prepare cAMP luciferase biosensors, a cAMP binding site is fused to a luciferase that is tolerant to modification. Positions in click beetle and firefly luciferases that are tolerant to modification, e.g., for circular permutation or insertion of heterologous sequences, are disclosed in U.S. published application 20050153310, U.S. Ser. No. 11/732,105, PCT/US2004/032705 and PCT/US2007/008176, the disclosures of which are incorporated by reference herein.

Example II

Generation of Mutations in the Human RIIβB Site

To identify improved biosensors for cAMP, constructs were prepared with substitutions in a human cAMP binding domain (subsite B from the human PKA regulatory subunit type IIβ (RIIβB; Genbank Accession No. BC075800, residues 266-414). Substitutions in RIIβB were generated using the oligo-based site-directed mutatagenesis kit (Kunkel, PNAS USA 82(2):488 (1985)), Quik Change (Stratagene) on the human RIIβB site or the error-prone, mutagenic PCR-based system (Daugherty, PNAS USA 97(5):2029 (2000)), GeneMorph II (Stratagene) on the circularly-permuted firefly luciferase construct (Met-(FF luc 359-544)-(RIIβB)-(FF luc 4-355)-Val) according to the manufacture's instructions.

Example III

Screening of Human RIIβB Mutants

Biosensor constructs containing mutations to RIIβB (Example 2) were inserted into a circularly permuted firefly luciferase (CP-FF) construct (Met-(FF luc 359-544)-(RIIβB)-(FFluc4-355)-Val). These constructs were first screened in *E. coli* to identify mutant RIIβB sites which provided improved luminescence, improved response or both. Briefly, the constructs were overexpressed in *E. coli* in the presence or absence of 50 μM cAMP. Those constructs which demonstrated improved luminescence were screened for enhanced signal or enhanced response to agents that increase cAMP in HEK293 cells. The performance of these mutant biosensors was compared to that of the parent construct (GS358) with primary sequence Met-(FF luc 359-544)-GSSGGSGGSGGG (SEQ ID NO:41)-(RIIβB)-(FF-luc4-355)-Val.

Methods and Results

On day 1, 15,000 HEK293 cells were plated to the individual wells of a 96-well plate. On day 2, cells were transiently transfected with plasmid DNAs encoding various biosensor mutants (with mutations in the RIIβB cAMP binding domain) using the TransIT-LT1 reagent from Mirus Bio. Plasmids also carried a gene for constitutive expression of *Renilla* luciferase to act as a transfection control. Cells were equilibrated for 2 hours at room temperature using 2 mM endotoxin-free luciferin (EF-luc). Isoproterenol or forskolin (FSK) were added to 10 μM final concentration to the individual wells, and luminescence was monitored continuously in time (Mithras luminometer; 1 second integration time). Once measurements were complete (>30 minutes), cells were lysed, and *Renilla* luciferase activity was measured.

Biosensor luminescence (FF RLU) was normalized using the *Renilla* luminescence signal (RL norm), and fold-induction (response) was calculated by dividing the normalized biosensor luminescence from isoproterenol- or forskolin-treated wells by the normalized luminescence from control wells that received no compound addition (FIGS. 2-6).

As indicated in Table 1, some of the substitutions were found to improve only luminescent signal or response. Other substitutions, e.g., residues 389 and 333, were found to improve either luminescent signal or response depending on the amino acid substituted at that residue. Some substitutions, e.g., V333N, provided improvement in both the luminescent signal and response. Combinations of substitutions were also screened to determine if the substitutions had a cumulative effect on the improvement of the luminescent signal or response.

TABLE 1

| Agonist Signal Improvements | Agonist Response Improvements |
|---|---|
| M266Q | E284A |
| F282S | V291S |
| L286N | V296T |
| V296T | D308E |
| V333N, V333G | V316I |
| M389K | V333P, V333N |
| V404S | M389Y, M289S, M289C, M389V, M389L |
| | E284A + V316I |
| | E284A + V316I + V333P + M289Y |

Example IV

Generation of Mutated Linker Sequences

To identify if changes in the linker sequence of a cAMP biosensor could also improve luminescence, response to agents, or both, linker variants were prepared with substitutions in the parent linker sequence GS358, GSSGGSGGSGGG (SEQ ID NO:41). Linker variants were generated using a cassette-based cloning approach or by directly synthesizing annealed, duplex oligo linkers. The cassette based approach comprises the direct ligation of duplex library fragments or individual fragments into the sequence/gene. Briefly, linker variants were generated by amplification of single-stranded random sequences representing the linker region. The resulting duplex cassettes containing the appropriate restrication sites were ligated into the appropriate region of the sequence to create a plasmid-based library of linker variants. For linker variants synthesized directly, both strands of the linker cassette were synthesized (IDT), annealed, and cloned as in the cassette-based approach. Linker variants were screened for improved luminescence, improved response, or both in *E. coli*. The best linker variants were then used to rationally design linker composites (n=48) from the amino acid sequences of these best linker variants. These composites were synthesized (IDT), annealed and cloned into CP-FF Luc construct.

Table 2 identifies the variant linker sequences generated.

TABLE 2

| Variant ID | Sequence | SEQ ID NO |
|---|---|---|
| Parent-GS358 | GSSGGSGGSGGG | 41 |
| 5A7 | GSSSDSDSSAGS | 42 |
| 9H9 | GSNDSSGGSEGG | 43 |
| 9F1 | GSNGGFDSSEGG | 44 |
| 64C1 | GSRGGSVYSEGG | 46 |
| 36D1 | GSRGGSVYSEGG | 46 |
| 54B8 | GSSEGSSDFGGD | 47 |
| 72E8 | GSIVVSCSSEGG | 48 |
| 7A1 | GSNWDSGCSREG | 49 |
| 7A2 | GSSGCTGDAGGS | 51 |
| L9 | GSIAGCGDAGEG | 126 |

Example V

Screening of Mutated Linker Sequences

The linker variants of Example III were inserted into a CP-FF construct as in Example II. The construct further comprised a mutant RIIβb cAMP binding site containing the substitutions at E284A and V316I. As in Example II, the constructs were first screened in *E. coli* to identify linker sequences which provided improved luminescence, improved response or both. The linker variants were then screened for improved luminescence signal, response to isoproterenol, or both in HEK293 cells.

Methods and Results

On day 1, 15,000 HEK293 cells were plated to the individual wells of a 96-well plate. On day 2, cells were transiently transfected with plasmid DNAs encoding a cAMP biosensor variant comprising a variant linker sequence using the LT1 reagent from Mirus Bio. Plasmids also carried a gene for constitutive expression of *Renilla* luciferase to act as a transfection control. Cells were equilibrated for 2 hours at room temperature using 5 mM luciferin EF (EF-luc). Isoproterenol was added to 10 μM final concentration to the individual wells, and luminescence was monitored continuously in time (Mithras luminometer; 1 second integration time). Once measurements were complete (>30 minutes), cells were lysed, and *Renilla* luciferase activity was measured.

Biosensor luminescence (FF RLU) was normalized using the *Renilla* luminescence signal (RL norm), and fold-induction (response) was calculated by dividing the normalized biosensor luminescence from isoproterenol-treated wells by the normalized luminescence from control wells that received no compound addition (Figure). Table 3 provides a summary of the linker improvements. The data in Table 8 comprises fold improvement values in luminescent signal, response to Isoproterenol, or both over the parental GS358 construct (GS358 with E284A and V316I substitutions in RIIβB).

TABLE 3

| Linker Variant ID | Signal Improvement | Response Improvement |
|---|---|---|
| 5A7 | 4.8 | 0.9 |
| 9H9 | 3.2 | 1.2 |
| 9F1 | 3.1 | 1.1 |
| 64C1 | 0.9 | 1.8 |
| 36D1 | 1.5 | 1.7 |
| 54B8 | 2.0 | 1.6 |
| 72E8 | 2.4 | 1.3 |
| 7A1 | 2.4 | 1.4 |
| 7A2 | 2.7 | 1.5 |

Example VI

In Vitro Detection of cAMP with CPM-FF Luc/Mutant RIIβB cAMP Biosensors

Figure 9A:
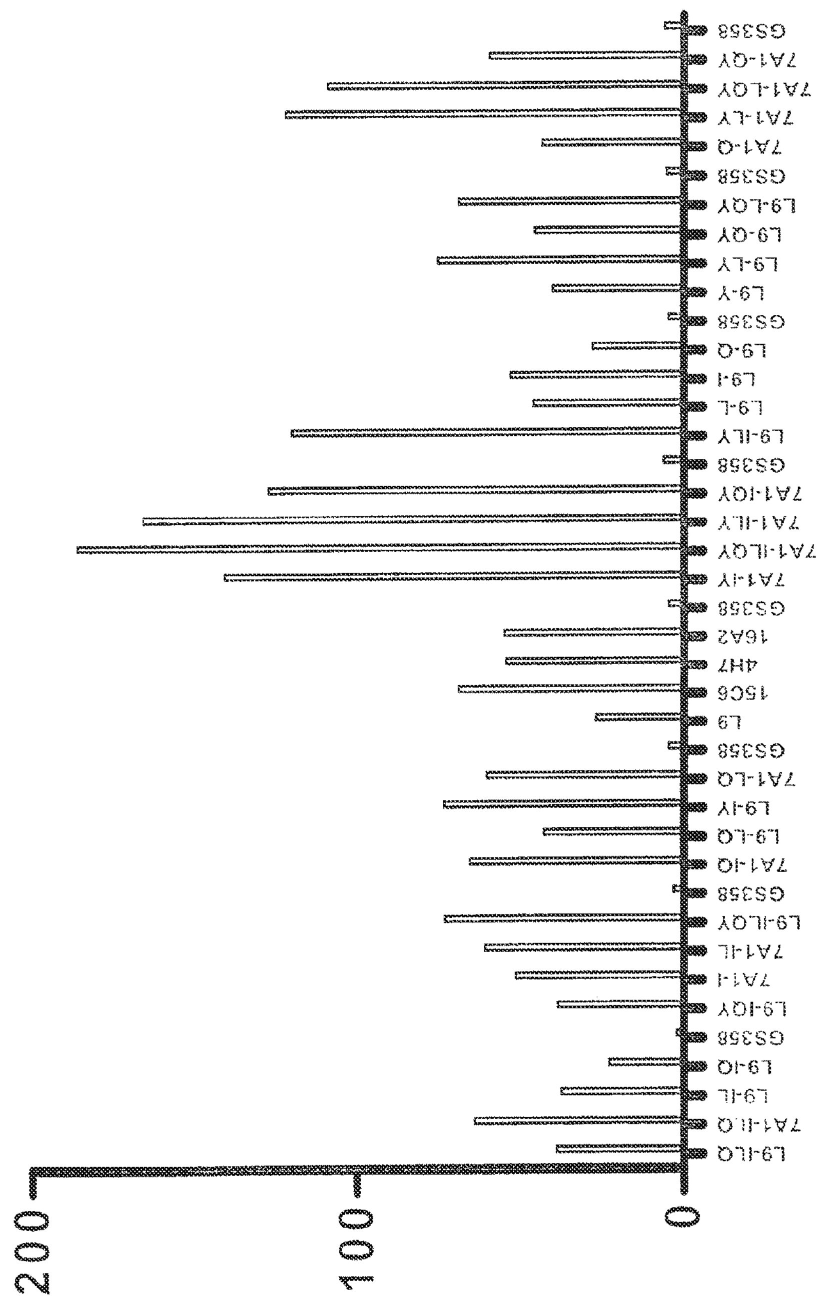
FIG. 9A, FIG. 9B, and FIG. 9C. Fold response for clones treated with various compounds and with FSK.
Figure 9B:
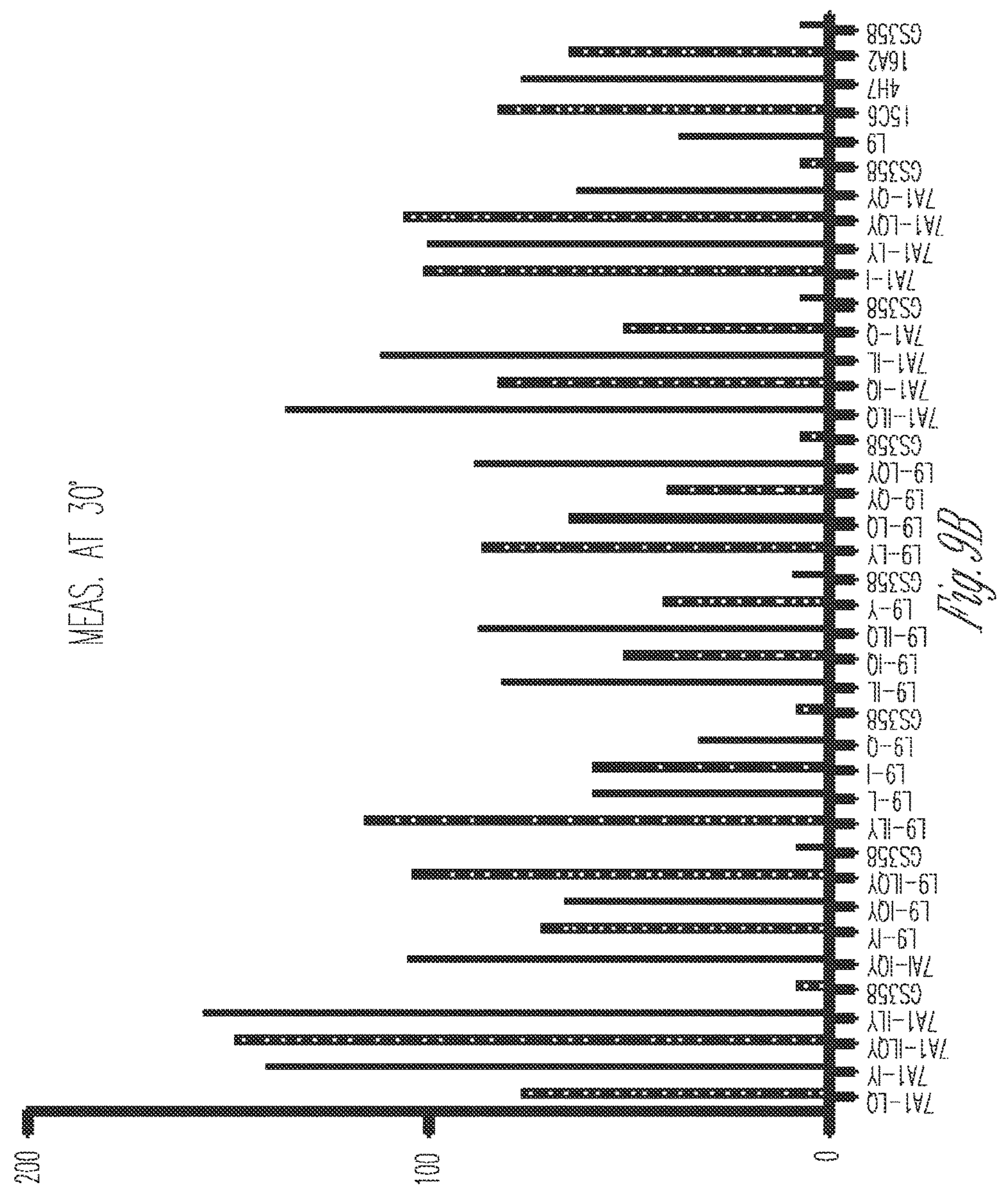
Figure 9C:
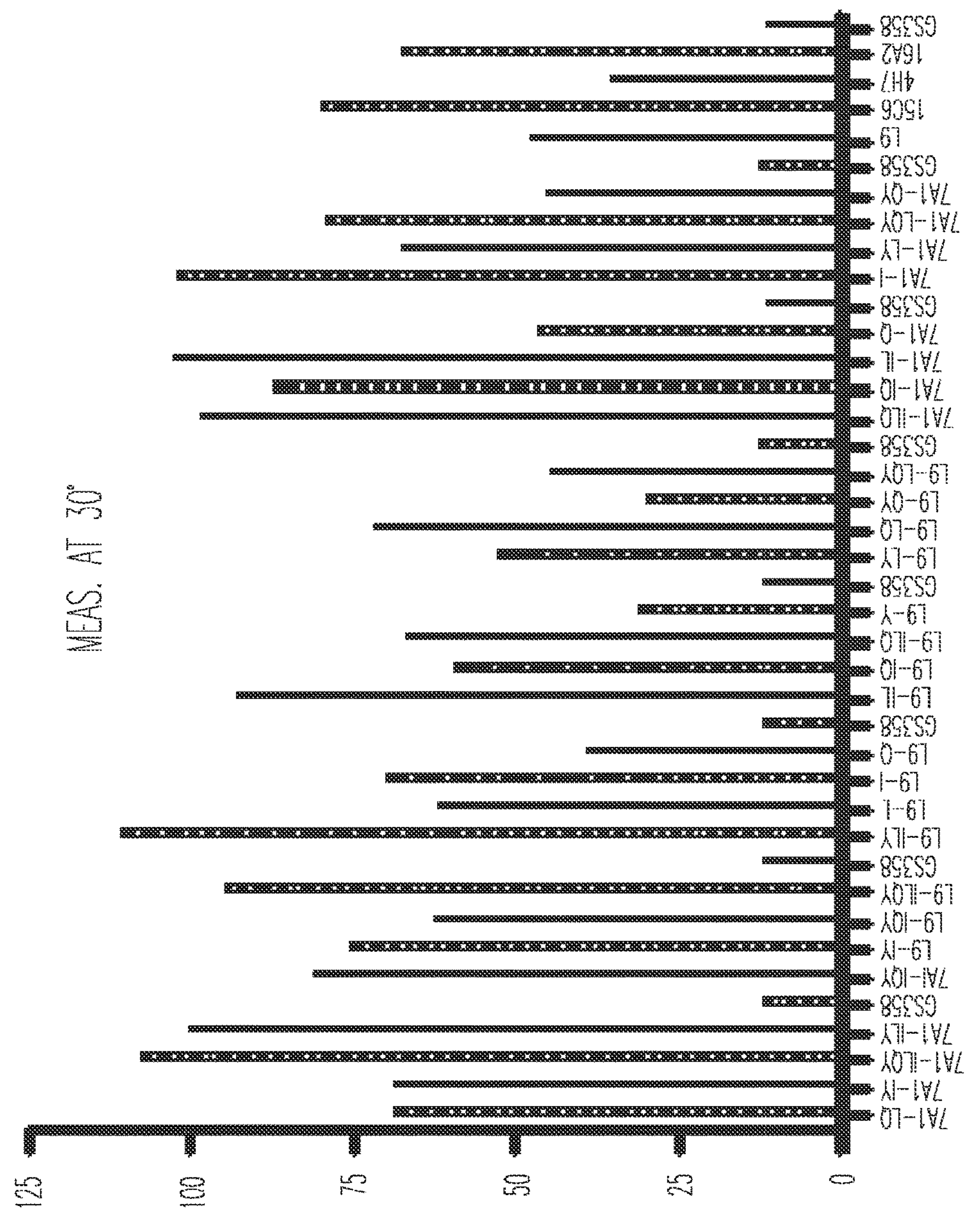

Plasmid DNA encoding cAMP biosensor variants were expressed in vitro using TnT® T7 Coupled Rabbit Reticulocyte Lysate System (Promega) according to the manufacturer's instructions for 1 hour at 30° C. cAMP biosensor variants expressed included: a double variant comprising substitutions V316I and E284I in RIIβB, clone 7A1 (SEQ ID NO: 113; SEQ ID NO:114) comprising V316I and E284 substitutions in RIIβB and the modified linker sequence GSNWDSGCSRE (SEQ ID NO: 127), clone L9 (SEQ ID NO:104; SEQ ID NO: 105) comprising substitutions E284A and V316I in RIIβB and the modified linker sequence GSIAGCGDAGEG (SEQ ID NO:56; SEQ ID NO: 128), and parental clone GS358 (SEQ ID NO:111; SEQ ID NO:112). Following expression, 20 μL of the TnT® reaction was combined with 2 μL of a 10× stock solution of cAMP diluted in $H_2O$. The mixture was incubated at room temperature for 15 minutes, and luminescence was measured from 5 μL of sample following injection of 90 μL of Luciferase Assay Reagent using a Glomax luminometer (0.5 second integration time). The three cAMP variants all right shifted which is indicative of reduced affinity for cAMP (FIG. 9).

Example VII

Figure 8A:
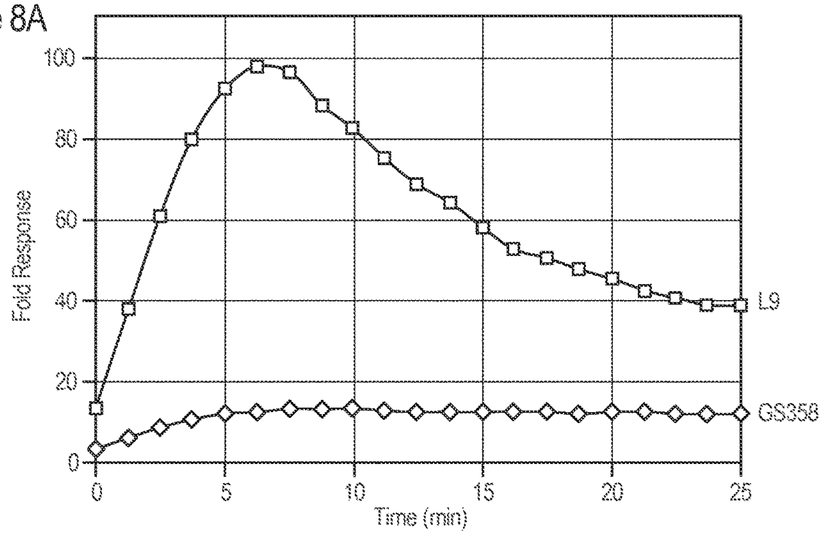
FIGS. 8A-B.
Figure 8B:
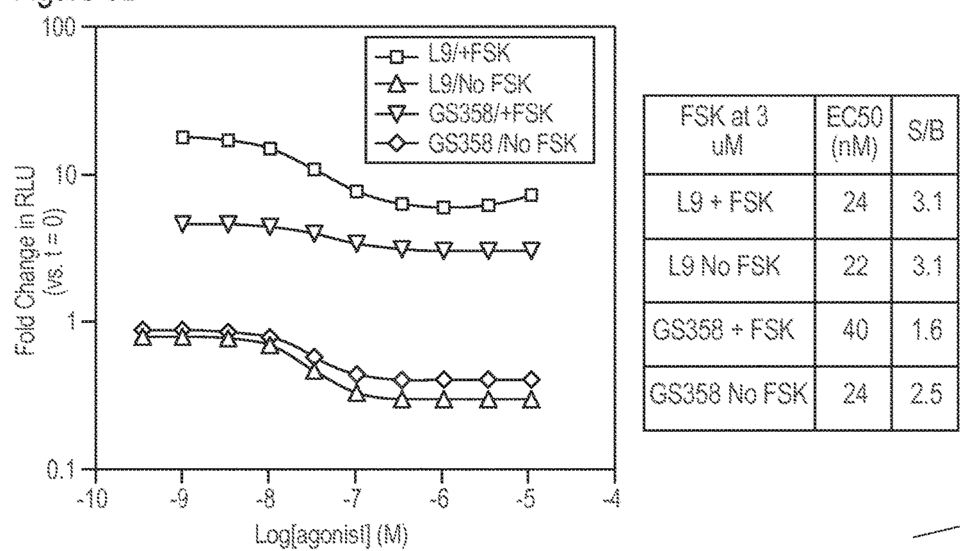

Increased Stimulatory Response to Isoproterenol by a CPM-FF Luc/Mutant RIIβB cAMP Biosensor with a Modified Linker Region A mutant cAMP biosensor (termed L9; SEQ ID NO: 104; SEQ ID NO: 105) having a mutant RIIβB binding site (substitutions E284A and V316I) and a modified linker sequence (GSIAGCGDAGEG, SEQ ID NO: 57; SEQ ID NO: 128) was screened for increased light output and increased fold response when expressed in mammalian cells (primary sequence Met-(*Photinus pyralis* luciferase residues 359-544)-(GSIAGCGDAGEG (SEQ ID NO: 57; SEQ ID NO: SEQ ID NO: 128))-(RIIβB E284A, V316I)-(*Photinus pyralis* luciferase residues 4-355)-Val). For a stimulatory response, transient expression in HEK293 cells was followed by treatment with 10 μM isoproterenol (agonist of the endogenous beta2-adrenergic receptor). For an inhibitory response, transient expression in HEK293 cells that stably express the dopamine D2 receptor was followed by simultaneous treatment with dopamine in the presence or absence of forskolin L9 transfected cells provide an improved fold response to isoproterenol induction of the Gs pathway (FIG. 8A) and also an improved fold response for the Gi pathway (FIG. 8B).

B. HEK293 cells were transiently transfected with plasmid DNAs encoding various biosensor mutants as above. These biosensor mutants contained the E284A and V316I mutation in the RIIbetaB cAMP binding domain and the modified linker sequence 7A1 (GSNWDSGCSREG; SEQ ID NO: 129). The clones also contained the additional mutations outlined in Table 5. Cells were equilibrated for 2 hours at room temperature with 2 mM EF-Luc. Luminescence was measured 5 and 15 minutes after addition of the isoproterenol and 15 minutes after addition of FSK. Fold response (response; Resp.) was calculated by dividing relative light units (RLUs) from induced cells by the RLUs from uninduced cells. As a control, the biosensor GS358 and 7A1 were included.

TABLE 4

| | Isoproterenol-5 minutes | | | Isoproterenol-15 minutes | | | Forskolin (FSK) | | |
|---|---|---|---|---|---|---|---|---|---|
| Clone | Un-induced | Induced | Resp | Un-induced | Induced | Resp | Un-induced | Induced | Resp |
| 4H7 | 493 | 42467 | 86 | 2665 | 207210 | 78 | 2665 | 88555 | 33 |
| 9G4 | 553 | 27930 | 50 | 5760 | 264500 | 46 | 5760 | 263020 | 46 |

TABLE 4-continued

| | Isoproterenol-5 minutes | | | Isoproterenol-15 minutes | | | Forskolin (FSK) | | |
|---|---|---|---|---|---|---|---|---|---|
| Clone | Un-induced | Induced | Resp | Un-induced | Induced | Resp | Un-induced | Induced | Resp |
| 1B3 | 1673 | 59767 | 36 | 6460 | 344375 | 53 | 6460 | 305500 | 47 |
| 15C6 | 560 | 47663 | 85 | 1970 | 141250 | 72 | 1970 | 162400 | 82 |
| 16A2 | 527 | 44890 | 85 | 2025 | 141135 | 70 | 2025 | 153670 | 76 |
| 15H6 | 1073 | 91567 | 85 | 4040 | 244700 | 61 | 4040 | 29500 | 57 |
| 16B3 | 2063 | 72003 | 35 | 6555 | 248415 | 38 | 6555 | 257605 | 39 |
| 7A1 | 1231 | 73287 | 60 | 3415 | 173340 | 51 | 3415 | 161755 | 47 |
| GS358 | 4943 | 41610 | 8 | 14895 | 184150 | 12 | 14895 | 195335 | 13 |

TABLE 5

| Clone | Substitution | SEQ ID NO |
|---|---|---|
| 15C6 | F369I, K541Q-substitutions in Luc2.0 (SEQ ID NO: 106) | 23, 24 |
| 16A2 | F518L-substitution in Luc2.0 | 60, 61 |
| 15H6 | F433Y, M493V-substitutions in Luc2.0; modified linker sequence: GSNWDSGCSRGC | 107, 108 |
| 4H7 | F407Y-substitution in RIIβb | 35, 36 |
| 16B3 | S440N-substitution in Luc2.0 | 72, 73 |
| 9G4 | E382K-substitution in RIIβb | 37, 38 |
| 1B3 | A338E-substitution in RIIβb | 33, 34 |

TABLE 6

| | Forskolin (FSK) | | | Dopamine | | Halo | |
|---|---|---|---|---|---|---|---|
| Clone | Un-induced | Induced | Re-sponse | Induced | Re-sponse | Induced | Re-sponse |
| 15C6 | 117 | 3520 | 30 | 1463 | 0.42 | 2918 | 2.0 |
| 16A2 | 147 | 4117 | 28 | 95 | 0.33 | 223 | 2.3 |
| 15H6 | 283 | 7177 | 25 | 30 | 0.56 | 65 | 2.2 |
| 4H7 | 230 | 3180 | 14 | 583 | 0.18 | 2778 | 4.8 |
| 16B3 | 370 | 6400 | 17 | 3050 | 0.48 | 6188 | 2.0 |
| 9G4 | 293 | 4133 | 14 | 1735 | 0.42 | 4370 | 2.5 |
| 1B3 | 460 | 8410 | 18 | 1898 | 0.23 | 5228 | 2.8 |
| 7A1 | 307 | 4709 | 15 | 1860 | 0.38 | 5429 | 2.9 |
| GS358 | 1704 | 9166 | 5 | 5153 | 0.56 | 9218 | 1.9 |

Example VIII

To measure changes in the intracellular concentration of cAMP, HEK293 cells are transiently transfected with mutant cAMP biosensors followed by treatment with compounds known to increase or decrease the intracellular cAMP concentration through GPCR activation of Gs- or Gi-coupled receptors, respectively. FSK (direct activator of endogenous adenylate cyclase) is used to elevate cAMP, dopamine is used to reduce cAMP (agonist of the Gi-coupled dopamine D2 receptor), and Haloperidol (dopamine D2 receptor antagonist) is used demonstrate the use of the assay in screens for Gi-coupled receptor antagonists.

Materials and Results

HEK293 cells stably expressing the dopamine D2 receptor were transiently transfected with the mutant cAMP biosensors from Example VIIB. Cells were also transfected with either 7A1 (Example III) or GS358 (parent biosensor) as controls. Cells were equilibrated for 2 hours at room temperature using 2 mM EF-luc. Antagonist assay wells were pre-treated for 10-15 minutes at room temperature with 10 μM Haloperidol (Halo). Next, the following reagents were added to their respective wells: media alone to "untreated" samples; 3 μM forskolin (FSK) to "forskolin-treated" samples; 3 μM FSK+0.3 μM dopamine to "agonist-treated" samples; and 3 μM FSK+0.3 μM dopamine to the aforementioned wells pre-treated with Halo. The cells were then incubated at room temperature for 10 minutes and luminescence was measured. Fold response for FSK was calculated by dividing the RLU from "forskolin-treated" cells by the RLU from the "untreated" cells. Fold response for dopamine treatment was calculated by dividing the RLU from the "agonist-treated" cells by the RLU from the "forskolin-treated" cells. Fold response for Haloperidol treatment was calculated by dividing the RLU from the cells treated with haloperidol then forskolin plus dopamine by the RLU of cells treated with forskolin plus dopamine alone.

Example IX cAMP mutant biosensor variants were generated which contained combinations of amino acid substitutions which seemed to provide the most improved response in Example VII. These amino acid substitutions included substitutions in Luc2.0: F369I (I), K541Q (Q), F518L (L) and/or RIIβB: F407Y (Y). The cAMP biosensor variants were generated in either the 7A1 or L9 background. Naming of the variants is provided as the background clone (7A1 or L9) plus the amino acid substitution(s) (I, Q, L and/or Y). These variants were screened for improved luminescence and/or response.

HEK293 cells stably expressing GPCR receptors GPR41 (Multispan, Inc.), GPR44 (Multispan), or dopamine D2 receptor were plated at 15,000 cells/well in individual wells of 96-well plates. After 24 hours, the cells were transiently transfected with one of the cAMP biosensor variants (Tables 7A and 7B). After another 24 hours, the cells were equilibrated for 2 hours at room temperature using 5 mM EF-luc in CO2 independent media with 10% FBS. Prior to the addition of the compounds, luminescence was measured. The compounds (12× stock in CO2 independent media without FBS) were then added to the cells. For GPR41 expressing cells, sodium proprionate CRC was added. For GPR44 expressing cells, 15(R)-prostaglandin D2 (PGD2) CRC was added. For dopamine D2 expressing cells, dopamine CRC was added. After a 5 minute incubation with the compounds, FSK was added to all cells. The cells were allowed to incubate another 30 minutes and luminescence read on a Varioskan Flash. $EC_{50}$ values and fold responses were calculated for each of the clones with each of the compounds with or without FSK. In addition, variants L9, 15C6 (Example VIIIB), 4H7 (Example VIIB), 16A2 (Example VIIB) and GS358 were also screened.

Figure 10A:
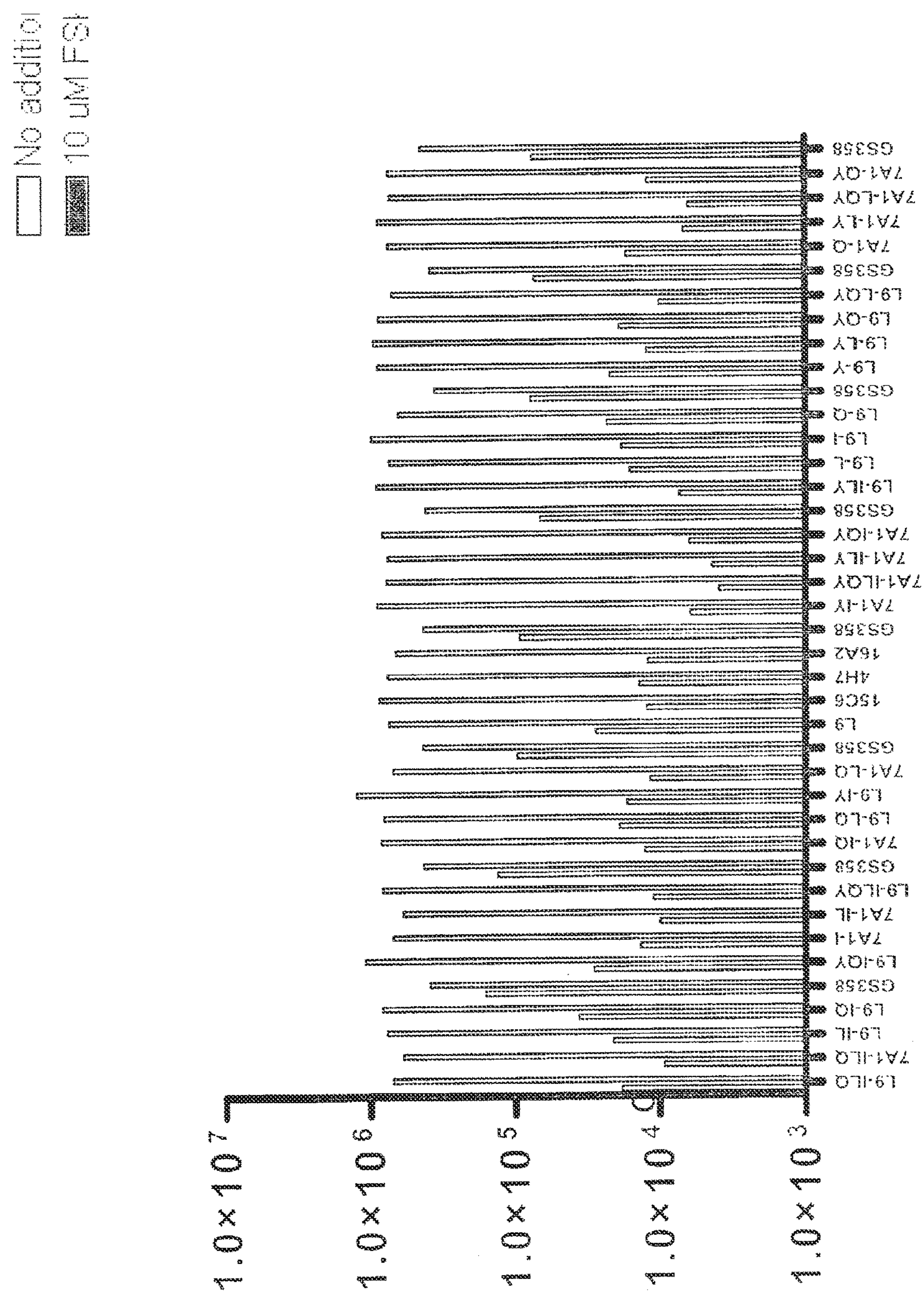
FIG. 10A, FIG. 10B, and FIG. 10C. Graph of the absolute RLUs for clones at 30 minutes with each compound and with or without FSK.
Figure 10B:
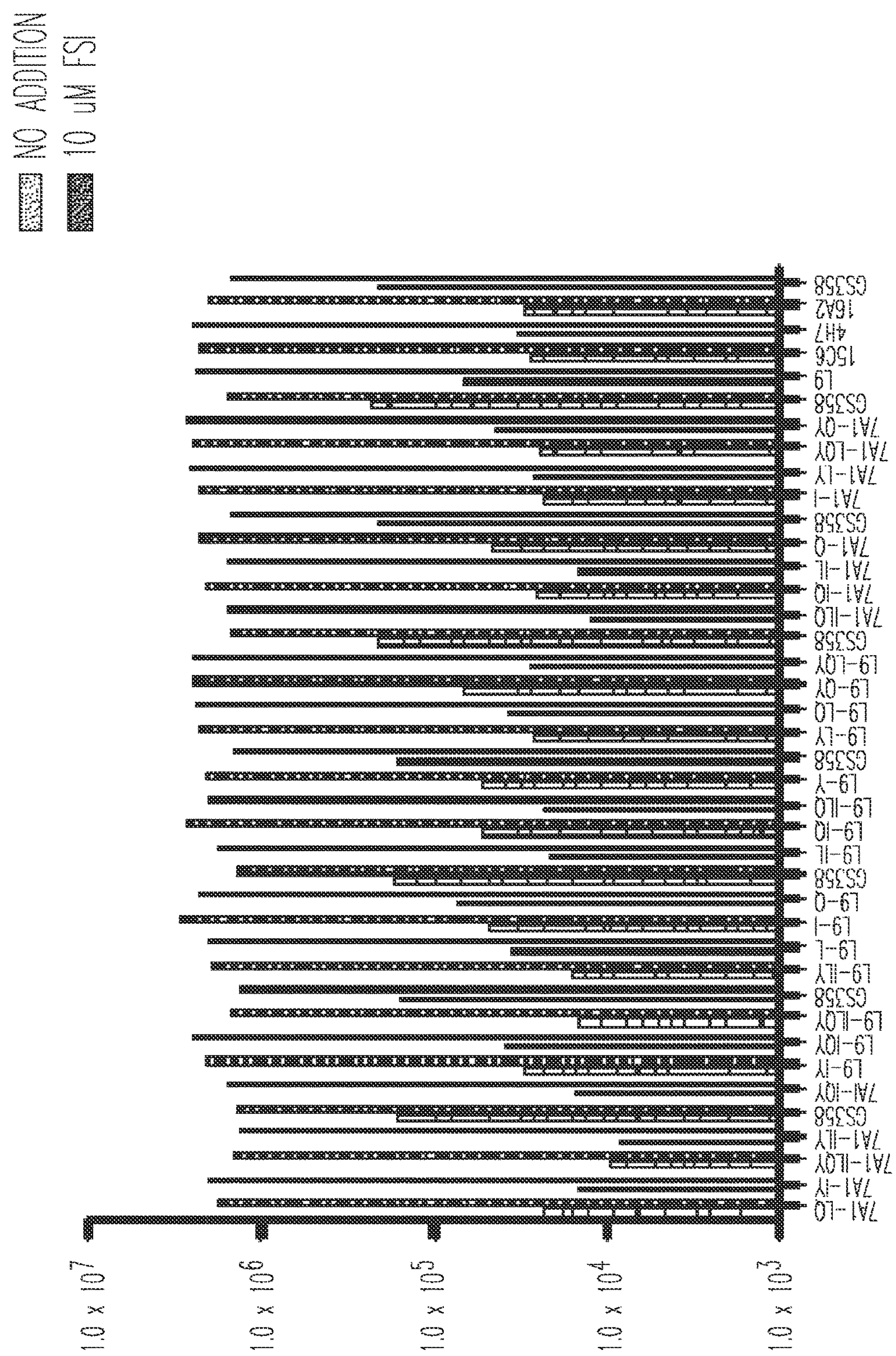
Figure 10C:
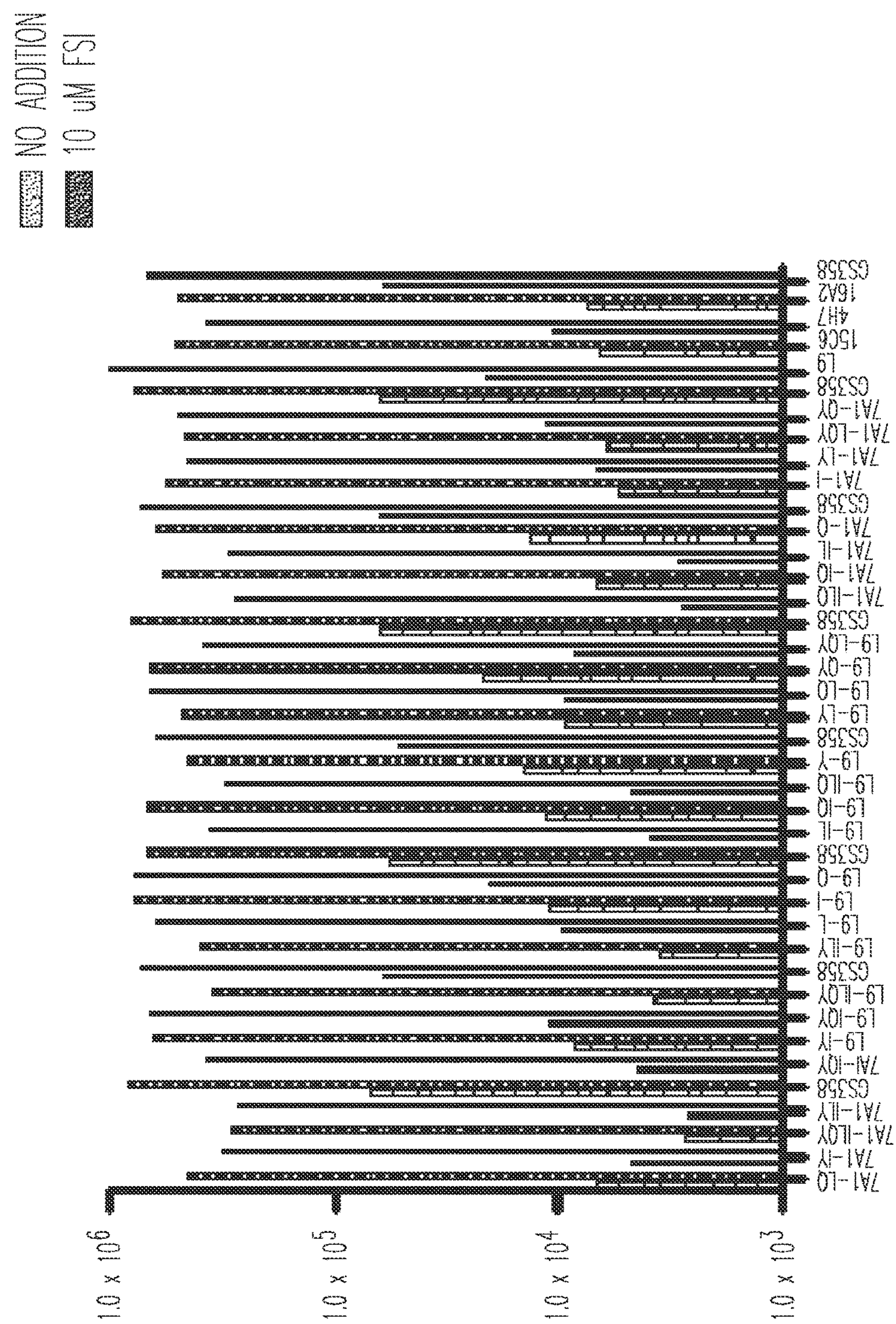

Tables 7A and 7B provide fold response (ratio of induced signal to uninduced signal) and fold signal change (ratio of RLU of FSK treated well to untreated well) for Na proprionate treated GPR41 cells. Tables 8A and 8B provide the $EC_{50}$ values obtained for each of the clones with each of the compounds with or without FSK. FIG. 9 (A=GPR44, B=GPR41, C=D2) provides the fold response seen in each clone with each of the compounds with FSK (versus without). Fold response is calculated by dividing the RLU at 30 minutes by the RLU prior to compound addition. FIG. 10 (A=GPR44, B=GRP41, C=D2) provides a graph of the absolute RLUs for each of the clones at 30 minutes with each compound with or without FSK.

TABLE 7A

| Clone | Fold Response Na proprionate | Fold Response Na proprionate + FSK(1 μM) | Fold Signal Change |
|---|---|---|---|
| L9 | 2.73 | 2.60 | 40.9 |
| L9-IY | 2.53 | NA | 86.4 |
| L9-IQY | 3.82 | NA | 96.0 |
| L9-ILQY | NA | NA | 152.7 |
| L9-ILY | 3.34 | 4.91 | 161.2 |
| L9-L | 3.04 | 5.72 | 72.2 |
| L9-I | 3.61 | 3.83 | 83.5 |
| L9-Q | 2.57 | 5.24 | 42.0 |
| L9-IL | 3.67 | 7.43 | 96.7 |
| L9-IQ | 3.41 | 5.17 | 64.0 |
| L9-ILQ | 4.13 | 10.21 | 140.4 |
| L9-Y | 2.17 | 3.88 | 55.8 |
| L9-LY | 2.07 | 5.57 | 126.7 |
| L9-LQ | 2.83 | 7.20 | 98.6 |
| L9-QY | 2.01 | 10.02 | 61.3 |
| L9-LQY | 1.95 | 13.78 | 136.0 |
| GS358 | 2.56 (n = 8) | 3.19 (n = 7) | 9.48 (n = 8) |
| 15C6 | 3.42 | 3.55 | 104.5 |
| 4H7 | 1.94 | 2.98 | 93.6 |
| 16A2 | 2.73 | 3.76 | 89.7 |

TABLE 7B

| Clone | Fold Response Na proprionate | Fold Response Na proprionate + FSK(1 μM) | Fold Signal Change |
|---|---|---|---|
| 7A1-LQ | 2.70 | 6.6 | 85.2 |
| 7A1-IY | 2.81 | 8.66 | 165.7 |
| 7A1-ILQY | 2.57 | 8.13 | 220.1 |
| 7A1-ILY | 2.49 | 8.96 | 194.6 |
| 7A1-IQY | 2.42 | NA | 128.0 |
| 7A1-ILQ | 4.09 | 5.68 | 181.8 |
| 7A1-IQ | 3.66 | 3.42 | 128.0 |
| 7A1-IL | 4.66 | 4.36 | 200.0 |
| 7A1-Q | 2.26 | 4.26 | 71.6 |
| 7A1-I | 3.07 | 6.60 | 133.9 |
| 7A1-LY | 2.15 | 62.19 | 141.7 |
| 7A1-LQY | 1.94 | NA | 153.1 |
| 7A1-QY | 1.68 | 161.29 | 87.6 |
| GS358 | 2.56 (n = 8) | 3.19 (n = 7) | 9.48 (n = 8) |
| 15C6 | 3.42 | 3.55 | 104.5 |
| 4H7 | 1.94 | 2.98 | 93.6 |
| 16A2 | 2.73 | 3.76 | 89.7 |

TABLE 8A

| | $EC_{50}$(nM) | | | | | |
|---|---|---|---|---|---|---|
| Clone | Na proprionate | Na proprionate + FSK(1 μM) | Dopamine | Dopamine + FSK (1 μM) | PGD2 | PGD2 + FSK(1 μM) |
| L9 | 13.7 | 20.4 | 110.33 | 5723.3 | 5.34 | 10.4 |
| L9-IY | 18.6 | NA | 66.65 | 88.4 | 3.40 | 13.3 |
| L9-IQY | 9.8 | NA | 59.24 | 77.2 | 5.39 | 11.4 |
| L9-ILQY | NA | NA | 86.89 | 75.4 | 4.52 | 8.6 |
| L9-ILY | 14.6 | 16.8 | 70.91 | 73.6 | 3.34 | 9.8 |
| L9-L | 16.1 | 29.7 | 80.36 | 66.4 | 5.59 | 10.2 |
| L9-I | 20.8 | 60.9 | 79.71 | 58.3 | 3.33 | 11.3 |
| L9-Q | 19.4 | 78.8 | 90.37 | 66.2 | 4.25 | 16.3 |
| L9-IL | 17.9 | 21.2 | 93.62 | 104.7 | 4.21 | 3.3 |
| L9-IQ | 18.7 | 36.7 | 77.66 | 105.3 | 6.43 | 10.3 |
| L9-ILQ | 19.3 | 57.7 | 89.54 | 108.4 | 5.51 | 9.1 |
| L9-Y | 13.1 | 45.4 | 91.29 | 262.4 | 3.26 | 6.5 |
| L9-LY | 21.4 | 11.6 | 91.06 | 103.6 | 4.80 | 0.1 |
| L9-LQ | 18.9 | 7.4 | 78.89 | 107.3 | 5.61 | 24.2 |
| L9-QY | 22.8 | 4.3 | 97.23 | 100.7 | 6.35 | 0.0 |
| L9-LQY | 24.7 | 6.8 | NA | 113.6 | 4.65 | 13.4 |
| GS358 | 20.0 (n = 8) | 55.4 (n = 8) | 88.6 (n = 8) | 1404.6 (n = 7) | 12.2 (n = 7) | 33.2 (n = 8) |
| 15C6 | 16.5 | 21.7 | 137.45 | 58016.0 | 5.72 | 10.1 |
| 4H7 | 13.4 | 28.8 | 106.15 | 59296.0 | 2.43 | 4.1 |
| 16A2 | 14.3 | 21.8 | 142.88 | 77197.0 | 5.00 | 7.6 |

TABLE 8B

| | $EC_{50}$(nM) | | | | | |
|---|---|---|---|---|---|---|
| Clone | Na proprionate | Na proprionate + FSK(1 μM) | Dopamine | Dopamine + FSK (1 μM) | PGD2 | PGD2 + FSK(1 μM) |
| 7A1-LQ | 13.6 | 17.0 | 65.41 | 69.0 | 4.16 | 1.5 |
| 7A1-IY | 8.7 | 4.6 | 65.66 | 94.0 | 2.10 | 15.4 |
| 7A1-ILQY | 21.9 | 8.9 | 61.98 | 70.8 | 2.89 | 3.5 |
| 7A1-ILY | 17.5 | 7.3 | 76.51 | 92.0 | 1.89 | 5.3 |

TABLE 8B-continued

| | EC50(nM) | | | | | |
|---|---|---|---|---|---|---|
| Clone | Na proprionate | Na proprionate + FSK(1 μM) | Dopamine | Dopamine + FSK (1 μM) | PGD2 | PGD2 + FSK(1 μM) |
| 7A1-IQY | 17.4 | | 81.64 | 98.4 | 5.40 | 0.0 |
| 7A1-ILQ | 16.3 | 24.4 | 94.35 | 108.6 | 5.09 | 4.1 |
| 7A1-IQ | 17.4 | 28.3 | 96.40 | 111.9 | 2.65 | 19.8 |
| 7A1-IL | 8.3 | 40.3 | 93.04 | 76.9 | 4.46 | 10.4 |
| 7A1-Q | 16.7 | 53.6 | 98.27 | 98.6 | 3.02 | 9.5 |
| 7A1-I | 19.9 | 25.1 | 125.31 | 18066.0 | 4.20 | 11.4 |
| 7A1-LY | 19.7 | 0.1 | 0.00 | 119.4 | 3.61 | 9.0 |
| 7A1-LQY | 14.0 | NA | 108.71 | 331.1 | 3.99 | 8.8 |
| 7A1-QY | 17.6 | NA | 102.88 | 177.4 | 3.0 | 8.2 |
| GS358 | 20.0 (n = 8) | 63.3 (n = 7) | 88.6 (n = 8) | 1404.6 (n = 7) | 12.2 (n = 7) | 33.2 (n = 8) |
| 15C6 | 16.5 | 21.7 | 137.45 | 58016.0 | 5.72 | 10.1 |
| 4H7 | 13.4 | 28.8 | 106.15 | 59296.0 | 2.43 | 4.1 |
| 16A2 | 14.3 | 21.8 | 142.88 | 77197.0 | 5.00 | 7.6 |

Exemplary cAMP biosensor clones include, but are not limited to, 15H6 (SEQ ID NO:107; SEQ ID NO:108); 7A1-QY (SEQ ID NO:109; SEQ ID NO:110); GS358 (SEQ ID NO:111; SEQ ID NO:112); 7A1 (SEQ ID NO:113; SEQ ID NO:114); 7A1-IQ (SEQ ID NO:23; SEQ ID NO:24); 7A1-LY (SEQ ID NO:25; SEQ ID NO:26); 7A1-ILY (SEQ ID NO:27; SEQ ID NO:28); 7A1-IQY (SEQ ID NO:29; SEQ ID NO:30); 7A1-ILQY (SEQ ID NO:31; SEQ ID NO:32); 1B3 (SEQ ID NO:33; SEQ ID NO:34); 4H7 (SEQ ID NO:35; SEQ ID NO:36); 9G4 (SEQ ID NO:37; SEQ ID NO:38); 7A1-IY (SEQ ID NO:39; SEQ ID NO:40); 7A1-LQY (SEQ ID NO:58; SEQ ID NO:59); 16A2 (SEQ ID NO:60; SEQ ID NO:61); 7A1-Q (SEQ ID NO:62; SEQ ID NO:63); 7A1-LQ (SEQ ID NO:64; SEQ ID NO:65); 7A1-I (SEQ ID NO:66; SEQ ID NO:67); 7A1-ILQ (SEQ ID NO:68; SEQ ID NO:69); 7A1-IL (SEQ ID NO:70; SEQ ID NO:71); 16B3 (SEQ ID NO:72; SEQ ID NO:73); L9-IQ (SEQ ID NO:74; SEQ ID NO:75); L9-IY (SEQ ID NO:76; SEQ ID NO:77); L9-IQY (SEQ ID NO:78; SEQ ID NO:79); L9-ILQY (SEQ ID NO:80; SEQ ID NO:81); L9-ILY (SEQ ID NO:82; SEQ ID NO:83); L9-IL (SEQ ID NO:84; SEQ ID NO:85); L9-ILQ (SEQ ID NO:86; SEQ ID NO:87); L9-LQY (SEQ ID NO:88; SEQ ID NO:89); L9-QY (SEQ ID NO:90; SEQ ID NO:91); L9-I (SEQ ID NO:92; SEQ ID NO:93); L9-L (SEQ ID NO:94; SEQ ID NO:95); L9-Q (SEQ ID NO:96; SEQ ID NO:97); L9-Y (SEQ ID NO:98; SEQ ID NO:99); L9-LY (SEQ ID NO:100; SEQ ID NO:101); L9-LQ (SEQ ID NO:102; SEQ ID NO:103); and L9 (SEQ ID NO:104; SEQ ID NO:105).

D7A1-ILY (SEQ ID NO:12) is a cAMP biosensor with three substitutions in the cAMP binding site, the 7AI linker (including NWDSGCSREG; SEQ ID NO: 130) and two substitutions in the luciferase sequence (Met-FF Luc2.0 (359-544)-7AI-cAMP binding site-FF Luc2.0 (4-355)-Val). DL9-IL (SEQ ID NO:13) is a cAMP biosensor with two substitutions in the cAMP binding site, the L9 linker (including IAGCGDAGEG; SEQ ID NO: 131), and two substitutions in the luciferase sequence (Met-FF Luc2.0 (359-544)-L9-cAMP binding site-FF Luc2.0 (4-355)-Val). These clones included mutant cAMP binding sites, linkers obtained by random cassette mutagenesis, and whole gene random mutageneis/error prone PCR/recombination. D7A1-ILY and DL9-IL have improved properties including enhanced luminescence and an enhanced response relative to GS358.

All publications, patents and patent applications are incorporated herein by reference. While in the foregoing specification, this invention has been described in relation to certain embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method to detect one or more modulators of a G protein coupled receptor, comprising:

a) contacting a sample with one or more test agents and reagents for a luminescence reaction, wherein the sample comprises a cell expressing a G-protein coupled receptor and a polynucleotide, wherein the G-protein coupled receptor is a Gs or Gi coupled receptor; and b) detecting or determining luminescence in the sample, wherein an increase or decrease in luminescence detected in the sample compared to a control sample indicates that the test agent is a modulator of the G protein coupled receptor, wherein the polynucleotide encodes a modified luciferase comprising luciferase sequences and a heterologous amino acid sequence for a mutant RIIβB cAMP binding site inserted at a site or region in the luciferase that is tolerant to modification, wherein the luciferase sequences in the modified luciferase are circularly permuted relative to a wild-type luciferase and are firefly luciferase sequences, wherein the permutation is in a region corresponding to residue 2 to 12, residue 32 to 53, residue 70 to 88, residue 102 to 126, residue 139 to 165, residue 183 to 203, residue 220 to 247, residue 262 to 273, residue 303 to 313, residue 353 to 408, residue 485 to 495, or residue 535 to 546 of SEQ ID NO: 106, 118, or 120, wherein the mutant RIIβB cAMP binding site has at least 80% amino acid sequence identity to the cAMP binding site of residue 266-414 of SEQ ID NO: 4, wherein the cAMP binding site is in a region corresponding to residue 2 to 12, residue 32 to 53, residue 70 to 88, residue 102 to 126, residue 139 to 165, residue 183 to 203, residue 220 to 247, residue 262 to 273, residue 303 to 313, residue 353 to 408, residue 485 to 495, or residue 535 to 546 of SEQ ID NO: 106, 118, or 120, wherein binding of cAMP to the mutant RIIβB cAMP binding site produces a response from the modified luciferase, wherein the mutant RIIβB cAMP binding site has one or more substitutions that enhance the luminescence signal of the modified luciferase, enhance the response of the modified luciferase to a change in the amount of cAMP in a cell, reduce affinity of wild-type cAMP binding, or a combination thereof, relative to a corresponding luciferase with a RIIβB cAMP binding site that lacks the one or more substitutions, wherein one or more of the substitutions are at a position corresponding to residue 266, 282, 284, 286, 296, 316, 333, 338, 382, 389, 404, or 407 of RIIβB having SEQ ID NO: 4.

2. The method of claim 1, wherein the mutant cAMP binding site is flanked by a peptide linker.

3. The method of claim 2, wherein the peptide linker comprises GSSGGSGGSGGG (SEQ ID NO:41), GSSSDSDSSAGS (SEQ ID NO:42), GSNDSSGGSEGG (SEQ ID NO:43), GSNGGFDSSEGG (SEQ ID NO:44), GSIRWSGLSGGD (SEQ ID NO:45), GSRGGSVYSEGG (SEQ ID NO:46), GSSEGSSDFGGD (SEQ ID NO:47), GSIVVSCSSEGG (SEQ ID NO:48), GSNWDSGCSREG (SEQ ID NO:49), GSNWDSGCSREC (SEQ ID NO:50), GSSGCTGDAGGS (SEQ ID NO:51), GSNWDSGCSRQC (SEQ ID NO:52), GSS/NS/D/GD/S/GS/FD/GS/GSA/EGS/G (SEQ ID NO:53), GSI/R/SR/G/EW/GSG/V/SL/Y/DS/FG/EGD/G (SEQ ID NO:54), GSI/N/SV/W/GV/D/CS/TC/GS/C/DS/AE/R/GG/EG/S (SEQ ID NO:55), GSI/SV/G/AV/GS/CG/DG/D/SS/AG/EG/EG/N (SEQ ID NO:56), GSI/N/SV/W/G/AV/D/C/GS/T/CC/GS/C/DS/AE/R/GG/EG/S (SEQ ID NO:57), GSIAGCGDAGEG (SEQ ID NO:126), GSNWDSGCSRE (SEQ ID NO: 127), GSNWDSGCSREG (SEQ ID NO:129), NWDSGCSREG (SEQ ID NO: 130), or IAGCGDAGEG (SEQ ID NO: 131).

* * * * *

SEQUENCE LISTING

```
<160> NUMBER OF SEQ ID NOS: 131

<210> SEQ ID NO 1
<211> LENGTH: 4
<212> TYPE: PRT
<213> ORGANISM: Artificial Sequence
<220> FEATURE:
<223> OTHER INFORMATION: A synthetic peptide

<400> SEQUENCE: 1

Arg Arg Phe Ser
 1


<210> SEQ ID NO 2
<211> LENGTH: 7
<212> TYPE: PRT
<213> ORGANISM: Artificial Sequence
<220> FEATURE:
```

<223> OTHER INFORMATION: A synthetic peptide

<400> SEQUENCE: 2

```
Leu Arg Arg Ala Ser Leu Gly
 1               5
```

<210> SEQ ID NO 3
<211> LENGTH: 6
<212> TYPE: PRT
<213> ORGANISM: Artificial Sequence
<220> FEATURE:
<223> OTHER INFORMATION: A synthetic peptide

<400> SEQUENCE: 3

```
Leu Val Pro Arg Glu Ser
 1               5
```

<210> SEQ ID NO 4
<211> LENGTH: 418
<212> TYPE: PRT
<213> ORGANISM: Artificial Sequence
<220> FEATURE:
<223> OTHER INFORMATION: A synthetic polypeptide

<400> SEQUENCE: 4

```
Met Ser Ile Glu Ile Pro Ala Gly Leu Thr Glu Leu Leu Gln Gly Phe
 1               5                   10                  15

Thr Val Glu Val Leu Arg His Gln Pro Ala Asp Leu Leu Glu Phe Ala
            20                  25                  30

Leu Gln His Phe Thr Arg Leu Gln Gln Glu Asn Glu Arg Lys Gly Thr
        35                  40                  45

Ala Arg Phe Cys His Glu Gly Arg Thr Trp Gly Asp Leu Gly Ala Ala
    50                  55                  60

Ala Gly Gly Gly Thr Pro Ser Lys Gly Val Asn Phe Ala Glu Glu Pro
65                  70                  75                  80

Met Gln Ser Asp Ser Glu Asp Gly Glu Glu Glu Glu Ala Ala Pro Ala
                85                  90                  95

Asp Ala Gly Ala Phe Asn Ala Pro Val Ile Asn Arg Phe Thr Arg Arg
            100                 105                 110

Ala Ser Val Cys Ala Glu Ala Tyr Asn Pro Asp Glu Glu Glu Asp Asp
        115                 120                 125

Ala Glu Ser Arg Ile Ile His Pro Lys Thr Asp Asp Gln Arg Asn Arg
    130                 135                 140

Leu Gln Glu Ala Cys Lys Asp Ile Leu Leu Phe Lys Asn Leu Asp Pro
145                 150                 155                 160

Glu Gln Met Ser Gln Val Leu Asp Ala Met Phe Glu Lys Leu Val Lys
                165                 170                 175

Asp Gly Glu His Val Ile Asp Gln Gly Asp Asp Gly Asp Asn Phe Tyr
            180                 185                 190

Val Ile Asp Arg Gly Thr Phe Asp Ile Tyr Val Lys Cys Asp Gly Val
        195                 200                 205

Gly Arg Cys Val Gly Asn Tyr Asp Asn Arg Gly Ser Phe Gly Glu Leu
    210                 215                 220

Ala Leu Met Tyr Asn Thr Pro Arg Ala Ala Thr Ile Thr Ala Thr Ser
225                 230                 235                 240

Pro Gly Ala Leu Trp Gly Leu Asp Arg Val Thr Phe Arg Arg Ile Ile
                245                 250                 255

Val Lys Asn Asn Ala Lys Lys Arg Lys Met Tyr Glu Ser Phe Ile Glu
```

```
            260                 265                 270

Ser Leu Pro Phe Leu Lys Ser Leu Glu Phe Ser Glu Arg Leu Lys Val
        275                 280                 285

Val Asp Val Ile Gly Thr Lys Val Tyr Asn Asp Gly Glu Gln Ile Ile
    290                 295                 300

Ala Gln Gly Asp Ser Ala Asp Ser Phe Phe Ile Val Glu Ser Gly Glu
305                 310                 315                 320

Val Lys Ile Thr Met Lys Arg Lys Gly Lys Ser Glu Val Glu Glu Asn
                325                 330                 335

Gly Ala Val Glu Ile Ala Arg Cys Ser Arg Gly Gln Tyr Phe Gly Glu
            340                 345                 350

Leu Ala Leu Val Thr Asn Lys Pro Arg Ala Ala Ser Ala His Ala Ile
        355                 360                 365

Gly Thr Val Lys Cys Leu Ala Met Asp Val Gln Ala Phe Glu Arg Leu
    370                 375                 380

Leu Gly Pro Cys Met Glu Ile Met Lys Arg Asn Ile Ala Thr Tyr Glu
385                 390                 395                 400

Glu Gln Leu Val Ala Leu Phe Gly Thr Asn Met Asp Ile Val Glu Pro
                405                 410                 415

Thr Ala


<210> SEQ ID NO 5
<211> LENGTH: 381
<212> TYPE: PRT
<213> ORGANISM: Artificial Sequence
<220> FEATURE:
<223> OTHER INFORMATION: A synthetic polypeptide

<400> SEQUENCE: 5

Met Glu Ser Gly Ser Thr Ala Ala Ser Glu Glu Ala Arg Ser Leu Arg
 1               5                  10                  15

Glu Cys Glu Leu Tyr Val Gln Lys His Asn Ile Gln Ala Leu Leu Lys
            20                  25                  30

Asp Ser Ile Val Gln Leu Cys Thr Ala Arg Pro Glu Arg Pro Met Ala
        35                  40                  45

Phe Leu Arg Glu Tyr Phe Glu Arg Leu Glu Lys Glu Glu Ala Lys Gln
    50                  55                  60

Ile Gln Asn Leu Gln Lys Ala Gly Thr Arg Thr Asp Ser Arg Glu Asp
65                  70                  75                  80

Glu Ile Ser Pro Pro Pro Pro Asn Pro Val Val Lys Gly Arg Arg Arg
                85                  90                  95

Arg Gly Ala Ile Ser Ala Glu Val Tyr Thr Glu Glu Asp Ala Ala Ser
            100                 105                 110

Tyr Val Arg Lys Val Ile Pro Lys Asp Tyr Lys Thr Met Ala Ala Leu
        115                 120                 125

Ala Lys Ala Ile Glu Lys Asn Val Leu Phe Ser His Leu Asp Asp Asn
    130                 135                 140

Glu Arg Ser Asp Ile Phe Asp Ala Met Phe Ser Val Ser Phe Ile Ala
145                 150                 155                 160

Gly Glu Thr Val Ile Gln Gln Gly Asp Glu Gly Asp Asn Phe Tyr Val
                165                 170                 175

Ile Asp Gln Gly Glu Thr Asp Val Tyr Val Asn Asn Glu Trp Ala Thr
            180                 185                 190

Ser Val Gly Glu Gly Gly Ser Phe Gly Glu Leu Ala Leu Ile Tyr Gly
        195                 200                 205
```

```
Thr Pro Arg Ala Ala Thr Val Lys Ala Lys Thr Asn Val Lys Leu Trp
    210                 215                 220

Gly Ile Asp Arg Asp Ser Tyr Arg Arg Ile Leu Met Gly Ser Thr Leu
225                 230                 235                 240

Arg Lys Arg Lys Met Tyr Glu Glu Phe Leu Ser Lys Val Ser Ile Leu
                245                 250                 255

Glu Ser Leu Asp Lys Trp Glu Arg Leu Thr Val Ala Asp Ala Leu Glu
            260                 265                 270

Pro Val Gln Phe Glu Asp Gly Gln Lys Ile Val Val Gln Gly Glu Pro
        275                 280                 285

Gly Asp Glu Phe Phe Ile Ile Leu Glu Gly Ser Ala Ala Val Leu Gln
    290                 295                 300

Arg Arg Ser Glu Asn Glu Glu Phe Val Glu Val Gly Arg Leu Gly Pro
305                 310                 315                 320

Ser Asp Tyr Phe Gly Glu Ile Ala Leu Leu Met Asn Arg Pro Arg Ala
                325                 330                 335

Ala Thr Val Val Ala Arg Gly Pro Leu Lys Cys Val Lys Leu Asp Arg
            340                 345                 350

Pro Arg Phe Glu Arg Val Leu Gly Pro Cys Ser Asp Ile Leu Lys Arg
        355                 360                 365

Asn Ile Gln Gln Tyr Asn Ser Phe Val Ser Leu Ser Val
    370                 375                 380


<210> SEQ ID NO 6
<211> LENGTH: 930
<212> TYPE: PRT
<213> ORGANISM: Artificial Sequence
<220> FEATURE:
<223> OTHER INFORMATION: A synthetic polypeptide

<400> SEQUENCE: 6

Met Thr His Asn Gly Gly Arg His Leu Leu Glu Ala Val Thr Leu Cys
 1               5                  10                  15

Gly Ser Ile Leu Thr Arg Tyr Lys Arg Ser Asn Met Lys Leu Asp Glu
            20                  25                  30

Ala Glu Val Arg Ala Leu Lys Glu Leu Phe Glu Lys Tyr Gln Asp Ile
        35                  40                  45

Leu Val Asp Gly Ser Pro Gly Leu Pro Thr His Ala Ser Gly Pro Met
    50                  55                  60

Ile Gln Pro Pro Val Thr Asn Met Val Ala Pro Tyr Asp Ser Pro Thr
65                  70                  75                  80

Asp Thr Ile Val Lys Phe Val Glu Gly Thr Ile Asn Leu Gln Arg Pro
                85                  90                  95

Ile Val Glu Val Leu His Val Met Asn Glu His Leu Ser Leu Val Leu
            100                 105                 110

Arg Ala Lys Asn Thr His Val Phe Tyr Val Asp Pro Val Asn Asn Leu
        115                 120                 125

Leu Tyr Asp Pro Ile His Gly Val Ala Ala Ala Leu Asp Glu Ser Ser
    130                 135                 140

Pro Ile Gly Lys Ala Ile Val Ser Gly Glu Arg Leu Asn Val Ala Gly
145                 150                 155                 160

Thr Leu Tyr Ile Pro Ile Ile Ser Glu Gly Met Pro Leu Gly Cys Val
                165                 170                 175

Leu Ser Pro Cys Gly Arg Ala Asp Tyr His Ala Ser Thr Met Leu Glu
            180                 185                 190
```

```
Ser Ser Leu Arg Val Ile Ser Thr Ser Leu Lys Asn Ile Ile Gln Ala
        195                 200                 205

Glu Lys Leu Asn Trp Asn Lys Glu Lys Ala Glu Ala Met Leu Arg Met
    210                 215                 220

Ala Thr Gln Leu Ala Arg Asp Asn Leu Glu Glu Thr Val Leu Ala Ser
225                 230                 235                 240

Ser Ile Met Asn Thr Val Lys Ser Leu Thr Glu Ser Ala Arg Cys Ser
                245                 250                 255

Leu Phe Leu Val Arg Gly Asp Val Leu Glu Ala His Phe Glu Asp Gly
            260                 265                 270

Asn Val Val Thr Ile Pro Arg Gly Ala Gly Ile Ala Gly Tyr Val Ala
        275                 280                 285

Gln Thr Gly Glu Thr Val Asn Ile Val Asp Ala Tyr Ala Asp Asp Arg
    290                 295                 300

Phe Asn Arg Glu Val Asp Lys Ala Thr Gly Tyr Arg Thr Lys Thr Ile
305                 310                 315                 320

Leu Cys Met Pro Val Met Tyr Glu Gly Thr Ile Val Ala Val Ala Gln
                325                 330                 335

Leu Ile Asn Lys Leu Asp Leu Thr Thr Glu Ser Gly Leu Arg Leu Pro
            340                 345                 350

Arg Val Phe Gly Lys Arg Asp Glu Glu Leu Phe Gln Thr Phe Ser Met
        355                 360                 365

Phe Ala Gly Ala Ser Leu Arg Asn Cys Arg Ile Asn Asp Arg Leu Leu
    370                 375                 380

Lys Glu Lys Lys Lys Ser Asp Val Ile Leu Asp Val Val Thr Val Leu
385                 390                 395                 400

Ser Asn Thr Asp Ile Arg Asp Val Asp Gly Ile Val Arg His Ala Leu
                405                 410                 415

His Gly Ala Lys Lys Leu Leu Asn Ala Asp Arg Ser Thr Leu Phe Leu
            420                 425                 430

Val Asp Lys Glu Arg Asn Glu Leu Cys Ser Arg Met Ala Asp Ser Val
        435                 440                 445

Ala Gly Lys Glu Ile Arg Phe Pro Cys Gly Gln Gly Ile Ala Gly Thr
    450                 455                 460

Val Ala Ala Ser Gly Val Gly Glu Asn Ile Gln Asp Ala Tyr Gln Asp
465                 470                 475                 480

Pro Arg Phe Asn Arg Glu Val Asp Lys Gln Leu Gly Tyr Arg Thr Gln
                485                 490                 495

Thr Ile Leu Cys Glu Pro Ile Ile Leu Asn Gly Glu Ile Leu Ala Val
            500                 505                 510

Val Gln Leu Val Asn Lys Leu Asp Thr Ser Gly Glu Val Thr Val Phe
        515                 520                 525

Thr Glu Asp Asp Arg Glu Thr Phe Arg Val Phe Ser Leu Phe Ala Gly
    530                 535                 540

Ile Ser Ile Asn Asn Ser His Leu Leu Glu Phe Ala Val Lys Ala Gly
545                 550                 555                 560

Arg Glu Val Met Glu Leu Asn Glu His Arg Ala Thr Leu Phe Asn Lys
                565                 570                 575

Asn Val Pro Ser Arg Ala Val Lys Arg Val Thr Ala Ile Thr Lys Val
            580                 585                 590

Glu Arg Glu Ala Val Leu Val Cys Glu Leu Pro Ser Phe Asp Val Thr
        595                 600                 605
```

```
Asp Val Glu Phe Asp Leu Phe Arg Ala Arg Glu Ser Thr Asp Lys Pro
    610                 615                 620

Leu Asp Val Ala Ala Ala Ile Ala Tyr Arg Leu Leu Leu Gly Ser Gly
625                 630                 635                 640

Leu Pro Gln Lys Phe Gly Cys Ser Asp Glu Val Leu Leu Asn Phe Ile
                645                 650                 655

Leu Gln Cys Arg Lys Lys Tyr Arg Asn Val Pro Tyr His Asn Phe Tyr
            660                 665                 670

His Val Val Asp Val Cys Gln Thr Ile Tyr Thr Phe Leu Tyr Arg Gly
        675                 680                 685

Asn Val Tyr Glu Lys Leu Thr Glu Leu Glu Cys Phe Val Leu Leu Ile
    690                 695                 700

Thr Ala Leu Val His Asp Leu Asp His Met Gly Leu Asn Asn Ser Phe
705                 710                 715                 720

Tyr Leu Lys Thr Glu Ser Pro Leu Gly Ile Leu Ser Ser Ala Ser Gly
                725                 730                 735

Asn Thr Ser Val Leu Glu Val His His Cys Asn Leu Ala Val Glu Ile
            740                 745                 750

Leu Ser Asp Pro Glu Ser Asp Val Phe Gly Gly Leu Glu Gly Ala Glu
        755                 760                 765

Arg Thr Leu Ala Phe Arg Ser Met Ile Asp Cys Val Leu Ala Thr Asp
    770                 775                 780

Met Ala Lys His Gly Ser Ala Leu Glu Ala Phe Leu Ala Ser Ala Ala
785                 790                 795                 800

Asp Gln Ser Ser Asp Glu Ala Ala Phe His Arg Met Thr Met Glu Ile
                805                 810                 815

Ile Leu Lys Ala Gly Asp Ile Ser Asn Val Thr Lys Pro Phe Asp Ile
            820                 825                 830

Ser Arg Gln Trp Ala Met Ala Val Thr Glu Glu Phe Tyr Arg Gln Gly
        835                 840                 845

Asp Met Glu Lys Glu Arg Gly Val Glu Val Leu Pro Met Phe Asp Arg
    850                 855                 860

Ser Lys Asn Met Glu Leu Ala Lys Gly Gln Ile Gly Phe Ile Asp Phe
865                 870                 875                 880

Val Ala Ala Pro Phe Phe Gln Lys Ile Val Asp Ala Cys Leu Gln Gly
                885                 890                 895

Met Gln Trp Thr Val Asp Arg Ile Lys Ser Asn Arg Ala Gln Trp Glu
            900                 905                 910

Arg Val Leu Glu Thr Arg Leu Ser Thr Ser Ser Gly Asn Asn Ser Ser
        915                 920                 925

Thr Arg
    930
```

<210> SEQ ID NO 7

<400> SEQUENCE: 7

000

<210> SEQ ID NO 8
<211> LENGTH: 1629
<212> TYPE: DNA
<213> ORGANISM: Artificial Sequence
<220> FEATURE:
<223> OTHER INFORMATION: A synthetic oligonucleotide

<400> SEQUENCE: 8

```
atgatgaaga gagagaaaaa tgttatatat ggacccgaac ccctacaccc cttggaagac     60
ttaacagcag gagaaatgct cttcagggcc cttcgaaaac attctcattt accgcaggct    120
ttagtagatg tgtttggtga cgaatcgctt tcctataaag agtttttga agctacatgc    180
ctcctagcgc aaagtctcca caattgtgga tacaagatga atgatgtagt gtcgatctgc    240
gccgagaata ataaaagatt ttttattccc attattgcag cttggtatat tggtatgatt    300
gtagcacctg ttaatgaaag ttacatccca gatgaactct gtaaggtcat gggtatatcg    360
aaaccacaaa tagtttttg tacaaagaac attttaaata aggtattgga ggtacagagc    420
agaactaatt tcataaaaag gatcatcata cttgatactg tagaaaacat acacggttgt    480
gaaagtcttc ccaattttat ttctcgttat tcggatggaa atattgccaa cttcaaacct    540
ttacattacg atcctgttga gcaagtggca gctatcttat gttcgtcagg cactactgga    600
ttaccgaaag gtgtaatgca aactcaccaa aatatttgtg tccgacttat acatgcttta    660
gaccccaggg caggaacgca acttattcct ggtgtgacag tcttagtata tctgcctttt    720
ttccatgctt ttgggttctc tataaacttg ggatacttca tggtgggtct tcgtgttatc    780
atgttaagac gatttgatca agaagcattt ctaaaagcta ttcaggatta tgaagttcga    840
agtgtaatta acgttccagc aataatattg ttcttatcga aaagtccttt ggttgacaaa    900
tacgatttat caagtttaag ggaattgtgt tgcggtgcgg caccattagc aaaagaagtt    960
gctgaggttg cagtaaaacg attaaacttg ccaggaattc gctgtggatt tggtttgaca   1020
gaatctactt cagctaatat acacagtctt ggggatgaat ttaaatcagg atcacttgga   1080
agagttactc ctttaatggc agctaaaata gcagataggg aaactggtaa agcattggga   1140
ccaaatcaag ttggtgaatt atgcgttaaa ggtcccatgg tatcgaaagg ttacgtgaac   1200
aatgtagaag ctaccaaaga agctattgat gatgatggtt ggcttcactc tggagacttt   1260
ggatactatg atgaggatga gcatttctat gtggtggacc gttacaagga attgattaaa   1320
tataagggct ctcaggtagc acctgcagaa ctagaagaga ttttattgaa aaatccatgt   1380
atcagagatg ttgctgtggt tggtattcct gatctagaag ctggagaact gccatctgcg   1440
tttgtggtta aacagcccgg aaaggagatt acagctaaag aagtgtacga ttatcttgcc   1500
gagagggtct cccatacaaa gtatttgcgt ggaggggttc gattcgttga tagcatacca   1560
aggaatgtta caggtaaaat tacaagaaag gaacttctga agcagttgct ggagaagagt   1620
tctaaactt                                                           1629
```

```
<210> SEQ ID NO 9
<211> LENGTH: 543
<212> TYPE: PRT
<213> ORGANISM: Artificial Sequence
<220> FEATURE:
<223> OTHER INFORMATION: A synthetic polypeptide

<400> SEQUENCE: 9

Met Met Lys Arg Glu Lys Asn Val Ile Tyr Gly Pro Glu Pro Leu His
 1               5                  10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Phe Gly Asp Glu
        35                  40                  45

Ser Leu Ser Tyr Lys Glu Phe Phe Glu Ala Thr Cys Leu Leu Ala Gln
    50                  55                  60
```

```
Ser Leu His Asn Cys Gly Tyr Lys Met Asn Asp Val Val Ser Ile Cys
65                  70                  75                  80

Ala Glu Asn Asn Lys Arg Phe Phe Ile Pro Ile Ile Ala Ala Trp Tyr
                85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Cys Thr
        115                 120                 125

Lys Asn Ile Leu Asn Lys Val Leu Glu Val Gln Ser Arg Thr Asn Phe
    130                 135                 140

Ile Lys Arg Ile Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Tyr Asp Pro Val Glu Gln Val Ala Ala Ile
            180                 185                 190

Leu Cys Ser Ser Gly Thr Thr Gly Leu Pro Lys Gly Val Met Gln Thr
        195                 200                 205

His Gln Asn Ile Cys Val Arg Leu Ile His Ala Leu Asp Pro Arg Ala
    210                 215                 220

Gly Thr Gln Leu Ile Pro Gly Val Thr Val Leu Val Tyr Leu Pro Phe
225                 230                 235                 240

Phe His Ala Phe Gly Phe Ser Ile Asn Leu Gly Tyr Phe Met Val Gly
                245                 250                 255

Leu Arg Val Ile Met Leu Arg Arg Phe Asp Gln Glu Ala Phe Leu Lys
            260                 265                 270

Ala Ile Gln Asp Tyr Glu Val Arg Ser Val Ile Asn Val Pro Ala Ile
        275                 280                 285

Ile Leu Phe Leu Ser Lys Ser Pro Leu Val Asp Lys Tyr Asp Leu Ser
    290                 295                 300

Ser Leu Arg Glu Leu Cys Cys Gly Ala Ala Pro Leu Ala Lys Glu Val
305                 310                 315                 320

Ala Glu Val Ala Val Lys Arg Leu Asn Leu Pro Gly Ile Arg Cys Gly
                325                 330                 335

Phe Gly Leu Thr Glu Ser Thr Ser Ala Asn Ile His Ser Leu Gly Asp
            340                 345                 350

Glu Phe Lys Ser Gly Ser Leu Gly Arg Val Thr Pro Leu Met Ala Ala
        355                 360                 365

Lys Ile Ala Asp Arg Glu Thr Gly Lys Ala Leu Gly Pro Asn Gln Val
    370                 375                 380

Gly Glu Leu Cys Val Lys Gly Pro Met Val Ser Lys Gly Tyr Val Asn
385                 390                 395                 400

Asn Val Glu Ala Thr Lys Glu Ala Ile Asp Asp Asp Gly Trp Leu His
                405                 410                 415

Ser Gly Asp Phe Gly Tyr Tyr Asp Glu Asp Glu His Phe Tyr Val Val
            420                 425                 430

Asp Arg Tyr Lys Glu Leu Ile Lys Tyr Lys Gly Ser Gln Val Ala Pro
        435                 440                 445

Ala Glu Leu Glu Glu Ile Leu Leu Lys Asn Pro Cys Ile Arg Asp Val
    450                 455                 460

Ala Val Val Gly Ile Pro Asp Leu Glu Ala Gly Glu Leu Pro Ser Ala
465                 470                 475                 480

Phe Val Val Lys Gln Pro Gly Lys Glu Ile Thr Ala Lys Glu Val Tyr
```

-continued

```
            485                 490                 495

Asp Tyr Leu Ala Glu Arg Val Ser His Thr Lys Tyr Leu Arg Gly Gly
        500                 505                 510

Val Arg Phe Val Asp Ser Ile Pro Arg Asn Val Thr Gly Lys Ile Thr
    515                 520                 525

Arg Lys Glu Leu Leu Lys Gln Leu Leu Glu Lys Ser Ser Lys Leu
530                 535                 540


<210> SEQ ID NO 10

<400> SEQUENCE: 10

000


<210> SEQ ID NO 11
<211> LENGTH: 8330
<212> TYPE: DNA
<213> ORGANISM: Artificial Sequence
<220> FEATURE:
<223> OTHER INFORMATION: A synthetic oligonucleotide

<400> SEQUENCE: 11

tcaatattgg ccattagcca tattattcat tggttatata gcataaatca atattggcta     60

ttggccattg catacgttgt atctatatca taatatgtac atttatattg gctcatgtcc    120

aatatgaccg ccatgttggc attgattatt gactagttat taatagtaat caattacggg    180

gtcattagtt catagcccat atatggagtt ccgcgttaca taacttacgg taaatggccc    240

gcctggctga ccgcccaacg acccccgccc attgacgtca ataatgacgt atgttcccat    300

agtaacgcca atagggactt tccattgacg tcaatgggtg gagtatttac ggtaaactgc    360

ccacttggca gtacatcaag tgtatcatat gccaagtccg ccccctattg acgtcaatga    420

cggtaaatgg cccgcctggc attatgccca gtacatgacc ttacgggact ttcctacttg    480

gcagtacatc tacgtattag tcatcgctat taccatggtg atgcggtttt ggcagtacac    540

caatgggcgt ggatagcggt ttgactcacg gggatttcca agtctccacc ccattgacgt    600

caatgggagt ttgttttggc accaaaatca acgggacttt ccaaaatgtc gtaataaccc    660

cgccccgttg acgcaaatgg gcggtaggcg tgtacggtgg gaggtctata taagcagagc    720

tggtttagtg aaccgtcaga tcactagaag ctttattgcg gtagtttatc acagttaaat    780

tgctaacgca gtcagtgctt ctgacacaac agtctcgaac ttaagctgca gaagttggtc    840

gtgaggcact gggcaggtaa gtatcaaggt tacaagacag gtttaaggag accaatagaa    900

actgggcttg tcgagacaga gaagactctt gcgtttctga taggcaccta ttggtcttac    960

tgacatccac tttgcctttc tctccacagg tgtccactcc cagttcaatt acagctctta   1020

aggctagagt attaatacga ctcactatag ggaattttaa ctttactaag gagcgatcgc   1080

catgcctggc gcagtaggca aggtggtgcc cttcatcgag gctaaggtgg tggacttgga   1140

caccggtaag acactgggtg tgaaccagcg cggcgagctg tgcgtccgtg gccccatgat   1200

catgagcggc tacgttaaca accccgaggc tacaaacgct ctcatcgaca aggacggctg   1260

gctgcacagc ggcgacatcg cctactggga cgaggacgag cacttcttca tcgtggaccg   1320

gctgaagagc ctgatcaaat acaagggcta ccaggtagcc ccagccgaac tggagagcat   1380

cctgctgcaa caccccaaca tcttcgacgc cggggtcgcc ggcctgcccg acgacgatgc   1440

cggcgagctg cccgccgcag tcgtcgtgct ggaacacggt aaaaccatga ccgagaagga   1500

gatcgtggac tatgtggcca gccaggttac aaccgccaag aagctgcgcg gtggtgttgt   1560
```

gttagtggac gaggtgccta aaggactgac cggcaagttg gacgcccgca agatccgcga 1620
gattctcatt aaggccaaga agggatccaa ttgggattct gggtgctcca gagaaggtat 1680
gtatgaaagc tttattgagt cactgccatt ccttaaatct ttggagtttt ctgcacgcct 1740
gaaagtagta gatgtgatag gcaccaaagt atacaacgat ggagaacaaa tcattgctca 1800
gggagattcg gctgattctt ttttcattat tgaatctgga gaagtgaaaa ttactatgaa 1860
aagaaagggt aaatcagaag tggaagagaa tggtgcagta gaaatcgctc gatgctcgcg 1920
gggacagtac tttggagagc ttgccctggt aactaacaaa cctcgagcag cttctgccca 1980
cgccattggg actgtcaaat gtttagcaat ggatgtgcaa gcatttgaaa ggcttctggg 2040
accttgcatg gaaattatga aaaggaacat cgctacctat gaagaacagt tagttgccct 2100
gtatggaacg aacatggata ttgtagccaa aaacattaag aagggcccag cgccattcta 2160
cccactcgaa gacgggaccg ccggcgagca gctgcacaaa gccatgaagc gctacgccct 2220
ggtgcccggc accatcgcct ttaccgacgc acatatcgag gtggacatta cctacgccga 2280
gtacttcgag atgagcgttc ggctggcaga agctatgaag cgctatgggc tgaatacaaa 2340
ccatcggatc gtggtgtgca gcgagaatag cttgcagttc ttcatgcccg tgttgggtgc 2400
cctgttcatc ggtgtggctg tggccccagc taacgacatc tacaacgagc gcgagctgct 2460
gaacagcatg ggcatcagcc agcccaccgt cgtattcgtg agcaagaaag ggctgcaaaa 2520
gatcctcaac gtgcaaaaga agctaccgat catacaaaag atcatcatca tggatagcaa 2580
gaccgactac cagggcttcc aaagcatgta caccttcgtg acttcccatt tgccacccgg 2640
cttcaacgag tacgacttcg tgcccgagag cttcgaccgg gacaaaacca tcgccctgat 2700
catgaacagt agtggcagta ccggattgcc caagggcgta gccctaccgc accgcaccgc 2760
ttgtgtccga ttcagtcatg cccgcgaccc catcttcggc aaccagatca tccccgacac 2820
cgctatcctc agcgtggtgc catttcacca cggcttcggc atgttcacca cgctgggcta 2880
cttgatctgc ggctttcggg tcgtgctcat gtaccgcttc gaggaggagc tattcttgcg 2940
cagcttgcaa gactataaga ttcaatctgc cctgctggtg cccacactat ttagcttctt 3000
cgctaagagc actctcatcg acaagtacga cctaagcaac ttgcacgaga tcgccagcgg 3060
cggggcgccg ctcagcaagg aggtaggtga ggccgtggcc aaacgcttcc acctaccagg 3120
catccgccag ggctacggcc tgacagaaac aaccagcgcc attctgatca ctccagaagg 3180
ggtttaaacg aattcgagct cggtacccgg ggttcctcta gagtcgacct gcaggcatgc 3240
aagctgatcc ggctgctaac aaagcccgaa aggaagctga gttggctgct gccaccgctg 3300
agcaataact agcataaccc cttggggcgg ccgcttcgag cagacatgat aagatacatt 3360
gatgagtttg gacaaaccac aactagaatg cagtgaaaaa aatgctttat ttgtgaaatt 3420
tgtgatgcta ttgctttatt tgtaaccatt ataagctgca ataaacaagt taacaacaac 3480
aattgcattc attttatgtt tcaggttcag ggggagatgt gggaggtttt tttaagcaag 3540
taaaacctct acaaatgtgg taaaatcgaa ttttaacaaa atattaacgc ttacaatttc 3600
ctgatgcggt attttctcct tacgcatctg tgcggtattt cacaccgcat acgcggatct 3660
gcgcagcacc atggcctgaa ataacctctg aaagaggaac ttggttaggt accttctgag 3720
gcggaaagaa ccagctgtgg aatgtgtgtc agttagggtg tggaaagtcc ccaggctccc 3780
cagcaggcag aagtatgcaa agcatgcatc tcaattagtc agcaaccagg tgtggaaagt 3840
ccccaggctc cccagcaggc agaagtatgc aaagcatgca tctcaattag tcagcaacca 3900

-continued

```
tagtcccgcc cctaactccg cccatcccgc ccctaactcc gcccagttcc gcccattctc   3960
cgccccatgg ctgactaatt ttttttattt atgcagaggc cgaggccgcc tcggcctctg   4020
agctattcca gaagtagtga ggaggctttt ttggaggcct aggcttttgc aaaaagcttg   4080
attcttctga cacaacagtc tcgaaccaaa ggctggagcc accatggctt ccaaggtgta   4140
cgaccccgag caacgcaaac gcatgatcac tgggcctcag tggtgggctc gctgcaagca   4200
aatgaacgtg ctggactcct tcatcaacta ctatgattcc gagaagcacg ccgagaacgc   4260
cgtgattttt ctgcatggta acgctgcctc cagctacctg tggaggcacg tcgtgcctca   4320
catcgagccc gtggctagat gcatcatccc tgatctgatc ggaatgggta agtccggcaa   4380
gagcgggaat ggctcatatc gcctcctgga tcactacaag tacctcaccg cttggttcga   4440
gctgctgaac cttccaaaga aaatcatctt tgtgggccac gactgggggg cttgtctggc   4500
ctttcactac tcctacgagc accaagacaa gatcaaggcc atcgtccatg ctgagagtgt   4560
cgtggacgtg atcgagtcct gggacgagtg gcctgacatc gaggaggata tcgccctgat   4620
caagagcgaa gagggcgaga aaatggtgct tgagaataac ttcttcgtcg agaccatgct   4680
cccaagcaag atcatgcgga aactggagcc tgaggagttc gctgcctacc tggagccatt   4740
caaggagaag ggcgaggtta gacggcctac cctctcctgg cctcgcgaga tccctctcgt   4800
taagggaggc aagcccgacg tcgtccagat tgtccgcaac tacaacgcct accttcgggc   4860
cagcgacgat ctgcctaaga tgttcatcga gtccgaccct gggttctttt ccaacgctat   4920
tgtcgaggga gctaagaagt tccctaacac cgagttcgtg aaggtgaagg gcctccactt   4980
cagccaggag gacgctccag atgaaatggg taagtacatc aagagcttcg tggagcgcgt   5040
gctgaagaac gagcagaccg gtggtgggag cggaggtggc ggatcaggtg gcggaggctc   5100
cggagggatt gaacaagatg gattgcacgc aggttctccg gccgcttggg tggagaggct   5160
attcggctat gactgggcac aacagacaat cggctgctct gatgccgccg tgttccggct   5220
gtcagcgcag gggcgcccgg ttctttttgt caagaccgac ctgtccggtg ccctgaatga   5280
actgcaggac gaggcagcgc ggctatcgtg gctggccacg acgggcgttc cttgcgcagc   5340
tgtgctcgac gttgtcactg aagcgggaag ggactggctg ctattgggcg aagtgccggg   5400
gcaggatctc ctgtcatctc accttgctcc tgccgagaaa gtatccatca tggctgatgc   5460
aatgcggcgg ctgcatacgc ttgatccggc tacctgccca ttcgaccacc aagcgaaaca   5520
tcgcatcgag cgagcacgta ctcggatgga agccggtctt gtcgatcagg atgatctgga   5580
cgaagagcat caggggctcg cgccagccga actgttcgcc aggctcaagg cgcgcatgcc   5640
cgacggcgag gatctcgtcg tgacccatgg cgatgcctgc ttgccgaata tcatggtgga   5700
aaatggccgc ttttctggat tcatcgactg tggccggctg ggtgtggcgg accgctatca   5760
ggacatagcg ttggctaccc gtgatattgc tgaagagctt ggcggcgaat gggctgaccg   5820
cttcctcgtg ctttacggta tcgccgctcc cgattcgcag cgcatcgcct tctatcgcct   5880
tcttgacgag ttcttctgag cgggactctg gggttcgaaa tgaccgacca agcgacgccc   5940
aacctgccat cacgatggcc gcaataaaat atctttattt tcattacatc tgtgtgttgg   6000
ttttttgtgt gaatcgatag cgataaggtt cctctttgcg cttgcgtttt cccttgtcca   6060
gatagcccag tagctgacat tcatccgggg tcagcaccgt ttctgcggac tggctttcta   6120
cgtaatggtt tcttagacgt caggtggcac ttttcgggga aatgtgcgcg gaacccctat   6180
ttgtttattt ttctaaatac attcaaatat gtatccgctc atgagacaat aaccctgata   6240
aatgcttcaa taatattgaa aaaggaagag tatgagtatt caacatttcc gtgtcgccct   6300
```

```
tattcccttt tttgcggcat tttgccttcc tgtttttgct cacccagaaa cgctggtgaa   6360

agtaaaagat gctgaagatc agttgggtgc acgagtgggt tacatcgaac tggatctcaa   6420

cagcggtaag atccttgaga gttttcgccc cgaagaacgt tttccaatga tgagcacttt   6480

caaagttctg ctatgtggcg cggtattatc ccgtattgac gccgggcaag agcaactcgg   6540

tcgccgcata cactattctc agaatgactt ggttgagtac tcaccagtca cagaaaagca   6600

tcttacggat ggcatgacag taagagaatt atgcagtgct gccataacca tgagtgataa   6660

cactgcggcc aacttacttc tgacaactat cggaggaccg aaggagctaa ccgctttttt   6720

gcacaacatg ggggatcatg taactcgcct tgatcgttgg gaaccggagc tgaatgaagc   6780

cataccaaac gacgagcgtg acaccacgat gcctgtagca atggcaacaa cgttgcgcaa   6840

actattaact ggcgaactac ttactctagc ttcccggcaa caattaatag actggatgga   6900

ggcggataaa gttgcaggac cacttctgcg ctcggccctt ccggctggct ggtttattgc   6960

tgataaatct ggagccggtg agcgtgggtc tcgcggtatc attgcagcac tggggccaga   7020

tggtaagccc tcccgtatcg tagttatcta cacgacgggg agtcaggcaa ctatggatga   7080

acgaaataga cagatcgctg agataggtgc ctcactgatt aagcattggt aattcgaaat   7140

gaccgaccaa gcgacgccca accggtatca gctcactcaa aggcggtaat acggttatcc   7200

acagaatcag gggataacgc aggaaagaac atgtgagcaa aaggccagca aaaggccagg   7260

aaccgtaaaa aggccgcgtt gctggcgttt ttccataggc tccgcccccc tgacgagcat   7320

cacaaaaatc gacgctcaag tcagaggtgg cgaaacccga caggactata aagataccag   7380

gcgtttcccc ctggaagctc cctcgtgcgc tctcctgttc cgaccctgcc gcttaccgga   7440

tacctgtccg cctttctccc ttcgggaagc gtggcgcttt ctcatagctc acgctgtagg   7500

tatctcagtt cggtgtaggt cgttcgctcc aagctgggct gtgtgcacga accccccgtt   7560

cagcccgacc gctgcgcctt atccggtaac tatcgtcttg agtccaaccc ggtaagacac   7620

gacttatcgc cactggcagc agccactggt aacaggatta gcagagcgag gtatgtaggc   7680

ggtgctacag agttcttgaa gtggtggcct aactacggct acactagaag gacagtattt   7740

ggtatctgcg ctctgctgaa gccagttacc ttcggaaaaa gagttggtag ctcttgatcc   7800

ggcaaacaaa ccaccgctgg tagcggtggt ttttttgttt gcaagcagca gattacgcgc   7860

agaaaaaaag gatttcaaga agatcctttg atcttttcta cggggtctga cgctcagtgg   7920

aacgaaaact cacgttaagg gattttggtc atgagattat caaaaaggat cttcacctag   7980

atccttttat agtccggaaa tacaggaacg cacgctggat ggcccttcgc tgggatggtg   8040

aaaccatgaa aaatggcagc ttcagtggat taagtggggg taatgtggcc tgtaccctct   8100

ggttgcatag gtattcatac ggttaaaatt tatcaggcgc gattgcggca gtttttcggg   8160

tggtttgttg ccatttttac ctgtctgctg ccgtgatcgc gctgaacgcg ttttagcggt   8220

gcgtacaatt aagggattat ggtaaatcca cttactgtct gccctcgtag ccatcgagat   8280

aaaccgcagt actccggcca cgatgcgtcc ggcgtagagg atcgagatct              8330
```

<210> SEQ ID NO 12
<211> LENGTH: 8330
<212> TYPE: DNA
<213> ORGANISM: Artificial Sequence
<220> FEATURE:
<223> OTHER INFORMATION: A synthetic oligonucleotide

<400> SEQUENCE: 12

```
tcaatattgg ccattagcca tattattcat tggttatata gcataaatca atattggcta     60
ttggccattg catacgttgt atctatatca taatatgtac atttatattg gctcatgtcc    120
aatatgaccg ccatgttggc attgattatt gactagttat taatagtaat caattacggg    180
gtcattagtt catagcccat atatggagtt ccgcgttaca taacttacgg taaatggccc    240
gcctggctga ccgcccaacg acccccgccc attgacgtca ataatgacgt atgttcccat    300
agtaacgcca atagggactt tccattgacg tcaatgggtg gagtatttac ggtaaactgc    360
ccacttggca gtacatcaag tgtatcatat gccaagtccg ccccctattg acgtcaatga    420
cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt ttgttttggc accaaaatca acgggacttt ccaaaatgtc gtaataaccc    660
cgccccgttg acgcaaatgg gcggtaggcg tgtacggtgg gaggtctata taagcagagc    720
tggtttagtg aaccgtcaga tcactagaag ctttattgcg gtagtttatc acagttaaat    780
tgctaacgca gtcagtgctt ctgacacaac agtctcgaac ttaagctgca gaagttggtc    840
gtgaggcact gggcaggtaa gtatcaaggt tacaagacag gtttaaggag accaatagaa    900
actgggcttg tcgagacaga gaagactctt gcgtttctga taggcaccta ttggtcttac    960
tgacatccac tttgcctttc tctccacagg tgtccactcc cagttcaatt acagctctta   1020
aggctagagt attaatacga ctcactatag ggaattttaa ctttactaag gagcgatcgc   1080
catgcctggc gcagtaggca aggtggtgcc cttcatcgag gctaaggtgg tggacttgga   1140
caccggtaag acactgggtg tgaaccagcg cggcgagctg tgcgtccgtg gccccatgat   1200
catgagcggc tacgttaaca accccgaggc tacaaacgct ctcatcgaca aggacggctg   1260
gctgcacagc ggcgacatcg cctactggga cgaggacgag cacttcttca tcgtggaccg   1320
gctgaagagc ctgatcaaat acaagggcta ccaggtagcc ccagccgaac tggagagcat   1380
cctgctgcaa caccccaaca tcttcgacgc cggggtcgcc ggcctgcccg acgacgatgc   1440
cggcgagctg cccgccgcag tcgtcgtgct ggaacacggt aaaaccatga ccgagaagga   1500
gatcgtggac tatgtggcca gccaggttac aaccgccaag aagctgcgcg gtggtgttgt   1560
gttagtggac gaggtgccta aaggactgac cggcaagttg gacgcccgca agatccgcga   1620
gattctcatt aaggccaaga agggatccat cgcaggttgt ggcgatgccg gcgaaggtat   1680
gtatgaaagc tttattgagt cactgccatt ccttaaatct ttggagtttt ctgcacgcct   1740
gaaagtagta gatgtgatag gcaccaaagt atacaacgat ggagaacaaa tcattgctca   1800
gggagattcg gctgattctt ttttcattat tgaatctgga gaagtgaaaa ttactatgaa   1860
aagaaagggt aaatcagaag tggaagagaa tggtgcagta gaaatcgctc gatgctcgcg   1920
gggacagtac tttggagagc ttgccctggt aactaacaaa cctcgagcag cttctgccca   1980
cgccattggg actgtcaaat gtttagcaat ggatgtgcaa gcatttgaaa ggcttctggg   2040
accttgcatg gaaattatga aaaggaacat cgctacctat gaagaacagt tagttgccct   2100
gtttggaacg aacatggata ttgtagccaa aaacattaag aagggcccag cgccattcta   2160
cccactcgaa gacgggaccg ccggcgagca gctgcacaaa gccatgaagc gctacgccct   2220
ggtgcccggc accatcgcct ttaccgacgc acatatcgag gtggacatta cctacgccga   2280
gtacttcgag atgagcgttc ggctggcaga agctatgaag cgctatgggc tgaatacaaa   2340
ccatcggatc gtggtgtgca gcgagaatag cttgcagttc ttcatgcccg tgttgggtgc   2400
```

```
cctgttcatc ggtgtggctg tggccccagc taacgacatc tacaacgagc gcgagctgct   2460
gaacagcatg ggcatcagcc agcccaccgt cgtattcgtg agcaagaaag ggctgcaaaa   2520
gatcctcaac gtgcaaaaga agctaccgat catacaaaag atcatcatca tggatagcaa   2580
gaccgactac cagggcttcc aaagcatgta caccttcgtg acttcccatt tgccacccgg   2640
cttcaacgag tacgacttcg tgcccgagag cttcgaccgg gacaaaacca tcgccctgat   2700
catgaacagt agtggcagta ccggattgcc caagggcgta gccctaccgc accgcaccgc   2760
ttgtgtccga ttcagtcatg cccgcgaccc catcttcggc aaccagatca tccccgacac   2820
cgctatcctc agcgtggtgc catttcacca cggcttcggc atgttcacca cgctgggcta   2880
cttgatctgc ggctttcggg tcgtgctcat gtaccgcttc gaggaggagc tattcttgcg   2940
cagcttgcaa gactataaga ttcaatctgc cctgctggtg cccacactat ttagcttctt   3000
cgctaagagc actctcatcg acaagtacga cctaagcaac ttgcacgaga tcgccagcgg   3060
cggggcgccg ctcagcaagg aggtaggtga ggccgtggcc aaacgcttcc acctaccagg   3120
catccgccag ggctacggcc tgacagaaac aaccagcgcc attctgatca ctccagaagg   3180
ggtttaaacg aattcgagct cggtacccgg ggttcctcta gagtcgacct gcaggcatgc   3240
aagctgatcc ggctgctaac aaagcccgaa aggaagctga gttggctgct gccaccgctg   3300
agcaataact agcataaccc cttggggcgg ccgcttcgag cagacatgat aagatacatt   3360
gatgagtttg gacaaaccac aactagaatg cagtgaaaaa aatgctttat ttgtgaaatt   3420
tgtgatgcta ttgctttatt tgtaaccatt ataagctgca ataaacaagt taacaacaac   3480
aattgcattc attttatgtt tcaggttcag ggggagatgt gggaggtttt tttaagcaag   3540
taaaacctct acaaatgtgg taaaatcgaa ttttaacaaa atattaacgc ttacaatttc   3600
ctgatgcggt attttctcct tacgcatctg tgcggtattt cacaccgcat acgcggatct   3660
gcgcagcacc atggcctgaa ataacctctg aaagaggaac ttggttaggt accttctgag   3720
gcggaaagaa ccagctgtgg aatgtgtgtc agttagggtg tggaaagtcc ccaggctccc   3780
cagcaggcag aagtatgcaa agcatgcatc tcaattagtc agcaaccagg tgtggaaagt   3840
ccccaggctc cccagcaggc agaagtatgc aaagcatgca tctcaattag tcagcaacca   3900
tagtcccgcc cctaactccg cccatcccgc ccctaactcc gcccagttcc gcccattctc   3960
cgccccatgg ctgactaatt ttttttattt atgcagaggc cgaggccgcc tcggcctctg   4020
agctattcca gaagtagtga ggaggctttt ttggaggcct aggcttttgc aaaaagcttg   4080
attcttctga cacaacagtc tcgaaccaaa ggctggagcc accatggctt ccaaggtgta   4140
cgaccccgag caacgcaaac gcatgatcac tgggcctcag tggtgggctc gctgcaagca   4200
aatgaacgtg ctggactcct tcatcaacta ctatgattcc gagaagcacg ccgagaacgc   4260
cgtgattttt ctgcatggta acgctgcctc cagctacctg tggaggcacg tcgtgcctca   4320
catcgagccc gtggctagat gcatcatccc tgatctgatc ggaatgggta agtccggcaa   4380
gagcgggaat ggctcatatc gcctcctgga tcactacaag tacctcaccg cttggttcga   4440
gctgctgaac cttccaaaga aaatcatctt tgtgggccac gactgggggg cttgtctggc   4500
ctttcactac tcctacgagc accaagacaa gatcaaggcc atcgtccatg ctgagagtgt   4560
cgtggacgtg atcgagtcct gggacgagtg gcctgacatc gaggaggata tcgccctgat   4620
caagagcgaa gagggcgaga aaatggtgct tgagaataac ttcttcgtcg agaccatgct   4680
cccaagcaag atcatgcgga aactggagcc tgaggagttc gctgcctacc tggagccatt   4740
```

```
caaggagaag ggcgaggtta gacggcctac cctctcctgg cctcgcgaga tccctctcgt   4800
taagggaggc aagcccgacg tcgtccagat tgtccgcaac tacaacgcct accttcgggc   4860
cagcgacgat ctgcctaaga tgttcatcga gtccgaccct gggttctttt ccaacgctat   4920
tgtcgaggga gctaagaagt tccctaacac cgagttcgtg aaggtgaagg gcctccactt   4980
cagccaggag gacgctccag atgaaatggg taagtacatc aagagcttcg tggagcgcgt   5040
gctgaagaac gagcagaccg gtggtgggag cggaggtggc ggatcaggtg gcggaggctc   5100
cggagggatt gaacaagatg gattgcacgc aggttctccg gccgcttggg tggagaggct   5160
attcggctat gactgggcac aacagacaat cggctgctct gatgccgccg tgttccggct   5220
gtcagcgcag gggcgcccgg ttctttttgt caagaccgac ctgtccggtg ccctgaatga   5280
actgcaggac gaggcagcgc ggctatcgtg gctggccacg acgggcgttc cttgcgcagc   5340
tgtgctcgac gttgtcactg aagcgggaag ggactggctg ctattgggcg aagtgccggg   5400
gcaggatctc ctgtcatctc accttgctcc tgccgagaaa gtatccatca tggctgatgc   5460
aatgcggcgg ctgcatacgc ttgatccggc tacctgccca ttcgaccacc aagcgaaaca   5520
tcgcatcgag cgagcacgta ctcggatgga agccggtctt gtcgatcagg atgatctgga   5580
cgaagagcat caggggctcg cgccagccga actgttcgcc aggctcaagg cgcgcatgcc   5640
cgacggcgag gatctcgtcg tgacccatgg cgatgcctgc ttgccgaata tcatggtgga   5700
aaatggccgc ttttctggat tcatcgactg tggccggctg ggtgtggcgg accgctatca   5760
ggacatagcg ttggctaccc gtgatattgc tgaagagctt ggcggcgaat gggctgaccg   5820
cttcctcgtg ctttacggta tcgccgctcc cgattcgcag cgcatcgcct tctatcgcct   5880
tcttgacgag ttcttctgag cgggactctg gggttcgaaa tgaccgacca agcgacgccc   5940
aacctgccat cacgatggcc gcaataaaat atctttattt tcattacatc tgtgtgttgg   6000
tttttgtgt gaatcgatag cgataaggtt cctctttgcg cttgcgtttt cccttgtcca   6060
gatagcccag tagctgacat tcatccgggg tcagcaccgt ttctgcggac tggctttcta   6120
cgtaatggtt tcttagacgt caggtggcac ttttcgggga aatgtgcgcg gaacccctat   6180
ttgtttattt ttctaaatac attcaaatat gtatccgctc atgagacaat aaccctgata   6240
aatgcttcaa taatattgaa aaaggaagag tatgagtatt caacatttcc gtgtcgccct   6300
tattcccttt tttgcggcat tttgccttcc tgtttttgct cacccagaaa cgctggtgaa   6360
agtaaaagat gctgaagatc agttgggtgc acgagtgggt tacatcgaac tggatctcaa   6420
cagcggtaag atccttgaga gttttcgccc cgaagaacgt tttccaatga tgagcacttt   6480
caaagttctg ctatgtggcg cggtattatc ccgtattgac gccgggcaag agcaactcgg   6540
tcgccgcata cactattctc agaatgactt ggttgagtac tcaccagtca cagaaaagca   6600
tcttacggat ggcatgacag taagagaatt atgcagtgct gccataacca tgagtgataa   6660
cactgcggcc aacttacttc tgacaactat cggaggaccg aaggagctaa ccgctttttt   6720
gcacaacatg ggggatcatg taactcgcct tgatcgttgg gaaccggagc tgaatgaagc   6780
cataccaaac gacgagcgtg acaccacgat gcctgtagca atggcaacaa cgttgcgcaa   6840
actattaact ggcgaactac ttactctagc ttcccggcaa caattaatag actggatgga   6900
ggcggataaa gttgcaggac cacttctgcg ctcggccctt ccggctggct ggtttattgc   6960
tgataaatct ggagccggtg agcgtgggtc tcgcggtatc attgcagcac tggggccaga   7020
tggtaagccc tcccgtatcg tagttatcta cacgacgggg agtcaggcaa ctatggatga   7080
acgaaataga cagatcgctg agataggtgc ctcactgatt aagcattggt aattcgaaat   7140
```

```
gaccgaccaa gcgacgccca accggtatca gctcactcaa aggcggtaat acggttatcc   7200
acagaatcag gggataacgc aggaaagaac atgtgagcaa aaggccagca aaaggccagg   7260
aaccgtaaaa aggccgcgtt gctggcgttt ttccataggc tccgcccccc tgacgagcat   7320
cacaaaaatc gacgctcaag tcagaggtgg cgaaacccga caggactata aagataccag   7380
gcgtttcccc ctggaagctc cctcgtgcgc tctcctgttc cgaccctgcc gcttaccgga   7440
tacctgtccg cctttctccc ttcgggaagc gtggcgcttt ctcatagctc acgctgtagg   7500
tatctcagtt cggtgtaggt cgttcgctcc aagctgggct gtgtgcacga accccccgtt   7560
cagcccgacc gctgcgcctt atccggtaac tatcgtcttg agtccaaccc ggtaagacac   7620
gacttatcgc cactggcagc agccactggt aacaggatta gcagagcgag gtatgtaggc   7680
ggtgctacag agttcttgaa gtggtggcct aactacggct acactagaag gacagtattt   7740
ggtatctgcg ctctgctgaa gccagttacc ttcggaaaaa gagttggtag ctcttgatcc   7800
ggcaaacaaa ccaccgctgg tagcggtggt ttttttgttt gcaagcagca gattacgcgc   7860
agaaaaaaag gatttcaaga agatcctttg atcttttcta cggggtctga cgctcagtgg   7920
aacgaaaact cacgttaagg gattttggtc atgagattat caaaaaggat cttcacctag   7980
atccttttat agtccggaaa tacaggaacg cacgctggat ggcccttcgc tgggatggtg   8040
aaaccatgaa aaatggcagc ttcagtggat taagtggggg taatgtggcc tgtaccctct   8100
ggttgcatag gtattcatac ggttaaaatt tatcaggcgc gattgcggca gtttttcggg   8160
tggtttgttg ccatttttac ctgtctgctg ccgtgatcgc gctgaacgcg ttttagcggt   8220
gcgtacaatt aagggattat ggtaaatcca cttactgtct gccctcgtag ccatcgagat   8280
aaaccgcagt actccggcca cgatgcgtcc ggcgtagagg atcgagatct              8330
```

```
<210> SEQ ID NO 13
<211> LENGTH: 1652
<212> TYPE: DNA
<213> ORGANISM: Artificial Sequence
<220> FEATURE:
<223> OTHER INFORMATION: A synthetic oligonucleotide

<400> SEQUENCE: 13

atggaagatg ccaaaaacat taagaagggc ccagcgccat tctacccact cgaagacggg     60
accgccggcg agcagctgca caaagccatg aagcgctacg ccctggtgcc cggcaccatc    120
gcctttaccg acgcacatat cgaggtggac attacctacg ccgagtactt cgagatgagc    180
gttcggctgg cagaagctat gaagcgctat gggctgaata caaaccatcg gatcgtggtg    240
tgcagcgaga atagcttgca gttcttcatg cccgtgttgg gtgccctgtt catcggtgtg    300
gctgtggccc cagctaacga catctacaac gagcgcgagc tgctgaacag catgggcatc    360
agccagccca ccgtcgtatt cgtgagcaag aaagggctgc aaaagatcct caacgtgcaa    420
aagaagctac cgatcataca aaagatcatc atcatggata gcaagaccga ctaccagggc    480
ttccaaagca tgtacacctt cgtgacttcc catttgccac ccggcttcaa cgagtacgac    540
ttcgtgcccg agagcttcga ccgggacaaa accatcgccc tgatcatgaa cagtagtggc    600
agtaccggat tgcccaaggg cgtagcccta ccgcaccgca ccgcttgtgt ccgattcagt    660
catgcccgcg accccatctt cggcaaccag atcatccccg acaccgctat cctcagcgtg    720
gtgccatttc accacggctt cggcatgttc accacgctgg gctacttgat ctgcggcttt    780
cgggtcgtgc tcatgtaccg cttcgaggag gagctattct tgcgcagctt gcaagactat    840
```

```
aagattcaat ctgccctgct ggtgcccaca ctatttagct tcttcgctaa gagcactctc    900

atcgacaagt acgacctaag caacttgcac gagatcgcca gcggcggggc gccgctcagc    960

aaggaggtag gtgaggccgt ggccaaacgc ttccacctac caggcatccg ccagggctac   1020

ggcctgacag aaacaaccag cgccattctg atcacccccg aaggggacga caagcctggc   1080

gcagtaggca aggtggtgcc cttcttcgag gctaaggtgg tggacttgga caccggtaag   1140

acactgggtg tgaaccagcg cggcgagctg tgcgtccgtg gccccatgat catgagcggc   1200

tacgttaaca accccgaggc tacaaacgct ctcatcgaca aggacggctg gctgcacagc   1260

ggcgacatcg cctactggga cgaggacgag cacttcttca tcgtggaccg gctgaagagc   1320

ctgatcaaat acaagggcta ccaggtagcc ccagccgaac tggagagcat cctgctgcaa   1380

caccccaaca tcttcgacgc cggggtcgcc ggcctgcccg acgacgatgc cggcgagctg   1440

cccgccgcag tcgtcgtgct ggaacacggt aaaaccatga ccgagaagga gatcgtggac   1500

tatgtggcca gccaggttac aaccgccaag aagctgcgcg gtggtgttgt gttcgtggac   1560

gaggtgccta aaggactgac cggcaagttg gacgcccgca agatccgcga gattctcatt   1620

aaggccaaga agggcggcaa gatcgccgtg ta                                 1652
```

<210> SEQ ID NO 14
<211> LENGTH: 8
<212> TYPE: PRT
<213> ORGANISM: Artificial Sequence
<220> FEATURE:
<223> OTHER INFORMATION: A synthetic peptide

<400> SEQUENCE: 14

```
Asp Tyr Lys Asp Asp Asp Asp Lys
 1               5
```

<210> SEQ ID NO 15
<211> LENGTH: 5
<212> TYPE: PRT
<213> ORGANISM: Artificial Sequence
<220> FEATURE:
<223> OTHER INFORMATION: A synthetic peptide

<400> SEQUENCE: 15

```
His His His His His
 1               5
```

<210> SEQ ID NO 16
<211> LENGTH: 6
<212> TYPE: PRT
<213> ORGANISM: Artificial Sequence
<220> FEATURE:
<223> OTHER INFORMATION: A synthetic peptide

<400> SEQUENCE: 16

```
His His His His His His
 1               5
```

<210> SEQ ID NO 17
<211> LENGTH: 10
<212> TYPE: PRT
<213> ORGANISM: Artificial Sequence
<220> FEATURE:
<223> OTHER INFORMATION: A synthetic peptide

<400> SEQUENCE: 17

```
Glu Gln Lys Leu Ile Ser Glu Glu Asp Leu
 1               5                  10
```

<210> SEQ ID NO 18
<211> LENGTH: 8
<212> TYPE: PRT
<213> ORGANISM: Artificial Sequence
<220> FEATURE:
<223> OTHER INFORMATION: A synthetic peptide

<400> SEQUENCE: 18

Trp Ser His Pro Gln Phe Glu Lys
1 5

<210> SEQ ID NO 19
<211> LENGTH: 9
<212> TYPE: PRT
<213> ORGANISM: Artificial Sequence
<220> FEATURE:
<223> OTHER INFORMATION: A synthetic peptide

<400> SEQUENCE: 19

Tyr Pro Tyr Asp Val Pro Asp Tyr Ala
1 5

<210> SEQ ID NO 20
<211> LENGTH: 5
<212> TYPE: PRT
<213> ORGANISM: Artificial Sequence
<220> FEATURE:
<223> OTHER INFORMATION: A synthetic peptide

<400> SEQUENCE: 20

Arg Tyr Ile Arg Ser
1 5

<210> SEQ ID NO 21
<211> LENGTH: 4
<212> TYPE: PRT
<213> ORGANISM: Artificial Sequence
<220> FEATURE:
<223> OTHER INFORMATION: A synthetic peptide

<400> SEQUENCE: 21

Phe His His Thr
1

<210> SEQ ID NO 22
<211> LENGTH: 17
<212> TYPE: PRT
<213> ORGANISM: Artificial Sequence
<220> FEATURE:
<223> OTHER INFORMATION: A synthetic peptide

<400> SEQUENCE: 22

Trp Glu Ala Ala Ala Arg Glu Ala Cys Cys Arg Glu Cys Cys Ala Arg
1 5 10 15

Ala

<210> SEQ ID NO 23
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 23
atgcctggcg cagtaggcaa ggtggtgccc ttcatcgagg ctaaggtggt ggacttggac 60

```
accggtaaga cactgggtgt gaaccagcgc ggcgagctgt gcgtccgtgg ccccatgatc    120
atgagcggct acgttaacaa ccccgaggct acaaacgctc tcatcgacaa ggacggctgg    180
ctgcacagcg gcgacatcgc ctactgggac gaggacgagc acttcttcat cgtggaccgg    240
ctgaagagcc tgatcaaata caagggctac caggtagccc cagccgaact ggagagcatc    300
ctgctgcaac accccaacat cttcgacgcc ggggtcgccg gcctgcccga cgacgatgcc    360
ggcgagctgc ccgccgcagt cgtcgtgctg gaacacggta aaaccatgac cgagaaggag    420
atcgtggact atgtggccag ccaggttaca accgccaaga agctgcgcgg tggtgttgtg    480
ttcgtggacg aggtgcctaa aggactgacc ggcaagttgg acgcccgcaa gatccgcgag    540
attctcattc aggccaagaa gggatccaat tgggattctg ggtgctccag agaaggtatg    600
tatgaaagct ttattgagtc actgccattc cttaaatctt tggagttttc tgcacgcctg    660
aaagtagtag atgtgatagg caccaaagta tacaacgatg gagaacaaat cattgctcag    720
ggagattcgg ctgattcttt tttcattatt gaatctggag aagtgaaaat tactatgaaa    780
agaaagggta aatcagaagt ggaagagaat ggtgcagtag aaatcgctcg atgctcgcgg    840
ggacagtact ttggagagct tgccctggta actaacaaac ctcgagcagc ttctgcccac    900
gccattggga ctgtcaaatg tttagcaatg gatgtgcaag catttgaaag gcttctggga    960
ccttgcatgg aaattatgaa aaggaacatc gctacctatg aagaacagtt agttgccctg   1020
tttggaacga acatggatat tgtagccaaa aacattaaga agggcccagc gccattctac   1080
ccactcgaag acgggaccgc cggcgagcag ctgcacaaag ccatgaagcg ctacgccctg   1140
gtgcccggca ccatcgcctt taccgacgca catatcgagg tggacattac ctacgccgag   1200
tacttcgaga tgagcgttcg gctggcagaa gctatgaagc gctatgggct gaatacaaac   1260
catcggatcg tggtgtgcag cgagaatagc ttgcagttct tcatgcccgt gttgggtgcc   1320
ctgttcatcg gtgtggctgt ggccccagct aacgacatct acaacgagcg cgagctgctg   1380
aacagcatgg gcatcagcca gcccaccgtc gtattcgtga gcaagaaagg gctgcaaaag   1440
atcctcaacg tgcaaaagaa gctaccgatc atacaaaaga tcatcatcat ggatagcaag   1500
accgactacc agggcttcca aagcatgtac accttcgtga cttcccattt gccacccggc   1560
ttcaacgagt acgacttcgt gcccgagagc ttcgaccggg acaaaaccat cgccctgatc   1620
atgaacagta gtggcagtac cggattgccc aagggcgtag ccctaccgca ccgcaccgct   1680
tgtgtccgat tcagtcatgc ccgcgacccc atcttcggca accagatcat ccccgacacc   1740
gctatcctca gcgtggtgcc atttcaccac ggcttcggca tgttcaccac gctgggctac   1800
ttgatctgcg gctttcgggt cgtgctcatg taccgcttcg aggaggagct attcttgcgc   1860
agcttgcaag actataagat tcaatctgcc ctgctggtgc ccacactatt tagcttcttc   1920
gctaagagca ctctcatcga caagtacgac ctaagcaact tgcacgagat cgccagcggc   1980
ggggcgccgc tcagcaagga ggtaggtgag gccgtggcca aacgcttcca cctaccaggc   2040
atccgccagg gctacggcct gacagaaaca accagcgcca ttctgatcac tccagaaggg   2100
gtt                                                                 2103
```

<210> SEQ ID NO 24
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 24

```
Met Pro Gly Ala Val Gly Lys Val Val Pro Phe Ile Glu Ala Lys Val
 1               5                  10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Phe Val Asp Glu Val Pro Lys Gly Leu Thr Gly Lys Leu Asp Ala Arg
                165                 170                 175

Lys Ile Arg Glu Ile Leu Ile Gln Ala Lys Lys Gly Ser Asn Trp Asp
            180                 185                 190

Ser Gly Cys Ser Arg Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Phe Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415
```

```
Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700
```

<210> SEQ ID NO 25
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 25

```
atgcctggcg cagtaggcaa ggtggtgccc ttcttcgagg ctaaggtggt ggacttggac      60

accggtaaga cactgggtgt gaaccagcgc ggcgagctgt gcgtccgtgg ccccatgatc     120

atgagcggct acgttaacaa ccccgaggct acaaacgctc tcatcgacaa ggacggctgg     180

ctgcacagcg gcgacatcgc ctactgggac gaggacgagc acttcttcat cgtggaccgg     240

ctgaagagcc tgatcaaata caagggctac caggtagccc cagccgaact ggagagcatc     300

ctgctgcaac accccaacat cttcgacgcc ggggtcgccg gcctgcccga cgacgatgcc     360

ggcgagctgc ccgccgcagt cgtcgtgctg gaacacggta aaaccatgac cgagaaggag     420
```

```
atcgtggact atgtggccag ccaggttaca accgccaaga agctgcgcgg tggtgttgtg    480
ttagtggacg aggtgcctaa aggactgacc ggcaagttgg acgcccgcaa gatccgcgag    540
attctcatta aggccaagaa gggatccaat tgggattctg ggtgctccag agaaggtatg    600
tatgaaagct ttattgagtc actgccattc cttaaatctt tggagttttc tgcacgcctg    660
aaagtagtag atgtgatagg caccaaagta tacaacgatg gagaacaaat cattgctcag    720
ggagattcgg ctgattcttt tttcattatt gaatctggag aagtgaaaat tactatgaaa    780
agaaagggta aatcagaagt ggaagagaat ggtgcagtag aaatcgctcg atgctcgcgg    840
ggacagtact ttggagagct tgccctggta actaacaaac ctcgagcagc ttctgcccac    900
gccattggga ctgtcaaatg tttagcaatg gatgtgcaag catttgaaag gcttctggga    960
ccttgcatgg aaattatgaa aaggaacatc gctacctatg aagaacagtt agttgccctg   1020
tatggaacga acatggatat tgtagccaaa aacattaaga agggcccagc gccattctac   1080
ccactcgaag acgggaccgc cggcgagcag ctgcacaaag ccatgaagcg ctacgccctg   1140
gtgcccggca ccatcgcctt taccgacgca catatcgagg tggacattac ctacgccgag   1200
tacttcgaga tgagcgttcg gctggcagaa gctatgaagc gctatgggct gaatacaaac   1260
catcggatcg tggtgtgcag cgagaatagc ttgcagttct tcatgcccgt gttgggtgcc   1320
ctgttcatcg gtgtggctgt ggccccagct aacgacatct acaacgagcg cgagctgctg   1380
aacagcatgg gcatcagcca gcccaccgtc gtattcgtga gcaagaaagg gctgcaaaag   1440
atcctcaacg tgcaaaagaa gctaccgatc atacaaaaga tcatcatcat ggatagcaag   1500
accgactacc agggcttcca aagcatgtac accttcgtga cttcccattt gccacccggc   1560
ttcaacgagt acgacttcgt gcccgagagc ttcgaccggg acaaaaccat cgccctgatc   1620
atgaacagta gtggcagtac cggattgccc aagggcgtag ccctaccgca ccgcaccgct   1680
tgtgtccgat tcagtcatgc ccgcgacccc atcttcggca accagatcat ccccgacacc   1740
gctatcctca gcgtggtgcc atttcaccac ggcttcggca tgttcaccac gctgggctac   1800
ttgatctgcg gctttcgggt cgtgctcatg taccgcttcg aggaggagct attcttgcgc   1860
agcttgcaag actataagat tcaatctgcc ctgctggtgc ccacactatt tagcttcttc   1920
gctaagagca ctctcatcga caagtacgac ctaagcaact tgcacgagat cgccagcggc   1980
ggggcgccgc tcagcaagga ggtaggtgag gccgtggcca aacgcttcca cctaccaggc   2040
atccgccagg gctacggcct gacagaaaca accagcgcca ttctgatcac tccagaaggg   2100
gtt                                                                 2103
```

<210> SEQ ID NO 26
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 26

```
Met Pro Gly Ala Val Gly Lys Val Val Pro Phe Phe Glu Ala Lys Val
1               5                   10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60
```

```
Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Leu Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Asn Trp Asp
            180                 185                 190

Ser Gly Cys Ser Arg Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Tyr Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480
```

```
Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700
```

<210> SEQ ID NO 27
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 27

```
atgcctggcg cagtaggcaa ggtggtgccc ttcatcgagg ctaaggtggt ggacttggac      60

accggtaaga cactgggtgt gaaccagcgc ggcgagctgt gcgtccgtgg ccccatgatc     120

atgagcggct acgttaacaa ccccgaggct acaaacgctc tcatcgacaa ggacggctgg     180

ctgcacagcg gcgacatcgc ctactgggac gaggacgagc acttcttcat cgtggaccgg     240

ctgaagagcc tgatcaaata caagggctac caggtagccc cagccgaact ggagagcatc     300

ctgctgcaac accccaacat cttcgacgcc ggggtcgccg gcctgcccga cgacgatgcc     360

ggcgagctgc ccgccgcagt cgtcgtgctg gaacacggta aaaccatgac cgagaaggag     420

atcgtggact atgtggccag ccaggttaca accgccaaga agctgcgcgg tggtgttgtg     480

ttagtggacg aggtgcctaa aggactgacc ggcaagttgg acgcccgcaa gatccgcgag     540

attctcatta aggccaagaa gggatccaat tgggattctg ggtgctccag agaaggtatg     600

tatgaaagct ttattgagtc actgccattc cttaaatctt tggagttttc tgcacgcctg     660

aaagtagtag atgtgatagg caccaaagta tacaacgatg gagaacaaat cattgctcag     720

ggagattcgg ctgattcttt tttcattatt gaatctggag aagtgaaaat tactatgaaa     780

agaaagggta aatcagaagt ggaagagaat ggtgcagtag aaatcgctcg atgctcgcgg     840
```

```
ggacagtact ttggagagct tgccctggta actaacaaac ctcgagcagc ttctgcccac    900

gccattggga ctgtcaaatg tttagcaatg gatgtgcaag catttgaaag gcttctggga    960

ccttgcatgg aaattatgaa aaggaacatc gctacctatg aagaacagtt agttgccctg   1020

tatggaacga acatggatat tgtagccaaa aacattaaga agggcccagc gccattctac   1080

ccactcgaag acgggaccgc cggcgagcag ctgcacaaag ccatgaagcg ctacgccctg   1140

gtgcccggca ccatcgcctt taccgacgca catatcgagg tggacattac ctacgccgag   1200

tacttcgaga tgagcgttcg gctggcagaa gctatgaagc gctatgggct gaatacaaac   1260

catcggatcg tggtgtgcag cgagaatagc ttgcagttct tcatgcccgt gttgggtgcc   1320

ctgttcatcg gtgtggctgt ggccccagct aacgacatct acaacgagcg cgagctgctg   1380

aacagcatgg gcatcagcca gcccaccgtc gtattcgtga gcaagaaagg gctgcaaaag   1440

atcctcaacg tgcaaaagaa gctaccgatc atacaaaaga tcatcatcat ggatagcaag   1500

accgactacc agggcttcca aagcatgtac accttcgtga cttcccattt gccacccggc   1560

ttcaacgagt acgacttcgt gcccgagagc ttcgaccggg acaaaaccat cgccctgatc   1620

atgaacagta gtggcagtac cggattgccc aagggcgtag ccctaccgca ccgcaccgct   1680

tgtgtccgat tcagtcatgc ccgcgacccc atcttcggca accagatcat ccccgacacc   1740

gctatcctca gcgtggtgcc atttcaccac ggcttcggca tgttcaccac gctgggctac   1800

ttgatctgcg gctttcgggt cgtgctcatg taccgcttcg aggaggagct attcttgcgc   1860

agcttgcaag actataagat tcaatctgcc ctgctggtgc ccacactatt tagcttcttc   1920

gctaagagca ctctcatcga caagtacgac ctaagcaact tgcacgagat cgccagcggc   1980

ggggcgccgc tcagcaagga ggtaggtgag gccgtggcca aacgcttcca cctaccaggc   2040

atccgccagg gctacggcct gacagaaaca accagcgcca ttctgatcac tccagaaggg   2100

gtt                                                                 2103
```

<210> SEQ ID NO 28
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 28

```
Met Pro Gly Ala Val Gly Lys Val Val Pro Phe Ile Glu Ala Lys Val
1               5                   10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125
```

```
Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Leu Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Asn Trp Asp
            180                 185                 190

Ser Gly Cys Ser Arg Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Tyr Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
```

-continued

```
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700


<210> SEQ ID NO 29
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 29

atgcctggcg cagtaggcaa ggtggtgccc ttcatcgagg ctaaggtggt ggacttggac     60

accggtaaga cactgggtgt gaaccagcgc ggcgagctgt gcgtccgtgg ccccatgatc    120

atgagcggct acgttaacaa ccccgaggct acaaacgctc tcatcgacaa ggacggctgg    180

ctgcacagcg gcgacatcgc ctactgggac gaggacgagc acttcttcat cgtggaccgg    240

ctgaagagcc tgatcaaata caagggctac caggtagccc cagccgaact ggagagcatc    300

ctgctgcaac accccaacat cttcgacgcc ggggtcgccg gcctgcccga cgacgatgcc    360

ggcgagctgc ccgccgcagt cgtcgtgctg gaacacggta aaaccatgac cgagaaggag    420

atcgtggact atgtggccag ccaggttaca accgccaaga agctgcgcgg tggtgttgtg    480

ttcgtggacg aggtgcctaa aggactgacc ggcaagttgg acgcccgcaa gatccgcgag    540

attctcattc aggccaagaa gggatccaat tgggattctg ggtgctccag agaaggtatg    600

tatgaaagct ttattgagtc actgccattc cttaaatctt tggagttttc tgcacgcctg    660

aaagtagtag atgtgatagg caccaaagta tacaacgatg gagaacaaat cattgctcag    720

ggagattcgg ctgattcttt tttcattatt gaatctggag aagtgaaaat tactatgaaa    780

agaaagggta aatcagaagt ggaagagaat ggtgcagtag aaatcgctcg atgctcgcgg    840

ggacagtact ttggagagct tgccctggta actaacaaac ctcgagcagc ttctgcccac    900

gccattggga ctgtcaaatg tttagcaatg gatgtgcaag catttgaaag gcttctggga    960

ccttgcatgg aaattatgaa aaggaacatc gctacctatg aagaacagtt agttgccctg   1020

tatggaacga acatggatat tgtagccaaa aacattaaga agggcccagc gccattctac   1080

ccactcgaag acgggaccgc cggcgagcag ctgcacaaag ccatgaagcg ctacgccctg   1140

gtgcccggca ccatcgcctt taccgacgca catatcgagg tggacattac ctacgccgag   1200
```

```
tacttcgaga tgagcgttcg gctggcagaa gctatgaagc gctatgggct gaatacaaac   1260

catcggatcg tggtgtgcag cgagaatagc ttgcagttct tcatgcccgt gttgggtgcc   1320

ctgttcatcg gtgtggctgt ggccccagct aacgacatct acaacgagcg cgagctgctg   1380

aacagcatgg gcatcagcca gcccaccgtc gtattcgtga gcaagaaagg gctgcaaaag   1440

atcctcaacg tgcaaaagaa gctaccgatc atacaaaaga tcatcatcat ggatagcaag   1500

accgactacc agggcttcca aagcatgtac accttcgtga cttcccattt gccacccggc   1560

ttcaacgagt acgacttcgt gcccgagagc ttcgaccggg acaaaaccat cgccctgatc   1620

atgaacagta gtggcagtac cggattgccc aagggcgtag ccctaccgca ccgcaccgct   1680

tgtgtccgat tcagtcatgc ccgcgacccc atcttcggca accagatcat ccccgacacc   1740

gctatcctca gcgtggtgcc atttcaccac ggcttcggca tgttcaccac gctgggctac   1800

ttgatctgcg gctttcgggt cgtgctcatg taccgcttcg aggaggagct attcttgcgc   1860

agcttgcaag actataagat tcaatctgcc ctgctggtgc ccacactatt tagcttcttc   1920

gctaagagca ctctcatcga caagtacgac ctaagcaact tgcacgagat cgccagcggc   1980

ggggcgccgc tcagcaagga ggtaggtgag gccgtggcca aacgcttcca cctaccaggc   2040

atccgccagg gctacggcct gacagaaaca accagcgcca ttctgatcac tccagaaggg   2100

gtt                                                                 2103
```

<210> SEQ ID NO 30
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 30

```
Met Pro Gly Ala Val Gly Lys Val Val Pro Phe Ile Glu Ala Lys Val
1               5                   10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Phe Val Asp Glu Val Pro Lys Gly Leu Thr Gly Lys Leu Asp Ala Arg
                165                 170                 175

Lys Ile Arg Glu Ile Leu Ile Gln Ala Lys Lys Gly Ser Asn Trp Asp
            180                 185                 190

Ser Gly Cys Ser Arg Glu Gly Met Tyr Glu Ser Phe Ile Glu Ser Leu
```

```
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Tyr Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620
```

```
Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700


<210> SEQ ID NO 31
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 31

atgcctggcg cagtaggcaa ggtggtgccc ttcatcgagg ctaaggtggt ggacttggac      60

accggtaaga cactgggtgt gaaccagcgc ggcgagctgt gcgtccgtgg ccccatgatc     120

atgagcggct acgttaacaa ccccgaggct acaaacgctc tcatcgacaa ggacggctgg     180

ctgcacagcg gcgacatcgc ctactgggac gaggacgagc acttcttcat cgtggaccgg     240

ctgaagagcc tgatcaaata caagggctac caggtagccc cagccgaact ggagagcatc     300

ctgctgcaac accccaacat cttcgacgcc ggggtcgccg gcctgcccga cgacgatgcc     360

ggcgagctgc ccgccgcagt cgtcgtgctg gaacacggta aaaccatgac cgagaaggag     420

atcgtggact atgtggccag ccaggttaca accgccaaga agctgcgcgg tggtgttgtg     480

ttagtggacg aggtgcctaa aggactgacc ggcaagttgg acgcccgcaa gatccgcgag     540

attctcattc aggccaagaa gggatccaat tgggattctg ggtgctccag agaaggtatg     600

tatgaaagct ttattgagtc actgccattc cttaaatctt tggagttttc tgcacgcctg     660

aaagtagtag atgtgatagg caccaaagta tacaacgatg gagaacaaat cattgctcag     720

ggagattcgg ctgattcttt tttcattatt gaatctggag aagtgaaaat tactatgaaa     780

agaaagggta aatcagaagt ggaagagaat ggtgcagtag aaatcgctcg atgctcgcgg     840

ggacagtact ttggagagct tgccctggta actaacaaac ctcgagcagc ttctgcccac     900

gccattggga ctgtcaaatg tttagcaatg gatgtgcaag catttgaaag gcttctggga     960

ccttgcatgg aaattatgaa aaggaacatc gctacctatg aagaacagtt agttgccctg    1020

tatggaacga acatggatat tgtagccaaa aacattaaga agggcccagc gccattctac    1080

ccactcgaag acgggaccgc cggcgagcag ctgcacaaag ccatgaagcg ctacgccctg    1140

gtgcccggca ccatcgcctt taccgacgca catatcgagg tggacattac ctacgccgag    1200

tacttcgaga tgagcgttcg gctggcagaa gctatgaagc gctatgggct gaatacaaac    1260

catcggatcg tggtgtgcag cgagaatagc ttgcagttct tcatgcccgt gttgggtgcc    1320

ctgttcatcg gtgtggctgt ggccccagct aacgacatct acaacgagcg cgagctgctg    1380

aacagcatgg gcatcagcca gcccaccgtc gtattcgtga gcaagaaagg gctgcaaaag    1440

atcctcaacg tgcaaaagaa gctaccgatc atacaaaaga tcatcatcat ggatagcaag    1500

accgactacc agggcttcca aagcatgtac accttcgtga cttcccattt gccacccggc    1560

ttcaacgagt acgacttcgt gcccgagagc ttcgaccggg acaaaaccat cgccctgatc    1620
```

```
atgaacagta gtggcagtac cggattgccc aagggcgtag ccctaccgca ccgcaccgct   1680

tgtgtccgat tcagtcatgc ccgcgacccc atcttcggca accagatcat ccccgacacc   1740

gctatcctca gcgtggtgcc atttcaccac ggcttcggca tgttcaccac gctgggctac   1800

ttgatctgcg gctttcgggt cgtgctcatg taccgcttcg aggaggagct attcttgcgc   1860

agcttgcaag actataagat tcaatctgcc ctgctggtgc ccacactatt tagcttcttc   1920

gctaagagca ctctcatcga caagtacgac ctaagcaact tgcacgagat cgccagcggc   1980

ggggcgccgc tcagcaagga ggtaggtgag gccgtggcca aacgcttcca cctaccaggc   2040

atccgccagg gctacggcct gacagaaaca accagcgcca ttctgatcac tccagaaggg   2100

gtt                                                                 2103


<210> SEQ ID NO 32
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 32

Met Pro Gly Ala Val Gly Lys Val Val Pro Phe Ile Glu Ala Lys Val
1               5                   10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Leu Val Asp Glu Val Pro Lys Gly Leu Thr Gly Lys Leu Asp Ala Arg
                165                 170                 175

Lys Ile Arg Glu Ile Leu Ile Gln Ala Lys Lys Gly Ser Asn Trp Asp
            180                 185                 190

Ser Gly Cys Ser Arg Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270
```

```
Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Tyr Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685
```

```
Glu Thr Thr Ser Ala Ile Leu Ile Thr Pro Glu Gly Val
    690                 695                 700


<210> SEQ ID NO 33
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 33

atgcctggcg cagtaggcaa ggtggtgccc ttcttcgagg ctaaggtggt ggacttggac     60

accggtaaga cactgggtgt gaaccagcgc ggcgagctgt gcgtccgtgg ccccatgatc    120

atgagcggct acgttaacaa ccccgaggct acaaacgctc tcatcgacaa ggacggctgg    180

ctgcacagcg gcgacatcgc ctactgggac gaggacgagc acttcttcat cgtggaccgg    240

ctgaagagcc tgatcaaata caagggctac caggtagccc cagccgaact ggagagcatc    300

ctgctgcaac accccaacat cttcgacgcc ggggtcgccg gcctgcccga cgacgatgcc    360

ggcgagctgc ccgccgcagt cgtcgtgctg gaacacggta aaaccatgac cgagaaggag    420

atcgtggact atgtggccag ccaggttaca accgccaaga agctgcgcgg tggtgttgtg    480

ttcgtggacg aggtgcctaa aggactgacc ggcaagttgg acgcccgcaa gatccgcgag    540

attctcatta aggccaagaa gggatccaat tgggattctg ggtgctccag agaaggtatg    600

tatgaaagct ttattgagtc actgccattc cttaaatctt tggagttttc tgcacgcctg    660

aaagtagtag atgtgatagg caccaaagta tacaacgatg gagaacaaat cattgctcag    720

ggagattcgg ctgattcttt tttcattatt gaatctggag aagtgaaaat tactatgaaa    780

agaaagggta aatcagaagt ggaagagaat ggtgaagtag aaatcgctcg atgctcgcgg    840

ggacagtact ttggagagct tgccctggta actaacaaac ctcgagcagc ttctgcccac    900

gccattggga ctgtcaaatg tttagcaatg gatgtgcaag catttgaaag gcttctggga    960

ccttgcatgg aaattatgaa aaggaacatc gctacctatg aagaacagtt agttgccctg   1020

tttggaacga acatggatat tgtagccaaa aacattaaga agggcccagc gccattctac   1080

ccactcgaag acgggaccgc cggcgagcag ctgcacaaag ccatgaagcg ctacgccctg   1140

gtgcccggca ccatcgcctt taccgacgca catatcgagg tggacattac ctacgccgag   1200

tacttcgaga tgagcgttcg gctggcagaa gctatgaagc gctatgggct gaatacaaac   1260

catcggatcg tggtgtgcag cgagaatagc ttgcagttct tcatgcccgt gttgggtgcc   1320

ctgttcatcg gtgtggctgt ggccccagct aacgacatct acaacgagcg cgagctgctg   1380

aacagcatgg gcatcagcca gcccaccgtc gtattcgtga gcaagaaagg gctgcaaaag   1440

atcctcaacg tgcaaaagaa gctaccgatc atacaaaaga tcatcatcat ggatagcaag   1500

accgactacc agggcttcca aagcatgtac accttcgtga cttcccattt gccacccggc   1560

ttcaacgagt acgacttcgt gcccgagagc ttcgaccggg acaaaaccat cgccctgatc   1620

atgaacagta gtggcagtac cggattgccc aagggcgtag ccctaccgca ccgcaccgct   1680

tgtgtccgat tcagtcatgc ccgcgacccc atcttcggca accagatcat ccccgacacc   1740

gctatcctca gcgtggtgcc atttcaccac ggcttcggca tgttcaccac gctgggctac   1800

ttgatctgcg gctttcgggt cgtgctcatg taccgcttcg aggaggagct attcttgcgc   1860

agcttgcaag actataagat tcaatctgcc ctgctggtgc ccacactatt tagcttcttc   1920

gctaagagca ctctcatcga caagtacgac ctaagcaact tgcacgagat cgccagcggc   1980
```

```
ggggcgccgc tcagcaagga ggtaggtgag gccgtggcca aacgcttcca cctaccaggc   2040

atccgccagg gctacggcct gacagaaaca accagcgcca ttctgatcac tccagaaggg   2100

gtt                                                                  2103


<210> SEQ ID NO 34
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 34

Met Pro Gly Ala Val Gly Lys Val Val Pro Phe Phe Glu Ala Lys Val
1               5                   10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Phe Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Asn Trp Asp
            180                 185                 190

Ser Gly Cys Ser Arg Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Glu
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335
```

```
Leu Val Ala Leu Phe Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700
```

<210> SEQ ID NO 35
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 35

```
atgcctggcg cagtaggcaa ggtggtgccc ttcttcgagg ctaaggtggt ggacttggac     60

accggtaaga cactgggtgt gaaccagcgc ggcgagctgt gcgtccgtgg ccccatgatc    120

atgagcggct acgttaacaa ccccgaggct acaaacgctc tcatcgacaa ggacggctgg    180

ctgcacagcg gcgacatcgc ctactgggac gaggacgagc acttcttcat cgtggaccgg    240

ctgaagagcc tgatcaaata caagggctac caggtagccc cagccgaact ggagagcatc    300

ctgctgcaac accccaacat cttcgacgcc ggggtcgccg gcctgcccga cgacgatgcc    360

ggcgagctgc ccgccgcagt cgtcgtgctg gaacacggta aaaccatgac cgagaaggag    420

atcgtggact atgtggccag ccaggttaca accgccaaga agctgcgcgg tggtgttgtg    480

ttcgtggacg aggtgcctaa aggactgacc ggcaagttgg acgcccgcaa gatccgcgag    540

attctcatta aggccaagaa gggatccaat tgggattctg ggtgctccag agaaggtatg    600

tatgaaagct ttattgagtc actgccattc cttaaatctt tggagttttc tgcacgcctg    660

aaagtagtag atgtgatagg caccaaagta tacaacgatg gagaacaaat cattgctcag    720

ggagattcgg ctgattcttt tttcattatt gaatctggag aagtgaaaat tactatgaaa    780

agaaagggta aatcagaagt ggaagagaat ggtgcagtag aaatcgctcg atgctcgcgg    840

ggacagtact ttggagagct tgccctggta actaacaaac ctcgagcagc ttctgcccac    900

gccattggga ctgtcaaatg tttagcaatg gatgtgcaag catttgaaag gcttctggga    960

ccttgcatgg aaattatgaa aaggaacatc gctacctatg aagaacagtt agttgccctg   1020

tatggaacga acatggatat tgtagccaaa aacattaaga agggcccagc gccattctac   1080

ccactcgaag acgggaccgc cggcgagcag ctgcacaaag ccatgaagcg ctacgccctg   1140

gtgcccggca ccatcgcctt taccgacgca catatcgagg tggacattac ctacgccgag   1200

tacttcgaga tgagcgttcg gctggcagaa gctatgaagc gctatgggct gaatacaaac   1260

catcggatcg tggtgtgcag cgagaatagc ttgcagttct tcatgcccgt gttgggtgcc   1320

ctgttcatcg gtgtggctgt ggccccagct aacgacatct acaacgagcg cgagctgctg   1380

aacagcatgg gcatcagcca gcccaccgtc gtattcgtga gcaagaaagg gctgcaaaag   1440

atcctcaacg tgcaaaagaa gctaccgatc atacaaaaga tcatcatcat ggatagcaag   1500

accgactacc agggcttcca aagcatgtac accttcgtga cttcccattt gccacccggc   1560

ttcaacgagt acgacttcgt gcccgagagc ttcgaccggg acaaaaccat cgccctgatc   1620

atgaacagta gtggcagtac cggattgccc aagggcgtag ccctaccgca ccgcaccgct   1680

tgtgtccgat tcagtcatgc ccgcgacccc atcttcggca accagatcat ccccgacacc   1740

gctatcctca gcgtggtgcc atttcaccac ggcttcggca tgttcaccac gctgggctac   1800

ttgatctgcg gctttcgggt cgtgctcatg taccgcttcg aggaggagct attcttgcgc   1860

agcttgcaag actataagat tcaatctgcc ctgctggtgc ccacactatt tagcttcttc   1920

gctaagagca ctctcatcga caagtacgac ctaagcaact tgcacgagat cgccagcggc   1980

ggggcgccgc tcagcaagga ggtaggtgag gccgtggcca aacgcttcca cctaccaggc   2040

atccgccagg gctacggcct gacagaaaca accagcgcca ttctgatcac tccagaaggg   2100

gtt                                                                 2103
```

<210> SEQ ID NO 36
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 36

```
Met Pro Gly Ala Val Gly Lys Val Val Pro Phe Phe Glu Ala Lys Val
 1               5                  10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Phe Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Asn Trp Asp
            180                 185                 190

Ser Gly Cys Ser Arg Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Tyr Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
```

```
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700
```

<210> SEQ ID NO 37
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 37

```
atgcctggcg cagtaggcaa ggtggtgccc ttcttcgagg ctaaggtggt ggacttggac      60

accggtaaga cactgggtgt gaaccagcgc ggcgagctgt gcgtccgtgg ccccatgatc     120

atgagcggct acgttaacaa ccccgaggct acaaacgctc tcatcgacaa ggacggctgg     180

ctgcacagcg gcgacatcgc ctactgggac gaggacgagc acttcttcat cgtggaccgg     240

ctgaagagcc tgatcaaata caagggctac caggtagccc cagccgaact ggagagcatc     300

ctgctgcaac accccaacat cttcgacgcc ggggtcgccg gcctgcccga cgacgatgcc     360

ggcgagctgc ccgccgcagt cgtcgtgctg gaacacggta aaaccatgac cgagaaggag     420
```

```
atcgtggact atgtggccag ccaggttaca accgccaaga agctgcgcgg tggtgttgtg    480

ttcgtggacg aggtgcctaa aggactgacc ggcaagttgg acgcccgcaa gatccgcgag    540

attctcatta aggccaagaa gggatccaat tgggattctg ggtgctccag agaaggtatg    600

tatgaaagct ttattgagtc actgccattc cttaaatctt tggagttttc tgcacgcctg    660

aaagtagtag atgtgatagg caccaaagta tacaacgatg gagaacaaat cattgctcag    720

ggagattcgg ctgattcttt tttcattatt gaatctggag aagtgaaaat tactatgaaa    780

agaaagggta aatcagaagt ggaagagaat ggtgcagtag aaatcgctcg atgctcgcgg    840

ggacagtact ttggagagct tgccctggta actaacaaac ctcgagcagc ttctgcccac    900

gccattggga ctgtcaaatg tttagcaatg gatgtgcaag catttaaaag gcttctggga    960

ccttgcatgg aaattatgaa aaggaacatc gctacctatg aagaacagtt agttgccctg   1020

tttggaacga acatggatat tgtagccaaa aacattaaga agggcccagc gccattctac   1080

ccactcgaag acgggaccgc cggcgagcag ctgcacaaag ccatgaagcg ctacgccctg   1140

gtgcccggca ccatcgcctt taccgacgca catatcgagg tggacattac ctacgccgag   1200

tacttcgaga tgagcgttcg gctggcagaa gctatgaagc gctatgggct gaatacaaac   1260

catcggatcg tggtgtgcag cgagaatagc ttgcagttct tcatgcccgt gttgggtgcc   1320

ctgttcatcg gtgtggctgt ggccccagct aacgacatct acaacgagcg cgagctgctg   1380

aacagcatgg gcatcagcca gcccaccgtc gtattcgtga gcaagaaagg gctgcaaaag   1440

atcctcaacg tgcaaaagaa gctaccgatc atacaaaaga tcatcatcat ggatagcaag   1500

accgactacc agggcttcca aagcatgtac accttcgtga cttcccattt gccacccggc   1560

ttcaacgagt acgacttcgt gcccgagagc ttcgaccggg acaaaaccat cgccctgatc   1620

atgaacagta gtggcagtac cggattgccc aagggcgtag ccctaccgca ccgcaccgct   1680

tgtgtccgat tcagtcatgc ccgcgacccc atcttcggca accagatcat ccccgacacc   1740

gctatcctca gcgtggtgcc atttcaccac ggcttcggca tgttcaccac gctgggctac   1800

ttgatctgcg gctttcgggt cgtgctcatg taccgcttcg aggaggagct attcttgcgc   1860

agcttgcaag actataagat tcaatctgcc ctgctggtgc ccacactatt tagcttcttc   1920

gctaagagca ctctcatcga caagtacgac ctaagcaact tgcacgagat cgccagcggc   1980

ggggcgccgc tcagcaagga ggtaggtgag gccgtggcca aacgcttcca cctaccaggc   2040

atccgccagg gctacggcct gacagaaaca accagcgcca ttctgatcac tccagaaggg   2100

gtt                                                                 2103
```

<210> SEQ ID NO 38
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 38

```
Met Pro Gly Ala Val Gly Lys Val Val Pro Phe Phe Glu Ala Lys Val
 1               5                  10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
```

```
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Phe Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Asn Trp Asp
            180                 185                 190

Ser Gly Cys Ser Arg Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Lys Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Phe Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480
```

```
Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700
```

<210> SEQ ID NO 39
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 39

```
atgcctggcg cagtaggcaa ggtggtgccc ttcatcgagg ctaaggtggt ggacttggac     60

accggtaaga cactgggtgt gaaccagcgc ggcgagctgt gcgtccgtgg ccccatgatc    120

atgagcggct acgttaacaa ccccgaggct acaaacgctc tcatcgacaa ggacggctgg    180

ctgcacagcg gcgacatcgc ctactgggac gaggacgagc acttcttcat cgtggaccgg    240

ctgaagagcc tgatcaaata caagggctac caggtagccc cagccgaact ggagagcatc    300

ctgctgcaac accccaacat cttcgacgcc ggggtcgccg gcctgcccga cgacgatgcc    360

ggcgagctgc ccgccgcagt cgtcgtgctg gaacacggta aaaccatgac cgagaaggag    420

atcgtggact atgtggccag ccaggttaca accgccaaga agctgcgcgg tggtgttgtg    480

ttcgtggacg aggtgcctaa aggactgacc ggcaagttgg acgcccgcaa gatccgcgag    540

attctcatta aggccaagaa gggatccaat tgggattctg ggtgctccag agaaggtatg    600

tatgaaagct ttattgagtc actgccattc cttaaatctt tggagttttc tgcacgcctg    660

aaagtagtag atgtgatagg caccaaagta tacaacgatg gagaacaaat cattgctcag    720

ggagattcgg ctgattcttt tttcattatt gaatctggag aagtgaaaat tactatgaaa    780
```

```
agaaagggta aatcagaagt ggaagagaat ggtgcagtag aaatcgctcg atgctcgcgg    840

ggacagtact ttggagagct tgccctggta actaacaaac ctcgagcagc ttctgcccac    900

gccattggga ctgtcaaatg tttagcaatg gatgtgcaag catttgaaag gcttctggga    960

ccttgcatgg aaattatgaa aaggaacatc gctacctatg aagaacagtt agttgccctg   1020

tatggaacga acatggatat tgtagccaaa aacattaaga agggcccagc gccattctac   1080

ccactcgaag acgggaccgc cggcgagcag ctgcacaaag ccatgaagcg ctacgccctg   1140

gtgcccggca ccatcgcctt taccgacgca catatcgagg tggacattac ctacgccgag   1200

tacttcgaga tgagcgttcg gctggcagaa gctatgaagc gctatgggct gaatacaaac   1260

catcggatcg tggtgtgcag cgagaatagc ttgcagttct tcatgcccgt gttgggtgcc   1320

ctgttcatcg gtgtggctgt ggccccagct aacgacatct acaacgagcg cgagctgctg   1380

aacagcatgg gcatcagcca gcccaccgtc gtattcgtga gcaagaaagg gctgcaaaag   1440

atcctcaacg tgcaaaagaa gctaccgatc atacaaaaga tcatcatcat ggatagcaag   1500

accgactacc agggcttcca aagcatgtac accttcgtga cttcccattt gccacccggc   1560

ttcaacgagt acgacttcgt gcccgagagc ttcgaccggg acaaaaccat cgccctgatc   1620

atgaacagta gtggcagtac cggattgccc aagggcgtag ccctaccgca ccgcaccgct   1680

tgtgtccgat tcagtcatgc ccgcgacccc atcttcggca accagatcat ccccgacacc   1740

gctatcctca gcgtggtgcc atttcaccac ggcttcggca tgttcaccac gctgggctac   1800

ttgatctgcg gctttcgggt cgtgctcatg taccgcttcg aggaggagct attcttgcgc   1860

agcttgcaag actataagat tcaatctgcc ctgctggtgc ccacactatt tagcttcttc   1920

gctaagagca ctctcatcga caagtacgac ctaagcaact tgcacgagat cgccagcggc   1980

ggggcgccgc tcagcaagga ggtaggtgag gccgtggcca aacgcttcca cctaccaggc   2040

atccgccagg gctacggcct gacagaaaca accagcgcca ttctgatcac tccagaaggg   2100

gtt                                                                 2103
```

<210> SEQ ID NO 40
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 40

```
Met Pro Gly Ala Val Gly Lys Val Val Pro Phe Ile Glu Ala Lys Val
1               5                   10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125
```

```
Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Phe Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Asn Trp Asp
            180                 185                 190

Ser Gly Cys Ser Arg Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Tyr Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540
```

```
Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700
```

<210> SEQ ID NO 41
<211> LENGTH: 12
<212> TYPE: PRT
<213> ORGANISM: Artificial Sequence
<220> FEATURE:
<223> OTHER INFORMATION: A synthetic peptide

<400> SEQUENCE: 41

```
Gly Ser Ser Gly Gly Ser Gly Gly Ser Gly Gly Gly
 1               5                  10
```

<210> SEQ ID NO 42
<211> LENGTH: 12
<212> TYPE: PRT
<213> ORGANISM: Artificial Sequence
<220> FEATURE:
<223> OTHER INFORMATION: A synthetic peptide

<400> SEQUENCE: 42

```
Gly Ser Ser Ser Asp Ser Asp Ser Ser Ala Gly Ser
 1               5                  10
```

<210> SEQ ID NO 43
<211> LENGTH: 12
<212> TYPE: PRT
<213> ORGANISM: Artificial Sequence
<220> FEATURE:
<223> OTHER INFORMATION: A synthetic peptide

<400> SEQUENCE: 43

```
Gly Ser Asn Asp Ser Ser Gly Gly Ser Glu Gly Gly
 1               5                  10
```

<210> SEQ ID NO 44
<211> LENGTH: 12
<212> TYPE: PRT
<213> ORGANISM: Artificial Sequence
<220> FEATURE:
<223> OTHER INFORMATION: A synthetic peptide

<400> SEQUENCE: 44

```
Gly Ser Asn Gly Gly Phe Asp Ser Ser Glu Gly Gly
 1               5                  10


<210> SEQ ID NO 45
<211> LENGTH: 12
<212> TYPE: PRT
<213> ORGANISM: Artificial Sequence
<220> FEATURE:
<223> OTHER INFORMATION: A synthetic peptide

<400> SEQUENCE: 45

Gly Ser Ile Arg Trp Ser Gly Leu Ser Gly Gly Asp
 1               5                  10


<210> SEQ ID NO 46
<211> LENGTH: 12
<212> TYPE: PRT
<213> ORGANISM: Artificial Sequence
<220> FEATURE:
<223> OTHER INFORMATION: A synthetic peptide

<400> SEQUENCE: 46

Gly Ser Arg Gly Gly Ser Val Tyr Ser Glu Gly Gly
 1               5                  10


<210> SEQ ID NO 47
<211> LENGTH: 12
<212> TYPE: PRT
<213> ORGANISM: Artificial Sequence
<220> FEATURE:
<223> OTHER INFORMATION: A synthetic peptide

<400> SEQUENCE: 47

Gly Ser Ser Glu Gly Ser Ser Asp Phe Gly Gly Asp
 1               5                  10


<210> SEQ ID NO 48
<211> LENGTH: 12
<212> TYPE: PRT
<213> ORGANISM: Artificial Sequence
<220> FEATURE:
<223> OTHER INFORMATION: A synthetic peptide

<400> SEQUENCE: 48

Gly Ser Ile Val Val Ser Cys Ser Ser Glu Gly Gly
 1               5                  10


<210> SEQ ID NO 49
<211> LENGTH: 12
<212> TYPE: PRT
<213> ORGANISM: Artificial Sequence
<220> FEATURE:
<223> OTHER INFORMATION: A synthetic peptide

<400> SEQUENCE: 49

Gly Ser Asn Trp Asp Ser Gly Cys Ser Arg Glu Gly
 1               5                  10


<210> SEQ ID NO 50
<211> LENGTH: 12
<212> TYPE: PRT
<213> ORGANISM: Artificial Sequence
<220> FEATURE:
<223> OTHER INFORMATION: A synthetic peptide

<400> SEQUENCE: 50

Gly Ser Asn Trp Asp Ser Gly Cys Ser Arg Glu Cys
```

```
 1               5                   10


<210> SEQ ID NO 51
<211> LENGTH: 12
<212> TYPE: PRT
<213> ORGANISM: Artificial Sequence
<220> FEATURE:
<223> OTHER INFORMATION: A synthetic peptide

<400> SEQUENCE: 51

Gly Ser Ser Gly Cys Thr Gly Asp Ala Gly Gly Ser
 1               5                   10


<210> SEQ ID NO 52
<211> LENGTH: 12
<212> TYPE: PRT
<213> ORGANISM: Artificial Sequence
<220> FEATURE:
<223> OTHER INFORMATION: A synthetic peptide

<400> SEQUENCE: 52

Gly Ser Asn Trp Asp Ser Gly Cys Ser Arg Gln Cys
 1               5                   10


<210> SEQ ID NO 53
<211> LENGTH: 12
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 3
<223> OTHER INFORMATION: Xaa = S or N
<220> FEATURE:
<221> NAME/KEY: SITE
<222> LOCATION: 4
<223> OTHER INFORMATION: Xaa = S, D or G
<220> FEATURE:
<221> NAME/KEY: SITE
<222> LOCATION: 5
<223> OTHER INFORMATION: Xaa = D, S or G
<220> FEATURE:
<221> NAME/KEY: SITE
<222> LOCATION: 6
<223> OTHER INFORMATION: Xaa = S or F
<220> FEATURE:
<221> NAME/KEY: SITE
<222> LOCATION: 7
<223> OTHER INFORMATION: Xaa = D or G
<220> FEATURE:
<221> NAME/KEY: SITE
<222> LOCATION: (8)...(8)
<223> OTHER INFORMATION: Xaa = S or G
<220> FEATURE:
<221> NAME/KEY: SITE
<222> LOCATION: (10)...(10)
<223> OTHER INFORMATION: Xaa = A or E
<220> FEATURE:
<221> NAME/KEY: SITE
<222> LOCATION: (12)...(12)
<223> OTHER INFORMATION: Xaa = S or G

<400> SEQUENCE: 53

Gly Ser Xaa Xaa Xaa Xaa Xaa Xaa Ser Xaa Gly Xaa
 1               5                   10


<210> SEQ ID NO 54
<211> LENGTH: 12
<212> TYPE: PRT
<213> ORGANISM: Artificial Sequence
<220> FEATURE:
```

<223> OTHER INFORMATION: A synthetic peptide
<220> FEATURE:
<221> NAME/KEY: SITE
<222> LOCATION: 3
<223> OTHER INFORMATION: Xaa = I, R or S
<220> FEATURE:
<221> NAME/KEY: SITE
<222> LOCATION: 4
<223> OTHER INFORMATION: Xaa = R, G or E
<220> FEATURE:
<221> NAME/KEY: SITE
<222> LOCATION: 5
<223> OTHER INFORMATION: Xaa = W or G
<220> FEATURE:
<221> NAME/KEY: SITE
<222> LOCATION: 7
<223> OTHER INFORMATION: Xaa = G, V or S
<220> FEATURE:
<221> NAME/KEY: SITE
<222> LOCATION: 8
<223> OTHER INFORMATION: Xaa = L, Y or D
<220> FEATURE:
<221> NAME/KEY: SITE
<222> LOCATION: (9)...(9)
<223> OTHER INFORMATION: Xaa = S or F
<220> FEATURE:
<221> NAME/KEY: SITE
<222> LOCATION: (10)...(10)
<223> OTHER INFORMATION: Xaa = G or E
<220> FEATURE:
<221> NAME/KEY: SITE
<222> LOCATION: (12)...(12)
<223> OTHER INFORMATION: Xaa = D or G

<400> SEQUENCE: 54

```
Gly Ser Xaa Xaa Xaa Ser Xaa Xaa Xaa Xaa Gly Xaa
 1               5                  10
```

<210> SEQ ID NO 55
<211> LENGTH: 12
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 3
<223> OTHER INFORMATION: Xaa = I, N or S
<220> FEATURE:
<221> NAME/KEY: SITE
<222> LOCATION: 4
<223> OTHER INFORMATION: Xaa = V, W or G
<220> FEATURE:
<221> NAME/KEY: SITE
<222> LOCATION: 5
<223> OTHER INFORMATION: Xaa = V, D or C
<220> FEATURE:
<221> NAME/KEY: SITE
<222> LOCATION: 6
<223> OTHER INFORMATION: Xaa = S or T
<220> FEATURE:
<221> NAME/KEY: SITE
<222> LOCATION: 7
<223> OTHER INFORMATION: Xaa = C or G
<220> FEATURE:
<221> NAME/KEY: SITE
<222> LOCATION: (8)...(8)
<223> OTHER INFORMATION: Xaa = S, C or D
<220> FEATURE:
<221> NAME/KEY: SITE
<222> LOCATION: (9)...(9)
<223> OTHER INFORMATION: Xaa = S or A
<220> FEATURE:
<221> NAME/KEY: SITE
<222> LOCATION: (10)...(10)
<223> OTHER INFORMATION: Xaa = E, R or G
<220> FEATURE:

```
<221> NAME/KEY: SITE
<222> LOCATION: (11)...(11)
<223> OTHER INFORMATION: Xaa = G or E
<220> FEATURE:
<221> NAME/KEY: SITE
<222> LOCATION: (12)...(12)
<223> OTHER INFORMATION: Xaa = G or S

<400> SEQUENCE: 55

Gly Ser Xaa Xaa Xaa Xaa Xaa Xaa Xaa Xaa Xaa Xaa
 1               5                   10


<210> SEQ ID NO 56
<211> LENGTH: 12
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 3
<223> OTHER INFORMATION: Xaa = I or S
<220> FEATURE:
<221> NAME/KEY: SITE
<222> LOCATION: 4
<223> OTHER INFORMATION: Xaa = V, G or A
<220> FEATURE:
<221> NAME/KEY: SITE
<222> LOCATION: 5
<223> OTHER INFORMATION: Xaa = V or G
<220> FEATURE:
<221> NAME/KEY: SITE
<222> LOCATION: 6
<223> OTHER INFORMATION: Xaa = S or C
<220> FEATURE:
<221> NAME/KEY: SITE
<222> LOCATION: 7
<223> OTHER INFORMATION: Xaa = G or D
<220> FEATURE:
<221> NAME/KEY: SITE
<222> LOCATION: (8)...(8)
<223> OTHER INFORMATION: Xaa = G, D or S
<220> FEATURE:
<221> NAME/KEY: SITE
<222> LOCATION: (9)...(9)
<223> OTHER INFORMATION: Xaa = S or A
<220> FEATURE:
<221> NAME/KEY: SITE
<222> LOCATION: (10)...(11)
<223> OTHER INFORMATION: Xaa = G or E
<220> FEATURE:
<221> NAME/KEY: SITE
<222> LOCATION: (12)...(12)
<223> OTHER INFORMATION: Xaa = G or N

<400> SEQUENCE: 56

Gly Ser Xaa Xaa Xaa Xaa Xaa Xaa Xaa Xaa Xaa Xaa
 1               5                   10


<210> SEQ ID NO 57
<211> LENGTH: 12
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 3
<223> OTHER INFORMATION: Xaa = I, N or S
<220> FEATURE:
<221> NAME/KEY: SITE
<222> LOCATION: 4
<223> OTHER INFORMATION: Xaa = V, W, G or A
<220> FEATURE:
<221> NAME/KEY: SITE
```

<222> LOCATION: 5
<223> OTHER INFORMATION: Xaa = V, D, C or G
<220> FEATURE:
<221> NAME/KEY: SITE
<222> LOCATION: 6
<223> OTHER INFORMATION: Xaa = S, T or C
<220> FEATURE:
<221> NAME/KEY: SITE
<222> LOCATION: 7
<223> OTHER INFORMATION: Xaa = C or G
<220> FEATURE:
<221> NAME/KEY: SITE
<222> LOCATION: (8)...(8)
<223> OTHER INFORMATION: Xaa = S, C or D
<220> FEATURE:
<221> NAME/KEY: SITE
<222> LOCATION: (9)...(9)
<223> OTHER INFORMATION: Xaa = S or A
<220> FEATURE:
<221> NAME/KEY: SITE
<222> LOCATION: (10)...(10)
<223> OTHER INFORMATION: Xaa = E, R or G
<220> FEATURE:
<221> NAME/KEY: SITE
<222> LOCATION: (11)...(11)
<223> OTHER INFORMATION: Xaa = G or E
<220> FEATURE:
<221> NAME/KEY: SITE
<222> LOCATION: (12)...(12)
<223> OTHER INFORMATION: Xaa = G or S

<400> SEQUENCE: 57

Gly Ser Xaa Xaa Xaa Xaa Xaa Xaa Xaa Xaa Xaa Xaa
 1               5                  10

<210> SEQ ID NO 58
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 58
atgcctggcg cagtaggcaa ggtggtgccc ttcttcgagg ctaaggtggt ggacttggac 60
accggtaaga cactgggtgt gaaccagcgc ggcgagctgt gcgtccgtgg ccccatgatc 120
atgagcggct acgttaacaa ccccgaggct acaaacgctc tcatcgacaa ggacggctgg 180
ctgcacagcg gcgacatcgc ctactgggac gaggacgagc acttcttcat cgtggaccgg 240
ctgaagagcc tgatcaaata caagggctac caggtagccc cagccgaact ggagagcatc 300
ctgctgcaac accccaacat cttcgacgcc ggggtcgccg gcctgcccga cgacgatgcc 360
ggcgagctgc ccgccgcagt cgtcgtgctg gaacacggta aaaccatgac cgagaaggag 420
atcgtggact atgtggccag ccaggttaca accgccaaga agctgcgcgg tggtgttgtg 480
ttagtggacg aggtgcctaa aggactgacc ggcaagttgg acgcccgcaa gatccgcgag 540
attctcattc aggccaagaa gggatccaat tgggattctg ggtgctccag agaaggtatg 600
tatgaaagct ttattgagtc actgccattc cttaaatctt tggagttttc tgcacgcctg 660
aaagtagtag atgtgatagg caccaaagta tacaacgatg gagaacaaat cattgctcag 720
ggagattcgg ctgattcttt tttcattatt gaatctggag aagtgaaaat tactatgaaa 780
agaaagggta aatcagaagt ggaagagaat ggtgcagtag aaatcgctcg atgctcgcgg 840
ggacagtact ttggagagct tgccctggta actaacaaac ctcgagcagc ttctgcccac 900
gccattggga ctgtcaaatg tttagcaatg gatgtgcaag catttgaaag gcttctggga 960
ccttgcatgg aaattatgaa aaggaacatc gctacctatg aagaacagtt agttgccctg 1020

```
tatggaacga acatggatat tgtagccaaa aacattaaga agggcccagc gccattctac   1080

ccactcgaag acgggaccgc cggcgagcag ctgcacaaag ccatgaagcg ctacgccctg   1140

gtgcccggca ccatcgcctt taccgacgca catatcgagg tggacattac ctacgccgag   1200

tacttcgaga tgagcgttcg gctggcagaa gctatgaagc gctatgggct gaatacaaac   1260

catcggatcg tggtgtgcag cgagaatagc ttgcagttct tcatgcccgt gttgggtgcc   1320

ctgttcatcg gtgtggctgt ggccccagct aacgacatct acaacgagcg cgagctgctg   1380

aacagcatgg gcatcagcca gcccaccgtc gtattcgtga gcaagaaagg gctgcaaaag   1440

atcctcaacg tgcaaaagaa gctaccgatc atacaaaaga tcatcatcat ggatagcaag   1500

accgactacc agggcttcca aagcatgtac accttcgtga cttcccattt gccacccggc   1560

ttcaacgagt acgacttcgt gcccgagagc ttcgaccggg acaaaaccat cgccctgatc   1620

atgaacagta gtggcagtac cggattgccc aagggcgtag ccctaccgca ccgcaccgct   1680

tgtgtccgat tcagtcatgc ccgcgacccc atcttcggca accagatcat ccccgacacc   1740

gctatcctca gcgtggtgcc atttcaccac ggcttcggca tgttcaccac gctgggctac   1800

ttgatctgcg gctttcgggt cgtgctcatg taccgcttcg aggaggagct attcttgcgc   1860

agcttgcaag actataagat tcaatctgcc ctgctggtgc ccacactatt tagcttcttc   1920

gctaagagca ctctcatcga caagtacgac ctaagcaact tgcacgagat cgccagcggc   1980

ggggcgccgc tcagcaagga ggtaggtgag gccgtggcca aacgcttcca cctaccaggc   2040

atccgccagg gctacggcct gacagaaaca accagcgcca ttctgatcac tccagaaggg   2100

gtt                                                                 2103
```

<210> SEQ ID NO 59
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 59

```
Met Pro Gly Ala Val Gly Lys Val Val Pro Phe Phe Glu Ala Lys Val
 1               5                  10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160
```

```
Leu Val Asp Glu Val Pro Lys Gly Leu Thr Gly Lys Leu Asp Ala Arg
                165                 170                 175

Lys Ile Arg Glu Ile Leu Ile Gln Ala Lys Lys Gly Ser Asn Trp Asp
            180                 185                 190

Ser Gly Cys Ser Arg Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Tyr Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
```

```
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700


<210> SEQ ID NO 60
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 60

atgcctggcg cagtaggcaa ggtggtgcct ttcttcgagg ctaaggtggt ggacttggac     60

accggtaaga cactgggtgt gaaccagcgc ggcgagctgt gcgtccgtgg ccccatgatc    120

atgagcggct acgttaacaa ccccgaggct acaaacgctc tcatcgacaa ggacggctgg    180

ctgcacagcg gcgacatcgc ctactgggac gaggacgagc acttcttcat cgtggaccgg    240

ctgaagagcc tgatcaaata caagggctac caggtagccc cagccgaact ggagagcatc    300

ctgctgcaac accccaacat cttcgacgcc ggggtcgccg gcctgcccga cgacgatgcc    360

ggcgagctgc ccgccgcagt cgtcgtgctg gaacacggta aaaccatgac cgagaaggag    420

atcgtggact atgtggccag ccaggttaca accgccaaga agctgcgcgg tggtgttgtg    480

ttagtggacg aggtgcctaa aggactgacc ggcaagttgg acgcccgcaa gatccgcgag    540

attctcatta aggccaagaa gggatccaat tgggattctg ggtgctccag agaaggtatg    600

tacgaaagct ttattgagtc actgccattc cttaaatctt tggagttttc tgcacgcctg    660

aaagtagtag atgtgatagg caccaaagta tacaacgatg gagaacaaat cattgctcag    720

ggagattcgg ctgattcttt tttcattatt gaatctggag aagtgaaaat tactatgaaa    780

agaaagggta aatcagaagt ggaagagaat ggtgcagtag aaatcgctcg atgctcgcgg    840

ggacagtact ttggagagct tgccctggta actaacaaac ctcgagcagc ttctgcccac    900

gccattggga ctgtcaaatg tttagcaatg gatgtgcaag catttgaaag gcttctggga    960

ccttgcatgg aaattatgaa aaggaacatc gctacctatg aagaacagtt agttgccctg   1020

tttggaacga acatggatat tgtagccaaa aacattaaga agggcccagc gccattctac   1080

ccactcgaag acgggaccgc cggcgagcag ctgcacaaag ccatgaagcg ctacgccctg   1140

gtgcccggca ccatcgcctt taccgacgca catatcgagg tggacattac ctacgccgag   1200

tacttcgaga tgagcgttcg gctggcagaa gctatgaagc gctatgggct gaatacaaac   1260

catcggatcg tggtgtgcag cgagaatagc ttgcagttct tcatgcccgt gttgggtgcc   1320

ctgttcatcg gtgtggctgt ggccccagct aacgacatct acaacgagcg cgagctgctg   1380
```

-continued

```
aacagcatgg gcatcagcca gcccaccgtc gtattcgtga gcaagaaagg gctgcaaaag   1440

atcctcaacg tgcaaaagaa gctaccgatc atacaaaaga tcatcatcat ggatagcaag   1500

accgactacc agggcttcca aagcatgtac accttcgtga cttcccattt gccacccggc   1560

ttcaacgagt acgacttcgt gcccgagagc ttcgaccggg acaaaaccat cgccctgatc   1620

atgaacagta gtggcagtac cggattgccc aagggcgtag ccctaccgca ccgcaccgct   1680

tgtgtccgat tcagtcatgc ccgcgacccc atcttcggca accagatcat ccccgacacc   1740

gctatcctca gcgtggtgcc atttcaccac ggcttcggca tgttcaccac gctgggctac   1800

ttgatctgcg gctttcgggt cgtgctcatg taccgcttcg aggaggagct attcttgcgc   1860

agcttgcaag actataagat tcaatctgcc ctgctggtgc ccacactatt tagcttcttc   1920

gctaagagca ctctcatcga caagtacgac ctaagcaact tgcacgagat cgccagcggc   1980

ggggcgccgc tcagcaagga ggtaggtgag gccgtggcca aacgcttcca cctaccaggc   2040

atccgccagg gctacggcct gacagaaaca accagcgcca ttctgatcac tccagaaggg   2100

gtt                                                                 2103
```

<210> SEQ ID NO 61
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 61

```
Met Pro Gly Ala Val Gly Lys Val Val Pro Phe Phe Glu Ala Lys Val
 1               5                  10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Leu Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Asn Trp Asp
            180                 185                 190

Ser Gly Cys Ser Arg Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
```

```
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Phe Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655
```

```
Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700


<210> SEQ ID NO 62
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 62

atgcctggcg cagtaggcaa ggtggtgccc ttcttcgagg ctaaggtggt ggacttggac     60

accggtaaga cactgggtgt gaaccagcgc ggcgagctgt gcgtccgtgg ccccatgatc    120

atgagcggct acgttaacaa ccccgaggct acaaacgctc tcatcgacaa ggacggctgg    180

ctgcacagcg gcgacatcgc ctactgggac gaggacgagc acttcttcat cgtggaccgg    240

ctgaagagcc tgatcaaata caagggctac caggtagccc cagccgaact ggagagcatc    300

ctgctgcaac accccaacat cttcgacgcc ggggtcgccg gcctgcccga cgacgatgcc    360

ggcgagctgc ccgccgcagt cgtcgtgctg gaacacggta aaaccatgac cgagaaggag    420

atcgtggact atgtggccag ccaggttaca accgccaaga agctgcgcgg tggtgttgtg    480

ttcgtggacg aggtgcctaa aggactgacc ggcaagttgg acgcccgcaa gatccgcgag    540

attctcattc aggccaagaa gggatccaat tgggattctg ggtgctccag agaaggtatg    600

tatgaaagct ttattgagtc actgccattc cttaaatctt tggagttttc tgcacgcctg    660

aaagtagtag atgtgatagg caccaaagta tacaacgatg gagaacaaat cattgctcag    720

ggagattcgg ctgattcttt tttcattatt gaatctggag aagtgaaaat tactatgaaa    780

agaaagggta aatcagaagt ggaagagaat ggtgcagtag aaatcgctcg atgctcgcgg    840

ggacagtact ttggagagct tgccctggta actaacaaac ctcgagcagc ttctgcccac    900

gccattggga ctgtcaaatg tttagcaatg gatgtgcaag catttgaaag gcttctggga    960

ccttgcatgg aaattatgaa aaggaacatc gctacctatg aagaacagtt agttgccctg   1020

tttggaacga acatggatat tgtagccaaa aacattaaga agggcccagc gccattctac   1080

ccactcgaag acgggaccgc cggcgagcag ctgcacaaag ccatgaagcg ctacgccctg   1140

gtgcccggca ccatcgcctt taccgacgca catatcgagg tggacattac ctacgccgag   1200

tacttcgaga tgagcgttcg gctggcagaa gctatgaagc gctatgggct gaatacaaac   1260

catcggatcg tggtgtgcag cgagaatagc ttgcagttct tcatgcccgt gttgggtgcc   1320

ctgttcatcg gtgtggctgt ggccccagct aacgacatct acaacgagcg cgagctgctg   1380

aacagcatgg gcatcagcca gcccaccgtc gtattcgtga gcaagaaagg gctgcaaaag   1440

atcctcaacg tgcaaaagaa gctaccgatc atacaaaaga tcatcatcat ggatagcaag   1500

accgactacc agggcttcca aagcatgtac accttcgtga cttcccattt gccacccggc   1560

ttcaacgagt acgacttcgt gcccgagagc ttcgaccggg acaaaaccat cgccctgatc   1620

atgaacagta gtggcagtac cggattgccc aagggcgtag ccctaccgca ccgcaccgct   1680

tgtgtccgat tcagtcatgc ccgcgacccc atcttcggca accagatcat ccccgacacc   1740

gctatcctca gcgtggtgcc atttcaccac ggcttcggca tgttcaccac gctgggctac   1800
```

```
ttgatctgcg gctttcgggt cgtgctcatg taccgcttcg aggaggagct attcttgcgc   1860

agcttgcaag actataagat tcaatctgcc ctgctggtgc ccacactatt tagcttcttc   1920

gctaagagca ctctcatcga caagtacgac ctaagcaact tgcacgagat cgccagcggc   1980

ggggcgccgc tcagcaagga ggtaggtgag gccgtggcca aacgcttcca cctaccaggc   2040

atccgccagg gctacggcct gacagaaaca accagcgcca ttctgatcac tccagaaggg   2100

gtt                                                                 2103
```

<210> SEQ ID NO 63
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 63

```
Met Pro Gly Ala Val Gly Lys Val Val Pro Phe Phe Glu Ala Lys Val
1               5                   10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Phe Val Asp Glu Val Pro Lys Gly Leu Thr Gly Lys Leu Asp Ala Arg
                165                 170                 175

Lys Ile Arg Glu Ile Leu Ile Gln Ala Lys Lys Gly Ser Asn Trp Asp
            180                 185                 190

Ser Gly Cys Ser Arg Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300
```

```
Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Phe Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700
```

<210> SEQ ID NO 64
<211> LENGTH: 2103

<212> TYPE: DNA
<213> ORGANISM: Artificial Sequence
<220> FEATURE:
<223> OTHER INFORMATION: A synthetic oligonucleotide

<400> SEQUENCE: 64

```
atgcctggcg cagtaggcaa ggtggtgccc ttcttcgagg ctaaggtggt ggacttggac     60

accggtaaga cactgggtgt gaaccagcgc ggcgagctgt gcgtccgtgg ccccatgatc    120

atgagcggct acgttaacaa ccccgaggct acaaacgctc tcatcgacaa ggacggctgg    180

ctgcacagcg gcgacatcgc ctactgggac gaggacgagc acttcttcat cgtggaccgg    240

ctgaagagcc tgatcaaata caagggctac caggtagccc cagccgaact ggagagcatc    300

ctgctgcaac accccaacat cttcgacgcc ggggtcgccg gcctgcccga cgacgatgcc    360

ggcgagctgc ccgccgcagt cgtcgtgctg gaacacggta aaaccatgac cgagaaggag    420

atcgtggact atgtggccag ccaggttaca accgccaaga agctgcgcgg tggtgttgtg    480

ttagtggacg aggtgcctaa aggactgacc ggcaagttgg acgcccgcaa gatccgcgag    540

attctcattc aggccaagaa gggatccaat tgggattctg ggtgctccag agaaggtatg    600

tatgaaagct ttattgagtc actgccattc cttaaatctt tggagttttc tgcacgcctg    660

aaagtagtag atgtgatagg caccaaagta tacaacgatg gagaacaaat cattgctcag    720

ggagattcgg ctgattcttt tttcattatt gaatctggag aagtgaaaat tactatgaaa    780

agaaagggta aatcagaagt ggaagagaat ggtgcagtag aaatcgctcg atgctcgcgg    840

ggacagtact ttggagagct tgccctggta actaacaaac ctcgagcagc ttctgcccac    900

gccattggga ctgtcaaatg tttagcaatg gatgtgcaag catttgaaag gcttctggga    960

ccttgcatgg aaattatgaa aaggaacatc gctacctatg aagaacagtt agttgccctg   1020

tttggaacga acatggatat tgtagccaaa aacattaaga agggcccagc gccattctac   1080

ccactcgaag acgggaccgc cggcgagcag ctgcacaaag ccatgaagcg ctacgccctg   1140

gtgcccggca ccatcgcctt taccgacgca catatcgagg tggacattac ctacgccgag   1200

tacttcgaga tgagcgttcg gctggcagaa gctatgaagc gctatgggct gaatacaaac   1260

catcggatcg tggtgtgcag cgagaatagc ttgcagttct tcatgcccgt gttgggtgcc   1320

ctgttcatcg gtgtggctgt ggccccagct aacgacatct acaacgagcg cgagctgctg   1380

aacagcatgg gcatcagcca gcccaccgtc gtattcgtga gcaagaaagg gctgcaaaag   1440

atcctcaacg tgcaaaagaa gctaccgatc atacaaaaga tcatcatcat ggatagcaag   1500

accgactacc agggcttcca aagcatgtac accttcgtga cttcccattt gccacccggc   1560

ttcaacgagt acgacttcgt gcccgagagc ttcgaccggg acaaaaccat cgccctgatc   1620

atgaacagta gtggcagtac cggattgccc aagggcgtag ccctaccgca ccgcaccgct   1680

tgtgtccgat tcagtcatgc ccgcgacccc atcttcggca accagatcat ccccgacacc   1740

gctatcctca gcgtggtgcc atttcaccac ggcttcggca tgttcaccac gctgggctac   1800

ttgatctgcg gctttcgggt cgtgctcatg taccgcttcg aggaggagct attcttgcgc   1860

agcttgcaag actataagat tcaatctgcc ctgctggtgc ccacactatt tagcttcttc   1920

gctaagagca ctctcatcga caagtacgac ctaagcaact tgcacgagat cgccagcggc   1980

ggggcgccgc tcagcaagga ggtaggtgag gccgtggcca aacgcttcca cctaccaggc   2040

atccgccagg gctacggcct gacagaaaca accagcgcca ttctgatcac tccagaaggg   2100

gtt                                                                 2103
```

<210> SEQ ID NO 65
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 65

```
Met Pro Gly Ala Val Gly Lys Val Val Pro Phe Phe Glu Ala Lys Val
 1               5                  10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Leu Val Asp Glu Val Pro Lys Gly Leu Thr Gly Lys Leu Asp Ala Arg
                165                 170                 175

Lys Ile Arg Glu Ile Leu Ile Gln Ala Lys Lys Gly Ser Asn Trp Asp
            180                 185                 190

Ser Gly Cys Ser Arg Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Phe Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365
```

```
Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700
```

<210> SEQ ID NO 66
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 66

```
atgcctggcg cagtaggcaa ggtggtgccc ttcatcgagg ctaaggtggt ggacttggac     60

accggtaaga cactgggtgt gaaccagcgc ggcgagctgt gcgtccgtgg ccccatgatc    120

atgagcggct acgttaacaa ccccgaggct acaaacgctc tcatcgacaa ggacggctgg    180
```

```
ctgcacagcg gcgacatcgc ctactgggac gaggacgagc acttcttcat cgtggaccgg    240

ctgaagagcc tgatcaaata caagggctac caggtagccc cagccgaact ggagagcatc    300

ctgctgcaac accccaacat cttcgacgcc ggggtcgccg gcctgcccga cgacgatgcc    360

ggcgagctgc ccgccgcagt cgtcgtgctg gaacacggta aaaccatgac cgagaaggag    420

atcgtggact atgtggccag ccaggttaca accgccaaga agctgcgcgg tggtgttgtg    480

ttcgtggacg aggtgcctaa aggactgacc ggcaagttgg acgcccgcaa gatccgcgag    540

attctcatta aggccaagaa gggatccaat tgggattctg ggtgctccag agaaggtatg    600

tatgaaagct ttattgagtc actgccattc cttaaatctt tggagttttc tgcacgcctg    660

aaagtagtag atgtgatagg caccaaagta tacaacgatg gagaacaaat cattgctcag    720

ggagattcgg ctgattcttt tttcattatt gaatctggag aagtgaaaat tactatgaaa    780

agaaagggta aatcagaagt ggaagagaat ggtgcagtag aaatcgctcg atgctcgcgg    840

ggacagtact ttggagagct tgccctggta actaacaaac ctcgagcagc ttctgcccac    900

gccattggga ctgtcaaatg tttagcaatg gatgtgcaag catttgaaag gcttctggga    960

ccttgcatgg aaattatgaa aaggaacatc gctacctatg aagaacagtt agttgccctg   1020

tttggaacga acatggatat tgtagccaaa aacattaaga agggcccagc gccattctac   1080

ccactcgaag acgggaccgc cggcgagcag ctgcacaaag ccatgaagcg ctacgccctg   1140

gtgcccggca ccatcgcctt taccgacgca catatcgagg tggacattac ctacgccgag   1200

tacttcgaga tgagcgttcg gctggcagaa gctatgaagc gctatgggct gaatacaaac   1260

catcggatcg tggtgtgcag cgagaatagc ttgcagttct tcatgcccgt gttgggtgcc   1320

ctgttcatcg gtgtggctgt ggccccagct aacgacatct acaacgagcg cgagctgctg   1380

aacagcatgg gcatcagcca gcccaccgtc gtattcgtga gcaagaaagg gctgcaaaag   1440

atcctcaacg tgcaaaagaa gctaccgatc atacaaaaga tcatcatcat ggatagcaag   1500

accgactacc agggcttcca aagcatgtac accttcgtga cttcccattt gccacccggc   1560

ttcaacgagt acgacttcgt gcccgagagc ttcgaccggg acaaaaccat cgccctgatc   1620

atgaacagta gtggcagtac cggattgccc aagggcgtag ccctaccgca ccgcaccgct   1680

tgtgtccgat tcagtcatgc ccgcgacccc atcttcggca accagatcat ccccgacacc   1740

gctatcctca gcgtggtgcc atttcaccac ggcttcggca tgttcaccac gctgggctac   1800

ttgatctgcg gctttcgggt cgtgctcatg taccgcttcg aggaggagct attcttgcgc   1860

agcttgcaag actataagat tcaatctgcc ctgctggtgc ccacactatt tagcttcttc   1920

gctaagagca ctctcatcga caagtacgac ctaagcaact tgcacgagat cgccagcggc   1980

ggggcgccgc tcagcaagga ggtaggtgag gccgtggcca aacgcttcca cctaccaggc   2040

atccgccagg gctacggcct gacagaaaca accagcgcca ttctgatcac tccagaaggg   2100

gtt                                                                 2103
```

<210> SEQ ID NO 67
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 67

```
Met Pro Gly Ala Val Gly Lys Val Val Pro Phe Ile Glu Ala Lys Val
 1               5                  10                  15
```

```
Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Phe Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Asn Trp Asp
            180                 185                 190

Ser Gly Cys Ser Arg Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Phe Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
```

```
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700
```

<210> SEQ ID NO 68
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 68

```
atgcctggcg cagtaggcaa ggtggtgccc ttcatcgagg ctaaggtggt ggacttggac      60

accggtaaga cactgggtgt gaaccagcgc ggcgagctgt gcgtccgtgg ccccatgatc     120

atgagcggct acgttaacaa ccccgaggct acaaacgctc tcatcgacaa ggacggctgg     180

ctgcacagcg gcgacatcgc ctactgggac gaggacgagc acttcttcat cgtggaccgg     240

ctgaagagcc tgatcaaata caagggctac caggtagccc cagccgaact ggagagcatc     300

ctgctgcaac accccaacat cttcgacgcc ggggtcgccg gcctgcccga cgacgatgcc     360

ggcgagctgc ccgccgcagt cgtcgtgctg gaacacggta aaaccatgac cgagaaggag     420

atcgtggact atgtggccag ccaggttaca accgccaaga agctgcgcgg tggtgttgtg     480

ttagtggacg aggtgcctaa aggactgacc ggcaagttgg acgcccgcaa gatccgcgag     540

attctcattc aggccaagaa gggatccaat tgggattctg ggtgctccag agaaggtatg     600
```

```
tatgaaagct ttattgagtc actgccattc cttaaatctt tggagttttc tgcacgcctg    660
aaagtagtag atgtgatagg caccaaagta tacaacgatg gagaacaaat cattgctcag    720
ggagattcgg ctgattcttt tttcattatt gaatctggag aagtgaaaat tactatgaaa    780
agaaagggta aatcagaagt ggaagagaat ggtgcagtag aaatcgctcg atgctcgcgg    840
ggacagtact ttggagagct tgccctggta actaacaaac ctcgagcagc ttctgcccac    900
gccattggga ctgtcaaatg tttagcaatg gatgtgcaag catttgaaag gcttctggga    960
ccttgcatgg aaattatgaa aaggaacatc gctacctatg aagaacagtt agttgccctg   1020
tttggaacga acatggatat tgtagccaaa aacattaaga agggcccagc gccattctac   1080
ccactcgaag acgggaccgc cggcgagcag ctgcacaaag ccatgaagcg ctacgccctg   1140
gtgcccggca ccatcgcctt taccgacgca catatcgagg tggacattac ctacgccgag   1200
tacttcgaga tgagcgttcg gctggcagaa gctatgaagc gctatgggct gaatacaaac   1260
catcggatcg tggtgtgcag cgagaatagc ttgcagttct tcatgcccgt gttgggtgcc   1320
ctgttcatcg gtgtggctgt ggccccagct aacgacatct acaacgagcg cgagctgctg   1380
aacagcatgg gcatcagcca gcccaccgtc gtattcgtga gcaagaaagg gctgcaaaag   1440
atcctcaacg tgcaaaagaa gctaccgatc atacaaaaga tcatcatcat ggatagcaag   1500
accgactacc agggcttcca aagcatgtac accttcgtga cttcccattt gccacccggc   1560
ttcaacgagt acgacttcgt gcccgagagc ttcgaccggg acaaaaccat cgccctgatc   1620
atgaacagta gtggcagtac cggattgccc aagggcgtag ccctaccgca ccgcaccgct   1680
tgtgtccgat tcagtcatgc ccgcgacccc atcttcggca accagatcat ccccgacacc   1740
gctatcctca gcgtggtgcc atttcaccac ggcttcggca tgttcaccac gctgggctac   1800
ttgatctgcg gctttcgggt cgtgctcatg taccgcttcg aggaggagct attcttgcgc   1860
agcttgcaag actataagat tcaatctgcc ctgctggtgc ccacactatt tagcttcttc   1920
gctaagagca ctctcatcga caagtacgac ctaagcaact tgcacgagat cgccagcggc   1980
ggggcgccgc tcagcaagga ggtaggtgag gccgtggcca aacgcttcca cctaccaggc   2040
atccgccagg gctacggcct gacagaaaca accagcgcca ttctgatcac tccagaaggg   2100
gtt                                                                 2103
```

```
<210> SEQ ID NO 69
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 69

Met Pro Gly Ala Val Gly Lys Val Val Pro Phe Ile Glu Ala Lys Val
 1               5                  10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
```

```
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Leu Val Asp Glu Val Pro Lys Gly Leu Thr Gly Lys Leu Asp Ala Arg
                165                 170                 175

Lys Ile Arg Glu Ile Leu Ile Gln Ala Lys Lys Gly Ser Asn Trp Asp
            180                 185                 190

Ser Gly Cys Ser Arg Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Phe Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510
```

```
Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700
```

```
<210> SEQ ID NO 70
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 70

atgcctggcg cagtaggcaa ggtggtgccc ttcatcgagg ctaaggtggt ggacttggac      60

accggtaaga cactgggtgt gaaccagcgc ggcgagctgt gcgtccgtgg ccccatgatc     120

atgagcggct acgttaacaa ccccgaggct acaaacgctc tcatcgacaa ggacggctgg     180

ctgcacagcg gcgacatcgc ctactgggac gaggacgagc acttcttcat cgtggaccgg     240

ctgaagagcc tgatcaaata caagggctac caggtagccc cagccgaact ggagagcatc     300

ctgctgcaac accccaacat cttcgacgcc ggggtcgccg gcctgcccga cgacgatgcc     360

ggcgagctgc ccgccgcagt cgtcgtgctg gaacacggta aaaccatgac cgagaaggag     420

atcgtggact atgtggccag ccaggttaca accgccaaga agctgcgcgg tggtgttgtg     480

ttagtggacg aggtgcctaa aggactgacc ggcaagttgg acgcccgcaa gatccgcgag     540

attctcatta aggccaagaa gggatccaat tgggattctg ggtgctccag agaaggtatg     600

tatgaaagct ttattgagtc actgccattc cttaaatctt tggagttttc tgcacgcctg     660

aaagtagtag atgtgatagg caccaaagta tacaacgatg gagaacaaat cattgctcag     720

ggagattcgg ctgattcttt tttcattatt gaatctggag aagtgaaaat tactatgaaa     780

agaaagggta aatcagaagt ggaagagaat ggtgcagtag aaatcgctcg atgctcgcgg     840

ggacagtact ttggagagct tgccctggta actaacaaac ctcgagcagc ttctgcccac     900

gccattggga ctgtcaaatg tttagcaatg gatgtgcaag catttgaaag gcttctggga     960
```

```
ccttgcatgg aaattatgaa aaggaacatc gctacctatg aagaacagtt agttgccctg   1020

tttggaacga acatggatat tgtagccaaa aacattaaga agggcccagc gccattctac   1080

ccactcgaag acgggaccgc cggcgagcag ctgcacaaag ccatgaagcg ctacgccctg   1140

gtgcccggca ccatcgcctt taccgacgca catatcgagg tggacattac ctacgccgag   1200

tacttcgaga tgagcgttcg gctggcagaa gctatgaagc gctatgggct gaatacaaac   1260

catcggatcg tggtgtgcag cgagaatagc ttgcagttct tcatgcccgt gttgggtgcc   1320

ctgttcatcg gtgtggctgt ggccccagct aacgacatct acaacgagcg cgagctgctg   1380

aacagcatgg gcatcagcca gcccaccgtc gtattcgtga gcaagaaagg gctgcaaaag   1440

atcctcaacg tgcaaaagaa gctaccgatc atacaaaaga tcatcatcat ggatagcaag   1500

accgactacc agggcttcca aagcatgtac accttcgtga cttcccattt gccacccggc   1560

ttcaacgagt acgacttcgt gcccgagagc ttcgaccggg acaaaaccat cgccctgatc   1620

atgaacagta gtggcagtac cggattgccc aagggcgtag ccctaccgca ccgcaccgct   1680

tgtgtccgat tcagtcatgc ccgcgacccc atcttcggca accagatcat ccccgacacc   1740

gctatcctca gcgtggtgcc atttcaccac ggcttcggca tgttcaccac gctgggctac   1800

ttgatctgcg gctttcgggt cgtgctcatg taccgcttcg aggaggagct attcttgcgc   1860

agcttgcaag actataagat tcaatctgcc ctgctggtgc ccacactatt tagcttcttc   1920

gctaagagca ctctcatcga caagtacgac ctaagcaact tgcacgagat cgccagcggc   1980

ggggcgccgc tcagcaagga ggtaggtgag gccgtggcca aacgcttcca cctaccaggc   2040

atccgccagg gctacggcct gacagaaaca accagcgcca ttctgatcac tccagaaggg   2100

gtt                                                                 2103
```

<210> SEQ ID NO 71
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 71

```
Met Pro Gly Ala Val Gly Lys Val Val Pro Phe Ile Glu Ala Lys Val
1               5                   10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160
```

```
Leu Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Asn Trp Asp
            180                 185                 190

Ser Gly Cys Ser Arg Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Phe Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575
```

```
Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700


<210> SEQ ID NO 72
<211> LENGTH: 2102
<212> TYPE: DNA
<213> ORGANISM: Artificial Sequence
<220> FEATURE:
<223> OTHER INFORMATION: A synthetic oligonucleotide

<400> SEQUENCE: 72

atgcctggcg cagtaggcaa ggtggtgccc ttcttcgagg ctaaggtggt ggacttggac      60

accggtaaga cactgggtgt gaaccagcgc ggcgagctgt gcgtccgtgg ccccatgatc     120

atgagcggct acgttaacaa ccccgaggct acaaacgctc tcatcgacaa ggacggctgg     180

ctgcacagcg gcgacatcgc ctactgggac gaggacgagc acttcttcat cgtggaccgg     240

ctgaagaacc tgatcaaata caaaggctac caggtagccc cagccgaact ggagagcatc     300

ctgctgcaac accccaacat cttcgacgcc ggggtcgccg gcctgcccga cgacgatgcc     360

ggcgagctgc ccgccgcagt cgtcgtgctg gaacacggta aaaccatgac cgagaaggag     420

atcgtggact atgtggccag ccaggttaca accgccaaga agctacgcgg tggtgttgtg     480

ttcgtggacg aggtgcctaa aggactgacc ggcaagttgg acgcccgcaa gatccgcgag     540

attctcatta aggccaagaa gggatccaat tgggattctg ggtgctccag agaaggtatg     600

tatgaaagct ttattgagtc actgccattc cttaaatctt tggagttttc tgcacgcctg     660

aaagtagtag atgtgatagg caccaaagta tacaacgatg gagaacaaat cattgctcag     720

ggagattcgg ctgattcttt tttcattatt gaatctggag aagtgaaaat tactatgaaa     780

agaaagggta aatcagaagt ggaagagaat ggtgcagtag aaatcgctcg atgctcgcgg     840

ggacagtact ttggagagct tgccctggta actaacaaac ctcgagcagc ttctgcccac     900

gccattggga ctgtcaaatg tttagcaatg gatgtgcaag catttgaaag gcttctggga     960

ccttgcatgg aaattatgaa aaggaacatc gctacctatg aagaacagtt agttgccctg    1020

tttggaacga acatggatat tgtagccaaa aacattaaga agggcccagc gccattctac    1080

ccactcgaag acgggaccgc cggcgagcag ctgcacaaag ccatgaagcg ctacgccctg    1140

gtgcccggca ccatcgcctt taccgacgca catatcgagg tggacattac ctacgccgag    1200

tacttcgaga tgagcgttcg gctggcagaa gctatgaagc gctatgggct gaatacaaac    1260

catcggatcg tggtgtgcag cgagaatagc ttgcagttct tcatgcccgt gttgggtgcc    1320

ctgttcatcg gtgtggctgt ggccccagct aacgacatct acaacgagcg cgagctgctg    1380
```

```
aacagcatgg gcatcagcca gcccaccgtc gtattcgtga gcaagaaagg gctgcaaaag   1440

atcctcaacg tgcaaaagaa gctaccgatc atacaaaaga tcatcatcat ggatagcaag   1500

accgactacc agggcttcca aagcatgtac accttcgtga cttcccattt gccacccggc   1560

ttcaacgagt acgacttcgt gcccgagagc ttcgaccggg acaaaaccat cgccctgatc   1620

atgaacagta gtggcagtac cggattgccc aagggcgtag ccctaccgca ccgcaccgct   1680

tgtgtccgat tcagtcatgc ccgcgacccc atcttcggca accagatcat ccccgacacc   1740

gctatcctca gcgtggtgcc atttcaccac ggcttcggca tgttcaccac gctgggctac   1800

ttgatctgcg gctttcgggt cgtgctcatg taccgcttcg aggaggagct attcttgcgc   1860

agcttgcaag actataagat tcaatctgcc ctgctggtgc ccacactatt tagcttcttc   1920

gctaagagca ctctcatcga caagtacgac ctaagcaact tgcacgagat cgccagcggc   1980

ggggcgccgc tcagcaagga ggtaggtgag gccgtggcca aacgcttcca cctaccaggc   2040

atccgccagg gctacggcct gacagaaaca accagcgcca ttctgatcac tccagaaggg   2100

gt                                                                  2102
```

<210> SEQ ID NO 73
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 73

```
Met Pro Gly Ala Val Gly Lys Val Val Pro Phe Phe Glu Ala Lys Val
1               5                   10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Asn Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Phe Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Asn Trp Asp
            180                 185                 190

Ser Gly Cys Ser Arg Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220
```

```
Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Phe Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
```

```
            645                 650                 655

Ile Ala Ser Gly Gly Ala Pro Leu Ser Lys Glu Val Gly Glu Ala Val
        660                 665                 670

Ala Lys Arg Phe His Leu Pro Gly Ile Arg Gln Gly Tyr Gly Leu Thr
    675                 680                 685

Glu Thr Thr Ser Ala Ile Leu Ile Thr Pro Glu Gly Val
690                 695                 700
```

<210> SEQ ID NO 74
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 74

```
atgcctggcg cagtaggcaa ggtggtgccc ttcatcgagg ctaaggtggt ggacttggac     60

accggtaaga cactgggtgt gaaccagcgc ggcgagctgt gcgtccgtgg ccccatgatc    120

atgagcggct acgttaacaa ccccgaggct acaaacgctc tcatcgacaa ggacggctgg    180

ctgcacagcg gcgacatcgc ctactgggac gaggacgagc acttcttcat cgtggaccgg    240

ctgaagagcc tgatcaaata caagggctac caggtagccc cagccgaact ggagagcatc    300

ctgctgcaac accccaacat cttcgacgcc ggggtcgccg gcctgcccga cgacgatgcc    360

ggcgagctgc ccgccgcagt cgtcgtgctg gaacacggta aaaccatgac cgagaaggag    420

atcgtggact atgtggccag ccaggttaca accgccaaga agctgcgcgg tggtgttgtg    480

ttcgtggacg aggtgcctaa aggactgacc ggcaagttgg acgcccgcaa gatccgcgag    540

attctcattc aggccaagaa gggatccatc gcaggttgtg gcgatgccgg cgaaggtatg    600

tatgaaagct ttattgagtc actgccattc cttaaatctt tggagttttc tgcacgcctg    660

aaagtagtag atgtgatagg caccaaagta tacaacgatg gagaacaaat cattgctcag    720

ggagattcgg ctgattcttt tttcattatt gaatctggag aagtgaaaat tactatgaaa    780

agaaagggta aatcagaagt ggaagagaat ggtgcagtag aaatcgctcg atgctcgcgg    840

ggacagtact ttggagagct tgccctggta actaacaaac ctcgagcagc ttctgcccac    900

gccattggga ctgtcaaatg tttagcaatg gatgtgcaag catttgaaag gcttctggga    960

ccttgcatgg aaattatgaa aaggaacatc gctacctatg aagaacagtt agttgccctg   1020

tttggaacga acatggatat tgtagccaaa aacattaaga agggcccagc gccattctac   1080

ccactcgaag acgggaccgc cggcgagcag ctgcacaaag ccatgaagcg ctacgccctg   1140

gtgcccggca ccatcgcctt taccgacgca catatcgagg tggacattac ctacgccgag   1200

tacttcgaga tgagcgttcg gctggcagaa gctatgaagc gctatgggct gaatacaaac   1260

catcggatcg tggtgtgcag cgagaatagc ttgcagttct tcatgcccgt gttgggtgcc   1320

ctgttcatcg gtgtggctgt ggccccagct aacgacatct acaacgagcg cgagctgctg   1380

aacagcatgg gcatcagcca gcccaccgtc gtattcgtga gcaagaaagg gctgcaaaag   1440

atcctcaacg tgcaaaagaa gctaccgatc atacaaaaga tcatcatcat ggatagcaag   1500

accgactacc agggcttcca aagcatgtac accttcgtga cttcccattt gccacccggc   1560

ttcaacgagt acgacttcgt gcccgagagc ttcgaccggg acaaaaccat cgccctgatc   1620

atgaacagta gtggcagtac cggattgccc aagggcgtag ccctaccgca ccgcaccgct   1680

tgtgtccgat tcagtcatgc ccgcgacccc atcttcggca accagatcat ccccgacacc   1740
```

```
gctatcctca gcgtggtgcc atttcaccac ggcttcggca tgttcaccac gctgggctac   1800

ttgatctgcg gctttcgggt cgtgctcatg taccgcttcg aggaggagct attcttgcgc   1860

agcttgcaag actataagat tcaatctgcc ctgctggtgc ccacactatt tagcttcttc   1920

gctaagagca ctctcatcga caagtacgac ctaagcaact tgcacgagat cgccagcggc   1980

ggggcgccgc tcagcaagga ggtaggtgag gccgtggcca aacgcttcca cctaccaggc   2040

atccgccagg gctacggcct gacagaaaca accagcgcca ttctgatcac tccagaaggg   2100

gtt                                                                 2103
```

```
<210> SEQ ID NO 75
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 75

Met Pro Gly Ala Val Gly Lys Val Val Pro Phe Ile Glu Ala Lys Val
1               5                   10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Phe Val Asp Glu Val Pro Lys Gly Leu Thr Gly Lys Leu Asp Ala Arg
                165                 170                 175

Lys Ile Arg Glu Ile Leu Ile Gln Ala Lys Lys Gly Ser Ile Ala Gly
            180                 185                 190

Cys Gly Asp Ala Gly Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
```

```
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Phe Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700

<210> SEQ ID NO 76
```

```
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 76

atgcctggcg cagtaggcaa ggtggtgccc ttcatcgagg ctaaggtggt ggacttggac     60
accggtaaga cactgggtgt gaaccagcgc ggcgagctgt gcgtccgtgg ccccatgatc    120
atgagcggct acgttaacaa ccccgaggct acaaacgctc tcatcgacaa ggacggctgg    180
ctgcacagcg gcgacatcgc ctactgggac gaggacgagc acttcttcat cgtggaccgg    240
ctgaagagcc tgatcaaata caagggctac caggtagccc cagccgaact ggagagcatc    300
ctgctgcaac accccaacat cttcgacgcc ggggtcgccg gcctgcccga cgacgatgcc    360
ggcgagctgc ccgccgcagt cgtcgtgctg gaacacggta aaaccatgac cgagaaggag    420
atcgtggact atgtggccag ccaggttaca accgccaaga agctgcgcgg tggtgttgtg    480
ttcgtggacg aggtgcctaa aggactgacc ggcaagttgg acgcccgcaa gatccgcgag    540
attctcatta aggccaagaa gggatccatc gcaggttgtg gcgatgccgg cgaaggtatg    600
tatgaaagct ttattgagtc actgccattc cttaaatctt tggagttttc tgcacgcctg    660
aaagtagtag atgtgatagg caccaaagta tacaacgatg gagaacaaat cattgctcag    720
ggagattcgg ctgattcttt tttcattatt gaatctggag aagtgaaaat tactatgaaa    780
agaaagggta aatcagaagt ggaagagaat ggtgcagtag aaatcgctcg atgctcgcgg    840
ggacagtact ttggagagct tgccctggta actaacaaac ctcgagcagc ttctgcccac    900
gccattggga ctgtcaaatg tttagcaatg gatgtgcaag catttgaaag gcttctggga    960
ccttgcatgg aaattatgaa aaggaacatc gctacctatg aagaacagtt agttgccctg   1020
tatggaacga acatggatat tgtagccaaa aacattaaga agggcccagc gccattctac   1080
ccactcgaag acgggaccgc cggcgagcag ctgcacaaag ccatgaagcg ctacgccctg   1140
gtgcccggca ccatcgcctt taccgacgca catatcgagg tggacattac ctacgccgag   1200
tacttcgaga tgagcgttcg gctggcagaa gctatgaagc gctatgggct gaatacaaac   1260
catcggatcg tggtgtgcag cgagaatagc ttgcagttct tcatgcccgt gttgggtgcc   1320
ctgttcatcg gtgtggctgt ggccccagct aacgacatct acaacgagcg cgagctgctg   1380
aacagcatgg gcatcagcca gcccaccgtc gtattcgtga gcaagaaagg gctgcaaaag   1440
atcctcaacg tgcaaaagaa gctaccgatc atacaaaaga tcatcatcat ggatagcaag   1500
accgactacc agggcttcca aagcatgtac accttcgtga cttcccattt gccacccggc   1560
ttcaacgagt acgacttcgt gcccgagagc ttcgaccggg acaaaaccat cgccctgatc   1620
atgaacagta gtggcagtac cggattgccc aagggcgtag ccctaccgca ccgcaccgct   1680
tgtgtccgat tcagtcatgc ccgcgacccc atcttcggca accagatcat ccccgacacc   1740
gctatcctca gcgtggtgcc atttcaccac ggcttcggca tgttcaccac gctgggctac   1800
ttgatctgcg gctttcgggt cgtgctcatg taccgcttcg aggaggagct attcttgcgc   1860
agcttgcaag actataagat tcaatctgcc ctgctggtgc ccacactatt tagcttcttc   1920
gctaagagca ctctcatcga caagtacgac ctaagcaact tgcacgagat cgccagcggc   1980
ggggcgccgc tcagcaagga ggtaggtgag gccgtggcca aacgcttcca cctaccaggc   2040
atccgccagg gctacggcct gacagaaaca accagcgcca ttctgatcac tccagaaggg   2100
gtt                                                                 2103
```

<210> SEQ ID NO 77
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 77

```
Met Pro Gly Ala Val Gly Lys Val Val Pro Phe Ile Glu Ala Lys Val
1               5                   10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Phe Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Ile Ala Gly
            180                 185                 190

Cys Gly Asp Ala Gly Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Tyr Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365
```

```
Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700
```

<210> SEQ ID NO 78
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 78

```
atgcctggcg cagtaggcaa ggtggtgccc ttcatcgagg ctaaggtggt ggacttggac     60

accggtaaga cactgggtgt gaaccagcgc ggcgagctgt gcgtccgtgg ccccatgatc    120

atgagcggct acgttaacaa ccccgaggct acaaacgctc tcatcgacaa ggacggctgg    180
```

```
ctgcacagcg gcgacatcgc ctactgggac gaggacgagc acttcttcat cgtggaccgg    240

ctgaagagcc tgatcaaata caagggctac caggtagccc cagccgaact ggagagcatc    300

ctgctgcaac accccaacat cttcgacgcc ggggtcgccg gcctgcccga cgacgatgcc    360

ggcgagctgc ccgccgcagt cgtcgtgctg gaacacggta aaaccatgac cgagaaggag    420

atcgtggact atgtggccag ccaggttaca accgccaaga agctgcgcgg tggtgttgtg    480

ttcgtggacg aggtgcctaa aggactgacc ggcaagttgg acgcccgcaa gatccgcgag    540

attctcattc aggccaagaa gggatccatc gcaggttgtg gcgatgccgg cgaaggtatg    600

tatgaaagct ttattgagtc actgccattc cttaaatctt tggagttttc tgcacgcctg    660

aaagtagtag atgtgatagg caccaaagta tacaacgatg gagaacaaat cattgctcag    720

ggagattcgg ctgattcttt tttcattatt gaatctggag aagtgaaaat tactatgaaa    780

agaaagggta aatcagaagt ggaagagaat ggtgcagtag aaatcgctcg atgctcgcgg    840

ggacagtact ttggagagct tgccctggta actaacaaac ctcgagcagc ttctgcccac    900

gccattggga ctgtcaaatg tttagcaatg gatgtgcaag catttgaaag gcttctggga    960

ccttgcatgg aaattatgaa aaggaacatc gctacctatg aagaacagtt agttgccctg   1020

tatggaacga acatggatat tgtagccaaa aacattaaga agggcccagc gccattctac   1080

ccactcgaag acgggaccgc cggcgagcag ctgcacaaag ccatgaagcg ctacgccctg   1140

gtgcccggca ccatcgcctt taccgacgca catatcgagg tggacattac ctacgccgag   1200

tacttcgaga tgagcgttcg gctggcagaa gctatgaagc gctatgggct gaatacaaac   1260

catcggatcg tggtgtgcag cgagaatagc ttgcagttct tcatgcccgt gttgggtgcc   1320

ctgttcatcg gtgtggctgt ggccccagct aacgacatct acaacgagcg cgagctgctg   1380

aacagcatgg gcatcagcca gcccaccgtc gtattcgtga gcaagaaagg gctgcaaaag   1440

atcctcaacg tgcaaaagaa gctaccgatc atacaaaaga tcatcatcat ggatagcaag   1500

accgactacc agggcttcca aagcatgtac accttcgtga cttcccattt gccacccggc   1560

ttcaacgagt acgacttcgt gcccgagagc ttcgaccggg acaaaaccat cgccctgatc   1620

atgaacagta gtggcagtac cggattgccc aagggcgtag ccctaccgca ccgcaccgct   1680

tgtgtccgat tcagtcatgc ccgcgacccc atcttcggca accagatcat ccccgacacc   1740

gctatcctca gcgtggtgcc atttcaccac ggcttcggca tgttcaccac gctgggctac   1800

ttgatctgcg gctttcgggt cgtgctcatg taccgcttcg aggaggagct attcttgcgc   1860

agcttgcaag actataagat tcaatctgcc ctgctggtgc ccacactatt tagcttcttc   1920

gctaagagca ctctcatcga caagtacgac ctaagcaact tgcacgagat cgccagcggc   1980

ggggcgccgc tcagcaagga ggtaggtgag gccgtggcca aacgcttcca cctaccaggc   2040

atccgccagg gctacggcct gacagaaaca accagcgcca ttctgatcac tccagaaggg   2100

gtt                                                                 2103
```

<210> SEQ ID NO 79
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 79

```
Met Pro Gly Ala Val Gly Lys Val Val Pro Phe Ile Glu Ala Lys Val
 1               5                  10                  15
```

```
Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Phe Val Asp Glu Val Pro Lys Gly Leu Thr Gly Lys Leu Asp Ala Arg
                165                 170                 175

Lys Ile Arg Glu Ile Leu Ile Gln Ala Lys Lys Gly Ser Ile Ala Gly
            180                 185                 190

Cys Gly Asp Ala Gly Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Tyr Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430
```

```
Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700
```

<210> SEQ ID NO 80
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 80

```
atgcctggcg cagtaggcaa ggtggtgccc ttcatcgagg ctaaggtggt ggacttggac      60

accggtaaga cactgggtgt gaaccagcgc ggcgagctgt gcgtccgtgg ccccatgatc     120

atgagcggct acgttaacaa ccccgaggct acaaacgctc tcatcgacaa ggacggctgg     180

ctgcacagcg gcgacatcgc ctactgggac gaggacgagc acttcttcat cgtggaccgg     240

ctgaagagcc tgatcaaata caagggctac caggtagccc cagccgaact ggagagcatc     300

ctgctgcaac accccaacat cttcgacgcc ggggtcgccg gcctgcccga cgacgatgcc     360

ggcgagctgc ccgccgcagt cgtcgtgctg gaacacggta aaaccatgac cgagaaggag     420

atcgtggact atgtggccag ccaggttaca accgccaaga agctgcgcgg tggtgttgtg     480

ttagtggacg aggtgcctaa aggactgacc ggcaagttgg acgcccgcaa gatccgcgag     540
```

```
attctcattc aggccaagaa gggatccatc gcaggttgtg gcgatgccgg cgaaggtatg    600
tatgaaagct ttattgagtc actgccattc cttaaatctt tggagttttc tgcacgcctg    660
aaagtagtag atgtgatagg caccaaagta tacaacgatg gagaacaaat cattgctcag    720
ggagattcgg ctgattcttt tttcattatt gaatctggag aagtgaaaat tactatgaaa    780
agaaagggta aatcagaagt ggaagagaat ggtgcagtag aaatcgctcg atgctcgcgg    840
ggacagtact ttggagagct tgccctggta actaacaaac ctcgagcagc ttctgcccac    900
gccattggga ctgtcaaatg tttagcaatg gatgtgcaag catttgaaag gcttctggga    960
ccttgcatgg aaattatgaa aaggaacatc gctacctatg aagaacagtt agttgccctg   1020
tatggaacga acatggatat tgtagccaaa aacattaaga agggcccagc gccattctac   1080
ccactcgaag acgggaccgc cggcgagcag ctgcacaaag ccatgaagcg ctacgccctg   1140
gtgcccggca ccatcgcctt taccgacgca catatcgagg tggacattac ctacgccgag   1200
tacttcgaga tgagcgttcg gctggcagaa gctatgaagc gctatgggct gaatacaaac   1260
catcggatcg tggtgtgcag cgagaatagc ttgcagttct tcatgcccgt gttgggtgcc   1320
ctgttcatcg gtgtggctgt ggccccagct aacgacatct acaacgagcg cgagctgctg   1380
aacagcatgg gcatcagcca gcccaccgtc gtattcgtga gcaagaaagg gctgcaaaag   1440
atcctcaacg tgcaaaagaa gctaccgatc atacaaaaga tcatcatcat ggatagcaag   1500
accgactacc agggcttcca aagcatgtac accttcgtga cttcccattt gccacccggc   1560
ttcaacgagt acgacttcgt gcccgagagc ttcgaccggg acaaaaccat cgccctgatc   1620
atgaacagta gtggcagtac cggattgccc aagggcgtag ccctaccgca ccgcaccgct   1680
tgtgtccgat tcagtcatgc ccgcgacccc atcttcggca accagatcat ccccgacacc   1740
gctatcctca gcgtggtgcc atttcaccac ggcttcggca tgttcaccac gctgggctac   1800
ttgatctgcg gctttcgggt cgtgctcatg taccgcttcg aggaggagct attcttgcgc   1860
agcttgcaag actataagat tcaatctgcc ctgctggtgc ccacactatt tagcttcttc   1920
gctaagagca ctctcatcga caagtacgac ctaagcaact tgcacgagat cgccagcggc   1980
ggggcgccgc tcagcaagga ggtaggtgag gccgtggcca aacgcttcca cctaccaggc   2040
atccgccagg gctacggcct gacagaaaca accagcgcca ttctgatcac tccagaaggg   2100
gtt                                                                 2103
```

<210> SEQ ID NO 81
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 81

```
Met Pro Gly Ala Val Gly Lys Val Val Pro Phe Ile Glu Ala Lys Val
 1               5                  10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80
```

```
Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Leu Val Asp Glu Val Pro Lys Gly Leu Thr Gly Lys Leu Asp Ala Arg
                165                 170                 175

Lys Ile Arg Glu Ile Leu Ile Gln Ala Lys Lys Gly Ser Ile Ala Gly
            180                 185                 190

Cys Gly Asp Ala Gly Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Tyr Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
```

```
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700
```

<210> SEQ ID NO 82
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 82

```
atgcctggcg cagtaggcaa ggtggtgccc ttcatcgagg ctaaggtggt ggacttggac     60

accggtaaga cactgggtgt gaaccagcgc ggcgagctgt gcgtccgtgg ccccatgatc    120

atgagcggct acgttaacaa ccccgaggct acaaacgctc tcatcgacaa ggacggctgg    180

ctgcacagcg gcgacatcgc ctactgggac gaggacgagc acttcttcat cgtggaccgg    240

ctgaagagcc tgatcaaata caagggctac caggtagccc cagccgaact ggagagcatc    300

ctgctgcaac accccaacat cttcgacgcc ggggtcgccg gcctgcccga cgacgatgcc    360

ggcgagctgc ccgccgcagt cgtcgtgctg gaacacggta aaaccatgac cgagaaggag    420

atcgtggact atgtggccag ccaggttaca accgccaaga agctgcgcgg tggtgttgtg    480

ttagtggacg aggtgcctaa aggactgacc ggcaagttgg acgcccgcaa gatccgcgag    540

attctcatta aggccaagaa gggatccatc gcaggttgtg gcgatgccgg cgaaggtatg    600

tatgaaagct ttattgagtc actgccattc cttaaatctt tggagttttc tgcacgcctg    660

aaagtagtag atgtgatagg caccaaagta tacaacgatg gagaacaaat cattgctcag    720

ggagattcgg ctgattcttt tttcattatt gaatctggag aagtgaaaat tactatgaaa    780

agaaagggta aatcagaagt ggaagagaat ggtgcagtag aaatcgctcg atgctcgcgg    840

ggacagtact ttggagagct tgccctggta actaacaaac ctcgagcagc ttctgcccac    900

gccattggga ctgtcaaatg tttagcaatg gatgtgcaag catttgaaag gcttctggga    960
```

```
ccttgcatgg aaattatgaa aaggaacatc gctacctatg aagaacagtt agttgccctg   1020

tatggaacga acatggatat tgtagccaaa aacattaaga agggcccagc gccattctac   1080

ccactcgaag acgggaccgc cggcgagcag ctgcacaaag ccatgaagcg ctacgccctg   1140

gtgcccggca ccatcgcctt taccgacgca catatcgagg tggacattac ctacgccgag   1200

tacttcgaga tgagcgttcg gctggcagaa gctatgaagc gctatgggct gaatacaaac   1260

catcggatcg tggtgtgcag cgagaatagc ttgcagttct tcatgcccgt gttgggtgcc   1320

ctgttcatcg gtgtggctgt ggccccagct aacgacatct acaacgagcg cgagctgctg   1380

aacagcatgg gcatcagcca gcccaccgtc gtattcgtga gcaagaaagg gctgcaaaag   1440

atcctcaacg tgcaaaagaa gctaccgatc atacaaaaga tcatcatcat ggatagcaag   1500

accgactacc agggcttcca aagcatgtac accttcgtga cttcccattt gccacccggc   1560

ttcaacgagt acgacttcgt gcccgagagc ttcgaccggg acaaaaccat cgccctgatc   1620

atgaacagta gtggcagtac cggattgccc aagggcgtag ccctaccgca ccgcaccgct   1680

tgtgtccgat tcagtcatgc ccgcgacccc atcttcggca accagatcat ccccgacacc   1740

gctatcctca gcgtggtgcc atttcaccac ggcttcggca tgttcaccac gctgggctac   1800

ttgatctgcg gctttcgggt cgtgctcatg taccgcttcg aggaggagct attcttgcgc   1860

agcttgcaag actataagat tcaatctgcc ctgctggtgc ccacactatt tagcttcttc   1920

gctaagagca ctctcatcga caagtacgac ctaagcaact tgcacgagat cgccagcggc   1980

ggggcgccgc tcagcaagga ggtaggtgag gccgtggcca aacgcttcca cctaccaggc   2040

atccgccagg gctacggcct gacagaaaca accagcgcca ttctgatcac tccagaaggg   2100

gtt                                                                 2103
```

```
<210> SEQ ID NO 83
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 83

Met Pro Gly Ala Val Gly Lys Val Val Pro Phe Ile Glu Ala Lys Val
 1               5                  10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
```

```
145                 150                 155                 160

Leu Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Ile Ala Gly
            180                 185                 190

Cys Gly Asp Ala Gly Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Tyr Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575
```

```
Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700
```

<210> SEQ ID NO 84
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 84

```
atgcctggcg cagtaggcaa ggtggtgccc ttcatcgagg ctaaggtggt ggacttggac     60

accggtaaga cactgggtgt gaaccagcgc ggcgagctgt gcgtccgtgg ccccatgatc    120

atgagcggct acgttaacaa ccccgaggct acaaacgctc tcatcgacaa ggacggctgg    180

ctgcacagcg gcgacatcgc ctactgggac gaggacgagc acttcttcat cgtggaccgg    240

ctgaagagcc tgatcaaata caagggctac caggtagccc cagccgaact ggagagcatc    300

ctgctgcaac accccaacat cttcgacgcc ggggtcgccg gcctgcccga cgacgatgcc    360

ggcgagctgc ccgccgcagt cgtcgtgctg gaacacggta aaaccatgac cgagaaggag    420

atcgtggact atgtggccag ccaggttaca accgccaaga agctgcgcgg tggtgttgtg    480

ttagtggacg aggtgcctaa aggactgacc ggcaagttgg acgcccgcaa gatccgcgag    540

attctcatta aggccaagaa gggatccatc gcaggttgtg gcgatgccgg cgaaggtatg    600

tatgaaagct ttattgagtc actgccattc cttaaatctt tggagttttc tgcacgcctg    660

aaagtagtag atgtgatagg caccaaagta tacaacgatg gagaacaaat cattgctcag    720

ggagattcgg ctgattcttt tttcattatt gaatctggag aagtgaaaat tactatgaaa    780

agaaagggta aatcagaagt ggaagagaat ggtgcagtag aaatcgctcg atgctcgcgg    840

ggacagtact ttggagagct tgccctggta actaacaaac ctcgagcagc ttctgcccac    900

gccattggga ctgtcaaatg tttagcaatg gatgtgcaag catttgaaag gcttctggga    960

ccttgcatgg aaattatgaa aaggaacatc gctacctatg aagaacagtt agttgccctg   1020

tttggaacga acatggatat tgtagccaaa aacattaaga agggcccagc gccattctac   1080

ccactcgaag acgggaccgc cggcgagcag ctgcacaaag ccatgaagcg ctacgccctg   1140

gtgcccggca ccatcgcctt taccgacgca catatcgagg tggacattac ctacgccgag   1200

tacttcgaga tgagcgttcg gctggcagaa gctatgaagc gctatgggct gaatacaaac   1260

catcggatcg tggtgtgcag cgagaatagc ttgcagttct tcatgcccgt gttgggtgcc   1320
```

```
ctgttcatcg gtgtggctgt ggccccagct aacgacatct acaacgagcg cgagctgctg   1380

aacagcatgg gcatcagcca gcccaccgtc gtattcgtga gcaagaaagg gctgcaaaag   1440

atcctcaacg tgcaaaagaa gctaccgatc atacaaaaga tcatcatcat ggatagcaag   1500

accgactacc agggcttcca aagcatgtac accttcgtga cttcccattt gccacccggc   1560

ttcaacgagt acgacttcgt gcccgagagc ttcgaccggg acaaaaccat cgccctgatc   1620

atgaacagta gtggcagtac cggattgccc aagggcgtag ccctaccgca ccgcaccgct   1680

tgtgtccgat tcagtcatgc ccgcgacccc atcttcggca accagatcat ccccgacacc   1740

gctatcctca gcgtggtgcc atttcaccac ggcttcggca tgttcaccac gctgggctac   1800

ttgatctgcg gctttcgggt cgtgctcatg taccgcttcg aggaggagct attcttgcgc   1860

agcttgcaag actataagat tcaatctgcc ctgctggtgc ccacactatt tagcttcttc   1920

gctaagagca ctctcatcga caagtacgac ctaagcaact tgcacgagat cgccagcggc   1980

ggggcgccgc tcagcaagga ggtaggtgag gccgtggcca aacgcttcca cctaccaggc   2040

atccgccagg gctacggcct gacagaaaca accagcgcca ttctgatcac tccagaaggg   2100

gtt                                                                 2103
```

<210> SEQ ID NO 85
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 85

```
Met Pro Gly Ala Val Gly Lys Val Val Pro Phe Ile Glu Ala Lys Val
1               5                   10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Leu Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Ile Ala Gly
            180                 185                 190

Cys Gly Asp Ala Gly Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220
```

```
Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Phe Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640
```

```
Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700


<210> SEQ ID NO 86
<211> LENGTH: 2102
<212> TYPE: DNA
<213> ORGANISM: Artificial Sequence
<220> FEATURE:
<223> OTHER INFORMATION: A synthetic oligonucleotide

<400> SEQUENCE: 86

atgcctggcg cagtaggcaa ggtggtgccc ttcatcgagg ctaaggtggt ggacttggac     60

accggtaaga cactgggtgt gaaccagcgc ggcgagctgt gcgtccgtgg ccccatgatc    120

atgagcggct acgttaacaa ccccgaggct acaaacgctc tcatcgacaa ggacggctgg    180

ctgcacagcg gcgacatcgc ctactgggac gaggacgagc acttcttcat cgtggaccgg    240

ctgaagagcc tgatcaaata caagggctac caggtagccc cagccgaact ggagagcatc    300

ctgctgcaac accccaacat cttcgacgcc ggggtcgccg gcctgcccga cgacgatgcc    360

ggcgagctgc ccgccgcagt cgtcgtgctg gaacacggta aaaccatgac cgagaaggag    420

atcgtggact atgtggccag ccaggttaca accgccaaga agctgcgcgg tggtgttgtg    480

ttagtggacg aggtgcctaa aggactgacc ggcaagttgg acgcccgcaa gatccgcgag    540

attctcattc aggccaagaa gggatccatc gcaggttgtg gcgatgccgg cgaaggtatg    600

tatgaaagct ttattgagtc actgccattc cttaaatctt tggagttttc tgcacgcctg    660

aaagtagtag atgtgatagg caccaaagta tacaacgatg gagaacaaat cattgctcag    720

ggagattcgg ctgattcttt tttcattatt gaatctggag aagtgaaaat tactatgaaa    780

agaaagggta aatcagaagt ggaagagaat ggtgcagtag aaatcgctcg atgctcgcgg    840

ggacagtact ttggagagct tgccctggta actaacaaac ctcgagcagc ttctgcccac    900

gccattggga ctgtcaaatg tttagcaatg gatgtgcaag catttgaaag gcttctggga    960

ccttgcatgg aaattatgaa aaggaacatc gctacctatg aagaacagtt agttgccctg   1020

tttggaacga acatggatat tgtagccaaa aacattaaga agggcccagc gccattctac   1080

ccactcgaag acgggaccgc cggcgagcag ctgcacaaag ccatgaagcg ctacgccctg   1140

gtgcccggca ccatcgcctt taccgacgca catatcgagg tggacattac ctacgccgag   1200

tacttcgaga tgagcgttcg gctggcagaa gctatgaagc gctatgggct gaatacaaac   1260

catcggatcg tggtgtgcag cgagaatagc ttgcagttct tcatgcccgt gttgggtgcc   1320

ctgttcatcg gtgtggctgt ggccccagct aacgacatct acaacgagcg cgagctgctg   1380

aacagcatgg gcatcagcca gcccaccgtc gtattcgtga gcaagaaagg gctgcaaaag   1440

atcctcaacg tgcaaaagaa gctaccgatc atacaaaaga tcatcatcat ggatagcaag   1500

accgactacc agggcttcca aagcatgtac accttcgtga cttcccattt gccacccggc   1560

ttcaacgagt acgacttcgt gcccgagagc ttcgaccggg acaaaaccat cgccctgatc   1620

atgaacagta gtggcagtac cggattgccc aagggcgtag ccctaccgca ccgcaccgct   1680

tgtgtccgat tcagtcatgc ccgcgacccc atcttcggca accagatcat ccccgacacc   1740
```

```
gctatcctca gcgtggtgcc atttcaccac ggcttcggca tgttcaccac gctgggctac   1800

ttgatctgcg gctttcgggt cgtgctcatg taccgcttcg aggaggagct attcttgcgc   1860

agcttgcaag actataagat tcaatctgcc ctgctggtgc ccacactatt tagcttcttc   1920

gctaagagca ctctcatcga caagtacgac ctaagcaact tgcacgagat cgccagcggc   1980

ggggcgccgc tcagcaagga ggtaggtgag gccgtggcca aacgcttcca cctaccaggc   2040

atccgccagg gctacggcct gacagaaaca accagcgcca ttctgatcac tccagaaggg   2100

gt                                                                  2102


<210> SEQ ID NO 87
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 87

Met Pro Gly Ala Val Gly Lys Val Val Pro Phe Ile Glu Ala Lys Val
1               5                   10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Leu Val Asp Glu Val Pro Lys Gly Leu Thr Gly Lys Leu Asp Ala Arg
                165                 170                 175

Lys Ile Arg Glu Ile Leu Ile Gln Ala Lys Lys Gly Ser Ile Ala Gly
            180                 185                 190

Cys Gly Asp Ala Gly Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285
```

```
Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Phe Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700
```

<210> SEQ ID NO 88
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 88
atgcctggcg cagtaggcaa ggtggtgccc ttcttcgagg ctaaggtggt ggacttggac 60
accggtaaga cactgggtgt gaaccagcgc ggcgagctgt gcgtccgtgg ccccatgatc 120
atgagcggct acgttaacaa ccccgaggct acaaacgctc tcatcgacaa ggacggctgg 180
ctgcacagcg gcgacatcgc ctactgggac gaggacgagc acttcttcat cgtggaccgg 240
ctgaagagcc tgatcaaata caagggctac caggtagccc cagccgaact ggagagcatc 300
ctgctgcaac accccaacat cttcgacgcc ggggtcgccg gcctgcccga cgacgatgcc 360
ggcgagctgc ccgccgcagt cgtcgtgctg gaacacggta aaaccatgac cgagaaggag 420
atcgtggact atgtggccag ccaggttaca accgccaaga agctgcgcgg tggtgttgtg 480
ttagtggacg aggtgcctaa aggactgacc ggcaagttgg acgcccgcaa gatccgcgag 540
attctcattc aggccaagaa gggatccatc gcaggttgtg gcgatgccgg cgaaggtatg 600
tatgaaagct ttattgagtc actgccattc cttaaatctt tggagttttc tgcacgcctg 660
aaagtagtag atgtgatagg caccaaagta tacaacgatg gagaacaaat cattgctcag 720
ggagattcgg ctgattcttt tttcattatt gaatctggag aagtgaaaat tactatgaaa 780
agaaagggta aatcagaagt ggaagagaat ggtgcagtag aaatcgctcg atgctcgcgg 840
ggacagtact ttggagagct tgccctggta actaacaaac ctcgagcagc ttctgcccac 900
gccattggga ctgtcaaatg tttagcaatg gatgtgcaag catttgaaag gcttctggga 960
ccttgcatgg aaattatgaa aaggaacatc gctacctatg aagaacagtt agttgccctg 1020
tatggaacga acatggatat tgtagccaaa aacattaaga agggcccagc gccattctac 1080
ccactcgaag acgggaccgc cggcgagcag ctgcacaaag ccatgaagcg ctacgccctg 1140
gtgcccggca ccatcgcctt taccgacgca catatcgagg tggacattac ctacgccgag 1200
tacttcgaga tgagcgttcg gctggcagaa gctatgaagc gctatgggct gaatacaaac 1260
catcggatcg tggtgtgcag cgagaatagc ttgcagttct tcatgcccgt gttgggtgcc 1320
ctgttcatcg gtgtggctgt ggccccagct aacgacatct acaacgagcg cgagctgctg 1380
aacagcatgg gcatcagcca gcccaccgtc gtattcgtga gcaagaaagg gctgcaaaag 1440
atcctcaacg tgcaaaagaa gctaccgatc atacaaaaga tcatcatcat ggatagcaag 1500
accgactacc agggcttcca aagcatgtac accttcgtga cttcccattt gccacccggc 1560
ttcaacgagt acgacttcgt gcccgagagc ttcgaccggg acaaaaccat cgccctgatc 1620
atgaacagta gtggcagtac cggattgccc aagggcgtag ccctaccgca ccgcaccgct 1680
tgtgtccgat tcagtcatgc ccgcgacccc atcttcggca accagatcat ccccgacacc 1740
gctatcctca gcgtggtgcc atttcaccac ggcttcggca tgttcaccac gctgggctac 1800
ttgatctgcg gctttcgggt cgtgctcatg taccgcttcg aggaggagct attcttgcgc 1860
agcttgcaag actataagat tcaatctgcc ctgctggtgc ccacactatt tagcttcttc 1920
gctaagagca ctctcatcga caagtacgac ctaagcaact tgcacgagat cgccagcggc 1980
ggggcgccgc tcagcaagga ggtaggtgag gccgtggcca aacgcttcca cctaccaggc 2040
atccgccagg gctacggcct gacagaaaca accagcgcca ttctgatcac tccagaaggg 2100
gtt 2103

<210> SEQ ID NO 89
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 89

Met Pro Gly Ala Val Gly Lys Val Val Pro Phe Phe Glu Ala Lys Val
1 5 10 15

Val Asp Leu Asp Thr Gly Lys Thr Leu Gly Val Asn Gln Arg Gly Glu
20 25 30

Leu Cys Val Arg Gly Pro Met Ile Met Ser Gly Tyr Val Asn Asn Pro
35 40 45

Glu Ala Thr Asn Ala Leu Ile Asp Lys Asp Gly Trp Leu His Ser Gly
50 55 60

Asp Ile Ala Tyr Trp Asp Glu Asp Glu His Phe Phe Ile Val Asp Arg
65 70 75 80

Leu Lys Ser Leu Ile Lys Tyr Lys Gly Tyr Gln Val Ala Pro Ala Glu
85 90 95

Leu Glu Ser Ile Leu Leu Gln His Pro Asn Ile Phe Asp Ala Gly Val
100 105 110

Ala Gly Leu Pro Asp Asp Asp Ala Gly Glu Leu Pro Ala Ala Val Val
115 120 125

Val Leu Glu His Gly Lys Thr Met Thr Glu Lys Glu Ile Val Asp Tyr
130 135 140

Val Ala Ser Gln Val Thr Thr Ala Lys Lys Leu Arg Gly Gly Val Val
145 150 155 160

Leu Val Asp Glu Val Pro Lys Gly Leu Thr Gly Lys Leu Asp Ala Arg
165 170 175

Lys Ile Arg Glu Ile Leu Ile Gln Ala Lys Lys Gly Ser Ile Ala Gly
180 185 190

Cys Gly Asp Ala Gly Glu Gly Met Tyr Glu Ser Phe Ile Glu Ser Leu
195 200 205

Pro Phe Leu Lys Ser Leu Glu Phe Ser Ala Arg Leu Lys Val Val Asp
210 215 220

Val Ile Gly Thr Lys Val Tyr Asn Asp Gly Glu Gln Ile Ile Ala Gln
225 230 235 240

Gly Asp Ser Ala Asp Ser Phe Phe Ile Ile Glu Ser Gly Glu Val Lys
245 250 255

Ile Thr Met Lys Arg Lys Gly Lys Ser Glu Val Glu Glu Asn Gly Ala
260 265 270

Val Glu Ile Ala Arg Cys Ser Arg Gly Gln Tyr Phe Gly Glu Leu Ala
275 280 285

Leu Val Thr Asn Lys Pro Arg Ala Ala Ser Ala His Ala Ile Gly Thr
290 295 300

Val Lys Cys Leu Ala Met Asp Val Gln Ala Phe Glu Arg Leu Leu Gly
305 310 315 320

Pro Cys Met Glu Ile Met Lys Arg Asn Ile Ala Thr Tyr Glu Glu Gln
325 330 335

Leu Val Ala Leu Tyr Gly Thr Asn Met Asp Ile Val Ala Lys Asn Ile
340 345 350

Lys Lys Gly Pro Ala Pro Phe Tyr Pro Leu Glu Asp Gly Thr Ala Gly

```
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700


<210> SEQ ID NO 90
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 90

atgcctggcg cagtaggcaa ggtggtgccc ttcttcgagg ctaaggtggt ggacttggac      60

accggtaaga cactgggtgt gaaccagcgc ggcgagctgt gcgtccgtgg ccccatgatc     120
```

-continued

```
atgagcggct acgttaacaa ccccgaggct acaaacgctc tcatcgacaa ggacggctgg    180
ctgcacagcg gcgacatcgc ctactgggac gaggacgagc acttcttcat cgtggaccgg    240
ctgaagagcc tgatcaaata caagggctac caggtagccc cagccgaact ggagagcatc    300
ctgctgcaac accccaacat cttcgacgcc ggggtcgccg gcctgcccga cgacgatgcc    360
ggcgagctgc ccgccgcagt cgtcgtgctg gaacacggta aaaccatgac cgagaaggag    420
atcgtggact atgtggccag ccaggttaca accgccaaga agctgcgcgg tggtgttgtg    480
ttcgtggacg aggtgcctaa aggactgacc ggcaagttgg acgcccgcaa gatccgcgag    540
attctcattc aggccaagaa gggatccatc gcaggttgtg gcgatgccgg cgaaggtatg    600
tatgaaagct ttattgagtc actgccattc cttaaatctt tggagttttc tgcacgcctg    660
aaagtagtag atgtgatagg caccaaagta tacaacgatg gagaacaaat cattgctcag    720
ggagattcgg ctgattcttt tttcattatt gaatctggag aagtgaaaat tactatgaaa    780
agaaagggta aatcagaagt ggaagagaat ggtgcagtag aaatcgctcg atgctcgcgg    840
ggacagtact ttggagagct tgccctggta actaacaaac ctcgagcagc ttctgcccac    900
gccattggga ctgtcaaatg tttagcaatg gatgtgcaag catttgaaag gcttctggga    960
ccttgcatgg aaattatgaa aaggaacatc gctacctatg aagaacagtt agttgccctg   1020
tatggaacga acatggatat tgtagccaaa aacattaaga agggcccagc gccattctac   1080
ccactcgaag acgggaccgc cggcgagcag ctgcacaaag ccatgaagcg ctacgccctg   1140
gtgcccggca ccatcgcctt taccgacgca catatcgagg tggacattac ctacgccgag   1200
tacttcgaga tgagcgttcg gctggcagaa gctatgaagc gctatgggct gaatacaaac   1260
catcggatcg tggtgtgcag cgagaatagc ttgcagttct tcatgcccgt gttgggtgcc   1320
ctgttcatcg gtgtggctgt ggccccagct aacgacatct acaacgagcg cgagctgctg   1380
aacagcatgg gcatcagcca gcccaccgtc gtattcgtga gcaagaaagg gctgcaaaag   1440
atcctcaacg tgcaaaagaa gctaccgatc atacaaaaga tcatcatcat ggatagcaag   1500
accgactacc agggcttcca aagcatgtac accttcgtga cttcccattt gccacccggc   1560
ttcaacgagt acgacttcgt gcccgagagc ttcgaccggg acaaaaccat cgccctgatc   1620
atgaacagta gtggcagtac cggattgccc aagggcgtag ccctaccgca ccgcaccgct   1680
tgtgtccgat tcagtcatgc ccgcgacccc atcttcggca accagatcat ccccgacacc   1740
gctatcctca gcgtggtgcc atttcaccac ggcttcggca tgttcaccac gctgggctac   1800
ttgatctgcg gctttcgggt cgtgctcatg taccgcttcg aggaggagct attcttgcgc   1860
agcttgcaag actataagat tcaatctgcc ctgctggtgc ccacactatt tagcttcttc   1920
gctaagagca ctctcatcga caagtacgac ctaagcaact tgcacgagat cgccagcggc   1980
ggggcgccgc tcagcaagga ggtaggtgag gccgtggcca aacgcttcca cctaccaggc   2040
atccgccagg gctacggcct gacagaaaca accagcgcca ttctgatcac tccagaaggg   2100
gtt                                                                 2103
```

<210> SEQ ID NO 91
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 91

Met Pro Gly Ala Val Gly Lys Val Val Pro Phe Phe Glu Ala Lys Val

-continued

```
1               5                   10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Phe Val Asp Glu Val Pro Lys Gly Leu Thr Gly Lys Leu Asp Ala Arg
                165                 170                 175

Lys Ile Arg Glu Ile Leu Ile Gln Ala Lys Lys Gly Ser Ile Ala Gly
            180                 185                 190

Cys Gly Asp Ala Gly Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Tyr Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430
```

```
Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700
```

<210> SEQ ID NO 92
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 92

```
atgcctggcg cagtaggcaa ggtggtgccc ttcatcgagg ctaaggtggt ggacttggac     60

accggtaaga cactgggtgt gaaccagcgc ggcgagctgt gcgtccgtgg ccccatgatc    120

atgagcggct acgttaacaa ccccgaggct acaaacgctc tcatcgacaa ggacggctgg    180

ctgcacagcg gcgacatcgc ctactgggac gaggacgagc acttcttcat cgtggaccgg    240

ctgaagagcc tgatcaaata caagggctac caggtagccc cagccgaact ggagagcatc    300

ctgctgcaac accccaacat cttcgacgcc ggggtcgccg gcctgcccga cgacgatgcc    360

ggcgagctgc ccgccgcagt cgtcgtgctg gaacacggta aaaccatgac cgagaaggag    420

atcgtggact atgtggccag ccaggttaca accgccaaga agctgcgcgg tggtgttgtg    480

ttcgtggacg aggtgcctaa aggactgacc ggcaagttgg acgcccgcaa gatccgcgag    540
```

```
attctcatta aggccaagaa gggatccatc gcaggttgtg gcgatgccgg cgaaggtatg    600
tatgaaagct ttattgagtc actgccattc cttaaatctt tggagttttc tgcacgcctg    660
aaagtagtag atgtgatagg caccaaagta tacaacgatg gagaacaaat cattgctcag    720
ggagattcgg ctgattcttt tttcattatt gaatctggag aagtgaaaat tactatgaaa    780
agaaagggta aatcagaagt ggaagagaat ggtgcagtag aaatcgctcg atgctcgcgg    840
ggacagtact ttggagagct tgccctggta actaacaaac ctcgagcagc ttctgcccac    900
gccattggga ctgtcaaatg tttagcaatg gatgtgcaag catttgaaag gcttctggga    960
ccttgcatgg aaattatgaa aaggaacatc gctacctatg aagaacagtt agttgccctg   1020
tttggaacga acatggatat tgtagccaaa aacattaaga agggcccagc gccattctac   1080
ccactcgaag acgggaccgc cggcgagcag ctgcacaaag ccatgaagcg ctacgccctg   1140
gtgcccggca ccatcgcctt taccgacgca catatcgagg tggacattac ctacgccgag   1200
tacttcgaga tgagcgttcg gctggcagaa gctatgaagc gctatgggct gaatacaaac   1260
catcggatcg tggtgtgcag cgagaatagc ttgcagttct tcatgcccgt gttgggtgcc   1320
ctgttcatcg gtgtggctgt ggccccagct aacgacatct acaacgagcg cgagctgctg   1380
aacagcatgg gcatcagcca gcccaccgtc gtattcgtga gcaagaaagg gctgcaaaag   1440
atcctcaacg tgcaaaagaa gctaccgatc atacaaaaga tcatcatcat ggatagcaag   1500
accgactacc agggcttcca aagcatgtac accttcgtga cttcccattt gccacccggc   1560
ttcaacgagt acgacttcgt gcccgagagc ttcgaccggg acaaaaccat cgccctgatc   1620
atgaacagta gtggcagtac cggattgccc aagggcgtag ccctaccgca ccgcaccgct   1680
tgtgtccgat tcagtcatgc ccgcgacccc atcttcggca accagatcat ccccgacacc   1740
gctatcctca gcgtggtgcc atttcaccac ggcttcggca tgttcaccac gctgggctac   1800
ttgatctgcg gctttcgggt cgtgctcatg taccgcttcg aggaggagct attcttgcgc   1860
agcttgcaag actataagat tcaatctgcc ctgctggtgc ccacactatt tagcttcttc   1920
gctaagagca ctctcatcga caagtacgac ctaagcaact tgcacgagat cgccagcggc   1980
ggggcgccgc tcagcaagga ggtaggtgag gccgtggcca aacgcttcca cctaccaggc   2040
atccgccagg gctacggcct gacagaaaca accagcgcca ttctgatcac tccagaaggg   2100
gtt                                                                 2103
```

<210> SEQ ID NO 93
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 93

```
Met Pro Gly Ala Val Gly Lys Val Val Pro Phe Ile Glu Ala Lys Val
 1               5                  10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80
```

```
Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Phe Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Ile Ala Gly
            180                 185                 190

Cys Gly Asp Ala Gly Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Phe Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495
```

```
Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700
```

<210> SEQ ID NO 94
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 94

```
atgcctggcg cagtaggcaa ggtggtgccc ttcttcgagg ctaaggtggt ggacttggac      60

accggtaaga cactgggtgt gaaccagcgc ggcgagctgt gcgtccgtgg ccccatgatc     120

atgagcggct acgttaacaa ccccgaggct acaaacgctc tcatcgacaa ggacggctgg     180

ctgcacagcg gcgacatcgc ctactgggac gaggacgagc acttcttcat cgtggaccgg     240

ctgaagagcc tgatcaaata caagggctac caggtagccc cagccgaact ggagagcatc     300

ctgctgcaac accccaacat cttcgacgcc ggggtcgccg gcctgcccga cgacgatgcc     360

ggcgagctgc ccgccgcagt cgtcgtgctg gaacacggta aaaccatgac cgagaaggag     420

atcgtggact atgtggccag ccaggttaca accgccaaga agctgcgcgg tggtgttgtg     480

ttagtggacg aggtgcctaa aggactgacc ggcaagttgg acgcccgcaa gatccgcgag     540

attctcatta aggccaagaa gggatccatc gcaggttgtg gcgatgccgg cgaaggtatg     600

tatgaaagct ttattgagtc actgccattc cttaaatctt tggagttttc tgcacgcctg     660

aaagtagtag atgtgatagg caccaaagta tacaacgatg gagaacaaat cattgctcag     720

ggagattcgg ctgattcttt tttcattatt gaatctggag aagtgaaaat tactatgaaa     780

agaaagggta aatcagaagt ggaagagaat ggtgcagtag aaatcgctcg atgctcgcgg     840

ggacagtact ttggagagct tgccctggta actaacaaac ctcgagcagc ttctgcccac     900
```

```
gccattggga ctgtcaaatg tttagcaatg gatgtgcaag catttgaaag gcttctggga    960

ccttgcatgg aaattatgaa aaggaacatc gctacctatg aagaacagtt agttgccctg   1020

tttggaacga acatggatat tgtagccaaa aacattaaga agggcccagc gccattctac   1080

ccactcgaag acgggaccgc cggcgagcag ctgcacaaag ccatgaagcg ctacgccctg   1140

gtgcccggca ccatcgcctt taccgacgca catatcgagg tggacattac ctacgccgag   1200

tacttcgaga tgagcgttcg gctggcagaa gctatgaagc gctatgggct gaatacaaac   1260

catcggatcg tggtgtgcag cgagaatagc ttgcagttct tcatgcccgt gttgggtgcc   1320

ctgttcatcg gtgtggctgt ggccccagct aacgacatct acaacgagcg cgagctgctg   1380

aacagcatgg gcatcagcca gcccaccgtc gtattcgtga gcaagaaagg gctgcaaaag   1440

atcctcaacg tgcaaaagaa gctaccgatc atacaaaaga tcatcatcat ggatagcaag   1500

accgactacc agggcttcca aagcatgtac accttcgtga cttcccattt gccacccggc   1560

ttcaacgagt acgacttcgt gcccgagagc ttcgaccggg acaaaaccat cgccctgatc   1620

atgaacagta gtggcagtac cggattgccc aagggcgtag ccctaccgca ccgcaccgct   1680

tgtgtccgat tcagtcatgc ccgcgacccc atcttcggca accagatcat ccccgacacc   1740

gctatcctca gcgtggtgcc atttcaccac ggcttcggca tgttcaccac gctgggctac   1800

ttgatctgcg gctttcgggt cgtgctcatg taccgcttcg aggaggagct attcttgcgc   1860

agcttgcaag actataagat tcaatctgcc ctgctggtgc ccacactatt tagcttcttc   1920

gctaagagca ctctcatcga caagtacgac ctaagcaact tgcacgagat cgccagcggc   1980

ggggcgccgc tcagcaagga ggtaggtgag gccgtggcca aacgcttcca cctaccaggc   2040

atccgccagg gctacggcct gacagaaaca accagcgcca ttctgatcac tccagaaggg   2100

gtt                                                                 2103
```

```
<210> SEQ ID NO 95
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 95

Met Pro Gly Ala Val Gly Lys Val Val Pro Phe Phe Glu Ala Lys Val
1               5                   10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140
```

```
Val Ala Ser Gln Val Thr Thr Ala Lys Lys Leu Arg Gly Gly Val Val
145                 150                 155                 160

Leu Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Ile Ala Gly
            180                 185                 190

Cys Gly Asp Ala Gly Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Phe Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
```

```
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700


<210> SEQ ID NO 96
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 96

atgcctggcg cagtaggcaa ggtggtgccc ttcttcgagg ctaaggtggt ggacttggac      60

accggtaaga cactgggtgt gaaccagcgc ggcgagctgt gcgtccgtgg ccccatgatc     120

atgagcggct acgttaacaa ccccgaggct acaaacgctc tcatcgacaa ggacggctgg     180

ctgcacagcg gcgacatcgc ctactgggac gaggacgagc acttcttcat cgtggaccgg     240

ctgaagagcc tgatcaaata caagggctac caggtagccc cagccgaact ggagagcatc     300

ctgctgcaac accccaacat cttcgacgcc ggggtcgccg gcctgcccga cgacgatgcc     360

ggcgagctgc ccgccgcagt cgtcgtgctg gaacacggta aaaccatgac cgagaaggag     420

atcgtggact atgtggccag ccaggttaca accgccaaga agctgcgcgg tggtgttgtg     480

ttcgtggacg aggtgcctaa aggactgacc ggcaagttgg acgcccgcaa gatccgcgag     540

attctcattc aggccaagaa gggatccatc gcaggttgtg gcgatgccgg cgaaggtatg     600

tatgaaagct ttattgagtc actgccattc cttaaatctt tggagttttc tgcacgcctg     660

aaagtagtag atgtgatagg caccaaagta tacaacgatg gagaacaaat cattgctcag     720

ggagattcgg ctgattcttt tttcattatt gaatctggag aagtgaaaat tactatgaaa     780

agaaagggta aatcagaagt ggaagagaat ggtgcagtag aaatcgctcg atgctcgcgg     840

ggacagtact ttggagagct tgccctggta actaacaaac ctcgagcagc ttctgcccac     900

gccattggga ctgtcaaatg tttagcaatg gatgtgcaag catttgaaag gcttctggga     960

ccttgcatgg aaattatgaa aaggaacatc gctacctatg aagaacagtt agttgccctg    1020

tttggaacga acatggatat tgtagccaaa aacattaaga agggcccagc gccattctac    1080

ccactcgaag acgggaccgc cggcgagcag ctgcacaaag ccatgaagcg ctacgccctg    1140

gtgcccggca ccatcgcctt taccgacgca catatcgagg tggacattac ctacgccgag    1200

tacttcgaga tgagcgttcg gctggcagaa gctatgaagc gctatgggct gaatacaaac    1260

catcggatcg tggtgtgcag cgagaatagc ttgcagttct tcatgcccgt gttgggtgcc    1320
```

```
ctgttcatcg gtgtggctgt ggccccagct aacgacatct acaacgagcg cgagctgctg   1380

aacagcatgg gcatcagcca gcccaccgtc gtattcgtga gcaagaaagg gctgcaaaag   1440

atcctcaacg tgcaaaagaa gctaccgatc atacaaaaga tcatcatcat ggatagcaag   1500

accgactacc agggcttcca aagcatgtac accttcgtga cttcccattt gccacccggc   1560

ttcaacgagt acgacttcgt gcccgagagc ttcgaccggg acaaaaccat cgccctgatc   1620

atgaacagta gtggcagtac cggattgccc aagggcgtag ccctaccgca ccgcaccgct   1680

tgtgtccgat tcagtcatgc ccgcgacccc atcttcggca accagatcat ccccgacacc   1740

gctatcctca gcgtggtgcc atttcaccac ggcttcggca tgttcaccac gctgggctac   1800

ttgatctgcg gctttcgggt cgtgctcatg taccgcttcg aggaggagct attcttgcgc   1860

agcttgcaag actataagat tcaatctgcc ctgctggtgc ccacactatt tagcttcttc   1920

gctaagagca ctctcatcga caagtacgac ctaagcaact tgcacgagat cgccagcggc   1980

ggggcgccgc tcagcaagga ggtaggtgag gccgtggcca aacgcttcca cctaccaggc   2040

atccgccagg gctacggcct gacagaaaca accagcgcca ttctgatcac tccagaaggg   2100

gtt                                                                 2103
```

<210> SEQ ID NO 97
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 97

```
Met Pro Gly Ala Val Gly Lys Val Val Pro Phe Phe Glu Ala Lys Val
1               5                   10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Phe Val Asp Glu Val Pro Lys Gly Leu Thr Gly Lys Leu Asp Ala Arg
                165                 170                 175

Lys Ile Arg Glu Ile Leu Ile Gln Ala Lys Lys Gly Ser Ile Ala Gly
            180                 185                 190

Cys Gly Asp Ala Gly Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
```

```
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Phe Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640
```

```
Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700


<210> SEQ ID NO 98
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 98

atgcctggcg cagtaggcaa ggtggtgccc ttcttcgagg ctaaggtggt ggacttggac     60

accggtaaga cactgggtgt gaaccagcgc ggcgagctgt gcgtccgtgg ccccatgatc    120

atgagcggct acgttaacaa ccccgaggct acaaacgctc tcatcgacaa ggacggctgg    180

ctgcacagcg gcgacatcgc ctactgggac gaggacgagc acttcttcat cgtggaccgg    240

ctgaagagcc tgatcaaata caagggctac caggtagccc cagccgaact ggagagcatc    300

ctgctgcaac accccaacat cttcgacgcc ggggtcgccg gcctgcccga cgacgatgcc    360

ggcgagctgc ccgccgcagt cgtcgtgctg gaacacggta aaaccatgac cgagaaggag    420

atcgtggact atgtggccag ccaggttaca accgccaaga agctgcgcgg tggtgttgtg    480

ttcgtggacg aggtgcctaa aggactgacc ggcaagttgg acgcccgcaa gatccgcgag    540

attctcatta aggccaagaa gggatccatc gcaggttgtg gcgatgccgg cgaaggtatg    600

tatgaaagct ttattgagtc actgccattc cttaaatctt tggagttttc tgcacgcctg    660

aaagtagtag atgtgatagg caccaaagta tacaacgatg gagaacaaat cattgctcag    720

ggagattcgg ctgattcttt tttcattatt gaatctggag aagtgaaaat tactatgaaa    780

agaaagggta aatcagaagt ggaagagaat ggtgcagtag aaatcgctcg atgctcgcgg    840

ggacagtact ttggagagct tgccctggta actaacaaac ctcgagcagc ttctgcccac    900

gccattggga ctgtcaaatg tttagcaatg gatgtgcaag catttgaaag gcttctggga    960

ccttgcatgg aaattatgaa aaggaacatc gctacctatg aagaacagtt agttgccctg   1020

tatggaacga acatggatat tgtagccaaa aacattaaga agggcccagc gccattctac   1080

ccactcgaag acgggaccgc cggcgagcag ctgcacaaag ccatgaagcg ctacgccctg   1140

gtgcccggca ccatcgcctt taccgacgca catatcgagg tggacattac ctacgccgag   1200

tacttcgaga tgagcgttcg gctggcagaa gctatgaagc gctatgggct gaatacaaac   1260

catcggatcg tggtgtgcag cgagaatagc ttgcagttct tcatgcccgt gttgggtgcc   1320

ctgttcatcg gtgtggctgt ggccccagct aacgacatct acaacgagcg cgagctgctg   1380

aacagcatgg gcatcagcca gcccaccgtc gtattcgtga gcaagaaagg gctgcaaaag   1440

atcctcaacg tgcaaaagaa gctaccgatc atacaaaaga tcatcatcat ggatagcaag   1500

accgactacc agggcttcca aagcatgtac accttcgtga cttcccattt gccacccggc   1560

ttcaacgagt acgacttcgt gcccgagagc ttcgaccggg acaaaaccat cgccctgatc   1620

atgaacagta gtggcagtac cggattgccc aagggcgtag ccctaccgca ccgcaccgct   1680
```

```
tgtgtccgat tcagtcatgc ccgcgacccc atcttcggca accagatcat ccccgacacc   1740

gctatcctca gcgtggtgcc atttcaccac ggcttcggca tgttcaccac gctgggctac   1800

ttgatctgcg gctttcgggt cgtgctcatg taccgcttcg aggaggagct attcttgcgc   1860

agcttgcaag actataagat tcaatctgcc ctgctggtgc ccacactatt tagcttcttc   1920

gctaagagca ctctcatcga caagtacgac ctaagcaact tgcacgagat cgccagcggc   1980

ggggcgccgc tcagcaagga ggtaggtgag gccgtggcca aacgcttcca cctaccaggc   2040

atccgccagg gctacggcct gacagaaaca accagcgcca ttctgatcac tccagaaggg   2100

gtt                                                                 2103
```

<210> SEQ ID NO 99
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 99

```
Met Pro Gly Ala Val Gly Lys Val Val Pro Phe Phe Glu Ala Lys Val
1               5                   10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Phe Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Ile Ala Gly
            180                 185                 190

Cys Gly Asp Ala Gly Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285
```

```
Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Tyr Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700
```

<210> SEQ ID NO 100
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 100
atgcctggcg cagtaggcaa ggtggtgccc ttcttcgagg ctaaggtggt ggacttggac 60
accggtaaga cactgggtgt gaaccagcgc ggcgagctgt gcgtccgtgg ccccatgatc 120
atgagcggct acgttaacaa ccccgaggct acaaacgctc tcatcgacaa ggacggctgg 180
ctgcacagcg gcgacatcgc ctactgggac gaggacgagc acttcttcat cgtggaccgg 240
ctgaagagcc tgatcaaata caagggctac caggtagccc cagccgaact ggagagcatc 300
ctgctgcaac accccaacat cttcgacgcc ggggtcgccg gcctgcccga cgacgatgcc 360
ggcgagctgc ccgccgcagt cgtcgtgctg gaacacggta aaaccatgac cgagaaggag 420
atcgtggact atgtggccag ccaggttaca accgccaaga agctgcgcgg tggtgttgtg 480
ttagtggacg aggtgcctaa aggactgacc ggcaagttgg acgcccgcaa gatccgcgag 540
attctcatta aggccaagaa gggatccatc gcaggttgtg gcgatgccgg cgaaggtatg 600
tatgaaagct ttattgagtc actgccattc cttaaatctt tggagttttc tgcacgcctg 660
aaagtagtag atgtgatagg caccaaagta tacaacgatg gagaacaaat cattgctcag 720
ggagattcgg ctgattcttt tttcattatt gaatctggag aagtgaaaat tactatgaaa 780
agaaagggta aatcagaagt ggaagagaat ggtgcagtag aaatcgctcg atgctcgcgg 840
ggacagtact ttggagagct tgccctggta actaacaaac ctcgagcagc ttctgcccac 900
gccattggga ctgtcaaatg tttagcaatg gatgtgcaag catttgaaag gcttctggga 960
ccttgcatgg aaattatgaa aaggaacatc gctacctatg aagaacagtt agttgccctg 1020
tatggaacga acatggatat tgtagccaaa aacattaaga agggcccagc gccattctac 1080
ccactcgaag acgggaccgc cggcgagcag ctgcacaaag ccatgaagcg ctacgccctg 1140
gtgcccggca ccatcgcctt taccgacgca catatcgagg tggacattac ctacgccgag 1200
tacttcgaga tgagcgttcg gctggcagaa gctatgaagc gctatgggct gaatacaaac 1260
catcggatcg tggtgtgcag cgagaatagc ttgcagttct tcatgcccgt gttgggtgcc 1320
ctgttcatcg gtgtggctgt ggccccagct aacgacatct acaacgagcg cgagctgctg 1380
aacagcatgg gcatcagcca gcccaccgtc gtattcgtga gcaagaaagg gctgcaaaag 1440
atcctcaacg tgcaaaagaa gctaccgatc atacaaaaga tcatcatcat ggatagcaag 1500
accgactacc agggcttcca aagcatgtac accttcgtga cttcccattt gccacccggc 1560
ttcaacgagt acgacttcgt gcccgagagc ttcgaccggg acaaaaccat cgccctgatc 1620
atgaacagta gtggcagtac cggattgccc aagggcgtag ccctaccgca ccgcaccgct 1680
tgtgtccgat tcagtcatgc ccgcgacccc atcttcggca accagatcat ccccgacacc 1740
gctatcctca gcgtggtgcc atttcaccac ggcttcggca tgttcaccac gctgggctac 1800
ttgatctgcg gctttcgggt cgtgctcatg taccgcttcg aggaggagct attcttgcgc 1860
agcttgcaag actataagat tcaatctgcc ctgctggtgc ccacactatt tagcttcttc 1920
gctaagagca ctctcatcga caagtacgac ctaagcaact tgcacgagat cgccagcggc 1980
ggggcgccgc tcagcaagga ggtaggtgag gccgtggcca aacgcttcca cctaccaggc 2040
atccgccagg gctacggcct gacagaaaca accagcgcca ttctgatcac tccagaaggg 2100
gtt 2103

<210> SEQ ID NO 101
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 101

```
Met Pro Gly Ala Val Gly Lys Val Val Pro Phe Phe Glu Ala Lys Val
1               5                   10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Leu Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Ile Ala Gly
            180                 185                 190

Cys Gly Asp Ala Gly Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Tyr Gly Thr Asn Met Asp Ile Val Ala Lys Asn Ile
            340                 345                 350
```

```
Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700
```

<210> SEQ ID NO 102
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 102

```
atgcctggcg cagtaggcaa ggtggtgccc ttcttcgagg ctaaggtggt ggacttggac      60

accggtaaga cactgggtgt gaaccagcgc ggcgagctgt gcgtccgtgg ccccatgatc     120
```

```
atgagcggct acgttaacaa ccccgaggct acaaacgctc tcatcgacaa ggacggctgg    180
ctgcacagcg gcgacatcgc ctactgggac gaggacgagc acttcttcat cgtggaccgg    240
ctgaagagcc tgatcaaata caagggctac caggtagccc cagccgaact ggagagcatc    300
ctgctgcaac accccaacat cttcgacgcc ggggtcgccg gcctgcccga cgacgatgcc    360
ggcgagctgc ccgccgcagt cgtcgtgctg gaacacggta aaaccatgac cgagaaggag    420
atcgtggact atgtggccag ccaggttaca accgccaaga agctgcgcgg tggtgttgtg    480
ttagtggacg aggtgcctaa aggactgacc ggcaagttgg acgcccgcaa gatccgcgag    540
attctcattc aggccaagaa gggatccatc gcaggttgtg gcgatgccgg cgaaggtatg    600
tatgaaagct ttattgagtc actgccattc cttaaatctt tggagttttc tgcacgcctg    660
aaagtagtag atgtgatagg caccaaagta tacaacgatg gagaacaaat cattgctcag    720
ggagattcgg ctgattcttt tttcattatt gaatctggag aagtgaaaat tactatgaaa    780
agaaagggta aatcagaagt ggaagagaat ggtgcagtag aaatcgctcg atgctcgcgg    840
ggacagtact ttggagagct tgccctggta actaacaaac ctcgagcagc ttctgcccac    900
gccattggga ctgtcaaatg tttagcaatg gatgtgcaag catttgaaag gcttctggga    960
ccttgcatgg aaattatgaa aaggaacatc gctacctatg aagaacagtt agttgccctg   1020
tttggaacga acatggatat tgtagccaaa aacattaaga agggcccagc gccattctac   1080
ccactcgaag acgggaccgc cggcgagcag ctgcacaaag ccatgaagcg ctacgccctg   1140
gtgcccggca ccatcgcctt taccgacgca catatcgagg tggacattac ctacgccgag   1200
tacttcgaga tgagcgttcg gctggcagaa gctatgaagc gctatgggct gaatacaaac   1260
catcggatcg tggtgtgcag cgagaatagc ttgcagttct tcatgcccgt gttgggtgcc   1320
ctgttcatcg gtgtggctgt ggccccagct aacgacatct acaacgagcg cgagctgctg   1380
aacagcatgg gcatcagcca gcccaccgtc gtattcgtga gcaagaaagg gctgcaaaag   1440
atcctcaacg tgcaaaagaa gctaccgatc atacaaaaga tcatcatcat ggatagcaag   1500
accgactacc agggcttcca aagcatgtac accttcgtga cttcccattt gccacccggc   1560
ttcaacgagt acgacttcgt gcccgagagc ttcgaccggg acaaaaccat cgccctgatc   1620
atgaacagta gtggcagtac cggattgccc aagggcgtag ccctaccgca ccgcaccgct   1680
tgtgtccgat tcagtcatgc ccgcgacccc atcttcggca accagatcat ccccgacacc   1740
gctatcctca gcgtggtgcc atttcaccac ggcttcggca tgttcaccac gctgggctac   1800
ttgatctgcg gctttcgggt cgtgctcatg taccgcttcg aggaggagct attcttgcgc   1860
agcttgcaag actataagat tcaatctgcc ctgctggtgc ccacactatt tagcttcttc   1920
gctaagagca ctctcatcga caagtacgac ctaagcaact tgcacgagat cgccagcggc   1980
ggggcgccgc tcagcaagga ggtaggtgag gccgtggcca aacgcttcca cctaccaggc   2040
atccgccagg gctacggcct gacagaaaca accagcgcca ttctgatcac tccagaaggg   2100
gtt                                                                 2103
```

<210> SEQ ID NO 103
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 103

-continued

```
Met Pro Gly Ala Val Gly Lys Val Val Pro Phe Phe Glu Ala Lys Val
1               5                   10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Leu Val Asp Glu Val Pro Lys Gly Leu Thr Gly Lys Leu Asp Ala Arg
                165                 170                 175

Lys Ile Arg Glu Ile Leu Ile Gln Ala Lys Lys Gly Ser Ile Ala Gly
            180                 185                 190

Cys Gly Asp Ala Gly Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Phe Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
```

```
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700


<210> SEQ ID NO 104
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 104

atgcctggcg cagtaggcaa ggtggtgccc ttcttcgagg ctaaggtggt ggacttggac      60

accggtaaga cactgggtgt gaaccagcgc ggcgagctgt gcgtccgtgg ccccatgatc     120

atgagcggct acgttaacaa ccccgaggct acaaacgctc tcatcgacaa ggacggctgg     180

ctgcacagcg gcgacatcgc ctactgggac gaggacgagc acttcttcat cgtggaccgg     240

ctgaagagcc tgatcaaata caagggctac caggtagccc cagccgaact ggagagcatc     300

ctgctgcaac accccaacat cttcgacgcc ggggtcgccg gcctgcccga cgacgatgcc     360

ggcgagctgc ccgccgcagt cgtcgtgctg gaacacggta aaaccatgac cgagaaggag     420

atcgtggact atgtggccag ccaggttaca accgccaaga agctgcgcgg tggtgttgtg     480
```

```
ttcgtggacg aggtgcctaa aggactgacc ggcaagttgg acgcccgcaa gatccgcgag    540

attctcatta aggccaagaa gggatccatc gcaggttgtg gcgatgccgg cgaaggtatg    600

tatgaaagct ttattgagtc actgccattc cttaaatctt tggagttttc tgcacgcctg    660

aaagtagtag atgtgatagg caccaaagta tacaacgatg gagaacaaat cattgctcag    720

ggagattcgg ctgattcttt tttcattatt gaatctggag aagtgaaaat tactatgaaa    780

agaaagggta aatcagaagt ggaagagaat ggtgcagtag aaatcgctcg atgctcgcgg    840

ggacagtact ttggagagct tgccctggta actaacaaac ctcgagcagc ttctgcccac    900

gccattggga ctgtcaaatg tttagcaatg gatgtgcaag catttgaaag gcttctggga    960

ccttgcatgg aaattatgaa aaggaacatc gctacctatg aagaacagtt agttgccctg   1020

tttggaacga acatggatat tgtagccaaa aacattaaga agggcccagc gccattctac   1080

ccactcgaag acgggaccgc cggcgagcag ctgcacaaag ccatgaagcg ctacgccctg   1140

gtgcccggca ccatcgcctt taccgacgca catatcgagg tggacattac ctacgccgag   1200

tacttcgaga tgagcgttcg gctggcagaa gctatgaagc gctatgggct gaatacaaac   1260

catcggatcg tggtgtgcag cgagaatagc ttgcagttct tcatgcccgt gttgggtgcc   1320

ctgttcatcg gtgtggctgt ggccccagct aacgacatct acaacgagcg cgagctgctg   1380

aacagcatgg gcatcagcca gcccaccgtc gtattcgtga gcaagaaagg gctgcaaaag   1440

atcctcaacg tgcaaaagaa gctaccgatc atacaaaaga tcatcatcat ggatagcaag   1500

accgactacc agggcttcca aagcatgtac accttcgtga cttcccattt gccacccggc   1560

ttcaacgagt acgacttcgt gcccgagagc ttcgaccggg acaaaaccat cgccctgatc   1620

atgaacagta gtggcagtac cggattgccc aagggcgtag ccctaccgca ccgcaccgct   1680

tgtgtccgat tcagtcatgc ccgcgacccc atcttcggca accagatcat ccccgacacc   1740

gctatcctca gcgtggtgcc atttcaccac ggcttcggca tgttcaccac gctgggctac   1800

ttgatctgcg gctttcgggt cgtgctcatg taccgcttcg aggaggagct attcttgcgc   1860

agcttgcaag actataagat tcaatctgcc ctgctggtgc ccacactatt tagcttcttc   1920

gctaagagca ctctcatcga caagtacgac ctaagcaact tgcacgagat cgccagcggc   1980

ggggcgccgc tcagcaagga ggtaggtgag gccgtggcca aacgcttcca cctaccaggc   2040

atccgccagg gctacggcct gacagaaaca accagcgcca ttctgatcac tccagaaggg   2100

gtt                                                                 2103
```

<210> SEQ ID NO 105
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 105

```
Met Pro Gly Ala Val Gly Lys Val Val Pro Phe Phe Glu Ala Lys Val
 1               5                  10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
```

-continued

```
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Phe Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Ile Ala Gly
            180                 185                 190

Cys Gly Asp Ala Gly Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Phe Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495
```

```
Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700


<210> SEQ ID NO 106
<211> LENGTH: 550
<212> TYPE: PRT
<213> ORGANISM: Artificial Sequence
<220> FEATURE:
<223> OTHER INFORMATION: A synthetic polypeptide

<400> SEQUENCE: 106

Met Glu Asp Ala Lys Asn Ile Lys Lys Gly Pro Ala Pro Phe Tyr Pro
 1               5                  10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160
```

```
Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
    450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
    530                 535                 540

Gly Gly Lys Ile Ala Val
545                 550
```

<210> SEQ ID NO 107
<211> LENGTH: 2103

<212> TYPE: DNA
<213> ORGANISM: Artificial Sequence
<220> FEATURE:
<223> OTHER INFORMATION: A synthetic oligonucleotide

<400> SEQUENCE: 107

```
atgcctggcg cagtaggcaa ggtggtgccc ttcttcgagg ctaaggtggt ggacttggac     60

accggtaaga cactgggtgt gaaccagcgc ggcgagctgt gcgtccgtgg ccccatgatc    120

atgagcggct acgttaacaa ccccgaggct acaaacgctc tcatcgacaa ggacggctgg    180

ctgcacagcg gcgacatcgc ctactgggac gaggacgagc acttctacat cgtggaccgg    240

ctgaagagcc tgatcaaata caagggctac caggtagccc cagccgaact ggagagcatc    300

ctgctgcaac accccaacat cttcgacgcc ggggtcgccg gcctgcccga cgacgatgcc    360

ggcgagctgc ccgccgcagt cgtcgtgctg gaacacggta aaaccgtgac cgagaaggag    420

atcgtggact atgtggccag ccaggttaca accgccaaga agctgcgcgg tggtgttgtg    480

ttcgtggacg aggtgcctaa aggactgacc ggcaagttgg acgcccgcaa gatccgcgag    540

attctcatta aggccaagaa gggttccaat tgggattctg ggtgctccag agaatgtatg    600

tatgaaagct ttattgagtc actgccattc cttaaatctt tggagttttc tgcacgcctg    660

aaagtagtag atgtgatagg caccaaagta tacaacgatg gagaacaaat cattgctcag    720

ggagattcgg ctgattcttt tttcattatt gaatctggag aagtgaaaat tactatgaaa    780

agaaagggta aatcagaagt ggaagagaat ggtgcagtag aaatcgctcg atgctcgcgg    840

ggacagtact ttggagagct tgccctggta actaacaaac ctcgagcagc ttctgcccac    900

gccattggga ctgtcaaatg tttagcaatg gatgtgcaag catttgaaag gcttctggga    960

ccttgcatgg aaattatgaa aaggaacatc gctacctatg aagaacagtt agttgccctg   1020

tttggaacga acatggatat tgtagccaaa aacattaaga agggcccagc gccattctac   1080

ccactcgaag acgggaccgc cggcgagcag ctgcacaaag ccatgaagcg ctacgccctg   1140

gtgcccggca ccatcgcctt taccgacgca catatcgagg tggacattac ctacgccgag   1200

tacttcgaga tgagcgttcg gctggcagaa gctatgaagc gctatgggct gaatacaaac   1260

catcggatcg tggtgtgcag cgagaatagc ttgcagttct tcatgcccgt gttgggtgcc   1320

ctgttcatcg gtgtggctgt ggccccagct aacgacatct acaacgagcg cgagctgctg   1380

aacagcatgg gcatcagcca gcccaccgtc gtattcgtga gcaagaaagg gctgcaaaag   1440

atcctcaacg tgcaaaagaa gctaccgatc atacaaaaga tcatcatcat ggatagcaag   1500

accgactacc agggcttcca aagcatgtac accttcgtga cttcccattt gccacccggc   1560

ttcaacgagt acgacttcgt gcccgagagc ttcgaccggg acaaaaccat cgccctgatc   1620

atgaacagta gtggcagtac cggattgccc aagggcgtag ccctaccgca ccgcaccgct   1680

tgtgtccgat tcagtcatgc ccgcgacccc atcttcggca accagatcat ccccgacacc   1740

gctatcctca gcgtggtgcc atttcaccac ggcttcggca tgttcaccac gctgggctac   1800

ttgatctgcg gctttcgggt cgtgctcatg taccgcttcg aggaggagct attcttgcgc   1860

agcttgcaag actataagat tcaatctgcc ctgctggtgc ccacactatt tagcttcttc   1920

gctaagagca ctctcatcga caagtacgac ctaagcaact tgcacgagat cgccagcggc   1980

ggggcgccgc tcagcaagga ggtaggtgag gccgtggcca aacgcttcca cctaccaggc   2040

atccgccagg gctacggcct gacagaaaca accagcgcca ttctgatcac tccagaaggg   2100

gtt                                                                2103
```

<210> SEQ ID NO 108
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 108

```
Met Pro Gly Ala Val Gly Lys Val Val Pro Phe Phe Glu Ala Lys Val
 1               5                  10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Tyr Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Val Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Phe Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Asn Trp Asp
            180                 185                 190

Ser Gly Cys Ser Arg Glu Cys Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Phe Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365
```

```
Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700
```

<210> SEQ ID NO 109
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 109

```
atgcctggcg cagtaggcaa ggtggtgccc ttcttcgagg ctaaggtggt ggacttggac      60

accggtaaga cactgggtgt gaaccagcgc ggcgagctgt gcgtccgtgg ccccatgatc     120

atgagcggct acgttaacaa ccccgaggct acaaacgctc tcatcgacaa ggacggctgg     180
```

```
ctgcacagcg gcgacatcgc ctactgggac gaggacgagc acttcttcat cgtggaccgg    240
ctgaagagcc tgatcaaata caagggctac caggtagccc cagccgaact ggagagcatc    300
ctgctgcaac accccaacat cttcgacgcc ggggtcgccg gcctgcccga cgacgatgcc    360
ggcgagctgc ccgccgcagt cgtcgtgctg gaacacggta aaaccatgac cgagaaggag    420
atcgtggact atgtggccag ccaggttaca accgccaaga agctgcgcgg tggtgttgtg    480
ttcgtggacg aggtgcctaa aggactgacc ggcaagttgg acgcccgcaa gatccgcgag    540
attctcattc aggccaagaa gggatccaat tgggattctg ggtgctccag agaaggtatg    600
tatgaaagct ttattgagtc actgccattc cttaaatctt tggagttttc tgcacgcctg    660
aaagtagtag atgtgatagg caccaaagta tacaacgatg gagaacaaat cattgctcag    720
ggagattcgg ctgattcttt tttcattatt gaatctggag aagtgaaaat tactatgaaa    780
agaaagggta aatcagaagt ggaagagaat ggtgcagtag aaatcgctcg atgctcgcgg    840
ggacagtact ttggagagct tgccctggta actaacaaac ctcgagcagc ttctgcccac    900
gccattggga ctgtcaaatg tttagcaatg gatgtgcaag catttgaaag gcttctggga    960
ccttgcatgg aaattatgaa aaggaacatc gctacctatg aagaacagtt agttgccctg   1020
tatggaacga acatggatat tgtagccaaa aacattaaga agggcccagc gccattctac   1080
ccactcgaag acgggaccgc cggcgagcag ctgcacaaag ccatgaagcg ctacgccctg   1140
gtgcccggca ccatcgcctt taccgacgca catatcgagg tggacattac ctacgccgag   1200
tacttcgaga tgagcgttcg gctggcagaa gctatgaagc gctatgggct gaatacaaac   1260
catcggatcg tggtgtgcag cgagaatagc ttgcagttct tcatgcccgt gttgggtgcc   1320
ctgttcatcg gtgtggctgt ggccccagct aacgacatct acaacgagcg cgagctgctg   1380
aacagcatgg gcatcagcca gcccaccgtc gtattcgtga gcaagaaagg gctgcaaaag   1440
atcctcaacg tgcaaaagaa gctaccgatc atacaaaaga tcatcatcat ggatagcaag   1500
accgactacc agggcttcca aagcatgtac accttcgtga cttcccattt gccacccggc   1560
ttcaacgagt acgacttcgt gcccgagagc ttcgaccggg acaaaaccat cgccctgatc   1620
atgaacagta gtggcagtac cggattgccc aagggcgtag ccctaccgca ccgcaccgct   1680
tgtgtccgat tcagtcatgc ccgcgacccc atcttcggca accagatcat ccccgacacc   1740
gctatcctca gcgtggtgcc atttcaccac ggcttcggca tgttcaccac gctgggctac   1800
ttgatctgcg gctttcgggt cgtgctcatg taccgcttcg aggaggagct attcttgcgc   1860
agcttgcaag actataagat tcaatctgcc ctgctggtgc ccacactatt tagcttcttc   1920
gctaagagca ctctcatcga caagtacgac ctaagcaact tgcacgagat cgccagcggc   1980
ggggcgccgc tcagcaagga ggtaggtgag gccgtggcca aacgcttcca cctaccaggc   2040
atccgccagg gctacggcct gacagaaaca accagcgcca ttctgatcac tccagaaggg   2100
gtt                                                                 2103
```

<210> SEQ ID NO 110
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 110

```
Met Pro Gly Ala Val Gly Lys Val Val Pro Phe Phe Glu Ala Lys Val
 1               5                  10                  15
```

```
Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Phe Val Asp Glu Val Pro Lys Gly Leu Thr Gly Lys Leu Asp Ala Arg
                165                 170                 175

Lys Ile Arg Glu Ile Leu Ile Gln Ala Lys Lys Gly Ser Asn Trp Asp
            180                 185                 190

Ser Gly Cys Ser Arg Glu Gly Met Tyr Glu Ser Phe Ile Glu Ser Leu
        195                 200                 205

Pro Phe Leu Lys Ser Leu Glu Phe Ser Ala Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Ile Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Tyr Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
```

```
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700
```

<210> SEQ ID NO 111
<211> LENGTH: 2102
<212> TYPE: DNA
<213> ORGANISM: Artificial Sequence
<220> FEATURE:
<223> OTHER INFORMATION: A synthetic oligonucleotide

<400> SEQUENCE: 111

```
atgcctggcg cagtaggcaa ggtggtgccc ttcttcgagg ctaaggtggt ggacttggac     60

accggtaaga cactgggtgt gaaccagcgc ggcgagctgt gcgtccgtgg ccccatgatc    120

atgagcggct acgttaacaa ccccgaggct acaaacgctc tcatcgacaa ggacggctgg    180

ctgcacagcg gcgacatcgc ctactgggac gaggacgagc acttcttcat cgtggaccgg    240

ctgaagagcc tgatcaaata caagggctac caggtagccc cagccgaact ggagagcatc    300

ctgctgcaac accccaacat cttcgacgcc ggggtcgccg gcctgcccga cgacgatgcc    360

ggcgagctgc ccgccgcagt cgtcgtgctg gaacacggta aaccatgac cgagaaggag    420

atcgtggact atgtggccag ccaggttaca accgccaaga agctgcgcgg tggtgttgtg    480

ttcgtggacg aggtgcctaa aggactgacc ggcaagttgg acgcccgcaa gatccgcgag    540

attctcatta aggccaagaa gggctcgagc ggaggttcag gcggctccgg aggaggtatg    600
```

```
tatgaaagct ttattgagtc actgccattc cttaaatctt tggagttttc tgaacgcctg    660

aaagtagtag atgtgatagg caccaaagta tacaacgatg gagaacaaat cattgctcag    720

ggagattcgg ctgattcttt tttcattgta gaatctggag aagtgaaaat tactatgaaa    780

agaaagggta aatcagaagt ggaagagaat ggtgcagtag aaatcgctcg atgctcgcgg    840

ggacagtact ttggagagct tgccctggta actaacaaac ctcgagcagc ttctgcccac    900

gccattggga ctgtcaaatg tttagcaatg gatgtgcaag catttgaaag gcttctggga    960

ccttgcatgg aaattatgaa aaggaacatc gctacctatg aagaacagtt agttgccctg   1020

tttggaacga acatggatat tgtagccaaa aacattaaga agggcccagc gccattctac   1080

ccactcgaag acgggaccgc cggcgagcag ctgcacaaag ccatgaagcg ctacgccctg   1140

gtgcccggca ccatcgcctt taccgacgca catatcgagg tggacattac ctacgccgag   1200

tacttcgaga tgagcgttcg gctggcagaa gctatgaagc gctatgggct gaatacaaac   1260

catcggatcg tggtgtgcag cgagaatagc ttgcagttct tcatgcccgt gttgggtgcc   1320

ctgttcatcg gtgtggctgt ggccccagct aacgacatct acaacgagcg cgagctgctg   1380

aacagcatgg gcatcagcca gcccaccgtc gtattcgtga gcaagaaagg gctgcaaaag   1440

atcctcaacg tgcaaaagaa gctaccgatc atacaaaaga tcatcatcat ggatagcaag   1500

accgactacc agggcttcca aagcatgtac accttcgtga cttcccattt gccacccggc   1560

ttcaacgagt acgacttcgt gcccgagagc ttcgaccggg acaaaaccat cgccctgatc   1620

atgaacagta gtggcagtac cggattgccc aagggcgtag ccctaccgca ccgcaccgct   1680

tgtgtccgat tcagtcatgc ccgcgacccc atcttcggca accagatcat ccccgacacc   1740

gctatcctca gcgtggtgcc atttcaccac ggcttcggca tgttcaccac gctgggctac   1800

ttgatctgcg gctttcgggt cgtgctcatg taccgcttcg aggaggagct attcttgcgc   1860

agcttgcaag actataagat tcaatctgcc ctgctggtgc ccacactatt tagcttcttc   1920

gctaagagca ctctcatcga caagtacgac ctaagcaact tgcacgagat cgccagcggc   1980

ggggcgccgc tcagcaagga ggtaggtgag gccgtggcca aacgcttcca cctaccaggc   2040

atccgccagg gctacggcct gacagaaaca accagcgcca ttctgatcac tccagaaggg   2100

gt                                                                  2102
```

<210> SEQ ID NO 112
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 112

```
Met Pro Gly Ala Val Gly Lys Val Val Pro Phe Phe Glu Ala Lys Val
 1               5                  10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
```

```
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160

Phe Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Ser Gly Gly
            180                 185                 190

Ser Gly Gly Ser Gly Gly Gly Met Tyr Glu Ser Phe Ile Glu Ser Leu
        195                 200                 205

Pro Phe Leu Lys Ser Leu Glu Phe Ser Glu Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Val Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Phe Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510
```

```
Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700
```

<210> SEQ ID NO 113
<211> LENGTH: 2103
<212> TYPE: DNA
<213> ORGANISM: Artificial Sequence
<220> FEATURE:
<223> OTHER INFORMATION: A synthetic oligonucleotide

<400> SEQUENCE: 113

```
atgcctggcg cagtaggcaa ggtggtgccc ttcttcgagg ctaaggtggt ggacttggac     60

accggtaaga cactgggtgt gaaccagcgc ggcgagctgt gcgtccgtgg ccccatgatc    120

atgagcggct acgttaacaa ccccgaggct acaaacgctc tcatcgacaa ggacggctgg    180

ctgcacagcg gcgacatcgc ctactgggac gaggacgagc acttcttcat cgtggaccgg    240

ctgaagagcc tgatcaaata caagggctac caggtagccc cagccgaact ggagagcatc    300

ctgctgcaac accccaacat cttcgacgcc ggggtcgccg gcctgcccga cgacgatgcc    360

ggcgagctgc ccgccgcagt cgtcgtgctg gaacacggta aaaccatgac cgagaaggag    420

atcgtggact atgtggccag ccaggttaca accgccaaga agctgcgcgg tggtgttgtg    480

ttcgtggacg aggtgcctaa aggactgacc ggcaagttgg acgcccgcaa gatccgcgag    540

attctcatta aggccaagaa gggatccaat tgggattctg ggtgctccag agaaggtatg    600

tatgaaagct ttattgagtc actgccattc cttaaatctt tggagttttc tgcacgcctg    660

aaagtagtag atgtgatagg caccaaagta tacaacgatg gagaacaaat cattgctcag    720

ggagattcgg ctgattcttt tttcattatt gaatctggag aagtgaaaat tactatgaaa    780

agaaagggta aatcagaagt ggaagagaat ggtgcagtag aaatcgctcg atgctcgcgg    840

ggacagtact ttggagagct tgccctggta actaacaaac ctcgagcagc ttctgcccac    900

gccattggga ctgtcaaatg tttagcaatg gatgtgcaag catttgaaag gcttctggga    960
```

```
ccttgcatgg aaattatgaa aaggaacatc gctacctatg aagaacagtt agttgccctg   1020

tttggaacga acatggatat tgtagccaaa aacattaaga agggcccagc gccattctac   1080

ccactcgaag acgggaccgc cggcgagcag ctgcacaaag ccatgaagcg ctacgccctg   1140

gtgcccggca ccatcgcctt taccgacgca catatcgagg tggacattac ctacgccgag   1200

tacttcgaga tgagcgttcg gctggcagaa gctatgaagc gctatgggct gaatacaaac   1260

catcggatcg tggtgtgcag cgagaatagc ttgcagttct tcatgcccgt gttgggtgcc   1320

ctgttcatcg gtgtggctgt ggccccagct aacgacatct acaacgagcg cgagctgctg   1380

aacagcatgg gcatcagcca gcccaccgtc gtattcgtga gcaagaaagg gctgcaaaag   1440

atcctcaacg tgcaaaagaa gctaccgatc atacaaaaga tcatcatcat ggatagcaag   1500

accgactacc agggcttcca aagcatgtac accttcgtga cttcccattt gccacccggc   1560

ttcaacgagt acgacttcgt gcccgagagc ttcgaccggg acaaaaccat cgccctgatc   1620

atgaacagta gtggcagtac cggattgccc aagggcgtag ccctaccgca ccgcaccgct   1680

tgtgtccgat tcagtcatgc ccgcgacccc atcttcggca accagatcat ccccgacacc   1740

gctatcctca gcgtggtgcc atttcaccac ggcttcggca tgttcaccac gctgggctac   1800

ttgatctgcg gctttcgggt cgtgctcatg taccgcttcg aggaggagct attcttgcgc   1860

agcttgcaag actataagat tcaatctgcc ctgctggtgc ccacactatt tagcttcttc   1920

gctaagagca ctctcatcga caagtacgac ctaagcaact tgcacgagat cgccagcggc   1980

ggggcgccgc tcagcaagga ggtaggtgag gccgtggcca aacgcttcca cctaccaggc   2040

atccgccagg gctacggcct gacagaaaca accagcgcca ttctgatcac tccagaaggg   2100

gtt                                                                 2103
```

<210> SEQ ID NO 114
<211> LENGTH: 701
<212> TYPE: PRT
<213> ORGANISM: Artificial Sequence
<220> FEATURE:
<223> OTHER INFORMATION: A synthetic polypeptide

<400> SEQUENCE: 114

```
Met Pro Gly Ala Val Gly Lys Val Val Pro Phe Phe Glu Ala Lys Val
 1               5                  10                  15

Val Asp Leu Asp Thr Gly Lys Thr Leu Gly Val Asn Gln Arg Gly Glu
            20                  25                  30

Leu Cys Val Arg Gly Pro Met Ile Met Ser Gly Tyr Val Asn Asn Pro
        35                  40                  45

Glu Ala Thr Asn Ala Leu Ile Asp Lys Asp Gly Trp Leu His Ser Gly
    50                  55                  60

Asp Ile Ala Tyr Trp Asp Glu Asp Glu His Phe Phe Ile Val Asp Arg
65                  70                  75                  80

Leu Lys Ser Leu Ile Lys Tyr Lys Gly Tyr Gln Val Ala Pro Ala Glu
                85                  90                  95

Leu Glu Ser Ile Leu Leu Gln His Pro Asn Ile Phe Asp Ala Gly Val
            100                 105                 110

Ala Gly Leu Pro Asp Asp Asp Ala Gly Glu Leu Pro Ala Ala Val Val
        115                 120                 125

Val Leu Glu His Gly Lys Thr Met Thr Glu Lys Glu Ile Val Asp Tyr
    130                 135                 140

Val Ala Ser Gln Val Thr Thr Ala Lys Lys Leu Arg Gly Gly Val Val
145                 150                 155                 160
```

```
Phe Val Asp Glu Val Pro Lys Gly Leu Thr Gly Lys Leu Asp Ala Arg
                165                 170                 175

Lys Ile Arg Glu Ile Leu Ile Lys Ala Lys Lys Gly Ser Ser Gly Gly
            180                 185                 190

Ser Gly Gly Ser Gly Gly Gly Met Tyr Glu Ser Phe Ile Glu Ser Leu
        195                 200                 205

Pro Phe Leu Lys Ser Leu Glu Phe Ser Glu Arg Leu Lys Val Val Asp
    210                 215                 220

Val Ile Gly Thr Lys Val Tyr Asn Asp Gly Glu Gln Ile Ile Ala Gln
225                 230                 235                 240

Gly Asp Ser Ala Asp Ser Phe Phe Ile Val Glu Ser Gly Glu Val Lys
                245                 250                 255

Ile Thr Met Lys Arg Lys Gly Lys Ser Glu Val Glu Glu Asn Gly Ala
            260                 265                 270

Val Glu Ile Ala Arg Cys Ser Arg Gly Gln Tyr Phe Gly Glu Leu Ala
        275                 280                 285

Leu Val Thr Asn Lys Pro Arg Ala Ala Ser Ala His Ala Ile Gly Thr
    290                 295                 300

Val Lys Cys Leu Ala Met Asp Val Gln Ala Phe Glu Arg Leu Leu Gly
305                 310                 315                 320

Pro Cys Met Glu Ile Met Lys Arg Asn Ile Ala Thr Tyr Glu Glu Gln
                325                 330                 335

Leu Val Ala Leu Phe Gly Thr Asn Met Asp Ile Val Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
    370                 375                 380

Ile Ala Phe Thr Asp Ala His Ile Glu Val Asp Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Gly
    450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
    530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575
```

```
Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
    610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685

Glu Thr Thr Ser Ala Ile Leu Ile Thr Pro Glu Gly Val
    690                 695                 700


<210> SEQ ID NO 115
<211> LENGTH: 933
<212> TYPE: DNA
<213> ORGANISM: Artificial Sequence
<220> FEATURE:
<223> OTHER INFORMATION: A synthetic oligonucleotide

<400> SEQUENCE: 115

atgacttcga aagtttatga tccagaacaa aggaaacgga tgataactgg tccgcagtgg     60

tgggccagat gtaaacaaat gaatgttctt gattcattta ttaattatta tgattcagaa    120

aaacatgcag aaaatgctgt tatttttta catggtaacg cggcctcttc ttatttatgg    180

cgacatgttg tgccacatat tgagccagta gcgcggtgta ttataccaga tcttattggt    240

atgggcaaat caggcaaatc tggtaatggt tcttataggt tacttgatca ttacaaatat    300

cttactgcat ggtttgaact tcttaattta ccaaagaaga tcatttttgt cggccatgat    360

tggggtgctt gtttggcatt tcattatagc tatgagcatc aagataagat caaagcaata    420

gttcacgctg aaagtgtagt agatgtgatt gaatcatggg atgaatggcc tgatattgaa    480

gaagatattg cgttgatcaa atctgaagaa ggagaaaaaa tggttttgga gaataacttc    540

ttcgtggaaa ccatgttgcc atcaaaaatc atgagaaagt tagaaccaga agaatttgca    600

gcatatcttg aaccattcaa agagaaaggt gaagttcgtc gtccaacatt atcatggcct    660

cgtgaaatcc cgttagtaaa aggtggtaaa cctgacgttg tacaaattgt taggaattat    720

aatgcttatc tacgtgcaag tgatgattta ccaaaaatgt ttattgaatc ggatccagga    780

ttcttttcca atgctattgt tgaaggcgcc aagaagtttc ctaatactga atttgtcaaa    840

gtaaaaggtc ttcatttttc gcaagaagat gcacctgatg aaatgggaaa atatatcaaa    900

tcgttcgttg agcgagttct caaaaatgaa caa                                 933


<210> SEQ ID NO 116
<211> LENGTH: 311
<212> TYPE: PRT
<213> ORGANISM: Artificial Sequence
<220> FEATURE:
<223> OTHER INFORMATION: A synthetic polypeptide

<400> SEQUENCE: 116

Met Thr Ser Lys Val Tyr Asp Pro Glu Gln Arg Lys Arg Met Ile Thr
 1               5                  10                  15
```

```
Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310
```

<210> SEQ ID NO 117
<211> LENGTH: 1650
<212> TYPE: DNA
<213> ORGANISM: Artificial Sequence
<220> FEATURE:
<223> OTHER INFORMATION: A synthetic oligonucleotide

<400> SEQUENCE: 117

```
atggaagacg ccaaaaacat aaagaaaggc ccggcgccat tctatcctct agaggatgga     60

accgctggag agcaactgca taaggctatg aagagatacg ccctggttcc tggaacaatt    120

gcttttacag atgcacatat cgaggtgaac atcacgtacg cggaatactt cgaaatgtcc    180

gttcggttgg cagaagctat gaaacgatat gggctgaata caaatcacag aatcgtcgta    240

tgcagtgaaa actctcttca attctttatg ccggtgttgg gcgcgttatt tatcggagtt    300

gcagttgcgc ccgcgaacga catttataat gaacgtgaat tgctcaacag tatgaacatt    360
```

```
tcgcagccta ccgtagtgtt tgtttccaaa aaggggttgc aaaaaatttt gaacgtgcaa    420

aaaaaattac caataatcca gaaaattatt atcatggatt ctaaaacgga ttaccaggga    480

tttcagtcga tgtacacgtt cgtcacatct catctacctc ccggttttaa tgaatacgat    540

tttgtaccag agtcctttga tcgtgacaaa acaattgcac tgataatgaa ttcctctgga    600

tctactgggt tacctaaggg tgtggccctt ccgcatagaa ctgcctgcgt cagattctcg    660

catgccagag atcctatttt tggcaatcaa atcattccgg atactgcgat tttaagtgtt    720

gttccattcc atcacggttt tggaatgttt actacactcg gatatttgat atgtggattt    780

cgagtcgtct taatgtatag atttgaagaa gagctgtttt tacgatccct tcaggattac    840

aaaattcaaa gtgcgttgct agtaccaacc ctattttcat tcttcgccaa aagcactctg    900

attgacaaat acgatttatc taatttacac gaaattgctt ctgggggcgc acctctttcg    960

aaagaagtcg gggaagcggt tgcaaaacgc ttccatcttc cagggatacg acaaggatat   1020

gggctcactg agactacatc agctattctg attacacccg agggggatga taaaccgggc   1080

gcggtcggta aagttgttcc atttttttgaa gcgaaggttg tggatctgga taccgggaaa   1140

acgctgggcg ttaatcagag aggcgaatta tgtgtcagag gacctatgat tatgtccggt   1200

tatgtaaaca atccggaagc gaccaacgcc ttgattgaca aggatggatg gctacattct   1260

ggagacatag cttactggga cgaagacgaa cacttcttca tagttgaccg cttgaagtct   1320

ttaattaaat acaaaggata tcaggtggcc cccgctgaat tggaatcgat attgttacaa   1380

caccccaaca tcttcgacgc gggcgtggca ggtcttcccg acgatgacgc cggtgaactt   1440

cccgccgccg ttgttgtttt ggagcacgga aagacgatga cggaaaaaga gatcgtggat   1500

tacgtcgcca gtcaagtaac aaccgcgaaa aagttgcgcg gaggagttgt gtttgtggac   1560

gaagtaccga aaggtcttac cggaaaactc gacgcaagaa aaatcagaga gatcctcata   1620

aaggccaaga agggcggaaa gtccaaattg                                    1650
```

<210> SEQ ID NO 118
<211> LENGTH: 550
<212> TYPE: PRT
<213> ORGANISM: Artificial Sequence
<220> FEATURE:
<223> OTHER INFORMATION: A synthetic polypeptide

<400> SEQUENCE: 118

```
Met Glu Asp Ala Lys Asn Ile Lys Lys Gly Pro Ala Pro Phe Tyr Pro
 1               5                  10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
```

```
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
    450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
    530                 535                 540

Gly Gly Lys Ser Lys Leu
545                 550
```

<210> SEQ ID NO 119
<211> LENGTH: 1635
<212> TYPE: DNA
<213> ORGANISM: Artificial Sequence
<220> FEATURE:
<223> OTHER INFORMATION: A synthetic oligonucleotide

<400> SEQUENCE: 119

```
atggaagata aaaatatttt atatggacct gaaccatttt atcccttggc tgatgggacg     60
gctggagaac agatgtttta cgcattatct cgttatgcag atatttcagg atgcatagca    120
ttgacaaatg ctcatacaaa agaaaatgtt ttatatgaag agtttttaaa attgtcgtgt    180
cgtttagcgg aaagttttaa aaagtatgga ttaaaacaaa acgacacaat agcggtgtgt    240
agcgaaaatg gtttgcaatt tttccttcct ttaattgcat cattgtatct tggaataatt    300
gcagcacctg ttagtgataa atacattgaa cgtgaattaa tacacagtct tggtattgta    360
aaaccacgca taatttttg ttccaagaat acttttcaaa aagtactgaa tgtaaaatct    420
aaattaaaat atgtagaaac tattattata ttagacttaa atgaagactt aggaggttat    480
caatgcctca acaactttat ttctcaaaat tccgatatta atcttgacgt aaaaaaattt    540
aaaccaaatt cttttaatcg agacgatcag gttgcgttgg taatgttttc ttctggtaca    600
actggtgttt cgaagggagt catgctaact cacaagaata ttgttgcacg attttctcat    660
tgcaaagatc ctacttttgg taacgcaatt aatccaacga cagcaatttt aacggtaata    720
cctttccacc atggttttgg tatgactacc acattaggat actttacttg tggattccga    780
gttgctctaa tgcacacgtt tgaagaaaaa ctatttctac aatcattaca agattataaa    840
gtggaaagta ctttacttgt accaacatta atggcatttt ttgcaaaaag tgcattagtt    900
gaaaagtacg atttatcgca cttaaaagaa attgcatctg gtggcgcacc tttatcaaaa    960
gaaattgggg agatggtgaa aaaacggttt aaattaaact ttgtcaggca agggtatgga   1020
ttaacagaaa ccacttcggc tgttttaatt acaccggaca ctgacgtcag accgggatca   1080
actggtaaaa tagtaccatt tcacgctgtt aaagttgtcg atcctacaac aggaaaaatt   1140
ttggggccaa atgaaactgg agaattgtat tttaaaggcg acatgataat gaaaagttat   1200
tataataatg aagaagctac taaagcaatt attaacaaag acggatggtt gcgctctggt   1260
gatattgctt attatgacaa tgatggccat ttttatattg tggacaggct gaagtcatta   1320
attaaatata aaggttatca ggttgcacct gctgaaattg agggaatact cttacaacat   1380
ccgtatattg ttgatgccgg cgttactggt ataccggatg aagccgcggg cgagcttcca   1440
gctgcaggtg ttgtagtaca gactggaaaa tatctaaacg aacaaatcgt acaaaatttt   1500
gtttccagtc aagtttcaac agccaaatgg ctacgtggtg ggtgaaatt tttggatgaa   1560
attcccaaag gatcaactgg aaaaattgac agaaaagtgt taagacaaat gtttgaaaaa   1620
cacaaatcta agctg                                                    1635
```

<210> SEQ ID NO 120
<211> LENGTH: 545
<212> TYPE: PRT
<213> ORGANISM: Artificial Sequence
<220> FEATURE:
<223> OTHER INFORMATION: A synthetic polypeptide

<400> SEQUENCE: 120

```
Met Glu Asp Lys Asn Ile Leu Tyr Gly Pro Glu Pro Phe Tyr Pro Leu
 1               5                  10                  15
```

```
Ala Asp Gly Thr Ala Gly Glu Gln Met Phe Tyr Ala Leu Ser Arg Tyr
            20                  25                  30

Ala Asp Ile Ser Gly Cys Ile Ala Leu Thr Asn Ala His Thr Lys Glu
        35                  40                  45

Asn Val Leu Tyr Glu Glu Phe Leu Lys Leu Ser Cys Arg Leu Ala Glu
    50                  55                  60

Ser Phe Lys Lys Tyr Gly Leu Lys Gln Asn Asp Thr Ile Ala Val Cys
65                  70                  75                  80

Ser Glu Asn Gly Leu Gln Phe Phe Leu Pro Leu Ile Ala Ser Leu Tyr
                85                  90                  95

Leu Gly Ile Ile Ala Ala Pro Val Ser Asp Lys Tyr Ile Glu Arg Glu
            100                 105                 110

Leu Ile His Ser Leu Gly Ile Val Lys Pro Arg Ile Ile Phe Cys Ser
        115                 120                 125

Lys Asn Thr Phe Gln Lys Val Leu Asn Val Lys Ser Lys Leu Lys Tyr
    130                 135                 140

Val Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ile Asn Leu Asp
                165                 170                 175

Val Lys Lys Phe Lys Pro Asn Ser Phe Asn Arg Asp Asp Gln Val Ala
            180                 185                 190

Leu Val Met Phe Ser Ser Gly Thr Thr Gly Val Ser Lys Gly Val Met
        195                 200                 205

Leu Thr His Lys Asn Ile Val Ala Arg Phe Ser His Cys Lys Asp Pro
    210                 215                 220

Thr Phe Gly Asn Ala Ile Asn Pro Thr Thr Ala Ile Leu Thr Val Ile
225                 230                 235                 240

Pro Phe His His Gly Phe Gly Met Thr Thr Thr Leu Gly Tyr Phe Thr
                245                 250                 255

Cys Gly Phe Arg Val Ala Leu Met His Thr Phe Glu Glu Lys Leu Phe
            260                 265                 270

Leu Gln Ser Leu Gln Asp Tyr Lys Val Glu Ser Thr Leu Leu Val Pro
        275                 280                 285

Thr Leu Met Ala Phe Phe Ala Lys Ser Ala Leu Val Glu Lys Tyr Asp
    290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Thr Thr Ser Ala Val Leu Ile Thr Pro
            340                 345                 350

Asp Thr Asp Val Arg Pro Gly Ser Thr Gly Lys Ile Val Pro Phe His
        355                 360                 365

Ala Val Lys Val Val Asp Pro Thr Thr Gly Lys Ile Leu Gly Pro Asn
    370                 375                 380

Glu Thr Gly Glu Leu Tyr Phe Lys Gly Asp Met Ile Met Lys Ser Tyr
385                 390                 395                 400

Tyr Asn Asn Glu Glu Ala Thr Lys Ala Ile Ile Asn Lys Asp Gly Trp
                405                 410                 415

Leu Arg Ser Gly Asp Ile Ala Tyr Tyr Asp Asn Asp Gly His Phe Tyr
            420                 425                 430
```

```
Ile Val Asp Arg Leu Lys Ser Leu Ile Lys Tyr Lys Gly Tyr Gln Val
        435                 440                 445

Ala Pro Ala Glu Ile Glu Gly Ile Leu Leu Gln His Pro Tyr Ile Val
    450                 455                 460

Asp Ala Gly Val Thr Gly Ile Pro Asp Glu Ala Ala Gly Glu Leu Pro
465                 470                 475                 480

Ala Ala Gly Val Val Val Gln Thr Gly Lys Tyr Leu Asn Glu Gln Ile
                485                 490                 495

Val Gln Asn Phe Val Ser Ser Gln Val Ser Thr Ala Lys Trp Leu Arg
            500                 505                 510

Gly Gly Val Lys Phe Leu Asp Glu Ile Pro Lys Gly Ser Thr Gly Lys
        515                 520                 525

Ile Asp Arg Lys Val Leu Arg Gln Met Phe Glu Lys His Lys Ser Lys
    530                 535                 540

Leu
545
```

<210> SEQ ID NO 121
<211> LENGTH: 185
<212> TYPE: PRT
<213> ORGANISM: Artificial Sequence
<220> FEATURE:
<223> OTHER INFORMATION: A synthetic polypeptide

<400> SEQUENCE: 121

```
Met Gly Val Lys Val Leu Phe Ala Leu Ile Cys Ile Ala Val Ala Glu
 1               5                  10                  15

Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
        35                  40                  45

Gly Lys Lys Leu Pro Leu Glu Val Leu Lys Glu Met Glu Ala Asn Ala
    50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Gly Ile Gly Glu Ala Ile
            100                 105                 110

Val Asp Ile Pro Glu Ile Pro Gly Phe Lys Asp Leu Glu Pro Met Glu
        115                 120                 125

Gln Phe Ile Ala Gln Val Asp Leu Cys Val Asp Cys Thr Thr Gly Cys
    130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp
            180                 185
```

<210> SEQ ID NO 122
<211> LENGTH: 169
<212> TYPE: PRT
<213> ORGANISM: Artificial Sequence
<220> FEATURE:
<223> OTHER INFORMATION: A synthetic polypeptide

<400> SEQUENCE: 122

```
Phe Thr Leu Ala Asp Phe Val Gly Asp Trp Gln Gln Thr Ala Gly Tyr
 1               5                  10                  15

Asn Gln Asp Gln Val Leu Glu Gln Gly Gly Leu Ser Ser Leu Phe Gln
            20                  25                  30

Ala Leu Gly Val Ser Val Thr Pro Ile Gln Lys Val Val Leu Ser Gly
        35                  40                  45

Glu Asn Gly Leu Lys Ala Asp Ile His Val Ile Ile Pro Tyr Glu Gly
    50                  55                  60

Leu Ser Gly Phe Gln Met Gly Leu Ile Glu Met Ile Phe Lys Val Val
65                  70                  75                  80

Tyr Pro Val Asp Asp His His Phe Lys Ile Ile Leu His Tyr Gly Thr
                85                  90                  95

Leu Val Ile Asp Gly Val Thr Pro Asn Met Ile Asp Tyr Phe Gly Arg
            100                 105                 110

Pro Tyr Pro Gly Ile Ala Val Phe Asp Gly Lys Gln Ile Thr Val Thr
        115                 120                 125

Gly Thr Leu Trp Asn Gly Asn Lys Ile Tyr Asp Glu Arg Leu Ile Asn
    130                 135                 140

Pro Asp Gly Ser Leu Leu Phe Arg Val Thr Ile Asn Gly Val Thr Gly
145                 150                 155                 160

Trp Arg Leu Cys Glu Asn Ile Leu Ala
                165
```

<210> SEQ ID NO 123
<211> LENGTH: 993
<212> TYPE: PRT
<213> ORGANISM: Artificial Sequence
<220> FEATURE:
<223> OTHER INFORMATION: A synthetic polypeptide

<400> SEQUENCE: 123

```
Met Val Ala Ala His Ala Ala His Ser Gln Ser Ser Ala Glu Trp Ile
 1               5                  10                  15

Ala Cys Leu Asp Lys Arg Pro Leu Glu Arg Ser Ser Glu Asp Val Asp
            20                  25                  30

Ile Ile Phe Thr Arg Leu Lys Gly Val Lys Ala Phe Glu Lys Phe His
        35                  40                  45

Pro Asn Leu Leu Arg Gln Ile Cys Leu Cys Gly Tyr Tyr Glu Asn Leu
    50                  55                  60

Glu Lys Gly Ile Thr Leu Phe Arg Gln Gly Asp Ile Gly Thr Asn Trp
65                  70                  75                  80

Tyr Ala Val Leu Ala Gly Ser Leu Asp Val Lys Val Ser Glu Thr Ser
                85                  90                  95

Ser His Gln Asp Ala Val Thr Ile Cys Thr Leu Gly Ile Gly Thr Ala
            100                 105                 110

Phe Gly Glu Ser Ile Leu Asp Asn Thr Pro Arg His Ala Thr Ile Val
        115                 120                 125

Thr Arg Glu Ser Ser Glu Leu Leu Arg Ile Glu Gln Glu Asp Phe Lys
    130                 135                 140

Ala Leu Trp Glu Lys Tyr Arg Gln Tyr Met Ala Gly Leu Leu Ala Pro
145                 150                 155                 160

Pro Tyr Gly Val Met Glu Thr Gly Ser Asn Asn Asp Arg Ile Pro Asp
                165                 170                 175

Lys Glu Asn Val Pro Ser Glu Lys Ile Leu Arg Ala Gly Lys Ile Leu
            180                 185                 190
```

```
Arg Ile Ala Ile Leu Ser Arg Ala Pro His Met Ile Arg Asp Arg Lys
        195                 200                 205

Tyr His Leu Lys Thr Tyr Arg Gln Cys Cys Val Gly Thr Glu Leu Val
    210                 215                 220

Asp Trp Met Ile Gln Gln Thr Ser Cys Val His Ser Arg Thr Gln Ala
225                 230                 235                 240

Val Gly Met Trp Gln Val Leu Leu Glu Asp Gly Val Leu Asn His Val
                245                 250                 255

Asp Gln Glu Arg His Phe Gln Asp Lys Tyr Leu Phe Tyr Arg Phe Leu
            260                 265                 270

Asp Asp Glu Arg Glu Asp Ala Pro Leu Pro Thr Glu Glu Glu Lys Lys
        275                 280                 285

Glu Cys Asp Glu Glu Leu Gln Asp Thr Met Leu Leu Leu Ser Gln Met
    290                 295                 300

Gly Pro Asp Ala His Met Arg Met Ile Leu Arg Lys Pro Pro Gly Gln
305                 310                 315                 320

Arg Thr Val Asp Asp Leu Glu Ile Ile Tyr Asp Glu Leu Leu His Ile
                325                 330                 335

Lys Ala Leu Ser His Leu Ser Thr Thr Val Lys Arg Glu Leu Ala Gly
            340                 345                 350

Val Leu Ile Phe Glu Ser His Ala Lys Gly Gly Thr Val Leu Phe Asn
        355                 360                 365

Gln Gly Glu Glu Gly Thr Ser Trp Tyr Ile Ile Leu Lys Gly Ser Val
    370                 375                 380

Asn Val Val Ile Tyr Gly Lys Gly Val Val Cys Thr Leu His Glu Gly
385                 390                 395                 400

Asp Asp Phe Gly Lys Leu Ala Leu Val Asn Asp Ala Pro Arg Ala Ala
                405                 410                 415

Ser Ile Val Leu Arg Glu Asp Asn Cys His Phe Leu Arg Val Asp Lys
            420                 425                 430

Glu Asp Phe Asn Arg Ile Leu Arg Asp Val Glu Ala Asn Thr Val Arg
        435                 440                 445

Leu Lys Glu His Asp Gln Asp Val Leu Val Leu Glu Lys Val Pro Ala
    450                 455                 460

Gly Asn Arg Ala Ala Asn Gln Gly Asn Ser Gln Pro Gln Gln Lys Tyr
465                 470                 475                 480

Thr Val Met Ser Gly Thr Pro Glu Lys Ile Leu Glu His Phe Leu Glu
                485                 490                 495

Thr Ile Arg Leu Glu Pro Ser Leu Asn Glu Ala Thr Asp Ser Val Leu
            500                 505                 510

Asn Asp Phe Val Met Met His Cys Val Phe Met Pro Asn Thr Gln Leu
        515                 520                 525

Cys Pro Ala Leu Val Ala His Tyr His Ala Gln Pro Ser Gln Gly Thr
    530                 535                 540

Glu Gln Glu Arg Met Asp Tyr Ala Leu Asn Asn Lys Arg Arg Val Ile
545                 550                 555                 560

Arg Leu Val Leu Gln Trp Ala Ala Met Tyr Gly Asp Leu Leu Gln Glu
                565                 570                 575

Asp Asp Val Ala Met Ala Phe Leu Glu Glu Phe Tyr Val Ser Val Ser
            580                 585                 590

Asp Asp Ala Arg Met Met Ala Ala Phe Lys Glu Gln Leu Pro Glu Leu
        595                 600                 605
```

```
Glu Lys Ile Val Lys Gln Ile Ser Glu Asp Ala Lys Ala Pro Gln Lys
    610                 615                 620

Lys His Lys Val Leu Leu Gln Gln Phe Asn Thr Gly Asp Glu Arg Ala
625                 630                 635                 640

Gln Lys Arg Gln Pro Ile Arg Gly Ser Asp Glu Val Leu Phe Lys Val
                645                 650                 655

Tyr Cys Ile Asp His Thr Tyr Thr Thr Ile Arg Val Pro Val Ala Ala
            660                 665                 670

Ser Val Lys Glu Val Ile Ser Ala Val Ala Asp Lys Leu Gly Ser Gly
        675                 680                 685

Glu Gly Leu Ile Ile Val Lys Met Asn Ser Gly Gly Glu Lys Val Val
    690                 695                 700

Leu Lys Ser Asn Asp Val Ser Val Phe Thr Thr Leu Thr Ile Asn Gly
705                 710                 715                 720

Arg Leu Phe Ala Cys Pro Arg Glu Gln Phe Asp Ser Leu Thr Pro Leu
                725                 730                 735

Pro Glu Gln Glu Gly Pro Thr Thr Gly Thr Val Gly Thr Phe Glu Leu
            740                 745                 750

Met Ser Ser Lys Asp Leu Ala Tyr Gln Met Thr Thr Tyr Asp Trp Glu
        755                 760                 765

Leu Phe Asn Cys Val His Glu Leu Glu Leu Ile Tyr His Thr Phe Gly
    770                 775                 780

Arg His Asn Phe Lys Lys Thr Thr Ala Asn Leu Asp Leu Phe Leu Arg
785                 790                 795                 800

Arg Phe Asn Glu Ile Gln Phe Trp Val Val Thr Glu Val Cys Leu Cys
                805                 810                 815

Ser Gln Leu Ser Lys Arg Val Gln Leu Leu Lys Lys Phe Ile Lys Ile
            820                 825                 830

Ala Ala His Cys Lys Glu Tyr Lys Asn Leu Asn Ser Phe Phe Ala Ile
        835                 840                 845

Val Met Gly Leu Ser Asn Val Ala Val Ser Arg Leu Ala Leu Thr Trp
    850                 855                 860

Glu Lys Leu Pro Ser Lys Phe Lys Lys Phe Tyr Ala Glu Phe Glu Ser
865                 870                 875                 880

Leu Met Asp Pro Ser Arg Asn His Arg Ala Tyr Arg Leu Thr Ala Ala
                885                 890                 895

Lys Leu Glu Pro Pro Leu Ile Pro Phe Met Pro Leu Leu Ile Lys Asp
            900                 905                 910

Met Thr Phe Thr His Glu Gly Asn Lys Thr Phe Ile Asp Asn Leu Val
        915                 920                 925

Asn Phe Glu Lys Met Arg Met Ile Ala Asn Thr Ala Arg Thr Val Arg
    930                 935                 940

Tyr Tyr Arg Ser Gln Pro Phe Asn Pro Asp Ala Ala Gln Ala Asn Lys
945                 950                 955                 960

Asn His Gln Asp Val Arg Ser Tyr Val Arg Gln Leu Asn Val Ile Asp
                965                 970                 975

Asn Gln Arg Thr Leu Ser Gln Met Ser His Arg Leu Glu Pro Arg Arg
            980                 985                 990

Pro

<210> SEQ ID NO 124
 <211> LENGTH: 381
<212> TYPE: PRT
<213> ORGANISM: Artificial Sequence
```

<220> FEATURE:
<223> OTHER INFORMATION: A synthetic polypeptide

<400> SEQUENCE: 124

```
Met Glu Ser Gly Ser Thr Ala Ala Ser Glu Glu Ala Arg Ser Leu Arg
1               5                   10                  15

Glu Cys Glu Leu Tyr Val Gln Lys His Asn Ile Gln Ala Leu Leu Lys
            20                  25                  30

Asp Ser Ile Val Gln Leu Cys Thr Ala Arg Pro Glu Arg Pro Met Ala
        35                  40                  45

Phe Leu Arg Glu Tyr Phe Glu Arg Leu Glu Lys Glu Glu Ala Lys Gln
    50                  55                  60

Ile Gln Asn Leu Gln Lys Ala Gly Thr Arg Thr Asp Ser Arg Glu Asp
65                  70                  75                  80

Glu Ile Ser Pro Pro Pro Pro Asn Pro Val Val Lys Gly Arg Arg Arg
                85                  90                  95

Arg Gly Ala Ile Ser Ala Glu Val Tyr Thr Glu Glu Asp Ala Ala Ser
            100                 105                 110

Tyr Val Arg Lys Val Ile Pro Lys Asp Tyr Lys Thr Met Ala Ala Leu
        115                 120                 125

Ala Lys Ala Ile Glu Lys Asn Val Leu Phe Ser His Leu Asp Asp Asn
    130                 135                 140

Glu Arg Ser Asp Ile Phe Asp Ala Met Phe Ser Val Ser Phe Ile Ala
145                 150                 155                 160

Gly Glu Thr Val Ile Gln Gln Gly Asp Glu Gly Asp Asn Phe Tyr Val
                165                 170                 175

Ile Asp Gln Gly Glu Thr Asp Val Tyr Val Asn Asn Glu Trp Ala Thr
            180                 185                 190

Ser Val Gly Glu Gly Gly Ser Phe Gly Glu Leu Ala Leu Ile Tyr Gly
        195                 200                 205

Thr Pro Arg Ala Ala Thr Val Lys Ala Lys Thr Asn Val Lys Leu Trp
    210                 215                 220

Gly Ile Asp Arg Asp Ser Tyr Arg Arg Ile Leu Met Gly Ser Thr Leu
225                 230                 235                 240

Arg Lys Arg Lys Met Tyr Glu Glu Phe Leu Ser Lys Val Ser Ile Leu
                245                 250                 255

Glu Ser Leu Asp Lys Trp Glu Arg Leu Thr Val Ala Asp Ala Leu Glu
            260                 265                 270

Pro Val Gln Phe Glu Asp Gly Gln Lys Ile Val Val Gln Gly Glu Pro
        275                 280                 285

Gly Asp Glu Phe Phe Ile Ile Leu Glu Gly Ser Ala Ala Val Leu Gln
    290                 295                 300

Arg Arg Ser Glu Asn Glu Glu Phe Val Glu Val Gly Arg Leu Gly Pro
305                 310                 315                 320

Ser Asp Tyr Phe Gly Glu Ile Ala Leu Leu Met Asn Arg Pro Arg Ala
                325                 330                 335

Ala Thr Val Val Ala Arg Gly Pro Leu Lys Cys Val Lys Leu Asp Arg
            340                 345                 350

Pro Arg Phe Glu Arg Val Leu Gly Pro Cys Ser Asp Ile Leu Lys Arg
        355                 360                 365

Asn Ile Gln Gln Tyr Asn Ser Phe Val Ser Leu Ser Val
    370                 375                 380
```

<210> SEQ ID NO 125

```
<211> LENGTH: 941
<212> TYPE: PRT
<213> ORGANISM: Artificial Sequence
<220> FEATURE:
<223> OTHER INFORMATION: A synthetic polypeptide

<400> SEQUENCE: 125

Met Gly Gln Ala Cys Gly His Ser Ile Leu Cys Arg Ser Gln Gln Tyr
 1               5                  10                  15

Pro Ala Ala Arg Pro Ala Glu Pro Arg Gly Gln Gln Val Phe Leu Lys
            20                  25                  30

Pro Asp Glu Pro Pro Pro Pro Pro Gln Pro Cys Ala Asp Ser Leu Gln
        35                  40                  45

Asp Ala Leu Leu Ser Leu Gly Ser Val Ile Asp Ile Ser Gly Leu Gln
    50                  55                  60

Arg Ala Val Lys Glu Ala Leu Ser Ala Val Leu Pro Arg Val Glu Thr
65                  70                  75                  80

Val Tyr Thr Tyr Leu Leu Asp Gly Glu Ser Gln Leu Val Cys Glu Asp
                85                  90                  95

Pro Pro His Glu Leu Pro Gln Glu Gly Lys Val Arg Glu Ala Ile Ile
            100                 105                 110

Ser Gln Lys Arg Leu Gly Cys Asn Gly Leu Gly Phe Ser Asp Leu Pro
        115                 120                 125

Gly Lys Pro Leu Ala Arg Leu Val Ala Pro Leu Ala Pro Asp Thr Gln
    130                 135                 140

Val Leu Val Met Pro Leu Ala Asp Lys Glu Ala Gly Ala Val Ala Ala
145                 150                 155                 160

Val Ile Leu Val His Cys Gly Gln Leu Ser Asp Asn Glu Glu Trp Ser
                165                 170                 175

Leu Gln Ala Val Glu Lys His Thr Leu Val Ala Leu Arg Arg Val Gln
            180                 185                 190

Val Leu Gln Gln Arg Gly Pro Arg Glu Ala Pro Arg Ala Val Gln Asn
        195                 200                 205

Pro Pro Glu Gly Thr Ala Glu Asp Gln Lys Gly Gly Ala Ala Tyr Thr
    210                 215                 220

Asp Arg Asp Arg Lys Ile Leu Gln Leu Cys Gly Glu Leu Tyr Asp Leu
225                 230                 235                 240

Asp Ala Ser Ser Leu Gln Leu Lys Val Leu Gln Tyr Leu Gln Gln Glu
                245                 250                 255

Thr Arg Ala Ser Arg Cys Cys Leu Leu Leu Val Ser Glu Asp Asn Leu
            260                 265                 270

Gln Leu Ser Cys Lys Val Ile Gly Asp Lys Val Leu Gly Glu Glu Val
        275                 280                 285

Ser Phe Pro Leu Thr Gly Cys Leu Gly Gln Val Val Glu Asp Lys Lys
    290                 295                 300

Ser Ile Gln Leu Lys Asp Leu Thr Ser Glu Asp Val Gln Gln Leu Gln
305                 310                 315                 320

Ser Met Leu Gly Cys Glu Leu Gln Ala Met Leu Cys Val Pro Val Ile
                325                 330                 335

Ser Arg Ala Thr Asp Gln Val Val Ala Leu Ala Cys Ala Phe Asn Lys
            340                 345                 350

Leu Glu Gly Asp Leu Phe Thr Asp Glu Asp Glu His Val Ile Gln His
        355                 360                 365

Cys Phe His Tyr Thr Ser Thr Val Leu Thr Ser Thr Leu Ala Phe Gln
    370                 375                 380
```

```
Lys Glu Gln Lys Leu Lys Cys Glu Cys Gln Ala Leu Leu Gln Val Ala
385                 390                 395                 400

Lys Asn Leu Phe Thr His Leu Asp Asp Val Ser Val Leu Leu Gln Glu
                405                 410                 415

Ile Ile Thr Glu Ala Arg Asn Leu Ser Asn Ala Glu Ile Cys Ser Val
            420                 425                 430

Phe Leu Leu Asp Gln Asn Glu Leu Val Ala Lys Val Phe Asp Gly Gly
        435                 440                 445

Val Val Asp Asp Glu Ser Tyr Glu Ile Arg Ile Pro Ala Asp Gln Gly
    450                 455                 460

Ile Ala Gly His Val Ala Thr Thr Gly Gln Ile Leu Asn Ile Pro Asp
465                 470                 475                 480

Ala Tyr Ala His Pro Leu Phe Tyr Arg Gly Val Asp Asp Ser Thr Gly
                485                 490                 495

Phe Arg Thr Arg Asn Ile Leu Cys Phe Pro Ile Lys Asn Glu Asn Gln
            500                 505                 510

Glu Val Ile Gly Val Ala Glu Leu Val Asn Lys Ile Asn Gly Pro Trp
        515                 520                 525

Phe Ser Lys Phe Asp Glu Asp Leu Ala Thr Ala Phe Ser Ile Tyr Cys
    530                 535                 540

Gly Ile Ser Ile Ala His Ser Leu Leu Tyr Lys Lys Val Asn Glu Ala
545                 550                 555                 560

Gln Tyr Arg Ser His Leu Ala Asn Glu Met Met Met Tyr His Met Lys
                565                 570                 575

Val Ser Asp Asp Glu Tyr Thr Lys Leu Leu His Asp Gly Ile Gln Pro
            580                 585                 590

Val Ala Ala Ile Asp Ser Asn Phe Ala Ser Phe Thr Tyr Thr Pro Arg
        595                 600                 605

Ser Leu Pro Glu Asp Asp Thr Ser Met Ala Ile Leu Ser Met Leu Gln
    610                 615                 620

Asp Met Asn Phe Ile Asn Asn Tyr Lys Ile Asp Cys Pro Thr Leu Ala
625                 630                 635                 640

Arg Phe Cys Leu Met Val Lys Lys Gly Tyr Arg Asp Pro Pro Tyr His
                645                 650                 655

Asn Trp Met His Ala Phe Ser Val Ser His Phe Cys Tyr Leu Leu Tyr
            660                 665                 670

Lys Asn Leu Glu Leu Thr Asn Tyr Leu Glu Asp Ile Glu Ile Phe Ala
        675                 680                 685

Leu Phe Ile Ser Cys Met Cys His Asp Leu Asp His Arg Gly Thr Asn
    690                 695                 700

Asn Ser Phe Gln Val Ala Ser Lys Ser Val Leu Ala Ala Leu Tyr Ser
705                 710                 715                 720

Ser Glu Gly Ser Val Met Glu Arg His His Phe Ala Gln Ala Ile Ala
                725                 730                 735

Ile Leu Asn Thr His Gly Cys Asn Ile Phe Asp His Phe Ser Arg Lys
            740                 745                 750

Asp Tyr Gln Arg Met Leu Asp Leu Met Arg Asp Ile Ile Leu Ala Thr
        755                 760                 765

Asp Leu Ala His His Leu Arg Ile Phe Lys Asp Leu Gln Lys Met Ala
    770                 775                 780

Glu Val Gly Tyr Asp Arg Asn Asn Lys Gln His His Arg Leu Leu Leu
785                 790                 795                 800
```

```
Cys Leu Leu Met Thr Ser Cys Asp Leu Ser Asp Gln Thr Lys Gly Trp
                805                 810                 815

Lys Thr Thr Arg Lys Ile Ala Glu Leu Ile Tyr Lys Glu Phe Phe Ser
            820                 825                 830

Gln Gly Asp Leu Glu Lys Ala Met Gly Asn Arg Pro Met Glu Met Met
        835                 840                 845

Asp Arg Glu Lys Ala Tyr Ile Pro Glu Leu Gln Ile Ser Phe Met Glu
    850                 855                 860

His Ile Ala Met Pro Ile Tyr Lys Leu Leu Gln Asp Leu Phe Pro Lys
865                 870                 875                 880

Ala Ala Glu Leu Tyr Glu Arg Val Ala Ser Asn Arg Glu His Trp Thr
                885                 890                 895

Lys Val Ser His Lys Phe Thr Ile Arg Gly Leu Pro Ser Asn Asn Ser
            900                 905                 910

Leu Asp Phe Leu Asp Glu Glu Tyr Glu Val Pro Asp Leu Asp Gly Thr
        915                 920                 925

Arg Ala Pro Ile Asn Gly Cys Cys Ser Leu Asp Ala Glu
    930                 935                 940


<210> SEQ ID NO 126
<211> LENGTH: 12
<212> TYPE: PRT
<213> ORGANISM: Artificial Sequence
<220> FEATURE:
<223> OTHER INFORMATION: A synthetic peptide

<400> SEQUENCE: 126

Gly Ser Ile Ala Gly Cys Gly Asp Ala Gly Glu Gly
 1               5                  10


<210> SEQ ID NO 127
<211> LENGTH: 11
<212> TYPE: PRT
<213> ORGANISM: Artificial Sequence
<220> FEATURE:
<223> OTHER INFORMATION: A synthetic peptide

<400> SEQUENCE: 127

Gly Ser Asn Trp Asp Ser Gly Cys Ser Arg Glu
 1               5                  10


<210> SEQ ID NO 128
<211> LENGTH: 12
<212> TYPE: PRT
<213> ORGANISM: Artificial Sequence
<220> FEATURE:
<223> OTHER INFORMATION: A synthetic peptide

<400> SEQUENCE: 128

Gly Ser Ile Ala Gly Cys Gly Asp Ala Gly Glu Gly
 1               5                  10


<210> SEQ ID NO 129
<211> LENGTH: 12
<212> TYPE: PRT
<213> ORGANISM: Artificial Sequence
<220> FEATURE:
<223> OTHER INFORMATION: A synthetic peptide

<400> SEQUENCE: 129

Gly Ser Asn Trp Asp Ser Gly Cys Ser Arg Glu Gly
 1               5                  10
```

```
<210> SEQ ID NO 130
<211> LENGTH: 10
<212> TYPE: PRT
<213> ORGANISM: Artificial Sequence
<220> FEATURE:
<223> OTHER INFORMATION: A synthetic peptide

<400> SEQUENCE: 130

Asn Trp Asp Ser Gly Cys Ser Arg Glu Gly
 1               5                   10


<210> SEQ ID NO 131
<211> LENGTH: 10
<212> TYPE: PRT
<213> ORGANISM: Artificial Sequence
<220> FEATURE:
<223> OTHER INFORMATION: A synthetic peptide

<400> SEQUENCE: 131

Ile Ala Gly Cys Gly Asp Ala Gly Glu Gly
 1               5                   10
```